(12) United States Patent
Kim et al.

(10) Patent No.: US 11,084,824 B2
(45) Date of Patent: Aug. 10, 2021

(54) PYRAZOLOPYRIMIDINE DERIVATIVES, PREPARATION METHOD THEREOF, AND PHARMACEUTICAL COMPOSITION FOR USE IN PREVENTING OR TREATING CANCER, AUTOIMMUNE DISEASE AND BRAIN DISEASE CONTAINING THE SAME AS AN ACTIVE INGREDIENT

(71) Applicant: Korea Research Institute of Chemical Technology, Daejeon (KR)

(72) Inventors: Pilho Kim, Daejeon (KR); Sung Yun Cho, Daejeon (KR); Jae Du Ha, Daejeon (KR); Hyoung Rae Kim, Daejeon (KR); Jong Yeon Hwang, Jeollabuk-do (KR); Chang Soo Yun, Daejeon (KR); Hee Jung Jung, Daejeon (KR); Chi Hoon Park, Daejeon (KR); Chong Ock Lee, Seoul (KR); Chang Hoon Lee, Daejeon (KR); Sunjoo Ahn, Daejeon (KR)

(73) Assignee: KOREA RESEARCH INSTITUTE OF CHEMICAL TECHNOLOGY, Daejeon (KR)

( * ) Notice: Subject to any disclaimer, the term of this patent is extended or adjusted under 35 U.S.C. 154(b) by 0 days.

(21) Appl. No.: 16/612,592

(22) PCT Filed: May 14, 2018

(86) PCT No.: PCT/KR2018/005478
§ 371 (c)(1),
(2) Date: Nov. 11, 2019

(87) PCT Pub. No.: WO2018/208132
PCT Pub. Date: Nov. 15, 2018

(65) Prior Publication Data
US 2020/0199129 A1 Jun. 25, 2020

(30) Foreign Application Priority Data

May 12, 2017 (KR) .................. 10-2017-0059165
May 4, 2018 (KR) .................. 10-2018-0051686

(51) Int. Cl.
*A61K 31/519* (2006.01)
*A61P 25/16* (2006.01)
*A61P 35/00* (2006.01)
*A61P 37/00* (2006.01)
*C07D 487/04* (2006.01)
*A23L 33/10* (2016.01)

(52) U.S. Cl.
CPC ............ *C07D 487/04* (2013.01); *A23L 33/10* (2016.08); *A61P 25/16* (2018.01); *A61P 35/00* (2018.01); *A61P 37/00* (2018.01)

(58) Field of Classification Search
CPC ........ A61K 31/519; A61P 25/16; A61P 35/00; A61P 37/00; C07D 487/04
See application file for complete search history.

(56) References Cited

FOREIGN PATENT DOCUMENTS

| KR | 1020160062103 A | 6/2016 |
| WO | 2007024680 A1 | 3/2007 |
| WO | 2008112695 A2 | 9/2008 |
| WO | 2015048689 A1 | 4/2015 |

OTHER PUBLICATIONS

PCT International Search Report and Written Opinion dated Aug. 14, 2018 for Intl. App. No. PCT/KR2018/005478, from which the instant application is based, 11 pages.
Wu, S. et al., "Ack1 is a dopamine transporter endocytic brake that rescues a trafficking-dysregulated ADHD coding variant," Proceedings of the National Academy of Sciences, 2015, vol. 112, No. 50, pp. 15480-15485.
LEUNG, C. S. et al., "Methyl Effects on Protein-Ligand Binding," Journal of Medicinal Chemistry, 2012, vol. 55, No. 9, pp. 4489-4500.
English Abstract and Machine Translation for Korean Publication No. 10-2016-0062103 A, published Jun. 1, 2016, 199 pages.

*Primary Examiner* — Brenda L Coleman
(74) *Attorney, Agent, or Firm* — Fredrikson & Byron, P.A.

(57) ABSTRACT

The present invention relates to a pyrazolopyrimidine derivative, a preparation method thereof and a pharmaceutical composition comprising the same as an active ingredient for the prevention or treatment of cancer, autoimmune disease and brain disease. The pyrazolopyrimidine derivative of the present invention exhibits excellent Bruton's tyrosine kinase inhibition activity, so that it can be effectively used as a pharmaceutical composition for the prevention or treatment of cancer, autoimmune disease and Parkinson's disease.

6 Claims, 1 Drawing Sheet

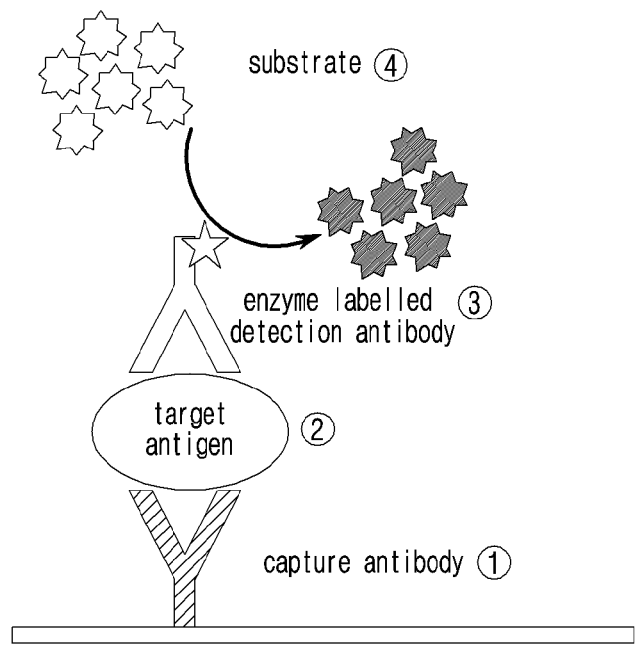

PYRAZOLOPYRIMIDINE DERIVATIVES, PREPARATION METHOD THEREOF, AND PHARMACEUTICAL COMPOSITION FOR USE IN PREVENTING OR TREATING CANCER, AUTOIMMUNE DISEASE AND BRAIN DISEASE CONTAINING THE SAME AS AN ACTIVE INGREDIENT

RELATED APPLICATIONS

This application is a 35 U.S.C. 371 national stage filing from International Application No. PCT/KR2018/005478, filed May 14, 2018, which claims priority to Korean Application No. 10-2018-0051686, filed May 4, 2018, and also claims priority to Korean Application No. 10-2017-0059165, filed May 12, 2017, the teachings of which are incorporated herein by reference.

TECHNICAL FIELD

The present invention relates to a pyrazolopyrimidine derivative, a preparation method thereof and a pharmaceutical composition comprising the same as an active ingredient for the prevention or treatment of cancer, autoimmune disease and brain disease.

BACKGROUND ART

Cancer is defined by the abnormal state of cells, wherein cell death is not controlled normally because of various changes in gene expression, and abnormal cell growth is induced. Cancer cells penetrate into neighboring tissues and destroy thereof, and migrate to other regions, which can result in human death.

The cause of cancer, that is, the mechanism by which normal cells are transfected into cancer cells, has not been clearly identified. It is known that the causes of cancer include environmental factors, external factors such as chemicals, radiation, and viruses, and internal factors such as genetic factors and immunological factors, and those factors interact complicate to cause cancer.

Cancer is largely divided into blood cancer characterized by abnormal blood cell number and solid cancer in the form of cell mass that has a certain degree of hardness and shape in the body. Cancer can be developed in blood and almost all parts of the body, which can be exemplified by lung cancer, stomach cancer, breast cancer, oral cancer, liver cancer, uterine cancer, esophageal cancer and skin cancer. Major treatment methods for cancer are surgery, radio-therapy, and chemo-therapy using a chemotherapeutic agent inhibiting cell proliferation.

A chemotherapeutic agent is not a target-specific agent that directly acts on the target of each cancer. Therefore, repeated chemotherapy treatments result in side effects due to cytotoxicity and resistance to the drugs, indicating that, despite the initial successful response to the anticancer drug, if the cancer treatment duration is prolonged or the cancer recurs, the treatment will fail because of such side effects and drug resistance. To overcome the limitations of the chemotherapeutic agent, it is necessary to develop a targeted therapeutic agent with clear anticancer mechanism.

To develop a targeted therapeutic agent, studies focused on specific molecular biological factors involved in tumorigenesis have been under-going. In particular, molecular biological factors are widely used to predict the prognosis of cancer or to determine the treatment method, either chemo-therapy or radio-therapy.

The conventional cancer drugs have been constructed by targeting the rapid cell division characteristics of tumor cells, indicating they are targeting not only tumor cells but also normal cells showing relatively fast cell division (for example, hair follicle cells, gastrointestinal cells, bone marrow cells, reproductive cells), which causes serious side effects. Therefore, it is required to develop a novel anticancer agent that is specifically expressed only in tumor cells and not expressed in normal cells or has no effect on normal cells.

Burton's tyrosine kinase (BTK) is a nonreceptor tyrosine kinase located on chromosome Xq22, which belongs to Tec family kinase. Bruton's tyrosine kinase (BTK) plays an important role in the downstream signaling of growth factors. B-cell antigens, chemokine receptors and innate immune receptors. That is. BTK is an important protein that plays an important role in various cell activities such as cell growth, survival, differentiation, pathogenesis, angiogenesis, signaling molecule production, and antigen presentation, and thus it is known to play a crucial role in signal transduction of B-cell immunity, inflammation, and anticancer.

Bruton's tyrosine kinase (BTK) is rarely expressed in other tissues than blood cells. Among blood cells, it is present only in B cells, not in T cells. Therefore. BTK inhibitor does not attack other tissues and is targeting only B cell tumor showing BTK activity, suggesting that the side effects can be minimized in patients.

Accordingly, studies on Bruton's tyrosine kinase (BTK) inhibitors have been actively undergoing (Patent Reference 1, Korean Patent Publication No. 10-2016-0062103). The irreversible BTK inhibitor now being used in clinically is Ibrutinib. However, it is still requested to develop a drug that can overcome the problems of resistance, side effects, and immuno-therapy.

Thus, the present inventors have tried to overcome the problems of resistance and side effects according to the co-treatment with immuno-therapy of the conventional BTK inhibitors and to develop a compound with significantly excellent anticancer effect by reversibly inhibiting BTK. In the course of our study, the present inventors confirmed that the compound of the present invention exhibited significantly excellent Bruton's tyrosine kinase inhibitory effect in animal tests, so that the compound could be used effectively in the treatment of cancer, autoimmune disease and Parkinson's disease, leading to the completion of the present invention.

DISCLOSURE OF INVENTION

Technical Problem

It is an object of the present invention to provide a pyrazolopyrimidine compound or a pharmaceutically acceptable sail thereof.

It is another object of the present invention to provide a preparation method of the pyrazolopyrimidine compound above.

It is also an object of the present invention to provide a pharmaceutical composition comprising the pyrazolopyrimidine compound above as an active ingredient for the prevention or treatment of cancer, autoimmune disease or Parkinson's disease.

It is further an object of the present invention to provide a health functional food comprising the pyrazolopyrimidine compound above as an active ingredient for the prevention or improvement of cancer, autoimmune disease or Parkinson's disease.

Solution to Problem

To achieve the objects above, the present invention provides a compound represented by formula 1 below or a pharmaceutically acceptable salt of the same:

[Formula 1]

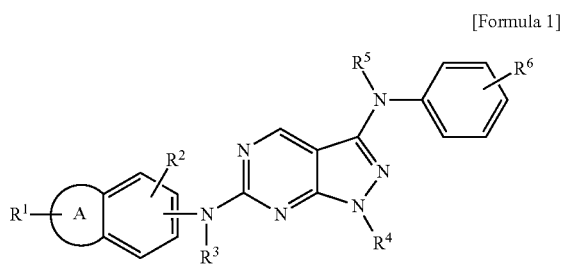

(In formula 1,
A, $R^1$, $R^2$, $R^3$, $R^4$, and $R^5$ are as defined in this specification).

The present invention also provides a preparation method of the compound represented by formula 1 comprising the step of preparing the compound represented by formula 1 by reacting the compound represented by formula 2 with the compound represented by formula 3 (step 1), as shown in reaction formula 1 below:

[Reaction Formula 1]

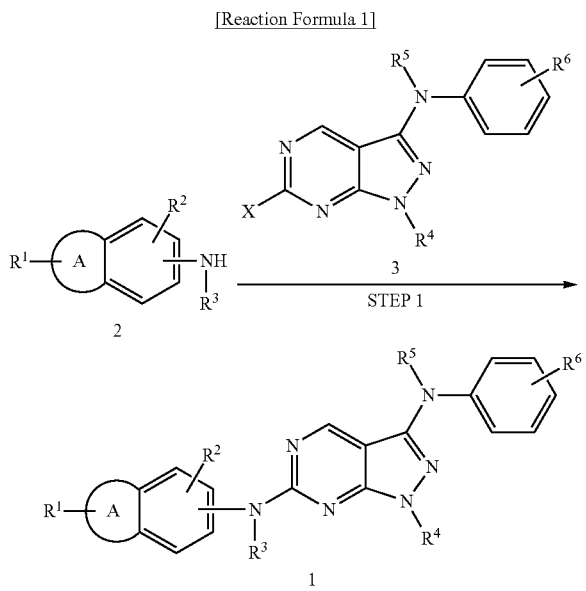

(in reaction formula 1.
A, $R^1$, $R^2$, $R^3$, $R^4$, $R^5$, and X are as defined in this specification).

In addition, the present invention provides a pharmaceutical composition comprising the compound represented by formula 1 or the pharmaceutically acceptable salt thereof as an active ingredient for the prevention or treatment of cancer, autoimmune disease or Parkinson's disease.

The present invention also provides a health functional food comprising the compound represented by formula 1 or the pharmaceutically acceptable salt thereof as an active ingredient for the prevention or improvement of cancer, autoimmune disease or Parkinson's disease.

The present invention also provides a method for the prevention or treatment of cancer, autoimmune disease or Parkinson's disease comprising the step of administering the pharmaceutical composition or the health functional food comprising the compound represented by formula 1 or the pharmaceutically acceptable salt thereof as an active ingredient to a subject in need.

In addition, the present invention provides a use of the pharmaceutical composition or the health functional food comprising the compound represented by formula 1 or the pharmaceutically acceptable salt thereof for the prevention or treatment of cancer, autoimmune disease or Parkinson's disease.

The present invention also provides a method of treating a subject having a cancer comprising administering an effective amount of the compound represented by formula 1 or the pharmaceutically acceptable salt thereof.

The present invention also provides a method of treating a subject having an autoimmune disease comprising administering an effective amount of the compound represented by formula 1 or the pharmaceutically acceptable salt thereof.

The present invention also provides a method of treating a subject having a Parkinson's disease comprising administering an effective amount of the compound represented by formula 1 or the pharmaceutically acceptable salt thereof.

The present invention also provides a compound represented by formula 1 or the pharmaceutically acceptable salt thereof for use in the treatment of a cancer.

The present invention also provides a compound represented by formula 1 or the pharmaceutically acceptable salt thereof for use in the treatment of an autoimmune disease.

The present invention also provides a compound represented by formula 1 or the pharmaceutically acceptable salt thereof for use in the treatment of a Parkinson's disease.

The present invention also provides a composition comprising a compound represented by formula 1 or the pharmaceutically acceptable salt thereof for use in the treatment of a cancer.

The present invention also provides a composition comprising a compound represented by formula 1 or the pharmaceutically acceptable salt thereof for use in the treatment of an autoimmune disease.

The present invention also provides a composition comprising a compound represented by formula 1 or the pharmaceutically acceptable salt thereof for use in the treatment of a Parkinson's disease.

The present invention also provides a composition comprising a compound represented by formula 1 or the pharmaceutically acceptable salt thereof for use as a medicament.

The present invention also provides a medicament comprising a compound represented by formula 1 or the pharmaceutically acceptable salt thereof.

Advantageous Effects of Invention

The pyrazolopyrimidine derivative of the present invention demonstrates an excellent Bruton's tyrosine kinase (BTK) inhibitory activity, so that a pharmaceutical composition comprising the compound of the invention as an active ingredient can be effectively used for the prevention or treatment of cancer, autoimmune disease and Parkinson's disease. The pyrazolopyrimidine derivative of the present invention can be used for immunotherapy because it does not inhibit ITK (Interlukin-2 receptor inducible T-cell kinase) and can be used as an autoimmune disease therapeutic agent for long-term administration because it is a reversible inhibitor. The derivative of the invention also shows an excellent pharmaceutical effect on Abl and Abl mutants along with excellent BBB permeability, so that it can be effectively used for the treatment of Parkinson's disease.

BRIEF DESCRIPTION OF DRAWINGS

The application of the preferred embodiments of the present invention is best understood with reference to the accompanying drawings, wherein:

The FIGURE is a schematic diagram illustrating the enzyme-linked immunosorbent assay performed for measuring the concentration of TNFa.

BEST MODE FOR CARRYING OUT THE INVENTION

Hereinafter, the present invention is described in detail.
The terms for the compound of the present invention are defined as follows:

"Heterocyclic ring" means a saturated or partially unsaturated heterocyclic ring of 3 to 8 ring atoms (refers to a carbocyclic radical having one or more double or triple bonds in the ring without directionality) which contains at least one of hetero atoms selected from the group consisting of N, O and S and the remaining ring atoms are carbon. In a preferred embodiment of the present invention, it refers to mono-heterocyclic consisting of one ring, wherein the hetero atom means a nitrogen atom or an oxygen atom. For example, it can be pyrrolidine, dihydrofuran, tetrahydrothiophene, tetrahydropyrane, dihydropyrane, tetrahydrothiopyran, piperidine, morpholine, thiomorpholine, thioxane, piperazine, azetidine, oxetane, thietane, oxepan, oxazepine, diazepine, thiazepine, 2-pyrroline, or 3-pyrroline.

"Cycloalkane" is a saturated or partly unsaturated (i.e., nonaromatic) group containing all carbon ring atoms. For example, it can be cyclohexene, cyclohexane, cyclopentene, cyclopentane, cyclobutene, cyclobutane, or cyclopropane.

"Alkyl" is a branched or straight-chain saturated aliphatic hydrocarbon group. In a preferred embodiment of the present invention, the alkyl contains 1~5 (e.g. 1-5) carbon atoms or 1~3 (e.g. 1-3) carbon atoms. For example, it can be methyl, ethyl, n-propyl, isopropyl, n-butyl, isobutyl, s-butyl, t-butyl, n-pentyl, isopentyl, t-pentyl, or neopentyl.

"Alkenyl" is a branched or straight-chain aliphatic hydrocarbon group having at least one carbon-carbon double bond that can occur along the chain at a stable point. In a preferred embodiment of the present invention, the alkenyl contains 2~5 (e.g. 2-5) carbon atoms. For example, it can be ethenyl or propenyl.

"Alkynyl" is a branched or straight-chain aliphatic hydrocarbon group having at least one carbon-carbon triple bond that can occur along the chain at any stable point. In a preferred embodiment of the present invention, the alkynyl contains 2~5 (e.g. 2-5) carbon atoms. For example, it can be ethynyl, propynyl, 1-butynyl, 2-butynyl, 3-butynyl, 1-pentynyl, 2-pentynyl, 3-pentynyl, or 4-pentynyl.

"Dialkyl" indicates an alkyl substituted group as defined above wherein two same or different alkyls are substituted.

"Alkoxy" is an alkyl group as defined above covalently bonded through an oxygen bridge (—O—).

"Hydroxyalkyl" is an alkyl group as described above substituted with one or more hydroxy substituents.

"Haloalkyl" indicates a branched or straight alkyl group substituted with one or more halogen atoms and up to a maximum number of halogen atoms. For example, it can be trifluoromethyl, monofluoromethyl, difluoromethyl, 2-fluoroethyl, or penta-fluoroethyl.

"Cycloalkyl" is a saturated or partly unsaturated (i.e., nonaromatic) group containing all carbon ring atoms. For example, it can be cyclohexenyl, cyclohexyl, cyclopentenyl, cyclopentyl, cyclobutenyl, cyclobutyl, or cyclopropyl.

"Alkyloxyalkyl" is an alkyl group as defined above wherein additional alkyl is covalently bonded through an oxygen bridge (—O—).

"Aryl" indicates an aromatic group containing only carbon in the aromatic ring. In a preferred embodiment of the present invention, it may be phenyl or naphthalenyl.

"Heteroaryl" indicates a stable 5~12 (e.g., 5-12) membered monocyclic aromatic ring, bicyclic or tricyclic system containing one or more hetero atoms selected from the group consisting of N, O and S and the remaining ring atoms are carbon. In a preferred embodiment of the present invention, the only hetero atom is nitrogen. The monocyclic heteroaryl group typically has 5~7 (e.g. 5-7) ring atoms. In a preferred embodiment of the present invention, the bicyclic heteroaryl group is a 9 or 10 membered heteroaryl group wherein a 5~7 (e.g., 5-7) membered aromatic ring is fused with the second aromatic or non-aromatic ring and 9~10 (e.g., 9-10) ring atoms are contained. The heteroaryl group is exemplified by pyridinyl (including 2-hydroxypyridinyl), imidazolyl, imidazolopyridinyl, pyrimidinyl (including 4-hydroxypyrimidinyl), pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, tetrahydroisoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, furazanyl, benzofurazanyl, benzothiophenyl, benzothiazolyl, benzoxazolyl, quinazolinyl, quinoxalinyl, naphthyridinyl, tetrahydrofuranyl, and furopyridinyl.

"Halo" or "halogen" independently represents any fluoro, chloro, bromo, and iodo.

The present invention provides a compound represented by formula 1 below or a pharmaceutically acceptable salt of the same:

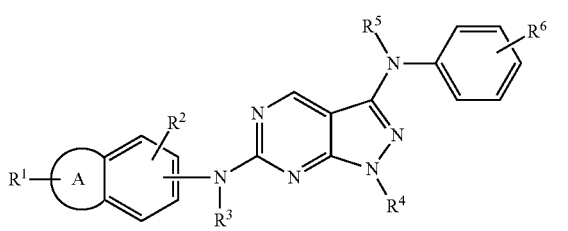

[Formula 1]

In formula 1.
A is 3~8 (e.g. 3-8) membered heterocyclic ring containing one or more hetero atoms selected from the group consisting of N, O and S or $C_{3-10}$ cycloalkane;

$R^1$ and $R^2$ are independently one or more substituents selected from the group consisting of hydrogen, carbonyl (=O), straight or branched $C_{1-5}$ alkyl, $C_{1-5}$ dialkyl, $C_{1-5}$ alkoxy or hydroxy $C_{1-5}$ alkyl, and —(C=O)$R^7$, $R^7$ is straight or branched $C_{1-5}$ alkyl, $C_{2-5}$ alkenyl having one or more double bonds, halo $C_{1-5}$ alkyl or hydroxy $C_{1-5}$ alkyl;

$C_{3-9}$ cycloalkyl; or $-N(CH_2)_nR^8R^9$; $R^8$ and $R^9$ are independently hydrogen or straight or branched $C_{1-5}$ alkyl, and n is an integer of 0~5 (e.g. 0-5);

$R^3$, $R^4$, and $R^5$ are independently hydrogen, straight or branched $C_{1-5}$ alkyl or $C_{3-8}$ cycloalkyl. At this time, the alkyl or cycloalkyl can be substituted with hydroxy; and $R^6$ is one or more substituents selected from the group consisting of hydrogen, $-OH$, $-CN$, $-NO_2$, halogen, straight or branched $C_{1-5}$ alkyl, $C_{2-5}$ alkenyl or $C_{2-5}$ alkynyl, $-OR^{10}$, $-NH(C=O)R^{10}$, $-(C=O)NHR^{10}$, and $-NH(C=O)NHR^{10}$, $R^{10}$ is straight or branched $C_{1-5}$ alkyl or $C_{1-5}$ alkyloxy $C_{1-5}$ alkyl; $C_{6-10}$ aryl; or 5~12 (e.g., 5-12) membered heteroaryl containing one or more hetero atoms selected from the group consisting of N, O, and S; and the aryl or heteroaryl can be substituted with one or more substituents selected from the group consisting of straight or branched $C_{1-5}$ alkyl, $C_{1-5}$ alkoxy and $C_{1-5}$ haloalkyl.

Preferably,

A is 3~6 (e.g. 3-6) membered heterocyclic ring containing one or more hetero atoms selected from the group consisting of N, O and S or $C_{5-7}$ cycloalkane;

$R^1$ and $R^2$ are independently one or more substituents selected from the group consisting of hydrogen, carbonyl (=O), straight or branched $C_{1-3}$ alkyl, $C_{1-3}$ dialkyl, $C_{1-3}$ alkoxy or hydroxy $C_{1-3}$ alkyl, and $-(C=O)R^7$, $R^7$ is straight or branched $C_{1-3}$ alkyl, $C_{2-3}$ alkenyl, halo $C_{1-3}$ alkyl or hydroxy $C_{1-3}$ alkyl; $C_{3-6}$ cycloalkyl; or $-N(CH_2)_nR^8R^9$; $R^8$ and $R^9$ are independently hydrogen or straight or branched $C_{1-3}$ alkyl, and n is an integer of 1~3 (e.g., 1-3);

$R^3$, $R^4$, and $R^5$ are independently hydrogen, straight or branched $C_{1-3}$ alkyl or $C_{3-6}$ cycloalkyl. At this time, the alkyl or cycloalkyl can be substituted with hydroxy; and $R^6$ is one or more substituents selected from the group consisting of hydrogen, straight or branched $C_{1-3}$ alkyl, $-OR^{10}$, $-NH(C=O)R^{10}$, $-(C=O)NHR^{10}$, and $-NH(C=O)NHR^{10}$, $R^{10}$ is straight or branched $C_{1-3}$ alkyl or $C_{1-3}$ alkyloxy $C_{1-3}$ alkyl; $C_{5-10}$ aryl; or 6~10 (e.g., 6-10) membered heteroaryl containing one or more nitrogen atoms; and the aryl or heteroaryl can be substituted with one or more substituents selected from the group consisting of straight or branched $C_{1-3}$ alkyl, $C_{1-3}$ alkoxy and $C_{1-3}$ haloalkyl.

More preferably,

A is piperidine, tetrahydropyrane, pyrrolidine, or cyclohexane;

$R^1$ is one or more substituents selected from the group consisting of hydrogen, carbonyl(=O), $-CH_3$, $-CH_2CH_3$, $-(CH_3)_2$, $-CH(CH_3)_2$, $-CH_2CH_2OH$, $-(C=O)CH_3$, $-(C=O)CF_3$, $-(C=O)CHCH_2$, $-(C=O)$cyclopropyl, $-(C=O)CH_2OH$, and $-(C=O)CH_2N(CH_3)_2$;

$R^2$ is hydrogen or methoxy;

$R^3$ is hydrogen;

$R^4$ is hydrogen, methyl, isopropyl, cyclopentyl, cyclohexyl, or (4-hydroxy)cyclohexyl;

$R_5$ is hydrogen; and $R^6$ is one or more substituents selected from the group consisting of hydrogen, methyl, ethyl, isopropyl, methoxy, chloro, fluoro, methoxyethoxy, phenoxy,

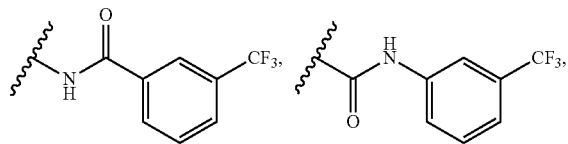

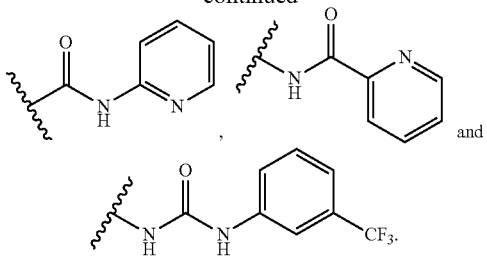

Most preferably, the compound represented by formula 1 above is any one selected from the group consisting of the following compounds:

(1) 1-(7-(3-(2,6-dimethylphenylamino)-1-methyl-1H-pyrazolo[3,4-d]pyrimidine-6-ylamino)-3,4-dihydroisoquinoline-2(1H)-yl)ethaneone;

(2) $N^3$-(2,6-dimethylphenyl)-1-methyl-$N^6$-(1,2,3,4-tetrahydroisoquinoline-7-yl)-1H-pyrazolo[3,4-d]pyrimidine-3,6-diamine;

(3) 1-(6-(3-(2,6-dimethylphenylamino)-1-methyl-1H-pyrazolo[3,4-d]pyrimidine-6-ylamino)-7-methoxy-3,4-dihydroisoquinoline-2(1H)-yl)-2,2,2-trifluoroethaneone;

(4) $N^3$-(2,6-dimethylphenyl)-$N^6$-(7-methoxy-1,2,3,4-tetrahydroisoquinoline-6-yl)-1-methyl-1H-pyrazolo[3,4-d]pyrimidine-3,6-diamine;

(5) 1-(6-(3-(2,6-dimethylphenylamino)-1-methyl-1H-pyrazolo[3,4-d]pyrimidine-6-ylamino)-7-methoxy-3,4-dihydroisoquinoline-2(1H)-yl)ethaneone;

(6) 1-(6-(3-(2,6-dimethylphenylamino)-1-methyl-1H-pyrazolo[3,4-d]pyrimidine-6-ylamino)-3,4-dihydroisoquinoline-2(1H)-yl)-2,2,2-trifluoroethaneone;

(7) $N^3$-(2,6-dimethylphenyl)-1-methyl-$N^6$-(1,2,3,4-tetrahydroisoquinoline-6-yl)-1H-pyrazolo[3,4-d]pyrimidine-3,6-diamine;

(8) 1-(6-(3-(2,6-dimethylphenylamino)-1-methyl-1H-pyrazolo[3,4-d]pyrimidine-6-ylamino)-3,4-dihydroisoquinoline-2(1H)-yl)ethaneone;

(9) 2,2,2-(trifluoro-1-(7-(1-methyl-3-(phenylamino)-1H-pyrazolo[3,4-d]pyrimidine-6-ylamino)-3,4-dihydroisoquinoline-2(1H)-yl)ethaneone;

(10) 1-methyl-$N^3$-phenyl-$N^6$-(1,2,3,4-tetrahydroisoquinolin-7-yl)-1H-pyrazolo[3,4-d]pyrimidine-3,6-diamine;

(11) 1-(7-(3-(2,6-dichlorophenylamino)-1-methyl-1H-pyrazolo[3,4-d]pyrimidine-6-ylamino)-3,4-dihydroisoquinoline-2(1H)-yl)-2,2,2-trifluoroethaneone;

(12) $N^3$-(2,6-dichlorophenyl)-1-methyl-$N^6$-(1,2,3,4-tetrahydroisoquinoline-7-yl)-1H-pyrazolo[3,4-d]pyrimidine-3,6-diamine;

(13) 1-(7-(3-(2,6-dichlorophenylamino)-1-methyl-1H-pyrazolo[3,4-d]pyrimidine-6-ylamino)-3,4-dihydroisoquinolin-2(1H)-yl)ethaneone;

(14) 1-(7-(3-(2,6-dimethylphenylamino)-1-methyl-1H-pyrazolo[3,4-d]pyrimidine-6-ylamino)-3,4-dihydroisoquinoline-2(H)-yl)prop-2-en-1-one;

(15) $N^3$-(2,6-dichlorophenyl)-1-methyl-$N^6$-(1,2,3,4-tetrahydroisoquinoline-6-yl)-1H-pyrazolo[3,4-d]pyrimidine-3,6-diamine;

(16) 1-(6-(3-(2,6-dichlorophenylamino)-1-methyl-1H-pyrazolo[3,4-d]pyrimidine-6-ylamino)-3,4-dihydroisoquinolin-2(1H)-yl)ethaneone;

(17) N-(2,6-dimethylphenyl)-1-methyl-$N^6$-(2-methyl-1,2,3,4-tetrahydroisoquinoline-7-yl)-1H-pyrazolo[3,4-d]pyrimidine-3,6-diamine;

(18) N-(2,6-dimethylphenyl)-N$^6$-(isochroman-7-yl)-1-methyl-1H-pyrazolo[3,4-d]pyrimidine-3,6-diamine;
(19) N$^3$-(2,6-dimethylphenyl)-N$^6$ (1,2,3,4-tetrahydroisoquinoline-7-yl)-1H-pyrazolo[3,4-d]pyrimidine-3,6-diamine;
(20) N$^3$(2,6-dimethylphenyl)-1-methyl-N$^6$-(1-methyl-1,2,3,4-tetrahydroisoquinoline-7-yl)-1H-pyrazolo[3,4-d]pyrimidine-3,6-diamine;
(21) N$^3$-(2,6-dimethylphenyl)-N$^6$-(2-isopropyl-1,2,3,4-tetrahydroisoquinoline-7-yl)-1-methyl-1H-pyrazolo[3,4-d]pyrimidine-3,6-diamine;
(22) 1-(7-(3-(2,6-dimethylphenylamino)-1-methyl-1H-pyrazolo[3,4-d]pyrimidine-6-ylamino)-3,4-dihydroisoquinoline-2(1H)-yl)-2-hydroxyethanone;
(23) cyclopropyl(7-(3-(2,6-dimethylphenylamino)-1-methyl-1H-pyrazolo[3,4-d]pyrimidine-6-ylamino)-3,4-dihydroisoquinoline-2(1H)-yl)methanone;
(24) 2-(7-((3-((2,6-dimethylphenyl)amino)-1-methyl-1H-pyrazolo[3,4-d]pyrimidine-6-yl)amino)-3,4-dihydroisoquinoline-2(1H)-yl)ethane-1-ol;
(25) 1-cyclopentyl-N$^3$-(2,6-dimethylphenyl)-N$^6$ (1,2,3,4-tetrahydroisoquinoline-7-yl)-1H-pyrazolo[3,4-d]pyrimidine-3,6-diamine;
(26) 1-cyclohexyl-N$^6$-(2,6-dimethylphenyl)-N$^6$ (1,2,3,4-tetrahydroisoquinoline-7-yl)-1H-pyrazolo[3,4-d]pyrimidine-3,6-diamine;
(27) N$^3$ (2,6-dimethylphenyl)-1-isopropyl-N6-(1,2,3,4-(tetrahydroisoquinoline-7-yl)-1H-pyrazolo[3,4-d]pyrimidine-3,6-diamine;
(28) N-(4-methyl-3-((1-methyl-6-((1,2,3,4-tetrahydroisoquinoline-7-yl)amino)-1H-pyrazolo[3,4-d]pyrimidine-3-yl)amino)phenyl)-3-(trifluoromethyl)benzamide;
(29) N-(2,4-dimethyl-3-(1-methyl-6-(1,2,3,4-tetrahydroisoquinoline-7-ylamino)-1H-pyrazolo[3,4-d]pyrimidine-3-ylamino)phenyl)-3-(trifluoromethyl)benzamide;
(30) N$^3$-(4-(2-methoxyethoxy)-2,6-dimethylphenyl)-1-methyl-N$^6$-(1,2,3,4-tetrahydroisoquinoline-7-yl)-1H-pyrazolo[3,4-d]pyrimidine-3,6-diamine;
(31) 2-(dimethylamino)-1-(7-(3-(2,6-dimethylphenylamino)-1-methyl-1H-pyrazolo[3,4-d]pyrimidine-6-ylamino)-3,4-dihydroisoquinoline-2(1H)-yl)ethanone;
(32) N$^3$-(2,6-dimethylphenyl)-N$^6$ (2-ethyl-1,2,3,4-tetrahydroisoquinoline-7-yl)-1-methyl-1H-pyrazolo[3,4-d]pyrimidine-3,6-diamine;
(33) N$^3$-(2,6-dimethyl-4-phenoxyphenyl)-1-methyl-N$^6$ (1,2,3,4-tetrahydroisoquinoline-7-yl)-1H-pyrazolo[3,4-d]pyrimidine-3,6-diamine;
(34) 3,5-dimethyl-4-(1-methyl-6-(1,2,3,4-tetrahydroisoquinoline-7-ylamino)-1H-pyrazolo[3,4-d]pyrimidine-3-ylamino)-N-(pyridine-2-yl)benzamide;
(35) N$^3$-(4-methoxy-2,6-dimethylphenyl)-1-methyl-N$^6$ (1,2,3,4-tetrahydroisoquinoline-7-yl)-1H-pyrazolo[3,4-d]pyrimidine-3,6-diamine;
(36) N$^3$-(2,6-diethylphenyl)-1-methyl-N$^6$ (1,2,3,4-tetrahydroisoquinoline-7-yl)-1H-pyrazolo[3,4-d]pyrimidine-3,6-diamine;
(37) N$^3$-(2,6-diisopropylphenyl)-1-methyl-N$^6$-(1,2,3,4-tetrahydroisoquinoline-7-yl)-1H-pyrazolo[3,4-d]pyrimidine-3,6-diamine;
(38) N$^3$-(2-chloro-3,5-dimethylphenyl)-1-methyl-N$^6$-(1,2,3,4-tetrahydroisoquinoline-7-yl)-1H-pyrazolo[3,4-d]pyrimidine-3,6-diamine;
(39) N$^3$-(2,4-dimethylphenyl)-1-methyl-N$^6$(1,2,3,4-tetrahydroisoquinoline-7-yl)-1H-pyrazolo[3,4-d]pyrimidine-3,6-diamine;
(40) 1-methyl-N$^6$-(1,2,3,4-tetrahydroisoquinoline-7-yl)-N$^3$-o-tolyl-1H-pyrazolo[3,4-d]pyrimidine-3,6-diamine;
(41) N$^3$-(3,5-dimethylphenyl)-1-methyl-N$^6$-(1,2,3,4-tetrahydroisoquinoline-7-yl)-1H-pyrazolo[3,4-d]pyrimidine-3,6-diamine;
(42) N$^3$-(2,6-difluorophenyl)-1-methyl-N$^6$-(1,2,3,4-tetrahydroisoquinoline-7-yl)-1H-pyrazolo[3,4-d]pyrimidine-3,6-diamine;
(43) N$^3$-(2,6-dimethoxyphenyl)-1-methyl-N$^6$-(1,2,3,4-tetrahydroisoquinoline-7-yl)-1H-pyrazolo[3,4-d]pyrimidine-3,6-diamine;
(44) N$^3$-(4-fluoro-2,6-dimethylphenyl)-1-methyl-N$^6$-(1,2,3,4-tetrahydroisoquinoline-7-yl)-1H-pyrazolo[3,4-d]pyrimidine-3,6-diamine;
(45) N$^3$-(2,5-dimethylphenyl)-1-methyl-N$^6$ (1,2,3,4-tetrahydroisoquinoline-7-yl)-1H-pyrazolo[3,4-d]pyrimidine-3,6-diamine;
(46) N$^3$-(4,4-dimethyl-1,2,3,4-tetrahydroisoquinoline-7-yl)-N$^6$ (2,6-dimethylphenyl)-1-methyl-1H-pyrazolo[3,4-d]pyrimidine-3,6-diamine;
(47) N-(4-methyl-3-(1-methyl-6-(1-methyl-1,2,3,4-tetrahydroisoquinoline-7-ylamino)-1H-pyrazolo[3,4-d]pyrimidine-3-ylamino)phenyl)-3-(trifluoromethyl)benzamide;
(48) N$^3$-(2-chloro-6-methylphenyl)-1-methyl-N$^6$-(1,2,3,4-tetrahydroisoquinoline-7-yl)-1H-pyrazolo[3,4-d]pyrimidine-3,6-diamine;
(49) N$^3$-(2,6-dimethylphenyl)-N$^6$ (1-isopropyl-1,2,3,4-tetrahydroisoquinoline-7-yl)-1-methyl-1H-pyrazolo[3,4-d]pyrimidine-3,6-diamine;
(50) N$^3$-(5-(2-methoxyethoxy)-2-methylphenyl)-1-methyl-N$^6$ (1,2,3,4-tetrahydroisoquinoline-7-yl)-1H-pyrazolo[3,4-d]pyrimidine-3,6-diamine;
(51) N-(4-methyl-3-(1-methyl-6-(1,2,3,4-tetrahydroisoquinoline-7-ylamino)-1H-pyrazolo[3,4-d]pyrimidine-3-ylamino)phenyl)picolineamide;
(52) 4-methyl-3-(1-methyl-6-(1,2,3,4-tetrahydroisoquinoline-7-ylamino)-1H-pyrazolo[3,4-d]pyrimidine-3-ylamino)-N-(3-(trifluoromethyl)phenyl)benzamide:
(53) N$^3$-(3,3-dimethyl-1,2,3,4-tetrahydroisoquinoline-7-yl)-N$^6$-(2,6-dimethylphenyl)-1-methyl-1H-pyrazolo[3,4-d]pyrimidine-3,6-diamine;
(54) 4-(3-((2,6-dimethylphenyl)amino)-6-((1,2,3,4-tetrahydroisoquinoline-7-yl)amino)-1H-pyrazolo[3,4-d]pyrimidine-1-yl)cyclohexane-1-ol;
(55) N$^3$-(2,6-dimethylphenyl)-1-methyl-N$^6$ (1,3,3-trimethyl-1,2,3,4-tetrahydroisoquinoline-7-yl)-1H-pyrazolo[3,4-d]pyrimidine-3,6-diamine;
(56) N$^3$-(2,6-dimethylphenyl)-N$^6$-(isoindolin-5-yl)-1-methyl-1H-pyrazolo[3,4-d]pyrimidine-3,6-diamine;
(57) 1-(4-methyl-3-((1-methyl-6-((1,2,3,4-tetrahydroisoquinoline-7-yl)amino)-1H-pyrazolo[3,4-d]pyrimidine-3-yl)amino)phenyl)-3-(3-(trifluoromethyl)phenyl)urea;
(58) N$^6$-(1,1-dimethyl-1,2,3,4-tetrahydroisoquinoline-7-yl)-N$^3$-(2,6-dimethylphenyl)-1-methyl-1H-pyrazolo[3,4-d]pyrimidine-3,6-diamine;
(59) N$^3$-(2,6-dimethylphenyl)-1-methyl-N$^6$ (1,1,2-trimethyl-1,2,3,4-tetrahydroisoquinoline-7-yl)-1H-pyrazolo[3,4-d]pyrimidine-3,6-diamine;
(60) 1-(7-((3-((2,6-dimethylphenyl)amino)-1-methyl-1H-pyrazolo[3,4-d]pyrimidine-6-yl)amino)-1,1-dimethyl-3,4-dihydroisoquinoline-2(1H)-yl)ethane-1-one;
(61) 1-(7-((3-((2,6-dimethylphenyl)amino)-1-methyl-1H-pyrazolo[3,4-d]pyrimidine-6-yl)amino)-1-methyl-3,4-dihydroisoquinoline-2(1H)-yl)ethane-1-one;
(62) N$^6$-(1,2-dimethyl-1,2,3,4-tetrahydroisoquinoline-7-yl)-N$^3$-(2,6-dimethylphenyl)-1-methyl-1H-pyrazolo[3,4-d]pyrimidine-3,6-diamine;

(63) N³-(2,6-dimethylphenyl)-1-methyl-N⁶-(2,4,4-trimethyl-1,2,3,4-tetrahydroisoquinoline-7-yl)-1H-pyrazolo[3,4-d]pyrimidine-3, 6-diamine:
(64) N-(3-((6-((1,2-dimethyl-1,2,3,4-tetrahydroisoquinoline-7-yl)amino)-1-methyl-1H-pyrazolo[3,4-d]pyrimidine-3-yl)amino)-4-methylphenyl)-3-(trifluoromethyl)benzamide;
(65) N³-(2,6-dimethylphenyl)-N⁶ (1-isopropyl-2-methyl-1,2,3,4-tetrahydroisoquinoline-7-yl)-1-methyl-1H-pyrazolo[3,4-d]pyrimidine-3,6-diamine;
(66) N³-(2,6-dimethylphenyl)-1-methyl-N⁶ (2,3,3-trimethyl-1,2,3,4-tetrahydroisoquinoline-7-yl)-1H-pyrazolo[3,4-d]pyrimidine-3, 6-diamine;
(67) N³-(2,6-dimethylphenyl)-1-methyl-N⁶-(1,2,3,3-tetramethyl-1,2,3,4-tetrahydroisoquinoline-7-yl)-1H-pyrazolo[3,4-d]pyrimidin c-3,6-diamine;
(68) 1-(7-((3-((2,6-dimethylphenyl)amino)-1-methyl-1H-pyrazolo[3,4-d]pyrimidine-6-yl)amino)-4,4-dimethyl-3,4-dihydroisoquinoline-2(1H)-yl)ethane-1-one;
(69) N-(3-((6-((2-acetyl-1-methyl-1,2,3,4-tetrahydroisoquinoline-7-yl)amino)-1-methyl-1H-pyrazolo[3,4-d]pyrimidine-3-yl)amino)-4-methylphenyl)-3-(trifluoromethyl)benzamide;
(70) 1-(7-((3-((2,6-dimethylphenyl)amino)-1-methyl-1H-pyrazolo[3,4-d]pyrimidine-6-yl)amino)-1-isopropyl-3,4-dihydroisoquinoline-2(1H)-yl)ethane-1-one;
(71) 1-(7-((3-((2,6-dimethylphenyl)amino)-1-methyl-1H-pyrazolo[3,4-d]pyrimidine-6-yl)amino)-3,3-dimethyl-3,4-dihydroisoquinoline-2(1H)-yl)ethane-1-one;
(72) 1-(5-((3-((2,6-dimethylphenyl)amino)-1-methyl-1H-pyrazolo[3,4-d]pyrimidine-6-yl)amino)isoindolin-2-yl)ethane-1-one;
(73) 1-(7-((3-((2,6-dimethylphenyl)amino)-1-methyl-1H-pyrazolo[3,4-d]pyrimidine-6-yl)amino)-1,3,3-trimethyl-3,4-dihydroisoquinoline-2(1H)-yl)ethane-1-one;
(74) N³-(2,6-dimethylphenyl)-1-methyl-N⁶ (2-methylisoindolin-5-yl)-1H-pyrazolo[3,4-d]pyrimidine-3,6-diamine;
(75) N³-(2,6-dimethylphenyl)-1-methyl-N⁶-(5,6,7,8-tetrahydronaphthalen-2-yl)-1H-pyrazolo[3,4-d]pyrimidine-3,6-diamine;
(76) N-(4-((3-((2,6-dimethylphenyl)amino)-1-methyl-1H-pyrazolo[3,4-d]pyrimidine-6-yl)amino)phenyl)acrylamide;
(77) 7-((3-((2,6-dimethylphenyl)amino)-1-methyl-1H-pyrazolo[3,4-d]pyrimidin-6-yl)amino)-3,4-dihydroisoquinoline-1(2H)-one;
(78) N⁶-(1-isopropyl-1,2,3,4-tetrahydroisoquinoline-7-yl)-N³ (4-(2-methoxyethoxy)-2,6-dimethylphenyl)-1-methyl-1H-pyrazolo[3,4-d]pyrimidine-3, 6-diamine;
(79) N⁶-(1,1-dimethyl-1,2,3,4-tetrahydroisoquinoline-7-yl)-N³-(4-(2-methoxyethoxy)-2,6-dimethylphenyl)-1-methyl-1H-pyrazolo[3,4-d]pyrimidine-3, 6-diamine.

The compound represented by formula 1 of the present invention can be used as a form of a pharmaceutically acceptable salt, in which the salt is preferably acid addition salt formed by pharmaceutically acceptable free acids. The acid addition sail herein can be obtained from inorganic acids such as hydrochloric acid, nitric acid, phosphoric acid, sulfuric acid, hydrobromic acid, hydroiodic acid, nitrous acid, and phosphorous acid; non-toxic organic acids such as aliphatic mono/dicarboxylate, phenyl-substituted alkanoate, hydroxy alkanoate, alkanedioic, aromatic acids, and aliphatic/aromatic sulfonic acids; or organic acids such as acetic acid, benzoic acid, citric acid, lactic acid, maleic acid, gluconic acid, methanesulfonic acid, 4-toluenesulfonic acid, tartaric acid, and fumaric acid. The pharmaceutically non-toxic salts are exemplified by sulfate, pyrosulfate, bisulfate, sulphite, bisulphite, nitrate, phosphate, monohydrogen phosphate, dihydrogen phosphate, metaphosphate, pyrophosphate, chloride, bromide, iodide, fluoride, acetate, propionate, decanoate, caprylate, acrylate, formate, isobutylate, caprate, heptanoate, propiolate, oxalate, malonate, succinate, suberate, cabacate, fumarat, maliate, butyne-1,4-dioate, hexane-1,6-dioate, benzoate, chlorobenzoate, methylbenzoate, dinitrobenzoate, hydroxybenzoate, methoxybenzoate, phthalate, teraphthalate, benzenesulfonate, toluenesulfonate, chlorobenzenesulfonate, xylenesulfonates, phenylacetate, phenylpropionate, phenylbutylate, citrate, lactate, hydroxybutylate, glycolate, malate, tartrate, methanesulfonate, propanesulfonate, naphthalene-1-sulfonate, naphthalene-2-sulfonate, and mandelate.

The acid addition salt in this invention can be prepared by the conventional method known to those in the ail. For example, the derivative represented by formula 1 is dissolved in an organic solvent such as methanol, ethanol, acetone, methylenechloride, or acetonitrile, to which organic acid or inorganic acid is added to induce precipitation. Then, the precipitate is filtered and dried to give the sail. Or the solvent and the excessive acid are distillated under reduced pressure, and dried to give the salt. Or the precipitate is crystallized in an organic solvent to give the same.

A pharmaceutically acceptable metal salt can be prepared by using a base. Alkali metal or alkali earth metal salt is obtained by the following processes: dissolving the compound in excessive alkali metal hydroxide or alkali earth metal hydroxide solution; filtering non-soluble compound salt; evaporating the remaining solution and drying thereof. At this time, the metal salt is preferably prepared in the pharmaceutically suitable form of sodium, potassium, or calcium salt. And the corresponding silver salt is prepared by the reaction of alkali metal or alkali earth metal salt with proper silver salt (ex: silver nitrate).

The present invention includes not only the compound represented by formula 1 but also a pharmaceutically acceptable salt thereof, and a solvate, an optical isomer, or a hydrate possibly produced from the same.

The present invention also provides a preparation method of the compound represented by formula 1 comprising the step of preparing the compound represented by formula 1 by reacting the compound represented by formula 2 with the compound represented by formula 3 (step 1), as shown in reaction formula 1 below:

[Reaction Formula 1]

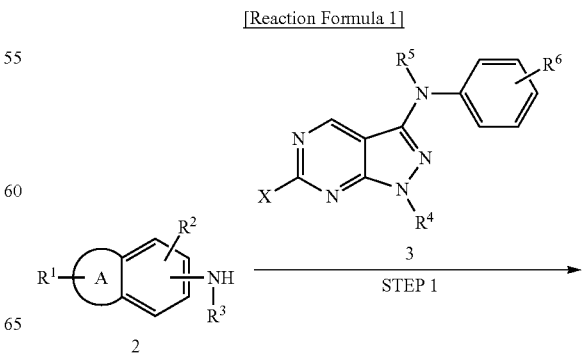

-continued

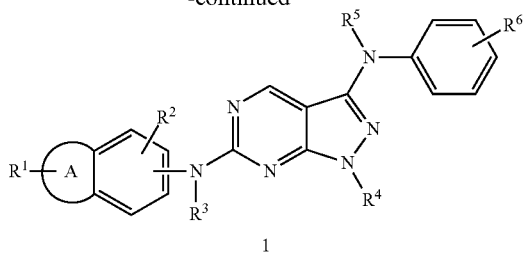

1

In reaction formula 1,

A, $R^1$, $R^2$, $R^3$, $R^4$, and $R^5$ are as defined in formula 1, and X is halogen.

In the preparation method of the compound represented by formula 1 according to the present invention, step 1 is to prepare the compound represented by formula 1 by reacting the compound represented by formula 2 with the compound represented by formula 3.

Particularly, step 1 is a step of condensing an amine group (—$NHR^5$) of the compound represented by formula 2 and a halogen group (X) of the compound represented by formula 3 in the presence of an acid.

Herein, the acid is not particularly limited as long as it is an acid generally used in the field, but trifluoroacetic acid (TFA), p-toluenesulfonic acid (p-TSA), hydrochloric acid (HCl) and formic acid can be used.

The reaction temperature is not limited but can be 10~150° C. (e.g., 10-150° C.), preferably 30~120° C. (e.g., 30-120° C.), and more preferably 50~100° C. (e.g., 50-100° C.). Most preferably, the reaction temperature can be the boiling point of the organic solvent used in the reaction.

Further, the reaction solvent is not particularly limited as long as it is an organic solvent generally used in the field, but isopropanol, butanol, and 1,4-dioxane can be used.

In the preparation method of the present invention, the compound represented by formula 3, which is the starting material, can be prepared by the following steps, as shown in reaction formula 2 below:

preparing the compound represented by formula 3-3 by reacting the compound represented by formula 3-1 with the compound represented by formula 3-2 via amidation (step 1);

preparing the compound represented by formula 3-5 by reacting the compound represented by formula 3-3 prepared in step 1 with the compound represented by formula 3-4 with the addition of hydrazine (step 2); and cyclizing the compound represented by formula 3-5 prepared in step 2 (step 3).

[Reaction Formula 2]

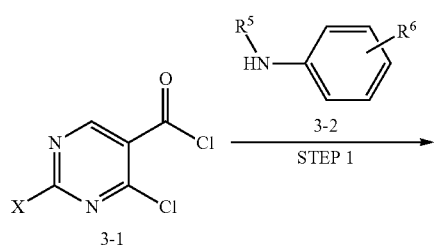

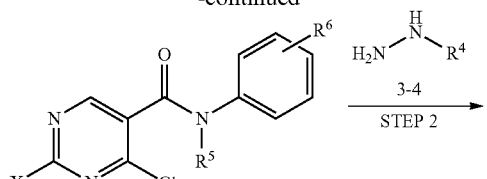

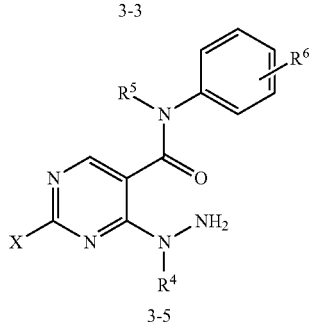

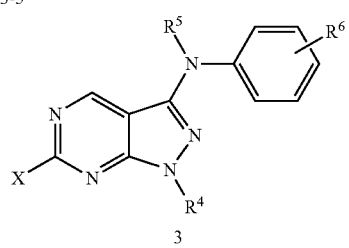

In reaction formula 2, $R^3$, $R^4$ and $R^5$ are as defined in formula 1, and X is halogen.

The reaction conditions for step 1 to step 3 shown in reaction formula 2 above are not particularly limited as long as they are generally used in the art, so that the detailed description is omitted herein.

The present invention also provides a pharmaceutical composition comprising the compound represented by formula 1 or the pharmaceutically acceptable salt thereof as an active ingredient for the prevention or treatment of cancer. Herein, the compound is characterized by being effective in preventing or treating cancer by inhibiting Bruton's tyrosine kinase (BTK). The cancer can be solid cancer or blood cancer.

The solid tumor can be selected from the group consisting of brain tumor, benign astrocytoma, malignant astrocytoma, pituitary adenoma, meningioma, brain lymphoma, oligodendroglioma, intracranial tumor, ependymoma, brain stem tumor, head and neck tumor, laryngeal cancer, uveal cancer, nasal cancer, nasopharyngeal cancer, salivary gland cancer, hypopharyngeal cancer, thyroid cancer, oral cancer, thoracic tumor, small cell lung cancer, non-small cell lung cancer, thymic cancer, mediastinal tumor, esophageal cancer, breast cancer, male breast cancer, abdominal tumor, stomach cancer, liver cancer, gallbladder cancer, biliary cancer, pancreatic cancer, small bowel cancer, colon cancer, anal cancer, bladder cancer, kidney cancer, male genital tumor, penile cancer, prostate cancer, female genital tumor, cervix cancer, endometrial cancer, ovarian cancer, uterine sarcoma, vaginal cancer, female external gonadal cancer, female urethral cancer, and skin cancer. The blood cancer can be leukemia, malignant lymphoma, multiple myeloma, or aplastic anemia.

The pharmaceutical composition comprising the compound represented by formula 1, the optical isomer thereof or the pharmaceutically acceptable salt thereof as an active ingredient for the prevention or treatment of cancer can be administered independently or co-administered with other anticancer agents in use.

Further, the present invention provides a pharmaceutical composition comprising the compound represented by formula 1 or the pharmaceutically acceptable salt thereof as an active ingredient for the prevention or treatment of autoimmune disease.

Herein, the compound is characterized by being effective in preventing or treating autoimmune disease by inhibiting Bruton's tyrosine kinase (BTK). The autoimmune disease can be selected from the group consisting of rheumatoid arthritis, psoriatic arthritis, osteoarthritis, Still's disease, juvenile arthritis, lupus, diabetes mellitus, myasthenia gravis, Hashimoto's thyroiditis, Graves' disease, Sjogren's syndrome, multiple sclerosis. Guilin Barre syndrome, acute sporadic encephalomyelitis, Addison's disease, ocular hepatocellular seizure-epileptic syndrome, ankylosing spondylitis, antiphospholipid antibody syndrome, aplastic anemia, autoimmune hepatitis, chronic digestive dysfunction, Goodpasture syndrome, idiopathic thrombocytopenic purpura, optic neuritis, scleroderma, primary dysplasia cirrhosis. Takayasu arteritis, temporal arteritis, autoimmune hemolytic anemia, Wegener's granulomatosis, psoriasis, systemic alopecia, Behcet's disease, chronic fatigue, autonomic nystagmus, endometriosis, interstitial cystitis, neuromuscular dystrophy, scleroderma, and vulvar pain.

The present invention also provides a pharmaceutical composition comprising the compound represented by formula 1 or the pharmaceutically acceptable salt thereof as an active ingredient for the prevention or treatment of Parkinson's disease.

The compound represented by formula 1 or the pharmaceutically acceptable salt thereof included in the pharmaceutical composition of the present invention can be administered orally or parenterally and be used in general forms of pharmaceutical formulation. That is, the composition of the present invention can be prepared for oral or parenteral administration by mixing with generally used diluents or excipients such as fillers, extenders, binders, wetting agents, disintegrating agents and surfactants.

The formulations for oral administration are exemplified by tablets, pills, hard/soft capsules, solution suspensions, emulsions, syrups, granules, elixirs, and troches, etc. These formulations can include diluents (for example, lactose, dextrose, sucrose, mannitol, sorbitol, cellulose, and/or glycine) and lubricants (for example, silica, talc, stearate and its magnesium or calcium salt, and/or polyethylene glycol) in addition to the active ingredient. Tablets can include binding agents such as magnesium aluminum silicate, starch paste, gelatin, methylcellulose, sodium carboxymethylcellulose and/or polyvinylpyrolidone, and if necessary disintegrating agents such as starch, agarose, alginic acid or its sodium salt or azeotropic mixtures and/or absorbents, coloring agents, flavours, and sweeteners can be additionally included thereto.

The pharmaceutical composition comprising the compound represented by formula 1 as an active ingredient can be administered by parenterally and the parenteral administration includes subcutaneous injection, intravenous injection, intramuscular injection, or intrathoracic injection.

To prepare the compound represented by formula 1 or the pharmaceutically acceptable salt thereof as a formulation for parenteral administration, the compound represented by formula 1 or the pharmaceutically acceptable salt thereof is mixed with a stabilizer or a buffering agent in water to produce a solution or suspension, which is then formulated as ampoules or vials. The composition herein can be sterilized and additionally contains preservatives, stabilizers, wettable powders or emulsifiers, salts and/or buffers for the regulation of osmotic pressure, and other therapeutically useful materials, and the composition can be formulated by the conventional mixing, granulating or coating method.

The effective dosage of the compound represented by formula 1 or the pharmaceutically acceptable salt thereof of the present invention can be determined according to age, weight, gender, administration method, health condition, and severity of disease. The dosage is generally 0.1~1000 mg/day (e.g., from 0.1 to 1000 mg/day), and preferably 1~500 mg/day (e.g., from 1 to 500 mg/day) based on an adult patient weighing 70 kg, which can be administered once or several times a day at intervals of a certain time depending on the judgment of a doctor or a pharmacist.

The pharmaceutical composition comprising the compound represented by formula 1, the optical isomer, or the pharmaceutically acceptable salt thereof as an active ingredient for the prevention or treatment of cancer can be administered as an individual therapeutic agent or in combination with other anticancer agents in use.

The present invention also provides a health functional food comprising the compound represented by formula 1 or the pharmaceutically acceptable salt thereof as an active ingredient for the prevention or improvement of cancer.

The present invention also provides a health functional food comprising the compound represented by formula 1 or the pharmaceutically acceptable salt thereof as an active ingredient for the prevention or improvement of autoimmune disease.

In addition, the present invention provides a health functional food comprising the compound represented by formula 1 or the pharmaceutically acceptable salt thereof as an active ingredient for the prevention or improvement of Parkinson's disease.

The compound represented by formula 1 of the present invention can be used as a food additive. In that case, the compound represented by formula 1 of the present invention can be added as it is or as mixed with other food components according to the conventional method. The mixing ratio of active ingredients can be regulated according to the purpose of use (prevention or improvement). In general, the compound of the present invention is preferably added to food or beverages by 0.1~90 (e.g., 0.1 to 90) weight part for the total weight of the food or beverages. However, if long term administration is required for health and hygiene or regulating health condition, the content can be lower than the above but higher content can be accepted as well since the compound of the present invention has been proved to be very safe.

The health beverage composition of the present invention can additionally include various flavors or natural carbohydrates, etc, like other beverages. The natural carbohydrates above can be one of monosaccharides such as glucose and fructose, disaccharides such as maltose and sucrose, polysaccharides such as dextrin and cyclodextrin, and sugar alcohols such as xilytole, sorbitol and erythritol. Besides, natural sweetening agents (thaumatin, stevia extract, for example rebaudioside A, glycyrrhizin, etc.) and synthetic sweetening agents (saccharin, aspartame, etc.) can be included as a sweetening agent. The content of the natural carbohydrate is preferably 1~20 g (e.g 1 to 20 g) and more preferably 5~12 g (e.g., 5 to 12 g) in 100 g of the composition of the invention.

In addition to the ingredients mentioned above, the compound represented by formula 1 of the present invention can include in variety of nutrients, vitamins, minerals (electrolytes), flavors including natural flavors and synthetic flavors, coloring agents and extenders (cheese, chocolate, etc.), pectic acid and its salts, alginic acid and its salts, organic acid, protective colloidal viscosifiers, pH regulators, stabilizers, antiseptics, glycerin, alcohols, carbonators which used to be added to soda, etc. The compound represented by formula 1 of the present invention can also include natural fruit juice, fruit beverages and fruit flesh addable to vegetable beverages.

The present invention also provides a method for the prevention or treatment of cancer, autoimmune disease or Parkinson's disease comprising the step of administering the pharmaceutical composition or the health functional food comprising the compound represented by formula 1 or the pharmaceutically acceptable salt thereof as an active ingredient to a subject in need.

In addition, the present invention provides a use of the pharmaceutical composition or the health functional food comprising the compound represented by formula 1 or the pharmaceutically acceptable salt thereof for the prevention or treatment of cancer, autoimmune disease or Parkinson's disease.

The present invention also provides a method of treating a subject having a cancer comprising administering an effective amount of the compound represented by formula 1 or the pharmaceutically acceptable salt thereof.

The present invention also provides a method of treating a subject having an autoimmune disease comprising administering an effective amount of the compound represented by formula 1 or the pharmaceutically acceptable salt thereof.

The present invention also provides a method of treating a subject having a Parkinson's disease comprising administering an effective amount of the compound represented by formula 1 or the pharmaceutically acceptable salt thereof.

The present invention also provides a compound represented by formula 1 or the pharmaceutically acceptable salt thereof for use in the treatment of a cancer.

The present invention also provides a compound represented by formula 1 or the pharmaceutically acceptable salt thereof for use in the treatment of an autoimmune disease.

The present invention also provides a compound represented by formula 1 or the pharmaceutically acceptable salt thereof for use in the treatment of a Parkinson's disease.

The present invention also provides a composition comprising a compound represented by formula 1 or the pharmaceutically acceptable salt thereof for use in the treatment of a cancer.

The present invention also provides a composition comprising a compound represented by formula 1 or the pharmaceutically acceptable salt thereof for use in the treatment of an autoimmune disease.

The present invention also provides a composition comprising a compound represented by formula 1 or the pharmaceutically acceptable salt thereof for use in the treatment of a Parkinson's disease.

The present invention also provides a composition comprising a compound represented by formula 1 or the pharmaceutically acceptable salt thereof for use as a medicament.

The present invention also provides a medicament comprising a compound represented by formula 1 or the pharmaceutically acceptable salt thereof.

The novel pyrazolopyrimidine compound of the present invention demonstrates an excellent BTK inhibitory activity at a low concentration, and therefore it can be used as a pharmaceutical composition for the prevention or treatment of cancer, autoimmune disease or Parkinson's disease, which is supported by the results of the following experiments.

MODE FOR THE INVENTION

Practical and presently preferred embodiments of the present invention are illustrative as shown in the following Examples.

However, it will be appreciated that those skilled in the art, on consideration of this disclosure, may make modifications and improvements within the spirit and scope of the present invention.

Preparative Example A-1: Preparation of 1-(7-amino-3,4-dihydroisoquinoline-2(1H)-yl)ethane-1-one Step 1: Preparation of N-(4-nitrophenetyl)acetamide

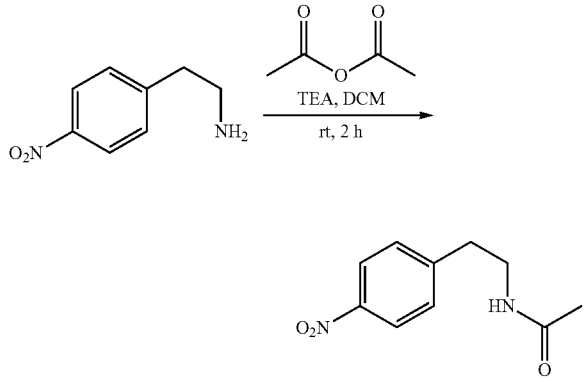

Acetic anhydride (1.36 mL, 14.4 mmol) was added to 2-(4-nitrophenyl)ethane-1-amine (2.0 g, 12.03 mmol) solution in DCM (50 mL), to which TEA (4.2 mL, 30.07 mmol) was added. The reaction mixture was stirred at room temperature for 2 hours. Upon completion of the reaction, water (50 mL) was added to the reaction mixture, followed by extraction with DCM (2×50 mL). The combined organic layer was washed with brine solution, which was then dried over $Na_2SO_4$. The solvent was eliminated in vacuum. The crude mixture was purified by re-crystallization. As a result, 1-(7-amino-3,4-dihydroisoquinoline-2(1H)-yl)ethane-1-one (2.25 g, 10.8 mmol, 90%) was obtained as a grey-white solid.

$^1$H NMR (300 MHz, $CDCl_3$) δ 8.17 (d, J=8.6 Hz, 2H), 7.36 (d, J=8.5 Hz, 2H), 5.52 (s, br, 1H), 3.55 (q, J=6.8 Hz, 2H), 2.95 (t, J=7.0 Hz, 2H), 1.96 (s 3H); LC/MS 209.2 [M+H$^+$].

Step 2: Preparation of 1-(7-nitro-3,4-dihydroisoquinoline-2(1H)-yl)ethane-1-one

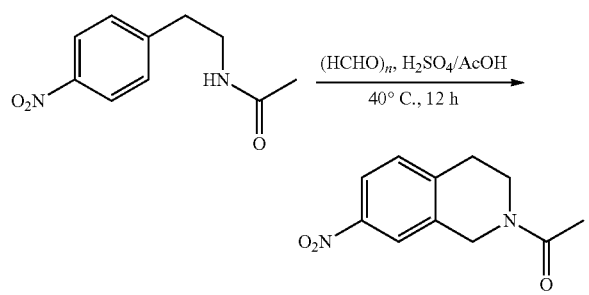

Compound of step 1 (1.0 g, 4.80 mmol) was dissolved in HOAc (5 mL), to which sulfuric acid (7.5 mL) and paraformaldehyde (231 mg, 7.68 mmol) were added at room temperature followed by stirring at 40° C. for 12 hours. The reaction mixture was poured carefully into approximately 100 mL of ice. The generated brown sludge suspension was extracted with EtOAc. The organic material was washed with saturated aqueous $NaHCO_3$ and brine, followed by drying over $MgSO_4$. The crude mixture was purified by column chromatography using MeOH/MC (1:4) as an eluent. As a result, 1-(7-nitro-3,4-dihydroisoquinoline-2(1H)-yl)ethane-1-one (900 mg, 4.08 mmol, 85%) was obtained as a white solid.

$^1H$ NMR (300 MHz, $CDCl_3$) δ 8.07-8.03 (m, 2H), 7.35-7.30 (m, 1H), 4.83-4.72 (m, 2H), 3.88-3.71 (m, 2H), 3.03-2.93 (m, 2H), 2.21-2.20 (m, 3H); LC/MS 221.2 [M+H$^+$].

Step 3: Preparation of 1-(7-amino-3,4-dihydroisoquinoline-2(1H)-yl)ethane-1-one

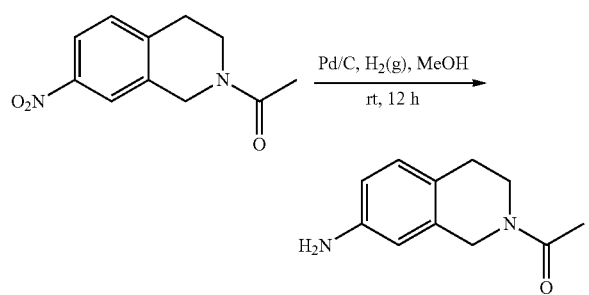

Pd/C (10 weight %) (20 mg, 0.93 mmol) was added to compound of step 2 (900 mg, 4.08 mmol) in MeOH (50 mL) at room temperature. The reaction mixture was stirred at room temperature under hydrogen balloon pressure for 12 hours. TLC analysis indicated the complete consumption of the starting material. The reaction mixture was filtered with a celite bed and concentrated to remove MeOH. The obtained crude mixture was purified by column chromatography using EtOAc/hexane. As a result, 1-(7-amino-3,4-dihydroisoquinoline-2(1H)-yl)ethane-1-one (580 mg, 3.04 mmol, 75%) was obtained as a grey-white solid.

$^1H$ NMR (300 MHz, $CDCl_3$) δ 6.95-6.91 (m, 1H), 6.57-6.51 (m, 1H), 6.47-6.43 (m, 1H), 4.63-4.51 (m, 2H), 3.80-3.60 (m, 4H), 2.80-2.70 (m, 2H), 2.15 (s, 3H); LC/MS 191.2 [M+H$^+$].

Preparative Example A-2: Preparation of 1-(6-amino-3,4-dihydroisoquinoline-2(1H)-yl)-2,2,2-trifluoroethane-1-one

Step 1: Preparation of N-(4-bromophenethyl)-2,2,2-trifluoroacetamide

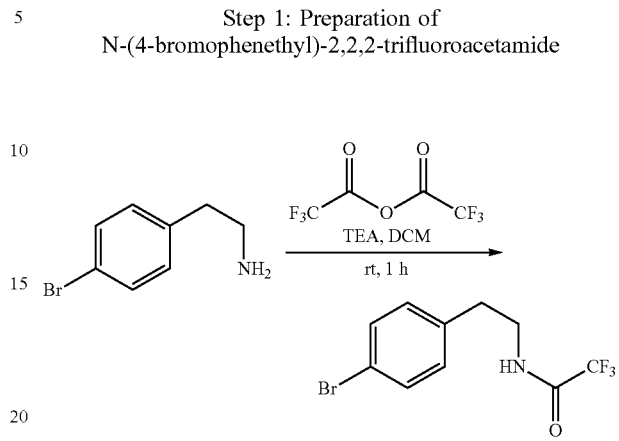

Trifluoro acetic anhydride (0.43 mL, 2.99 mmol) was added to 2-(4-bromophenyl)ethane-1-amine (500 mg, 2.50 mmol) solution in DCM (25 mL), to which TEA (0.87 mL, 6.25 mmol) was added. The reaction mixture was stirred at room temperature for 1 hour. Upon completion of the reaction, water (50 mL) was added to the reaction mixture, followed by extraction with DCM (2×50 mL). The combined organic layer was washed with saturated brine solution, which was dried over $Na_2SO_4$. The solvent was eliminated in vacuum. The crude mixture was purified by re-crystallization. As a result, N-(4-bromophenethyl)-2,2,2-trifluoroacetamide (700 mg, 2.36 mmol, 94%) was obtained as a white solid.

$^1H$ NMR (500 MHz, $CDCl_3$) δ 7.48 (d, J=8.3 Hz, 2H), 7.09 (d, J=8.3 Hz, 2H), 6.37 (s, br, 1H), 3.62 (q, J=6.6 Hz, 2H), 2.87 (t, J=7.0 Hz, 2H); LC/MS 296.2[M+H$^+$].

Step 2: Preparation of 1-(7-bromo-3,4-dihydroisoquinoline-2(1H)-yl)-2,2,2-trifluoroethane-1-one

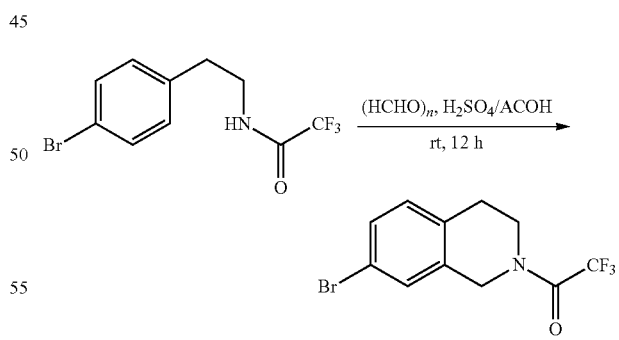

Compound of step 1 (250 mg, 0.844 mmol) was dissolved in HOAc (1.41 mL) and sulfuric acid (0.94 mL), to which paraformaldehyde (40 mg, 1.35 mmol) was added at room temperature, followed by stirring for 12 hours. The reaction mixture was poured carefully into approximately 10 mL of ice. The generated white sludge suspension was extracted with EtOAc. The organic material was washed with saturated aqueous $NaHCO_3$ and brine, followed by drying over $MgSO_4$. The crude mixture was purified by column chromatography using EtOAc/Hx (1:4) as an eluent. As a result, 1-(7-bromo-3,4-dihydroisoquinoline-2(1H)-yl)-2,2,2-trifluoroethane-1-one (225 mg, 0.730 mmol, 86%) was obtained as a white solid.

$^1$H NMR (300 MHz, CDCl$_3$) δ 7.37-7.28 (m, 2H), 7.07-7.02 (m, 1H), 4.76-4.71 (m, 2H), 3.89-3.81 (m, 2H), 2.93-2.87 (m, 2H); LC/MS 308.2 [M+H$^+$].

Step 3: Preparation of 1-(7-bromo-6-nitro-3,4-dihydroisoquinoline-2(1H)-yl)-2,2,2-trifluoroethane-1-one

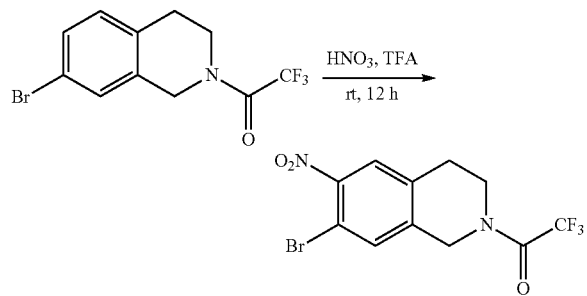

HNO$_3$ (187 mg, 1.785 mmol) was added to compound of step 2 (500 mg, 1.622 mmol) in TFA (15 mL) at 0° C. The reaction mixture was stirred for 12 hours. Ice was added to the reaction mixture and the generated solid was filtered. The obtained crude product was washed with NaHCO$_3$. The combined organic layer was dried over anhydrous Na$_2$SO$_4$. The solvent was eliminated under reduced pressure. The crude mixture was purified by column chromatography using EtOAc/Hx (1:4) as an eluent. As a result, 1-(7-bromo-6-nitro-3,4-dihydroisoquinoline-2(1H)-yl)-2,2,2-trifluoroethane-1-one (300 mg, 0.849 mmol, 52%) was obtained as a white solid.

$^1$H NMR (300 MHz, CDCl$_3$) δ 7.73-7.72 (m, 1H), 7.57-7.55 (m, 1H), 4.85-4.81 (m, 2H), 3.97-3.88 (m, 2H), 3.04-2.98 (m, 2H); LC/MS 355.2 [M+H$^+$].

Step 4: Preparation of 1-(6-amino-3,4-dihydroisoquinoline-2(1H)-yl)-2,2,2-trifluoroethane-1-one

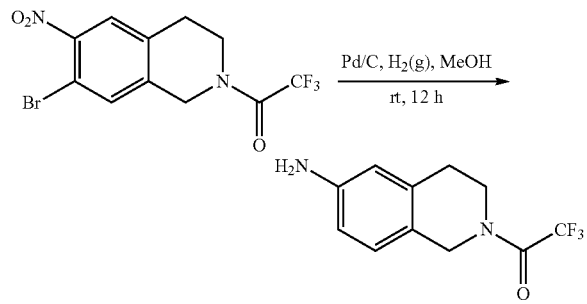

Pd/C (10 weight %) (36 mg, 0.34 mmol) was added to compound of step 3 (300 mg, 0.849 mmol) in MeOH (50 mL) at room temperature. The reaction mixture was stirred at room temperature under hydrogen balloon pressure for 12 hours. TLC analysis indicated the complete consumption of the starting material. The reaction mixture was filtered with a celite bed and concentrated to remove MeOH. The obtained crude mixture was purified by column chromatography using EtOAc/hexane. As a result, 1-(6-amino-3,4-dihydroisoquinoline-2(1H)-yl)-2,2,2-tri fluoroethane-1-one (100 mg, 0.409 mmol, 48%) was obtained as a grey-white solid.

$^1$H NMR (500 MHz, CDCl$_3$) δ 6.96-6.91 (m, 1H), 6.60-6.57 (m, 1H), 6.52-6.49 (m, 1H), 4.69-4.65 (m, 2H), 3.87-3.80 (m, 2H), 3.68 (s, br, 2H), 2.88-2.85 (m, 2H); LC/MS 245.2 [M+H]$^+$.

Preparative Example A-3: Preparation of 1-(7-amino-3,4-dihydroisoquinoline-2(1H)-yl)-2,2,2-trifluoroethane-1-one Step 1: Preparation of 2,2,2-trifluoro-N-(4-nitrophenetyl)acetamide

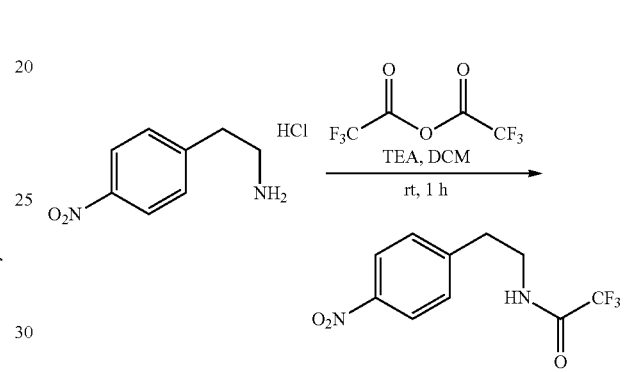

Trifluoro acetic anhydride (6.22 g, 29.61 mmol) was added to 2-(4-nitrophenyl)ethane-1-amine (5.0 g, 24.67 mmol) solution in DCM (100 mL), to which TEA (8.6 mL, 61.67 mmol) was added. The reaction mixture was stirred at room temperature for 2 hours. Upon completion of the reaction, water (50 mL) was added to the reaction mixture, followed by extraction with DCM (2×50 mL). The combined organic layer was washed with saturated brine solution, which was dried over Na$_2$SO$_4$. The solvent was eliminated in vacuum. The crude mixture was purified by re-crystallization. As a result, 2,2,2-trifluoro-N-(4-nitrophenetyl)acetamide (5.8 g, 22.1 mmol, 90%) was obtained as a grey-white solid.

$^1$H NMR (300 MHz, CDCl$_3$) δ 8.17 (d, J=8.6 Hz, 2H), 7.36 (d, J=8.6 Hz, 2H), 6.46 (s, br, 1H), 3.67 (q, J=6.8 Hz, 2H), 3.02 (t, J=7. Hz, 2H); LC/MS 262.2 [M+H$^+$].

Step 2: Preparation of 2,2,2-trifluoro-1-(7-nitro-3,4-dihydroisoquinoline-2(1H)-yl)ethane-1-one

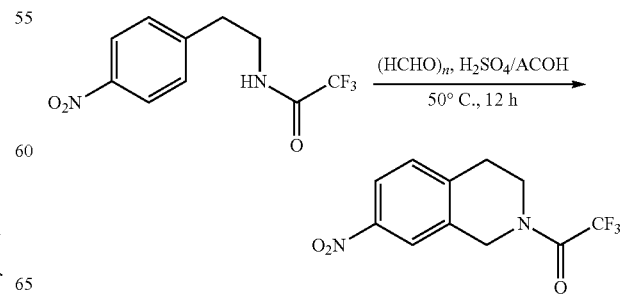

Compound of step 1 (750 mg, 2.86 mmol) was dissolved in HOAc (4 mL), to which sulfuric acid (7.5 mL) and paraformaldehyde (137 mg, 4.57 mmol) were added at room temperature, followed by stirring at 50° C. for 12 hours. The reaction mixture was poured carefully into approximately 100 mL of ice. The generated white sludge suspension was extracted with EtOAc. The organic material was washed with saturated aqueous NaHCO$_3$ and brine, followed by drying over MgSO$_4$. The crude mixture was purified by column chromatography using hexane/EA (1:4) as an eluent. As a result, 2,2,2-trifluoro-1-(7-nitro-3,4-dihydroisoquinoline-2(1H)-yl)ethane-1-one (660 mg, 2.40 mmol, 84%) was obtained as a white solid.

$^1$H NMR (300 MHz, CDCl$_3$) δ 8.12-8.04 (m, 2H), 7.38-7.33 (m, 1H), 4.89-4.85 (m, 2H), 3.97-3.88 (m, 2H), 3.09-3.04 (m 2H); LC/MS 275.2 [M+H$^+$]

Step 3: Preparation of 1-(7-amino-3,4-dihydroisoquinoline-2(1H)-yl)-2,2,2-trifluoroethane-1-one

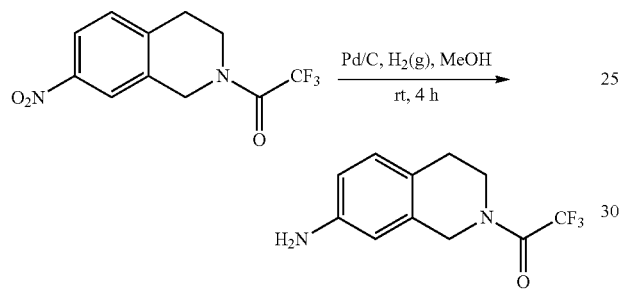

Pd/C (10 weight %) (60 mg, 0.54 mmol) was added to compound of step 2 (650 mg, 2.37 mmol) in MeOH (40 mL) at room temperature. The reaction mixture was stirred at room temperature under hydrogen balloon pressure for 4 hours. TLC analysis indicated the complete consumption of the starting material. The reaction mixture was filtered with a celite bed and concentrated to remove MeOH. The obtained crude mixture was purified by column chromatography using EtOAc/hexane. As a result, 1-(7-amino-3,4-dihydroisoquinoline-2(1H)-yl)-2,2,2-trifluoroethane-1-one (460 mg, 1.88 mmol, 80%) was obtained as a grey-white solid.

$^1$H NMR (300 MHz, CDCl$_3$) δ 6.97-6.92 (m, 1H), 6.59-6.54 (m, 1H), 6.46-6.43 (m, 1H), 4.68-4.63 (m, 2H), 3.86-3.78 (m, 2H), 3.64 (s, br, 2H), 2.85-2.80 (m, 2H); LC/MS 245.2 [M+H$^+$]

Preparative Example A-4: Preparation of isochroman-7-amine

Step 1: Preparation of 2-(1,3-diethoxy-1,3-dioxopropane-2-yl)-5-nitrobenzoic acid

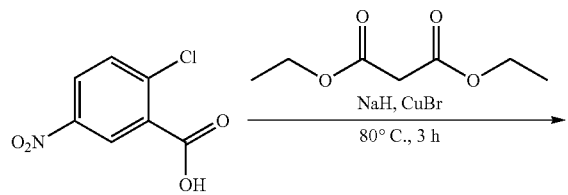

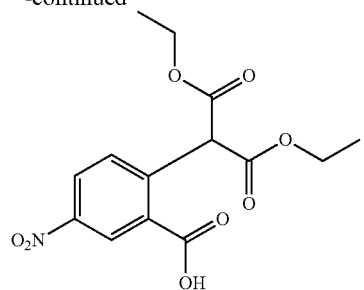

60% NaH (5.65 g, 141 mmol) was added to 90 ml of diethyl malonate and 2-chloro-5-nitrobenzoic acid (10 g, 49.6 mmol) in an ice bath under nitrogen atmosphere. Copper bromide (0.43 g, 0.06 mmol) was added thereto, followed by stirring at 80° C. for 3 hours. After cooling, 40 ml of water were added thereto, which was stirred and washed with hexane (40 ml×3). PH of the reaction mixture was adjusted to 2 with conc. HCl, and the insoluble materials were removed by filtration. The precipitated solid was filtered, washed with water, and dried to give 2-(1,3-diethoxy-1,3-dioxopropane-2-yl)-5-nitrobenzoic acid (12 g, 36.9 mmol, 74%) as a cream-type solid.

$^1$H NMR (300 MHz, CDCl$_3$) δ 8.99 (s, 1H), 8.45 (d, J=8.2 Hz, 1H), 7.75 (d, J=8.0 Hz, 1H), 5.88 (s, 1H), 4.30 (q, J=6.8 Hz, 4H), 1.32 (t, J=6.5 Hz, 6H); LC/MS 326.3 [M+H$^+$].

Step 2: Preparation of 2-(carboxymethyl)-5-nitrobenzoic acid

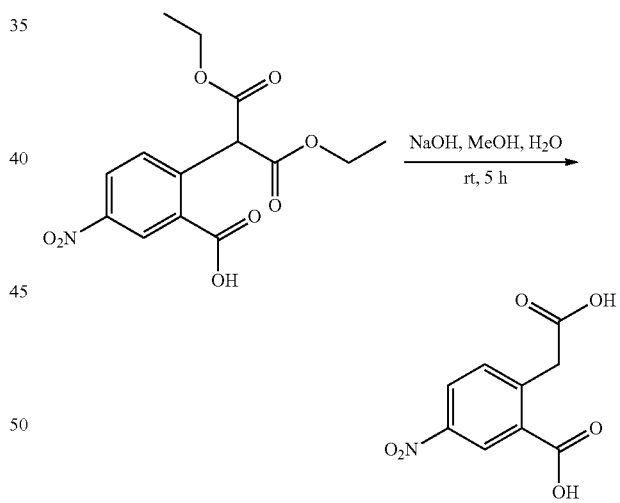

Compound of step 1 (4.0 g, 12.3 mmol) was dissolved in 30 mL of methanol, to which 30 mL of sodium hydroxide solution (2.7 g, 67.6 mmol) was added at room temperature, followed by stirring at room temperature for 5 hours. Most of methane was concentrated under reduced pressure, and pH of the residue was adjusted to 2 with conc. HCl. The solid was precipitated and filtered. The filtered cake was washed with water and dried. As a result, 2-(carboxymethyl)-5-nitrobenzoic acid (2.2 g, 9.77 mmol, 79%) was obtained as a cream type solid.

$^1$H NMR (300 MHz, DMSO-d6) δ 13.01 (s, br, 2H), 8.62 (d, J=2.5 Hz, 1H), 8.36 (dd, J=8.4, 2.6 Hz, 1H), 7.67 (d, J=8.5 Hz, 1H), 4.11 (s, 2H); LC/MS 226.3 [M+H+].

Step 3: Preparation of 2-(2-(hydroxymethyl)-4-nitrophenyl)ethane-1-ol

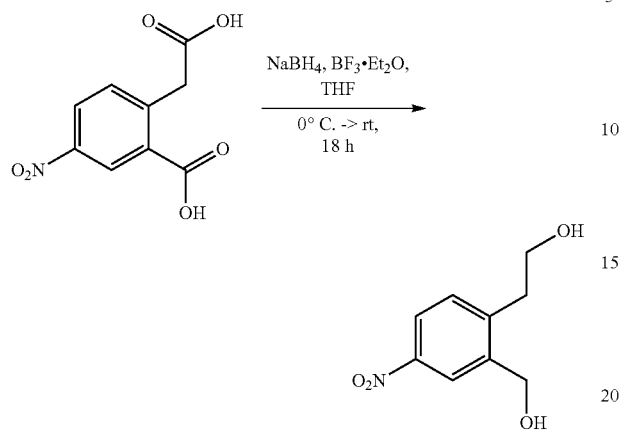

NaBH$_4$(1.07 g, 26.6 mmol) was added to compound of step 2 (2.0 g, 8.87 mmol) in THF (45 mL) for 5 minutes in the presence of N$_2$. The reaction mixture was cooled down to 0° C., to which BF$_3$·Et$_2$O (3.37 mL, 26.6 mmol) was added for 15 minutes, followed by stirring vigorously at room temperature for 18 hours. The reaction mixture was then cooled down to 0° C., which was treated with 1 N aqueous NaOH (35 mL). The reaction mixture was stirred at room temperature for 4 hours. THF was eliminated under reduced pressure and the generated precipitate was separated by filtration. The filtrate was extracted with MeOH/DCM. The precipitate was combined with the organic extract, which was diluted with MeOH/DCM. The mixture was dried over Na$_2$SO$_4$, followed by concentration under reduced pressure. As a result, 2-(2-(hydroxymethyl)-4-nitrophenyl)ethane-1-ol (1.3 g, 6.59 mmol, 74%) was obtained as a beige solid.

$^1$H NMR (300 MHz, CDCl$_3$) δ 8.25 (d, J=2.4 Hz, 1H), 8.14 (dd, J=8.4, 2.4 Hz, 1H), 7.42 (d, J=8.4 Hz, 1H), 4.76 (s, 2H), 3.97 (t, J=5.9 Hz, 2H), 3.37 (s, br, 1H), 3.05 (t, J=5.8 Hz, 2H), 2.41 (s, br, 1H); LC/MS 198.3 [M+H$^+$].

Step 4: Preparation of 3,4-dihydro-7-nitro-1H-2-benzopyran

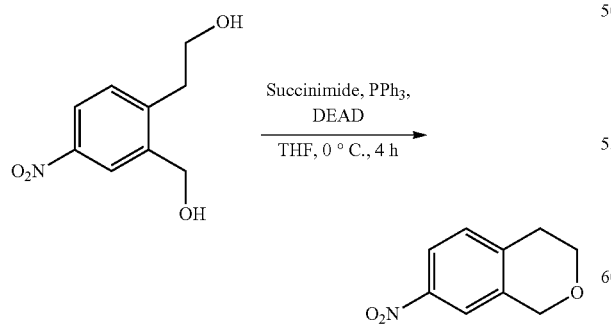

Diethyl azodicarboxylate (0.9 mL, 5.78 mmol) was added to compound of step 4 (1.0 g, 5.07 mmol), succinimide (0.5 g, 5.07 mmol) and triphenylphosphine (1.46 g, 5.57 mmol) in THF at 0° C. for 5 minutes in the presence of N$_2$. The mixture was stirred at 0° C. for 4 hours, followed by concentration under reduced pressure. The residue was purified by silica gel chromatography using EtOAc/hexane (10/90) as an eluent, followed by concentration. As a result, 3,4-dihydro-7-nitro-1H-2-benzopyran (600 mg, 3.35 mmol, 66%) was obtained as a white solid.

$^1$H NMR (300 MHz, CDCl$_3$) δ 8.03 (dd, J=8.4, 2.1 Hz, 1H), 7.89 (s, 1H), 7.28 (d, J=8.6 Hz, 1H), 4.84 (s, 2H), 4.01 (t, J=5.7 Hz, 2H), 2.96 (t, J=5.7 Hz, 2H); LC/MS 180.2 [M+H$^+$].

Step 5: Preparation of isochroman-7-amine

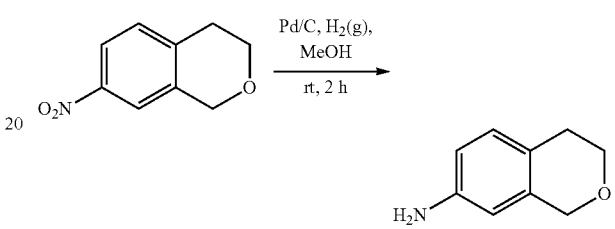

A mixture of PtO$_2$ (10 mol %, 25 mg) in MeOH (15 mL) was degassed and stirred for 25 minutes under hydrogen atmosphere (balloon) to activate the catalyst. Compound of step 4 (250 mg, 1.395 mmol) in MeOH (10 ml) was added thereto. The mixture was stirred for about 2 hours under hydrogen atmosphere (balloon). Then, the catalyst was eliminated by filtration using celite. The filtrate was concentrated under reduced pressure to give the crude product. The crude product was purified by silica gel chromatography using EtOAc/Hx (1/4) as an eluent. As a result, isochroman-7-amine (200 mg, 1.34 mmol, 96%) was obtained as a white solid.

$^1$H NMR (300 MHz, CDCl$_3$) δ 6.94 (d, J=8.1 Hz, 1H), 6.56 (dd, J=8.1, 2.2 Hz, 1H), 6.35 (s, 1H), 4.71 (s, 2H), 3.96 (t, J=5.7 Hz, 2H), 3.58 (s, br, 2H), 2.77 (1, J=5.7 Hz, 2H); LC/MS 150.2 [M+H$^+$].

Preparative Example A-5: Preparation of 1-(7-amino-4,4-dimethyl-3,4-dihydroquinoline-2(1H)-yl)-2,2,2-trifluoroethane-1-one

Step 1: Preparation of 2-methyl-2-(4-nitrophenyl)propanenitrile

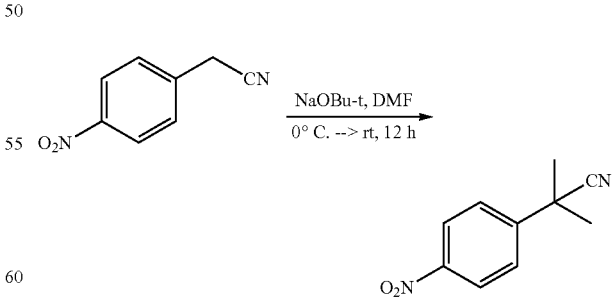

Sodium tert-butoxide (662 mg, 6.47 mmol) DMF (20 mL) suspension was added to 4-nitrophenylacetonitrile (1.0 g, 6.18 mmol) at 0° C., followed by stirring for 10 minutes. Methyl iodide (400 μL, 6.47 mmol) was loaded thereto for 15 minutes. The reaction mixture was stirred at 0-10° C. for 15 minutes, followed by stirring at room temperature for 15 minutes. Sodium tert-butoxide (662 mg, 6.47 mmol) was added to the purple solution above, followed by stirring for 15 minutes. Methyl iodide (400 μL, 6.47 mmol) was loaded thereto for 15 minutes, followed by stirring overnight. The reaction mixture was extracted with 1N HCl (50 mL) and EtOAc (75 mL). The combined organic layer was dried over NaSO₄, which was concentrated under reduced pressure. The residue was purified by column chromatography using EtOAc/Hx (1/4) as an eluent. As a result, 2-methy-2-(4-nitrophenyl)propanenitrile (1.01 g, 5.31 mmol, 86%) was obtained as a yellow solid.

¹H NMR (300 MHz, CDCl₃) δ 8.27 (d, J=8.8 Hz, 2H), 7.68 (d, J=8.8 Hz, 2H), 1.79 (s, 6H); LC/MS 191.2 [M+H⁺].

Step 2: Preparation of 2,2,2-trifluoro-N-(2-methyl-2-(4-nitrophenyl)propyl)acetamide

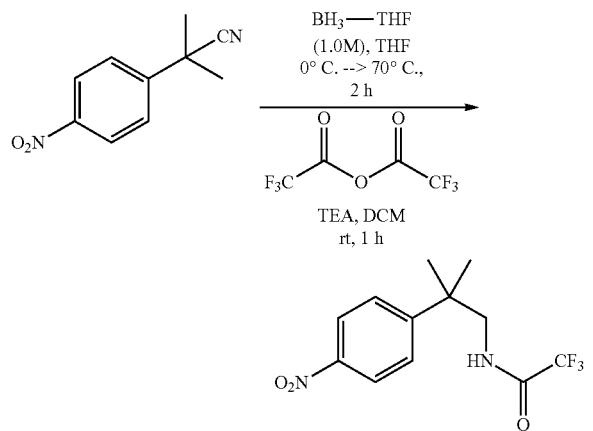

BH₃ THF (1.0 M) (21 mL, 21.03 mmol) was added to cold compound of step 1 (1.0 g, 5.25 mmol) THF (25 mL) solution at 0° C. The reaction mixture was stirred at 70° C. for 2 hours. The reaction was terminated with methanol, followed by concentration and drying 1.5 N HCl (15.00 mL) was added to the residue, followed by extraction with EtOAc. The aqueous layer was basified with NaOH solution and extracted with EtOAc (2×50 mL). The combined organic layer was washed with sodium sulfate and the remaining mixture was subjected to the following steps without any purification process. TEA (1.5 mL, 10.3 mmol) was added to DCM solution (40 mL) of the unpurified reaction mixture (0.8 g, 4.12 mmol), to which trifluoroacetic anhydride (0.7 mL, 4.94 mmol) was added. The reaction mixture was stirred at room temperature for 2 hours. Upon completion of the reaction, water was added to the reaction mixture, followed by extraction with DCM (2×50 mL). The combined organic layer was washed with saturated brine solution, followed by drying over NaSO₄. The solvent was eliminated under reduced pressure. The residue mixture was purified by re-crystallization. As a result, 2,2,2-trifluoro-N-(2-methy-2-(4-nitrophenyl)propyl)acetamide (0.85 g, 2.93 mmol, 71%) was obtained as a colorless oil.

¹H NMR (300 MHz, CDCl₃) δ 8.24 (d, J=8.9 Hz, 2H), 7.56 (d, J=8.9 Hz, 2H), 6.03 (s, 1H), 3.63 (d, J=6.5 Hz, 2H), 1.45 (s, 6H); LC/MS 291.2 [M+H⁺].

Step 3: Preparation of 1-(4,4-dimethyl-7-nitro-3,4-dihydroisoquinoline-2(1H)-yl)-2,2,2-trifluoroethane-1-one

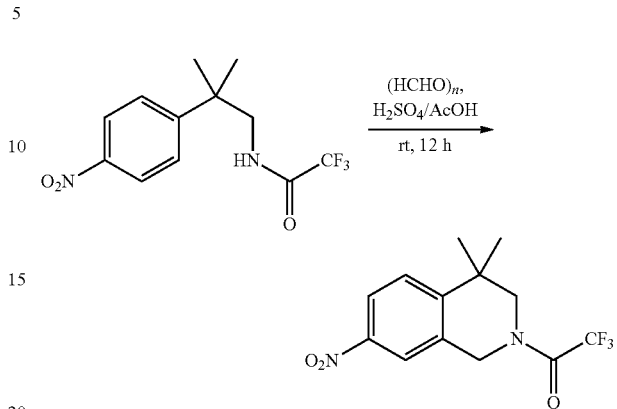

Compound of step 2 (300 mg, 1.03 mmol) was dissolved in HOAc (1.5 mL) and sulfuric acid (2.25 mL), to which paraformaldehyde (49.6 mg, 1.65 mmol) was added at room temperature. The solution above was stirred at 40° C. for 12 hours. The reaction mixture was poured carefully into approximately 100 mL of ice. The generated brown sludge suspension was extracted with EtOAc. The organic layer was washed with saturated aqueous NaHCO₃ and brine, followed by drying over MgSO₄. The residue mixture was purified by column chromatography using MeOH/MC (1:4) as an eluent. As a result, 1-(4,4-dimethyl-7-nitro-3,4-dihydroisoquinoline-2(1H)-yl)-2,2,2-trifluoroethane-1-one (190 mg, 0.628 mmol, 61%) was obtained as a white solid.

¹H NMR (300 MHz, CDCl₃) δ 8.18-8.11 (m, 1H), 8.10-7.99 (m, 1H), 7.56 (dd. J=8.7, 5.1 Hz, 1H), 4.92 (s, 2H), 3.78-3.60 (m, 2H), 1.43-1.36 (m, 6H); LC/MS 303.2 [M+H⁺].

Step 4: Preparation of 1-(7-amino-4,4-dimethyl-3,4-dihydroisoquinoline-2(1H)-yl)-2,2,2-trifluoroethane-1-on

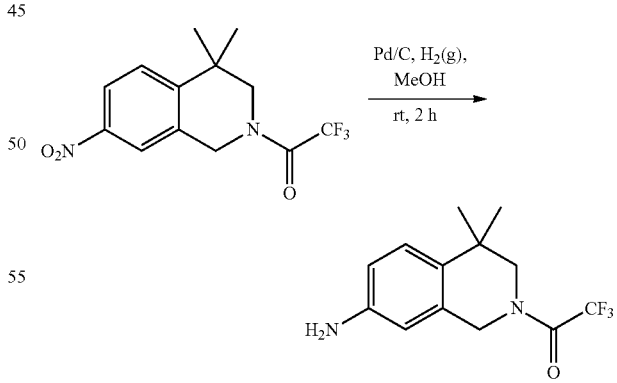

Pd/C (10 mol %, 20 mg) in MeOH (15 mL) was stirred for 25 minutes under hydrogen atmosphere (balloon) to activate the catalyst. Compound of step 3 (180 mg, 0.595 mmol) in MeOH (10 ml) was added thereto. The mixture was stirred for about 2 hours under hydrogen atmosphere (balloon). Then, the catalyst was eliminated by filtration using celite. The filtrate was concentrated under reduced pressure. The obtained crude product was purified by silica gel column chromatography using EtOAc/Hx (1/4) as an eluent. As a result, 1-(7-amino-4,4-dimethyl-3,4-dihydroisoquinoline-2(1H)-yl)-2,2,2-trifluoroethane-1-one (140 mg, 0.514 mmol, 86%) was obtained as a white solid.

$^1$H NMR (300 MHz, CDCl$_3$) δ 6.37 (m, 1H), 4.72 (s, 2H), 3.74-3.50 (m, 4H), 1.28 (s, 6H); LC/MS 273.4 [M+H$^+$].

Preparative Example A-6: Preparation of 1-(7-amino-1-isopropyl-3,4-dihydroisoquinoline-2(1H)-yl)-2,2,2-trifluoroethane-1-one Step 1: Preparation of N-phenethylisobutylamide

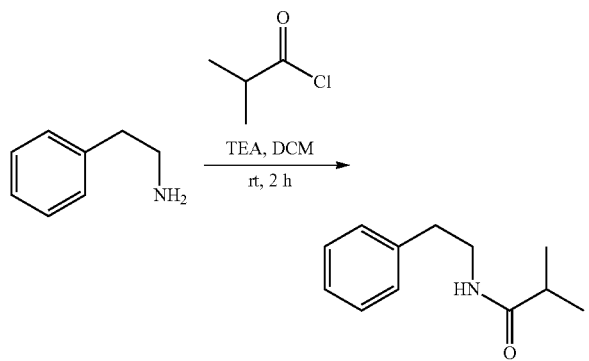

Isobutyryl chloride (4.83 g, 45.4 mmol) and TEA (14.42 mL, 103 mmol) were added to phenethylamine (5.0 g, 41.26 mmol) DCM (100 mL) solution. The reaction mixture was stirred at room temperature for 2 hours, Water (50 mL) was added to the reaction mixture, followed by extraction with DCM (2×50 mL). The combined organic layer was washed with saturated brine solution, and then dried over Na$_2$SO$_4$. The solvent was eliminated under reduced pressure. The residue mixture was purified by recrystallization. As a result, N-phenethylisobutylamide (7.1 g, 37.12 mmol, 90%) was obtained as a white solid.

$^1$H NMR (300 MHz, CDCl$_3$) δ 7.40-7.27 (m, 2H), 7.32-7.21 (m, 1H), 7.26-7.17 (m, 2H), 5.46 (s, 1H), 3.54 (q, J=6.6 Hz, 2H), 2.84 (t, J=6.9 Hz, 2H), 2.30 (sept, J=6.9 Hz, 1H), 1.14 (d, J=6.9 Hz, 6H); LC/MS 192.2 [M+H$^+$].

Step 2: Preparation of 1-isopropyl-3,4-dihydroisoquinoline

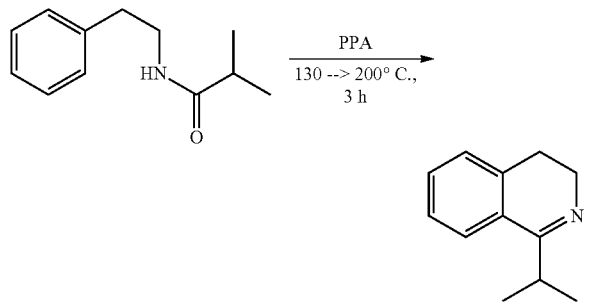

Compound of step 1 (1.0 g, 5.23 mmol) and PPA 115% (4.50 g, 46.0 mmol) were loaded in a round bottom flask. The round bottom flask was sealed with a rubber lid, followed by stirring at 130° C. for 30 minutes and then at 200° C. for 3 hours. The reaction mixture was cooled to room temperature and placed in an ice-filled beaker. Next, 25% (w/v) NH$_4$OH aqueous solution was added to the mixture until pH of the mixture reached 9. The mixture was extracted with dichloromethane (3×30 mL), followed by washing with saturated NaCl solution (3×20 mL). The organic layer was dried over MgSO$_4$, followed by distillation under reduced pressure. As a result, 1-isopropyl-3,4-dihydroisoquinoline (0.77 g, 4.44 mmol, 85%) was obtained as brown oil.

$^1$H NMR (300 MHz, CDCl$_3$) δ 7.54 (dd, J=7.0, 1.9 Hz, 1H), 7.39-7.29 (m, 2H), 7.25-7.18 (m, 1H), 3.74-3.62 (m, 2H), 3.29 (sept, J=6.8 Hz, 1H), 2.72-2.64 (m, 2H), 1.23 (d, J=6.8 Hz, 6H); LC/MS 174.2 [M+H$^+$].

Step 3: Preparation of 1-isopropyl-7-nitro-3,4-dihydroisoquinoline

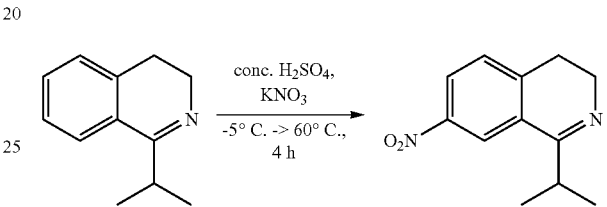

Conc. sulfuric acid (2.0 mL) solution containing potassium nitrate (252 mg, 2.49 mmol) was added to conc, sulfuric acid (2.0 mL) containing compound of step 2 (400 mg, 2.31 mmol) at −5° C. with stirring. The temperature of the mixture was raised to room temperature for 2 hours, followed by heating at 60° C. for 4 hours. The reaction mixture was placed in ice-water (10 mL) and basified with potassium hydroxide pellet (pH 9). The mixture was extracted with dichloromethane, followed by drying. The solvent was eliminated under reduced pressure. The crude product was purified by column chromatography using MeOH/DCM (1:9) as an eluent. As a result, 1-isopropyl-7-nitro-3,4-dihydroisoquinoline (400 mg, 1.83 mmol, 80%) was obtained as brown oil.

$^1$H NMR (300 MHz, CDCl$_3$) δ 8.39 (d, J=2.3 Hz, 1H), 8.24 (dd, J=8.3, 2.3 Hz. 1H), 7.40 (d, J=8.3 Hz, 1H), 3.80-3.71 (m, 2H), 3.34 (sept, J=6.7 Hz, 1H), 2.84-2.74 (m, 2H), 1.26 (d, J=6.8 Hz, 6H); LC/MS 219.3 [M+H]$^+$.

Step 4: Preparation of 2,2,2-trifluoro-1-(1-isopropyl-7-nitro-3,4-dihydroisoquinoline-2(1H)-yl)ethane-1-one

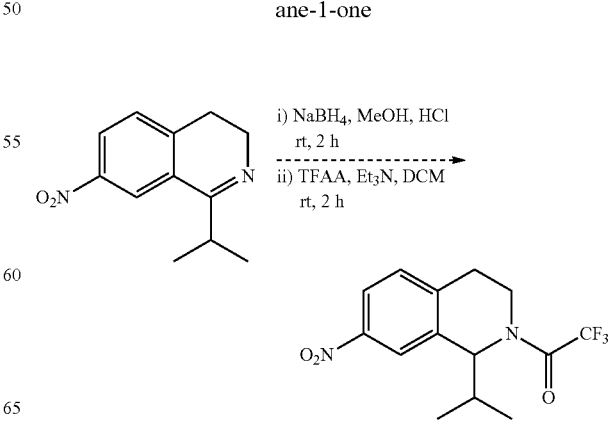

NaBH$_4$(138 mg, 3.66 mmol) was added to compound of step 3(400 mg, 1.83 mmol) MeOH (25 mL) solution at room temperature, followed by stirring for 2 hours. Upon completion of the reaction, HCl was added thereto. To eliminate MeOH, the mixture was concentrated. The mixture was basified with NaHCO$_3$, followed by extraction with DCM (15 mL×2). The reaction mixture was dried over sodium sulfate, followed by concentration. TEA (371 mg, 3.66 mmol) was added to DCM (45 mL) solution containing the reaction mixture, to which TFAA (577 mg, 2.75 mmol) was added, followed by stirring at room temperature for 2 hours. The reaction was terminated with water, followed by extraction with DCM (2×15 mL). The organic layer was washed with brine solution (2×5 mL), dried over sodium sulfate, and distillated under reduced pressure. The crude product was purified by column chromatography. As a result, 2,2,2-trifluoro-1-(1-isopropyl-7-nitro-3,4-dihydroisoquinoline-2 (1H)-yl)ethane-1-one (440 mg, 1.39 mmol, 76%) was obtained as colorless oil.

$^1$H NMR (300 MHz, CDCl$_3$) δ 8.15-7.97 (m, 2H), 7.39-7.32 (m, 1H), 5.36 (d, J=9.0 Hz, 0.8H), 4.66-4.55 (m, 0.2H), 4.52 (d, J=9.9 Hz, 0.2H), 4.19-4.07 (m, 0.8H), 3.85-3.72 (m, 0.8H), 3.56-3.43 (m, 0.2H), 3.27-3.04 (m, 2H), 2.24-2.04 (m, 1H), 1.15-0.99 (m, 6H); LC/MS 317.2 [M+H$^+$].

Step 5: Preparation of 1-(7-amino-1-isopropyl-3,4-dihydroisoquinoline-2(1H)-yl)-2,2,2-trifluoromethane-1-one

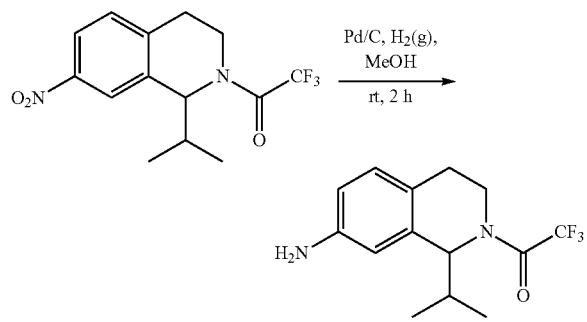

Pd/C (10 mol %, 80 mg) MeOH (50 mL) mixture was stirred for 25 minutes under hydrogen atmosphere (balloon) to activate the catalyst. Compound of step 4 (440 mg, 1.39 mmol) in MeOH (10 ml) was added thereto. The mixture was stirred for about 2 hours under hydrogen atmosphere (balloon). Then, the catalyst was eliminated by filtration using celite. The filtrate was concentrated under reduced pressure. The crude product was purified by silica gel chromatography using EtOAc/Hx (1/4). As a result, 1-(7-amino-1-isopropyl-3,4-dihydroisoquinoline-2(1H)-yl)-2,2,2-trifluoromethane-1-one (350 mg, 1.22 mmol, 88%) was obtained as a brown solid.

$^1$H NMR (300 MHz, CDCl$_3$) δ 6.95 (d, J=8.1 Hz, 1H), 6.60 (dd, J=8.1, 2.6 Hz, 1H), 6.54-6.40 (m, 1H), 5.15 (d, J=8.8 Hz, 0.8H), 4.47-4.35 (m, 0.2H), 4.28 (d, J=10.0 Hz, 0.2H), 4.06-3.93 (m, 0.8H), 3.81-3.68 (m, 0.8H), 3.64 (s, 2H), 3.53-3.41 (m, 0.2H), 3.03-2.80 (m, 2H), 2.19-2.08 (m, 1H), 1.12-0.95 (m, 6H); LC/MS 287.2 [M+H$^+$].

Preparative Example A-7: Preparation of 1-(7-amino-1,3,3-trimethyl-3,4-dihydroisoquinoline-2 (1H)-yl)-2,2,2-trifluoroethane-1-one Step 1: Preparation of 1,3,3-trimethyl-3,4-dihydroisoquinoline

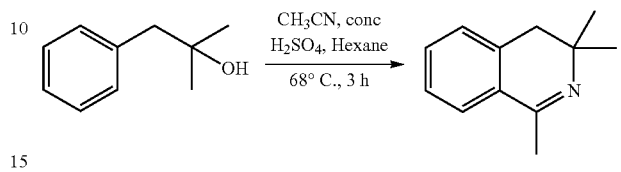

CH$_3$CN (0.55 mL) in hexane (10 mL) was loaded to cold conc. H$_2$SO$_4$ (15 mL) with magnetic stirring. Then, 2-methyl-1-methylpropanol (700 mg, 4.65 mmol) in hexane (15 mL) was added thereto. The temperature of the mixture was raised back to room temperature. The mixture was stirred at 68° C. for 2.5 hours. The solution was cooled to room temperature and ice water was poured under magnetic stirring. The solution was alkalized with ammonia. The organic layer was extracted with dichloromethane and the solution was washed with saturated brine. The mixture was dried over sodium sulfate, filtered, and then concentrated under reduced pressure. The obtained crude mixture was purified by column chromatography (MeOH/MC (1:4)). As a result, 1,3,3-trimethyl-3,4-dihydroisoquinoline (600 mg, 3.46 mmol, 74%) was obtained as colorless oil.

$^1$H NMR (300 MHz, CDCl$_3$) δ 7.50 (d, J=7.4 Hz, 1H), 7.36 (t, J=7.3 Hz, 1H), 7.33-7.28 (m, 1H), 7.16 (d, J=7.6 Hz, 1H), 2.71 (s, 2H), 2.40 (s, 3H), 1.22 (s, 6H); LC/MS 174.2 [M+H$^+$].

Step 2: Preparation of 1,3,3-trimethyl-7-nitro-3,4-dihydroisoquinoline

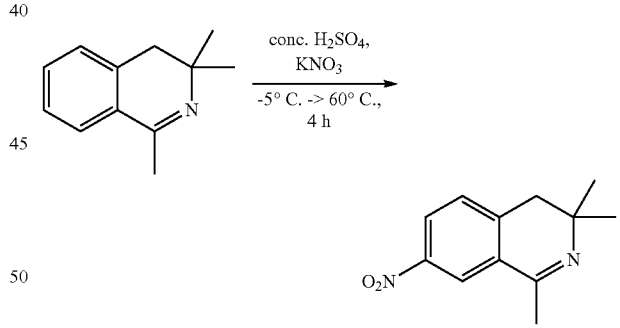

Conc. sulfuric acid (2.0 mL) solution containing potassium nitrate (252 mg, 2.49 mmol) was added to conc. sulfuric acid (2.0 mL) containing compound of step 1 (400 mg, 2.31 mmol) at −5° C. with stirring. The temperature of the mixture was raised to room temperature for 2 hours, followed by heating at 60° C. for 4 hours. The reaction mixture was placed in ice-water (10 mL) and basified with potassium hydroxide pellet (pH 9). The mixture was extracted with dichloromethane, followed by drying. The solvent was eliminated under reduced pressure. The crude product was purified by column chromatography (MeOH/DCM (1:9)). As a result, 1,3,3-trimethyl-7-nitro-3,4-dihydroisoquinoline (400 mg, 1.83 mmol, 80%) was obtained as brown oil.

$^1$H NMR (300 MHz, CDCl$_3$) δ 8.35 (d, J=2.2 Hz, 1H), 8.25 (dd, J=8.2, 2.3 Hz, 1H), 7.35 (d, J=8.2 Hz, 1H), 2.82 (s, 2H), 2.47 (s, 3H), 1.24 (s, 6H); LC/MS 219.2 [M+H$^+$].

Step 3: Preparation of 2,2,2-trifluoro-1-(1,3,3-trimethyl-7-nitro-3,4-dihydroisoquinoline-2(1H)-yl)ethane-1-one

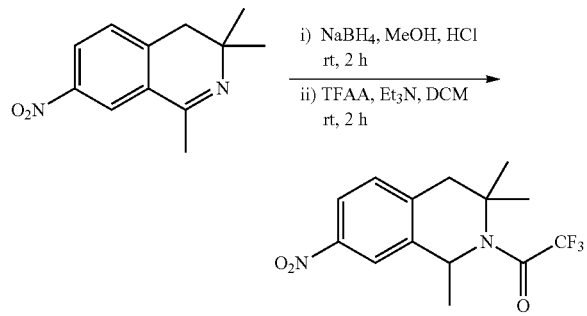

NaBH$_4$ (138 mg, 3.66 mmol) was added to compound of step 2 (400 mg, 1.83 mmol) MeOH (25 mL) solution at room temperature, followed by stirring for 2 hours. Upon completion of the reaction, HCl was added to the reaction mixture, followed by concentration to eliminate MeOH. The reaction mixture was basified with NaHCO$_3$, followed by extraction with DCM (15 mL×2). The mixture was dried over sodium sulfate and concentrated to obtain the crude mixture. TFAA (577 mg, 2.75 mmol) was added to DCM (45 mL) solution containing the reaction mixture, to which TEA (371 mg, 3.66 mmol) was added, followed by stirring for 2 hours. The reaction was quenched with water, followed by extraction with DCM (2×15 mL). The organic layer was washed with brine solution (2×5 mL), dried over sodium sulfate, and concentrated under reduced pressure. The crude product was purified by column chromatography. As a result, 2,2,2-trifluoro-1-(1,3,3-trimethyl-7-nitro-3,4-dihydroisoquinoline-2(1H)-yl)ethane-1-one (440 mg, 1.39 mmol, 76%) was obtained as a white solid.

$^1$H NMR (500 MHz, CDCl$_3$) δ 8.21 (dd, J=8.2, 2.2, 1H), 8.07 (d, J=2.2 Hz, 1H), 7.42 (d, J=8.2 Hz, 1H), 5.17 (q, J=7.0 Hz, 1H), 3.47 (d, J=15.7 Hz, 1H), 2.84 (d, J=15.7 Hz, 1H), 1.85 (s, 3H), 1.63 (d, J=6.9 Hz, 3H), 1.31 (s, 3H); LC/MS 317.2 [M+H$^+$].

Step 4: Preparation of 1-(7-amino-1,3,3-trimethyl-3,4-dihydroisoquinoline-2(1H)-yl)-2,2,2-trifluoroethane-1-one

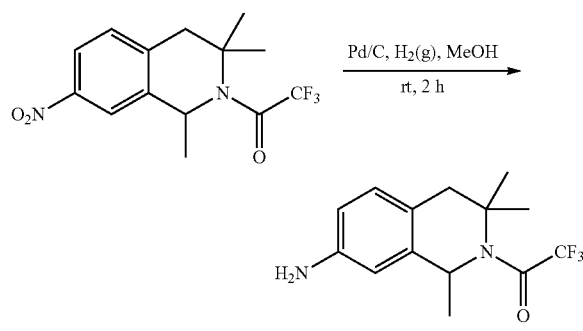

A mixture of Pd/C (10 mol %, 80 mg) in MeOH (50 mL) was degassed and stirred for 25 minutes under hydrogen atmosphere (balloon) to activate the catalyst. Compound of step 3 (400 mg, 1.26 mmol) in MeOH (10 ml) was added thereto. The reaction mixture was stirred for about 2 hours under hydrogen atmosphere (balloon). Then, the catalyst was eliminated by filtration using celite. The filtrate was concentrated under reduced pressure to give the crude product. The crude product was purified by silica gel column chromatography (EtOAc/Hx (1/4)). As a result, 1-(7-amino-1,3,3-trimethyl-3,4-dihydroisoquinoline-2(1H)-yl)-2,2,2-trifluoroethane-one (300 mg, 1.05 mmol, 83%) was obtained as brown oil.

$^1$H NMR (300 MHz, CDCl$_3$) δ 6.99 (d, J=7.9 Hz, 1H), 6.62 (d, J=7.7 Hz, 1H), 6.50 (s, 1H), 4.88 (q, J=7.1 Hz, 1H), 3.68 (s, 2H), 3.27 (d, J=15.3 Hz, 1H), 2.55 (d, J=15.1 Hz, 1H), 1.77 (s, 3H), 1.55 (d, J=6.9 Hz, 3H), 1.28 (s, 3H); LC/MS 287.2 [M+H$^+$].

Preparative Example A-8: Preparation of 1-(5-aminoisoindolin-2-yl)-2,2,2-trifluoroethane-1-one Step 1: Preparation of 2,2,2-trifluoro-1-(5-nitroisoindolin-2-yl)ethane-1-one

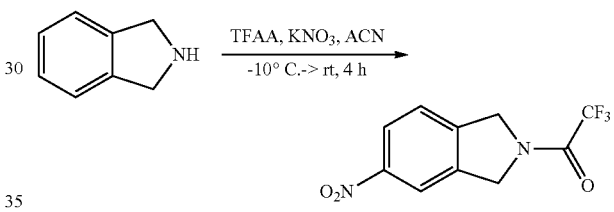

Trifluoroacetic anhydride (1.64 mL, 11.7 mmol) was added dropwise to cold isoindolin (400 mg, 3.35 mmol) acetonitrile (15 mL) solution at −10° C. Potassium nitrate (366 mg, 3.62 mmol) was added to the stirred mixture at once. The mixture was stirred at −10° C. for 1 hour. Saturated sodium bicarbonate aqueous solution (10 mL) was slowly added to the mixture. Active gas generation was observed. The mixture was stirred for 1 hour and then the temperature of the mixture was raised to mom temperature. The mixture was basified with saturated sodium carbonate (10 mL). The sticky turbid solution was filtered. The obtained solid was washed with water (20 mL) and then dissolved in dichloromethane (30 mL), followed by concentration under reduced pressure. The crude product was purified by column chromatography. As a result, 2,2,2-trifluoro-1-(5-nitroisoindolin-2-yl)ethane-1-one (600 mg, 2.30 mmol, 69%) was obtained as a white solid.

$^1$H NMR (300 MHz, CDCl$_3$) δ 8.32-8.18 (m, 2H), 7.52 (dd, J=16.3, 8.4 Hz, 1H), 5.16 (s, 2H), 5.04 (s, 2H); LC/MS 260.9 [M+H$^+$].

Step 2: Preparation of 1-(5-aminoisoindolin-2-yl)-2,2,2-trifluoroethane-1-one

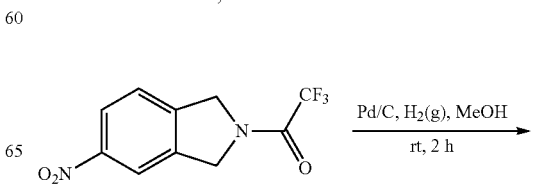

-continued

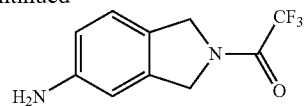

A target compound was prepared by the same manner as described in step 4 of Preparative Example A-7 except that 2,2,2-trifluoro-1-(5-nitroisoindolin-2-yl)ethane-1-one prepared in step 1 was used instead of 2,2,2-TRIFLUORO-1-(1,3,3-TRIMETHYL-7-NITRO-3,4-DIHYDROISOQUINOLIN E-2(1H)-YL)ETHANE-1-ONE.

$^1$H NMR (300 MHz, CDCl$_3$) δ 7.08 (dd, J=15.9, 8.1 Hz, 1H), 6.76-6.52 (m, 2H), 4.94 (s, 2H), 4.83 (d, J=4.3 Hz, 2H), 3.77 (s, 2H); LC/MS 231.2 [M+H$^+$].

Preparative Example A-9: Preparation of 1-(7-amino-1,1-dimethyl-3,4-dihydroisoquinoline-2(1H)-yl)-2,2,2-trifluoroethane-1-one Step 1: Preparation of N-(4-methoxyphenethyl)acetamide

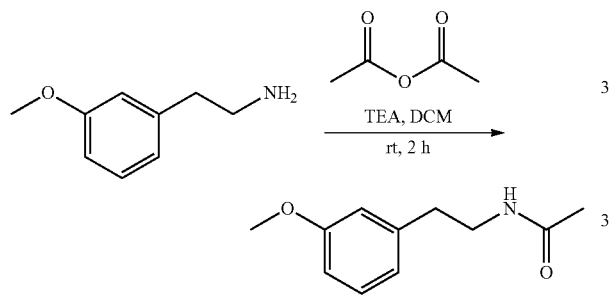

Acetic anhydride (1.5 mL, 15.87 mmol) was added to 2-(3-methoxyphenyl)ethane-1-amine (2.0 g, 13.22 mmol) DCM (50 mL) solution, to which TEA (4.6 mL, 33.0 mmol) was added, followed by stirring at room temperature for 2 hours. Upon completion of the reaction, water (100 mL) was added thereto, followed by extraction with DCM (2×150 mL). The combined organic layer was washed with saturated brine solution and then dried over Na$_2$SO$_4$. The solvent was removed under vacuum. The crude mixture was purified by column chromatography (EtOAc/Hx (2:8)). As a result, N-(4-methoxyphenethyl)acetamide (2.4 g, 12.42 mmol, 94%) was obtained as yellow oil.

$^1$H NMR (500 MHz, CDCl$_3$) δ 7.25 (t, J=7.8 Hz, 1H), 6.80 (dd, J=8.0, 2.3 Hz, 2H), 6.76 (t, J=2.0 Hz, 1H), 5.55 (s, 1H), 3.82 (s, 3H), 3.56-3.51 (m, 2H), 2.81 (t, J=6.9 Hz, 2H), 1.96 (s, 3H); LC/MS 193.9 [M+H$^+$].

Step 2: Preparation of 7-methoxy-1-methyl-3,4-dihydroisoquinoline

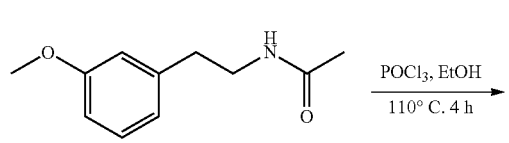

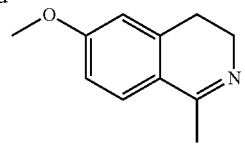

EtOH (1.7 mL, 28.9 mmol) was slowly added to compound of step 1 (2.0 g, 10.35 mmol) POCl$_3$ (7.9 mL, 84.86 mmol) solution at room temperature. The reaction mixture was refluxed for overnight. The mixture was cooled down at room temperature and POCl$_3$ was eliminated by evaporation. The crude mixture was basified with sat. NaHCO$_3$ (aq) (1000 mL), followed by extraction with DCM (3×500 mL). The combined organic layer was washed with saturated brine solution and then dried over Na$_2$SO$_4$. The solvent was removed under vacuum. The crude mixture was purified by column chromatography (MeOH/DCM (1:9)). As a result, 7-methoxy-1-methyl-3,4-dihydroisoquinolin (1.1 g, 6.27 mmol, 61%) was obtained as brown oil.

$^1$H NMR (300 MHz, CDCl$_3$) δ 7.49 (d, J=8.5 Hz, 1H), 6.83 (dd, J=8.6, 2.6 Hz, 1H), 6.74 (d, J=2.6 Hz, 1H), 3.87 (s, 3H), 3.69 (td, J=7.5, 1.6 Hz, 2H), 2.81-2.72 (m, 2H), 2.45 (t, J=1.4 Hz, 3H); LC/MS 175.8 [M+H$^+$].

Step 3: Preparation of 2-benzyl-6-methoxy-1-methyl-3,4-dihydroisoquinoline-2-inium bromide

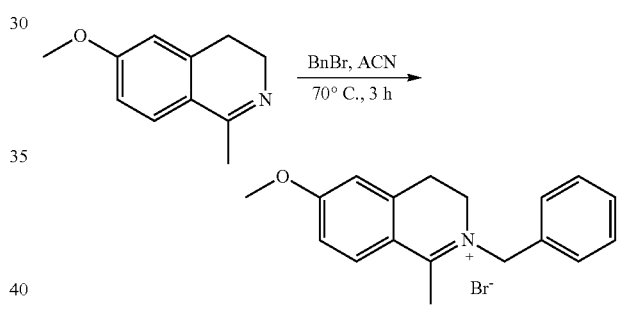

Benzyl bromide (0.68 mL, 5.70 mmol) was added to compound of step 2 (500 mg, 2.853 mmol) acetonitrile (40 mL) solution, followed by stirring at 70° C. for 3 hours. The solvent was evaporated. The crude mixture was purified by column chromatography (MeOH/DCM (1:9)). As a result, 2-benzyl-6-methoxy-1-methyl-3,4-dihydroisoquinoline-2-inium bromide (700 mg, 2.02 mmol, 70%) was obtained as a yellow foam-type solid.

$^1$H NMR (300 MHz, CDCl$_3$) δ 7.95 (d, J=9.0 Hz, 1H), 7.48-7.37 (m, 3H), 7.41-7.32 (m, 2H), 6.99 (dd, J=9.0, 2.6 Hz, 1H), 6.86 (dd, J=6.5, 2.5 Hz, 1H), 5.56 (s, 2H), 4.14 (t, J=7.6 Hz, 2H), 3.94 (s, 3H), 3.25 (t, J=7.5 Hz, 2H), 3.08 (s, 3H); LC/MS 266.2 [M−Br$^+$].

Step 4: Preparation of 2-benzyl-6-methoxy-1,1-dimethyl-1,2,3,4-tetrahydroisoquinoline

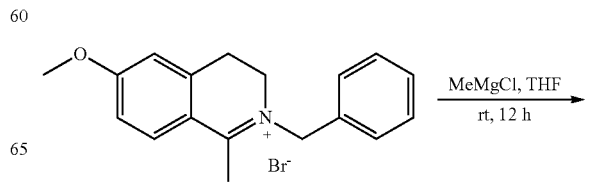

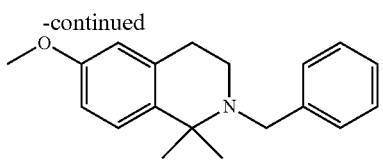

3.0 M McMgCl E120 (1.01 mL, 3.03 mmol) solution was added to compound of step 3 (700 mg, 2.021 mmol) THF (20 mL) turbid solution, followed by stirring at room temperature overnight. The reaction mixture was treated with saturated NH₄Cl (aq) (150 mL) solution, followed by extraction with EtOAc (200 mL×2). The organic layer was washed with water, and then washed again with saturated brine solution. The combined organic layer was concentrated under reduced pressure. The obtained crude mixture was purified by column chromatography (MeOH/MC (1:9)). As a result, 2-benzyl-6-methoxy-1,1-dimethyl-1,2,3,4-tetrahydroisoquinoline (300 mg, 1.066 mmol, 53%) was obtained as colorless oil.

$^1$H NMR (500 MHz, CDCl₃) δ 7.51-7.47 (m, 2H), 7.38 (t, J=7.6 Hz, 2H), 7.32-7.24 (m, 2H), 6.82 (dd, J=8.7, 2.8 Hz, 1H), 6.62 (d, J=2.7 Hz, 1H), 3.83 (s, 3H), 3.78 (s, 2H), 2.76 (s, 4H), 1.54 (s, 6H); LC/MS 282.1 [M+H⁺].

Step 5: Preparation of 2,2,2-trifluoro-1-(6-methoxy-1,1-dimethyl-3,4-dihydroisoquinoline-2(1H)-yl)ethane-1-one

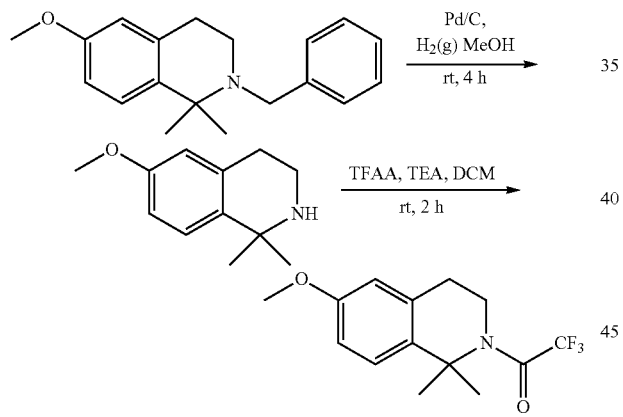

Pd/C (10 wt %) (30 mg, 0.281 mmol) was added to compound of step 4 (300 mg, 1.066 mmol) methanol (30 mL) solution, followed by stirring at room temperature under hydrogen balloon pressure for 4 hours. The reaction mixture was filtered with a celite bed. The solvent was evaporated under reduced pressure. The crude mixture was dissolved in DCM (75 mL), to which trifluoroacetic anhydride (0.18 mL, 1.279 mmol) was added. Triethylamine (0.3 mL, 2.132 mmol) was added thereto. The reaction mixture was stirred at room temperature for 2 hours, quenched with water (25 mL), and extracted with DCM (120 mL×2). The organic layer was washed with water, and then washed again with saturated brine. The combined organic layer was dried over anhydrous Na₂SO₄. The solvent was eliminated under reduced pressure. The obtained crude mixture was purified by column chromatography (EtOAc/Hexane). As a result, 2,2,2-trifluoro-1-(6-methoxy-1,1-dimethyl-3,4-dihydroisoquinoline-2(1H)-yl)ethaneone (200 mg, 0.696 mmol, 65%) was obtained as a white solid.

$^1$H NMR (300 MHz, CDCl₃) δ 7.24 (d, J=8.8 Hz, 1H), 6.86 (dd, J=8.9, 2.8 Hz, 1H), 6.65 (d, J=2.7 Hz, 1H), 3.83 (s, 3H), 3.72-3.62 (m, 2H), 2.94-2.85 (m, 2H), 1.83 (s, 6H); LC/MS 288.1 [M+H⁺].

Step 6: Preparation of 2,2,2-trifluoro-1-(6-methoxy-1,1-dimethyl-7-nitro-3,4-dihydroisoquinoline-2(1H)-yl)ethane-1-one

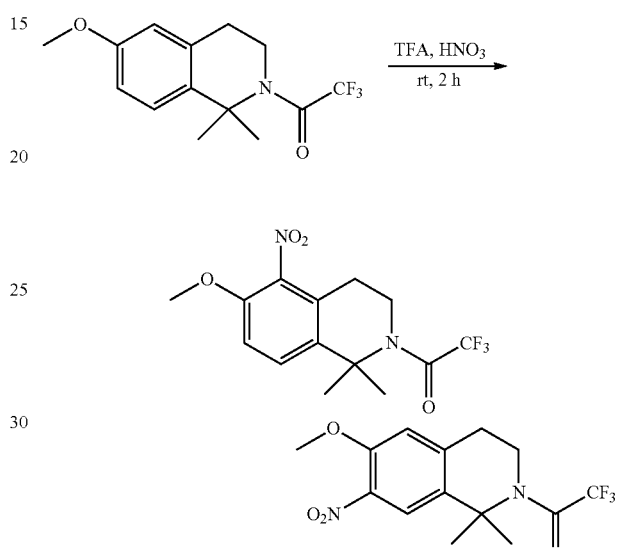

HNO₃ (80 mg, 0.765 mmol) TFA solution was added to 2,2,2-trifluoro-1-(6-methoxy-1,1-dimethyl-3,4-dihydroisoquinoline-2(1H)-yl)ethane-1-one (200 mg, 0.696 mmol) TFA (15 mL) solution, followed by stirring at room temperature for 2 hours. The reaction mixture was evaporated to eliminate TFA and basified with sat. NaHCO₃ solution. The mixture was extracted with EtOAc (15 mL×2). The organic layer was washed with water, and then washed again with saturated brine. The combined organic layer was dried over anhydrous Na₂SO₄. The solvent was eliminated under reduced pressure. The obtained crude mixture was purified by column chromatography (EtOAc/Hexane (3:7)). As a result, a mixture (80 mg, 0.240 mmol, 34%) of 2,2,2-trifluoro-1-(6-methoxy-1,1-dimethyl-5-nitro-3,4-dihydroisoquinolin-2(1H)-yl)ethanone (70 mg 0.210 mmol, 30%) and 2,2,2-trifluoro-1-(6-methoxy-1,1-dimethyl-7-nitro-3,4-dihydroisoquinoline-2(1H)-yl)ethane-1-1-one (45 mg, 0.135 mmol, 20%) was obtained as a white solid.

2,2,2-trifluoro-1-(6-methoxy-1,1-dimethyl-5-nitro-3,4-dihydroisoquinolin-2(1H)-yl)ethanone:

$^1$H NMR (300 MHz, CDCl₃) δ 7.42 (d, J=9.0 Hz, 1H), 7.03 (d, J=9.0 Hz, 1H), 3.93 (s, 3H), 3.67 (t, J=5.4 Hz, 2H), 2.96-2.73 (m, 2H), 1.85 (s, 6H); LC/MS 332.8 [M+H⁺].

2,2,2-trifluoro-1-(6-methoxy-1,1-dimethyl-7-nitro-3,4-dihydroisoquinoline-2(1H)-yl) ethane-1-one: $^1$H NMR (300 MHz, CDCl₃) δ 7.88 (s, 1H), 6.83 (s, 1H), 3.99 (s, 3H), 3.79-3.60 (m, 2H), 3.16-2.87 (m, 2H), 2.86 (s, 6H); LC/MS 332.8 [M+H⁺].

Step 7: Preparation of 2,2,2-trifluoro-1-(6-hydroxy-1,1-dimethyl-7-nitro-3,4-dihydroisoquinoline-2(1H)-yl)ethane-1-one

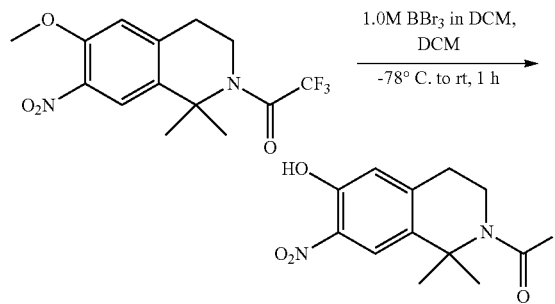

1.0 M BBr₃ DCM (0.54 mL, 0.54 mmol) was added to 2,2,2-trifluoro-1-(6-methoxy-1,1-dimethyl-7-nitro-3,4-dihydroisoquinoline-2(1H)-yl)ethane-1-one (45 mg, 0.135 mmol) DCM (10 mL) solution at −78° C. followed by stirring at −78° C. for 30 minutes. The temperature of the mixture was slowly raised to room temperature, followed by stirring for 1 hour. TLC analysis indicated the complete consumption of the starting material. The reaction mixture was quenched with NaHCO₃ solution, followed by extraction with DCM (15.0 mL). The organic layer was dried over Na₂SO₄, followed by evaporation under reduced pressure. The obtained crude mixture was purified by column chromatography (EtOAc/Hexane (3:7)). As a result, 2,2,2-trifluoro-1-(6-hydroxy-1,1-dimethyl-7-nitro-3,4-dihydroisoquinoline-2(1)-yl)ethane-1-one (32 mg, 0.100 mmol, 74%) was obtained as a yellow solid.

$^1$H NMR (300 MHz, CDCl₃) δ 10.40 (s, 1H), 8.09 (s, 1H), 6.93 (s, 1H), 3.85-3.45 (m, 2H), 3.02-2.83 (m, 2H), 1.86 (s, 6H); LC/MS 317.1 [M−H⁺].

Step 8: Preparation of 1,1-dimethyl-7-nitro-2-(2,2,2-trifluoroacetyl)-1,2,3,4-tetrahydroisoquinoline-6-yl trifluoromethanesulfonate

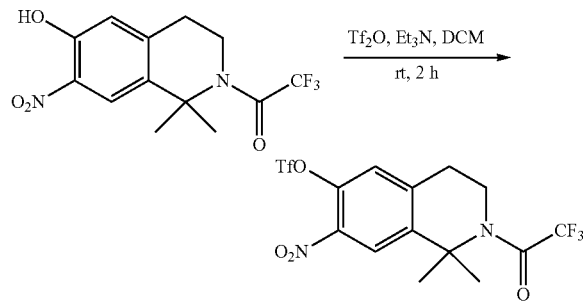

Tf2O (87 mg, 0.307 mmol) was added to 2,2,2-trifluoro-1-(6-hydroxy-1,1-dimethyl-7-nitro-3,4-dihydroisoquinoline-2(1H)-yl)ethane-1-one (70 mg, 0.219 mmol) DCM (15 mL) solution, to which TEA (67 mg, 0.659 mmol) was added, followed by stirring at room temperature for 2 hours. The reaction mixture was quenched with water, followed by extraction with DCM (2×15 mL). The organic layer was washed with brine (2×5 mL), dried over NaSO₄, and then concentrated under reduced pressure. The obtained crude product was purified by column chromatography. As a result, 1,1-dimethyl-7-nitro-2-(2,2,2-trifluoroacetyl)-1,2,3,4-tetrahydroisoquinoline-6-yl trifluoromethanesulfonate (75 mg, 0.166 mmol, 76%) was obtained as colorless oil.

$^1$H NMR (300 MHz, CDCl₃) δ 8.14 (s, 1H), 7.23 (s, 1H), 3.77-3.68 (m, 2H), 3.07-3.00 (m, 2H), 1.90 (s, 6H); LC/MS 450.8 [M+H⁺].

Step 9: Preparation of 1-(7-amino-1,1-dimethyl-3,4-dihydroisoquinoline-2(1H)-yl)-2,2,2-trifluoroethane-1-one

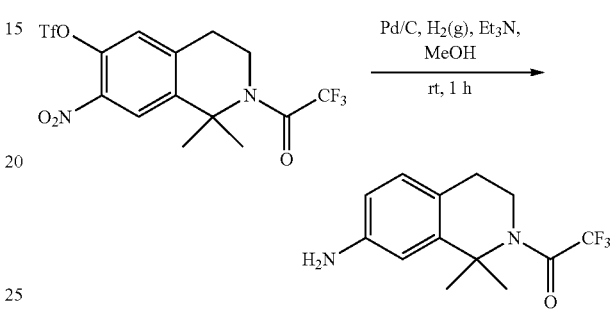

Pd/C (10 mol %, 80 mg) in MeOH (50 mL) was degassed and stirred for 25 minutes under hydrogen atmosphere (balloon) to activate the catalyst, 1,1-dimethyl-7-nitro-2-(2,2,2-trifluoroacetyl)-1,2,3,4-tetrahydroisoquinoline-6-yl trifluoromethanesulfonate (70 mg, 0.155 mmol) in MeOH (5 ml) was added thereto, to which Et₃N (16 mg, 0.155 mmol) was added. The reaction mixture was stirred for about 2 hours under hydrogen atmosphere (balloon). Then, the catalyst was eliminated by filtration using celite. The filtrate was concentrated under reduced pressure to give the crude product. The crude product was purified by silica gel column chromatography (EtOAc/Hx (1/4)). As a result, 1-(7-amino-1,1-dimethyl-3,4-dihydroisoquinoline-2(1H)-yl)-2,2,2-trifluoroethane-1-one (30 mg, 0.110 mmol, 71%) was obtained as a white solid.

$^1$H NMR (300 MHz, CDCl₃) δ 6.90 (d, J=8.1 Hz, 1H), 6.61 (d, J=2.2 Hz, 1H), 6.54 (dd, J=8.0, 2.3 Hz, 1H), 3.66-3.58 (n, 4H), 2.82-2.74 (m, 2H), 1.81 (s, 6H): LC/MS 273.4 [M+H⁺].

Preparative Example A-10: Preparation of N-(4-aminophenyl)acrylamide

Step 1: Preparation of N-(4-nitrophenyl)acrylamide

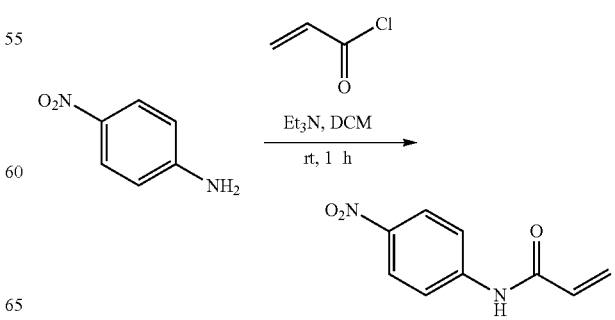

Acryloyl chloride (344 mg, 3.80 mmol) was added to DCM (25 mL) solution containing 4-nitroaniline (500 mg, 3.62 mmol) and triethylamine (1.0 mL, 7.24 mmol) at 0° C., followed by stirring for 1 hour. TLC analysis indicated the complete consumption of the starting material. The reaction mixture was quenched with water (25.0 mL), followed by extraction with DCM (25 mL×2). The combined organic layer was concentrated under reduced pressure. The obtained crude mixture was purified by column chromatography (EtOAc/Hexane (1:5)). As a result, N-(4-nitrophenyl)acrylamide (500 mg, 2.60 mmol, 72%) was obtained as a yellow solid.

$^1$H NMR (300 MHz, DMSO) δ 10.73 (s, 1H), 8.24 (d, J=9.1 Hz, 2H), 7.93 (d, J=8.3 Hz, 2H), 6.61-6.42 (m, 1H), 6.34 (d, J=15.3 Hz, 1H), 5.87 (d, J=9.9 Hz, 1H); LC/MS 193.2 [M+H$^+$].

Step 2: Preparation of N-(4-aminophenyl)acrylamide

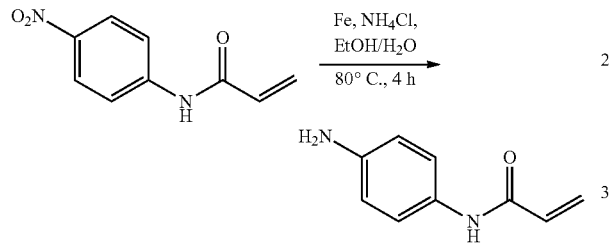

N-(4-nitrophenyl)acrylamide (200 mg, 1.04 mmol) was suspended in ethanol/water (5:1) mixture, to which Fe powder (116 mg, 2.08 mmol) and ammonium chloride solution (1 mL) were added. The mixture was heated to 80° C. for 4 hours. The reaction mixture was cooled at room temperature and filtered with a celite pad. The celite above was washed with ethanol (10 mL) and ethyl acetate (50 mL). The solution above was concentrated under vacuum. The reaction residue was fractionated with DCM (50 mL) and water (20 mL). The combined organic layer was concentrated under reduced pressure. The obtained crude mixture was purified by column chromatography (EtOAc/Hexane (1:5)). As a result, N-(4-aminophenyl)acrylamide (100 mg, 0.616 mmol, 60%) was obtained as a yellow solid.

$^1$H NMR (300 MHz, CDCl$_3$) δ 7.35 (d, J=8.0 Hz, 2H), 7.12 (s, 1H), 6.66 (d, J=8.6 Hz, 2H), 6.39 (d, J=16.8 Hz, H), 6.21 (dd, J=16.8, 10.1 Hz, 1H), 5.72 (d, J=10.1 Hz, 1H), 3.61 (s, 2H); LC/MS 163.2 [M+H$^+$].

Preparative Example A-11: Preparation of 7-amino-3,4-dihydroisoquinoline-1(2H)-one

Step 1: Preparation of 7-nitro-3,4-dihydroisoquinoline-1(2H)-one

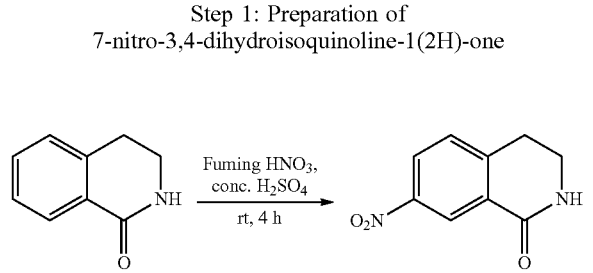

Fuming nitric acid (128 mg, 2.04 mmol) was added dropwise to −5° C. conc. sulfuric acid (2.0 mL) containing 3,4-dihydroisoquinolin-1(2H)-one (400 mg, 2.31 mmol) at 0° C. The temperature of the mixture was raised to room temperature for 2 hours. The reaction mixture was placed in ice-water (10 mL) and basified with potassium hydroxide pellet (pH 9). The mixture was extracted with dichloromethane, followed by drying. The solvent was eliminated under reduced pressure. The crude product was purified by column chromatography (MeOH/DCM (1:9)). As a result, 7-nitro-3,4-dihydroisoquinoline-1(2H)-one (300 mg, 1.56 mmol, 76%) was obtained as brown oil.

$^1$H NMR (500 MHz, CDCl$_3$) δ 8.94 (d, J=2.5 Hz, 1H), 8.33 (dd, J=8.3, 2.5 Hz, 1H), 7.45 (d, J=8.3 Hz, 1H), 6.42 (s, 1H), 3.67 (td, J=6.6, 2.9 Hz, 2H), 3.16 (t, J=6.6 Hz, 2H); LC/MS 193.2 [M+H$^+$].

Step 2: Preparation of 7-amino-3,4-dihydroisoquinoline-1(2H)-one

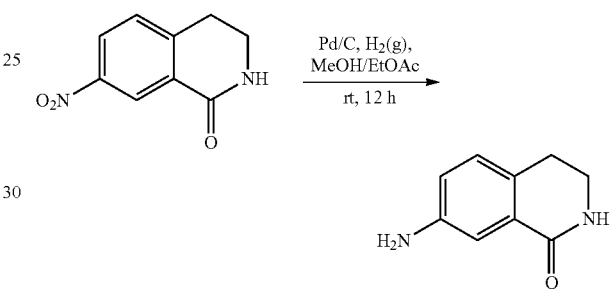

A target compound was prepared by the same manner as described in step 4 of Preparative Example A-7 except that 7-nitro-3,4-dihydroisoquinoline-(2H)-one prepared in step 1 was used instead of 2,2,2-TRIFLUORO-1-(1,3,3-TRIMETHYL-7-NITRO-3,4-DIHYDROISOQUINOLINE-2(1H)-YL)ETHANE-1-ONE.

$^1$H NMR (300 MHz, CDCl$_3$) δ 7.20-7.11 (n, 1H), 6.67-6.58 (m, 1H), 6.48-6.37 (m, 1H), 4.72 (s, 2H), 3.74-3.50 (m, 4H), 1.28 (s, 6H); LC/MS 163.2 [M+H$^+$].

Preparative Example B-1: Preparation of 6-chloro-N-(2,6-dimethylphenyl)-1-methyl-1H-pyrazolo[3,4-d]pyrimidine-3-amine

Step 1: Preparation of 2,4-dichloropyrimidine-5-carbonyl chloride

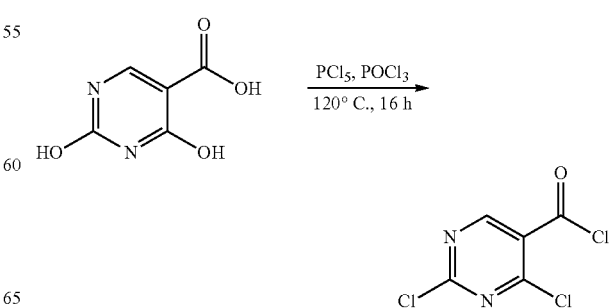

2,4-Dihydroxypyrimidine-5-carboxylic acid (10.0 g, 64 mmol) was added to POCl$_3$ (45 mL, 71 mmol) in a round bottom flask at 0° C. little by little, to which PCl$_5$ (46.6 g, 229 mmol) was slowly added. The temperature of the reaction mixture was raised to room temperature, and the mixture was heated to reflux for 16 hours. The mixture was concentrated to dry and slurried with DCM (dichloromethane, 30 mL). The precipitated solid was filtered and washed with DCM (2×20 mL). The filtrate was evaporated under reduced pressure. As a result, the target compound (10.2 g, 48 mmol, 75%) was obtained as yellow oil.

Step 2: Preparation of 2,4-dichloro-N-(2,6-dimethylphenyl)pyrimidine-5-carboxamide

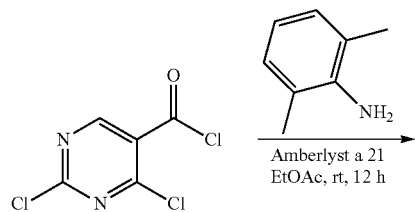

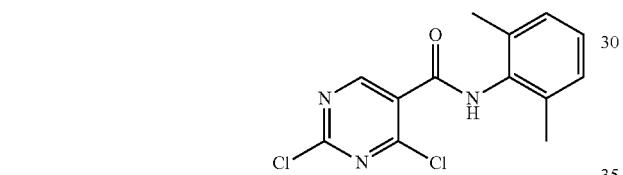

2,6-Dimethylaniline (5.81 g, 48 mmol) was added to 2,4-dichloropyrimidine-5-carbonyl chloride (10.2 g, 48 mmol) in EtOAc (400 mL) at room temperature, to which amberlyst 21 resin (2.0 g) was added. The mixture was stirred at room temperature for 12 hours, followed by filtering. The filtrate was washed serially with water, 1.5 N HCl (15 mL), NaOH, and brine in that order. The combined organic layer was dried over sodium sulfate, and then concentrated under reduced pressure. The obtained crude product was recrystallized by using DCM. As a result, 2,4-DICHLORO-N-(2,6-DIMETHYLPHENYL)PYRIMIDINE-5-CARBOXAMIDE(11.0 g, 37.14 mmol, 77%) was obtained as a grey-white solid.

$^1$H NMR (300 MHz, CDCl$_3$) δ 9.05 (s, 1H), 7.70 (s, br, 1H), 7.22-7.13 (m, 3H), 2.31 (s, 6H); LC/MS 296.2 [M+H$^+$].

Step 3: Preparation of 2-chloro-N-(2,6-dimethylphenyl)-4-(1-methylhydrazinyl)pyrimidine-5-carboxamide

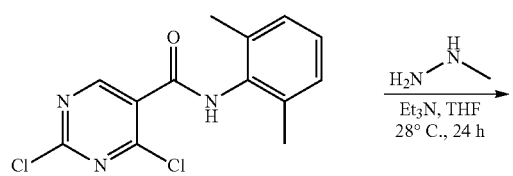

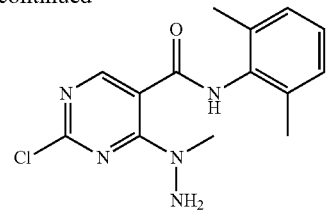

Methyl hydrazine (205 mg, 4.45 mmol) was added to 2,4-DICHLORO-N-(2,6-DIMETHYLPHENYL)PYRIMIDINE-5-CARBOXAMIDE (10.2 g, 4.05 mmol) in THF (30 mL) at room temperature, to which Et$_3$N (1.42 mL, 10.1 mmol) was added. The mixture was stirred at room temperature for 24 hours, which was concentrated to eliminate THF. The reaction mixture was washed with water, and the organic layer was dried over sodium sulfate, followed by concentration under reduced pressure. The obtained crude product was purified by silica gel column chromatography using EtOAc/Hx (1/4). As a result, 2-CHLORO-N-(2,6-DIMETHYLPHENYL)-4-(1-METHYLHYDRAZINYL) PYRIMIDINE-5-CARBOXAMIDE (1.0 g, 3.27 mmol, 80%) was obtained as a white solid.

$^1$H NMR (300 MHz, CDCl$_3$) δ 8.34 (s, 1H), 7.17-7.13 (m, 4H), 4.14 (s, br, 2H), 3.47 (s, 3H), 2.34 (s, 6H); LC/MS 306.2 [M+H$^+$].

Step 4: Preparation of 6-chloro-N-(2,6-dimethylphenyl)-1-methyl-1H-pyrazolo[3,4-d]pyrimidine-3-amine

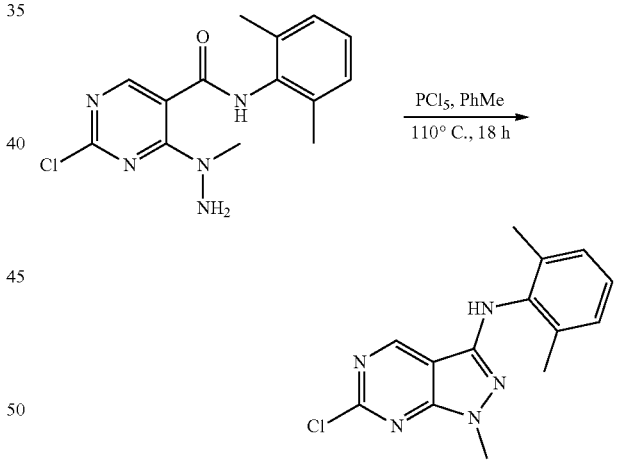

PCl$_5$ (681 mg, 3.27 mmol) was added to 2-CHLORO-N-(2,6-DIMETHYLPHENYL)-4-(1-METHYLHYDRAZINYL)PYRIMIDINE-5-CARBOXAMIDE (1.0 g, 3.27 mmol) in toluene (40 mL) at room temperature. The mixture was stirred at room temperature for 24 hours, which was concentrated to eliminate toluene. The reaction mixture was washed with sodium bicarbonate, and the organic layer was dried over sodium sulfate, followed by concentration under reduced pressure. The obtained crude product was purified by silica gel column chromatography using EtOAc/Hx (1/4). As a result, 6-CHLORO-N-(2,6-DIMETHYLPHENYL)-1-METHYL-1H-PYRAZOLO[3,4-D]PYRIMIDINE-3-AMINE (800 g, 2.78 mmol, 85%) was obtained as a yellow solid.

¹H NMR (300 MHz, CDCl₃) δ 7.54 (s, 1H), 7.25-7.16 (m, 3H), 6.12 (s, br, 1H), 3.89 (s, 3H), 2.26 (s, 6H); LC/MS 288.2 [M+H⁺].

Preparative Example B-2: Preparation of 6-chloro-1-methyl-N-phenyl-1H-pyrazolo[3,4-d]pyrimidine-3-amine Step 1: Preparation of 2,4-dichloro-N-phenyl pyrimidine-5-carboxamide

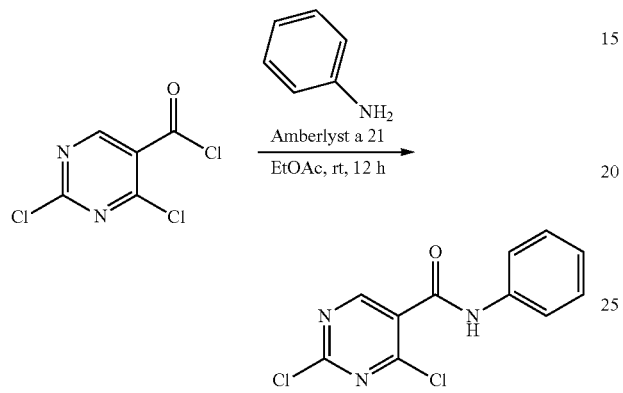

Aniline (440 mg, 4.72 mmol) was added to 2,4-dichloropyrimidin-5-carbonyl chloride (1.0 g, 4.72 mmol) in EtOAc (40 mL) at room temperature, to which amberlyst 21 resin (100 mg) was added. The mixture was stirred at room temperature for 12 hours, followed by filtering. The filtrate was washed with water, 1.5 N HCl (15 mL), NaOH, and brine in that order. The combined organic layer was dried over sodium sulfate, and then concentrated under reduced pressure. The obtained crude product was recrystallized by using DCM. As a result, 2,4-dichloro-N-phenyl pyrimidine-5-carboxamide (900 mg, 3.35 mmol, 71%) was obtained as a grey-white solid.

¹H NMR (300 MHz, DMSO-d6) δ 10.75 (s, 1H), 9.09 (s, 1H), 7.67 (d, J=7.7 Hz, 2H), 7.39 (t, J=7.6 Hz, 2H), 7.16 (t, J=7.4 Hz, 1H); LC/MS 268.2 [M+H⁴].

Step 2: Preparation of 2-chloro-4-(1-methylhydrazinyl)-N-phenylpyrimidine-5-carboxamide

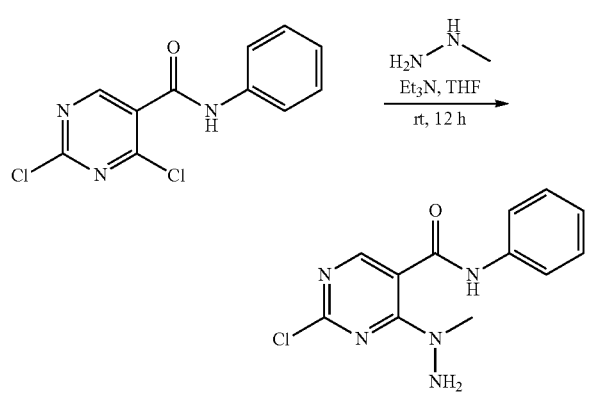

Methyl hydrazine (47 mg, 1.02 mmol) was added to 2,4-dichloro-N-phenyl pyrimidin-5-carboxamide (250 mg, 0.932 mmol) in THF (30 mL) at room temperature, to which Et₃N (0.32 mL, 2.33 mmol) was added. The mixture was stirred at room temperature for 12 hours, which was concentrated to eliminate THF. The reaction mixture was washed with water, and the organic layer was dried over sodium sulfate, followed by concentration under reduced pressure. The obtained crude product was purified by silica gel column chromatography using EtOAc/Hx (1/4). As a result. 2-chloro-4-(1-methylhydrazinyl)-N-phenylpyrimidine-5-carboxamide (210 mg, 0.756 mmol, 81%) was obtained as a white solid.

¹H NMR (500 MHz, DMSO-d6) δ 10.01 (s, 1H), 8.03 (s, 1H), 7.62 (d, J=7.85 Hz, 2H), 7.31 (t, J=7.70 Hz, 2H), 7.05 (t, J=7.35 Hz, 1H), 4.95 (s, 2H), 3.27 (s, 3H); LC/MS 278.2 [M+H⁺].

Step 3: Preparation of 6-chloro-1-methyl-N-phenyl-1H-pyrazolo[3,4-d]pyrimidine-3-amine

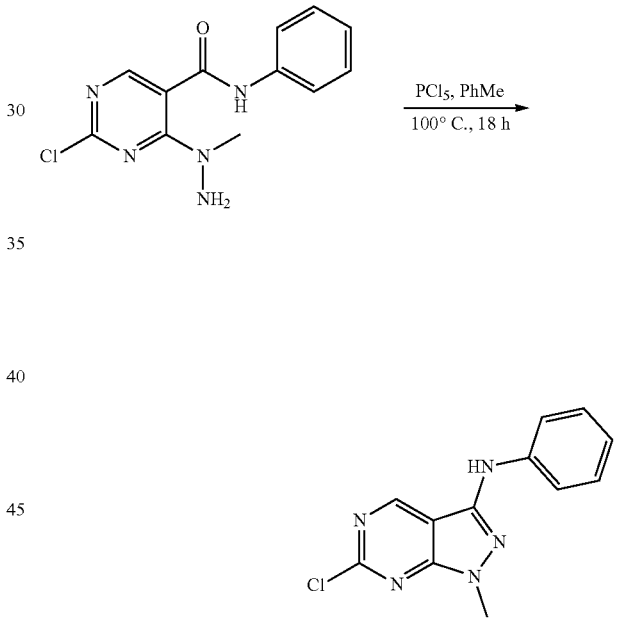

PCl₅ (150 mg, 0.720 mmol) was added to 2-chloro-4-(1-methylhydrazinyl)-N-phenylpyrimidine-5-carboxamide (200 mg, 0.720 mmol) in toluene (20 mL) at room temperature. The mixture was stirred at 100° C. for 18 hours, which was concentrated to eliminate toluene. The reaction mixture was washed with sodium bicarbonate, and the organic layer was dried over sodium sulfate, followed by concentration under reduced pressure. The obtained crude product was purified by silica gel column chromatography using EtOAc/Hx (1/4). As a result, 6-chloro-1-methyl-N-phenyl-1H-pyrazolo[3,4-d]pyrimidine-3-amine (150 mg, 0.577 mmol, 80%) was obtained as a yellow solid.

¹H NMR (300 MHz, CDCl₃) δ 8.76 (s, 1H), 7.47 (d, J=7.56 Hz, 2H), 7.38 (t, J=7.35 Hz, 2H), 7.09 (t, J=7.23 Hz, 1H), 6.53 (s, br 1H), 3.98 (s, 3H); LC/MS 260.2 [M+H⁺].

Preparative Example B-3: Preparation of 6-chloro-N-(2,6-dichlorophenyl)-1-methyl-1H-pyrazolo[3,4-d]pyrimidine-3-amine Step 1: Preparation of 2,4-dichloro-N-(2,6-dichlorophenyl)pyrimidine-5-carboxamide

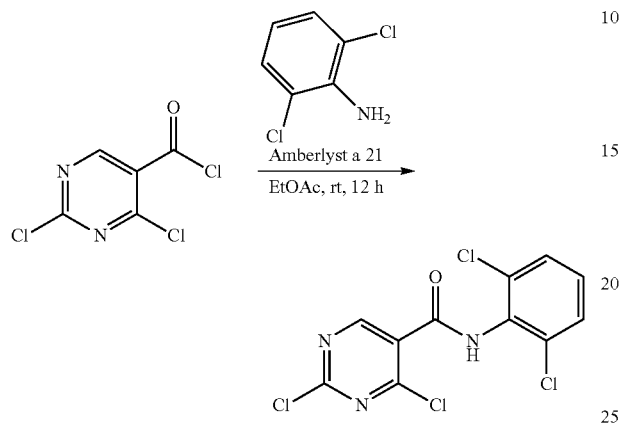

2,6-Dichloroaniline (383 mg, 2.36 mmol) was added to 2,4-dichloropyrimidine-5-carbonyl chloride (500 mg, 2.36 mmol) in EtOAc (40 mL) at room temperature, to which amberlyst 21 resin (100 mg) was added. The mixture was stirred for 12 hours, followed by filtering. The filtrate was washed with water, 1.5 N HCl (15 mL), NaOH, and brine in that order. The combined organic layer was dried over sodium sulfate, and then concentrated under reduced pressure. The obtained crude product was recrystallized by using DCM. As a result, 2,4-dichloro-N-(2,6-dichlorophenyl)pyrimidine-5-carboxamide (650 mg, 1.93 mmol, 81%) was obtained as a grey-white solid.

$^1$H NMR (300 MHz, DMSO-d6) δ 10.83 (s, 1H), 9.01 (s, 1H), 7.62 (d, J=8.1 Hz, 2H), 7.44 (t, J=7.8 Hz, 1H); LC/MS 337.2 [M+H$^+$].

Step 2: Preparation of 2-chloro-N-(2,6-dichlorophenyl)-4-(1-methylhydrazinyl)pyrimidine-5-carboxamide

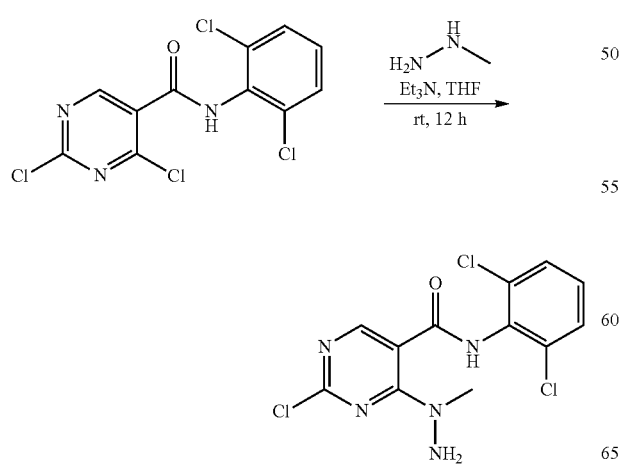

Methyl hydrazine (37 mg, 0.81 mmol) was added to 2,4-dichloro-N-(2,6-dichlorophenyl)pyrimidine-5-carboxamide (250 mg, 0.74 mmol) in THF (30 mL) at room temperature, to which Et$_3$N (0.26 mL, 1.85 mmol) was added. The mixture was stirred at room temperature for 12 hours, which was concentrated to eliminate THF. The reaction mixture was washed with water, and the organic layer was dried over sodium sulfate, followed by concentration under reduced pressure. The obtained crude product was purified by silica gel column chromatography using EtOAc/Hx (1/4). As a result, 2-chloro-N-(2,6-dichlorophenyl)-4-(1-methylhydrazinyl)pyrimidine-5-carboxamide (180 mg, 0.519 mmol, 70%) was obtained as a white solid.

$^1$H NMR (500 MHz, DMSO-d6) δ 10.17 (s, 1H), 8.14 (s, 1H), 7.55 (d, J=8.1 Hz, 2H), 7.37 (t, J=8.05 Hz, 1H), 4.99 (s, 2H), 3.30 (s, 3H); LC/MS 346.2 [M+H$^+$].

Step 3: Preparation of 6-chloro-N-(2,6-dichlorophenyl)-1-methyl-1H-pyrazolo[3,4-d]pyrimidine-3-amine

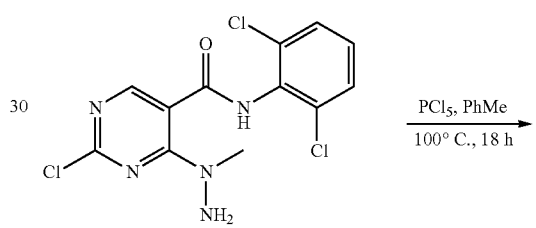

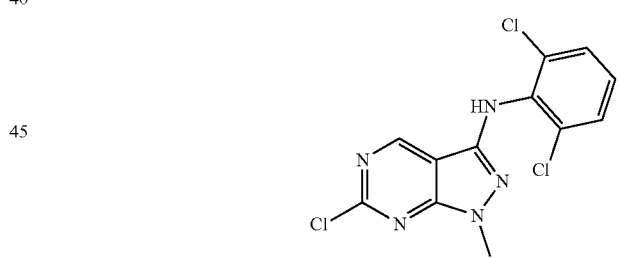

PCl$_5$ (120 mg, 0.577 mmol) was added to 2-chloro-N-(2,6-dichlorophenyl)-4-(1-methylhydrazinyl)pyrimidine-5-carboxamide (200 mg, 0.577 mmol) in toluene (20 mL) at room temperature. The mixture was stirred at 100° C. for 18 hours, which was concentrated to eliminate toluene. The reaction mixture was washed with sodium bicarbonate, and the organic layer was dried over sodium sulfate, followed by concentration under reduced pressure. The obtained crude product was purified by silica gel column chromatography using EtOAc/Hx (1/4). As a result, 6-chloro-N-(2,6-dichlorophenyl)-1-methyl-1H-pyrazolo[3,4-d]pyrimidine-3-amine (30 mg, 0.395 mmol, 68%) was obtained as a yellow solid.

$^1$H NMR (300 MHz, CDCl$_3$) δ 8.27 (s, 1H), 7.46 (d, J=8.1 Hz, 2H), 7.21 (t, J=7.8 Hz, 1H), 6.40 (s, 1H), 3.95 (s, 3H); LC/MS 328.2 [M+H$^+$].

Preparative Example B-4: Preparation of 6-chloro-N-(2,6-dimethylphenyl)-1H-pyrazolo[3,4-d]pyrimidine-3-amine

Step 1: Preparation of tertbutyl-2-(2-chloro-5-((2,6-dimethylphenyl)carbamoyl)pyrimidine-4-yl)hydrazine-1-carboxylate

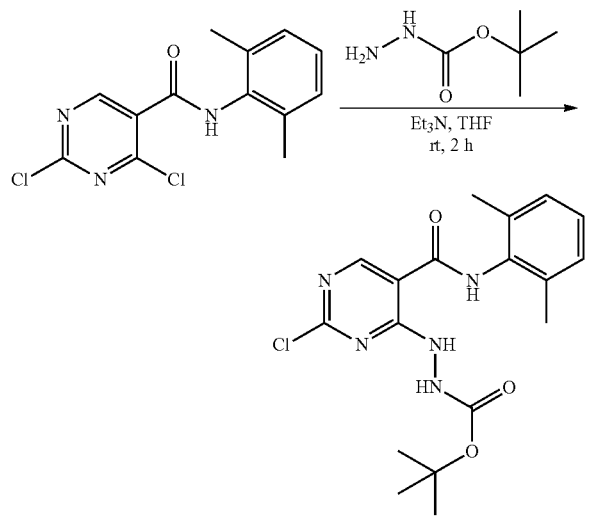

Tert-butyl carbazate (268 mg, 2.026 mmol) was added to 2,4-dichloro-N-(2,6-dimethylphenyl)pyrimidin-5-carboxamide (500 mg, 1.688 mmol) in THF (30 mL) at room temperature, to which Et$_3$N (0.6 mL, 4.22 mmol) was added. The mixture was stirred for 12 hours, which was concentrated to eliminate THF. The reaction mixture was washed with water, and the organic layer was dried over sodium sulfate, followed by concentration under reduced pressure. The obtained crude product was purified by silica gel column chromatography using EtOAc/Hx (1/4). As a result, tert-butyl-2-(2-chloro-5-((2,6-dimethylphenyl)carbamoyl)pyrimidine-4-yl)hydrazine-1-carboxylate (560 mg, 1.429 mmol, 84%) was obtained as a white solid.

$^1$H NMR (300 MHz, CDCl$_3$) δ 9.97 (s, br, 1H), 8.60 (s, 1H), 7.45 (s, br, 1H), 7.22-7.14 (m, 3H), 6.57 (s, br, 1H), 2.27 (s, 6H), 1.52 (s, 9H); LC/MS 391.2 [M+H$^+$].

Step 2: Preparation of 6-chloro-N-(2,6-dimethylphenyl)-1H-pyrazolo[3,4-d]pyrimidine-3-amine

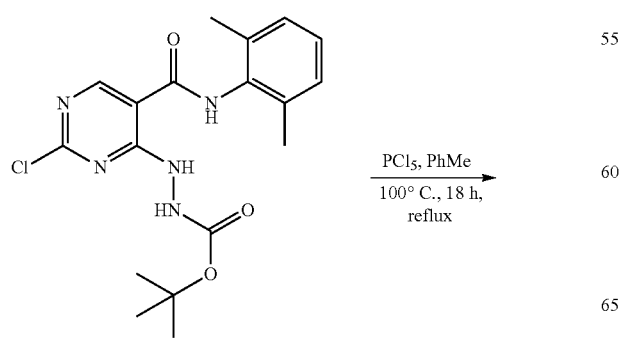

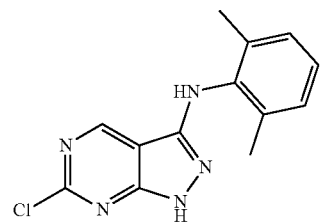

PCl$_5$ (297 mg, 1.429 mmol) was added to tertbutyl-2-(2-chloro-5-((2,6-dimethylphenyl)carbamoyl)pyrimidine-4-yl)hydrazine-1-carboxylate (560 mg, 1.429 mmol) in toluene (50 mL) at room temperature. The mixture was stirred at 100° C. for 18 hours, which was concentrated to eliminate toluene. The reaction mixture was washed with sodium bicarbonate, and the organic layer was dried over sodium sulfate, followed by concentration under reduced pressure. The obtained crude product was purified by silica gel column chromatography using EtOAc/Hx (1/4). As a result, 6-chloro-N-(2,6-dimethylphenyl)-1H-pyrazolo[3,4-d]pyrimidine-3-amine (65 mg, 0.237 mmol, 16%) was obtained as a yellow solid.

$^1$H NMR (300 MHz, CDCl$_3$) δ 10.31 (s, 1H), 7.69 (s, 1H), 7.24-7.13 (m, 3H), 6.29 (s, 1H), 2.26 (s, 6H); LC/MS 273.9 [M+H$^+$].

Preparative Example B-5: Preparation of 6-chloro-1-cyclopentyl-N-(2,6-dimethylphenyl)-1H-pyrazolo[3,4-d]pyrimidine-3-amine

Step 1: Preparation of 2-chloro-4-(1-cyclopentylhydrazinyl)-N-(2,6-dimethylphenyl)pyrimidine-5-carboxamide

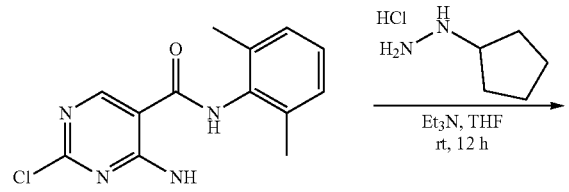

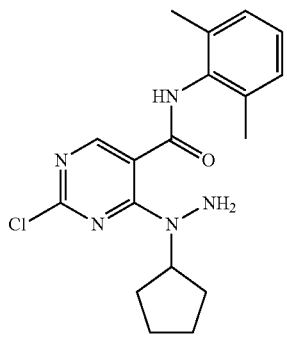

Et₃N (0.24 mL, 1.68 mmol) was added to 2,4-dichloro-N-(2,6-dimethylphenyl)pyrimidine-5-carboxamide (200 mg, 0.675 mmol) in THF (20 mL), to which cyclopentyl hydrazine HCl (101.5 mg, 0.742 mmol) was added at room temperature. The mixture was stirred at room temperature for 12 hours, which was concentrated to eliminate THF. The reaction mixture was washed with sodium bicarbonate, and the organic layer was dried over sodium sulfate, followed by concentration under reduced pressure. The obtained crude product was purified by column chromatography using EtOAc/Hx (1/4). As a result, 2-chloro-4-(1-cyclopentylhydrazinyl)-N-(2,6-dimethylphenyl)pyrimidine-5-carboxamide (180 mg, 0.500 mmol, 74%) was obtained as a white solid.

¹H NMR (300 MHz, CDCl₃) δ 8.27 (s, 1H), 7.35 (s, br, 1H), 7.16-7.09 (m, 3H), 5.25 (pent, J=8.1 Hz, 1H), 3.85 (s, 2H), 2.30 (s, 6H), 2.03-1.88 (m, 2H), 1.76-1.57 (m, 6H); LC/MS 359.9 [M+H⁺].

Step 2: Preparation of 6-chloro-1-cyclopentyl-N-(2,6-dimethylphenyl)-1H-pyrazolo[3,4-d]pyrimidine-3-amine

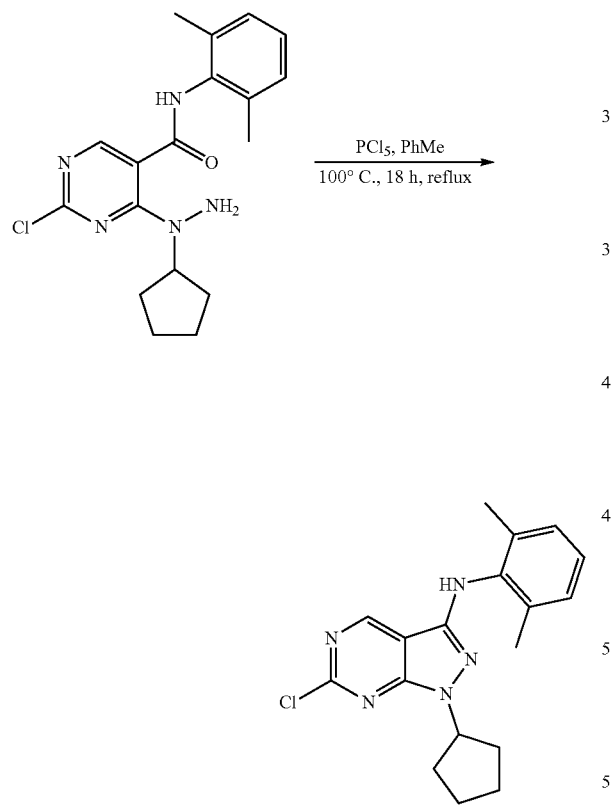

PCl₅ (104 mg, 0.500 mmol) was added to 2-chloro-4-(1-cyclopentylhydrazinyl)-N-(2,6-dimethylphenyl)pyrimidine-5-carboxamide (180 mg, 0.500 mmol) in toluene (20 mL) at room temperature. The mixture was stirred at 100° C. for 18 hours, which was concentrated to eliminate toluene. The reaction mixture was washed with sodium bicarbonate, and the organic layer was dried over sodium sulfate, followed by concentration under reduced pressure. The obtained crude product was purified by column chromatography using EtOAc/Hx (1/4). As a result, 6-chloro-1-cyclopentyl-N-(2,6-dimethylphenyl)-1H-pyrazolo[3,4-d]pyrimidine-3-amine (120 mg, 0.351 mmol, 70%) was obtained as a yellow solid.

¹H NMR (300 MHz, CDCl₃) δ 7.46 (s, 1H), 7.25-7.12 (m, 3H), 6.14 (s, 1H), 5.18 (pent, J=7.8 Hz, 1H), 2.27 (s, 6H), 2.16-2.02 (m, 4H), 1.98-1.86 (m, 2H), 1.80-1.67 (m, 2H); LC/MS 342.2 [M+H⁺].

Preparative Example B-6: Preparation of 6-chloro-1-cyclohexyl-N-(2,6-dimethylphenyl)-1H-pyrazolo[3,4-d]pyrimidine-3-amine Step 1: Preparation of 2-chloro-4-(1-cyclohexylhydrazinyl)-N-(2,6-dimethylphenyl)pyrimidine-5-carboxamide

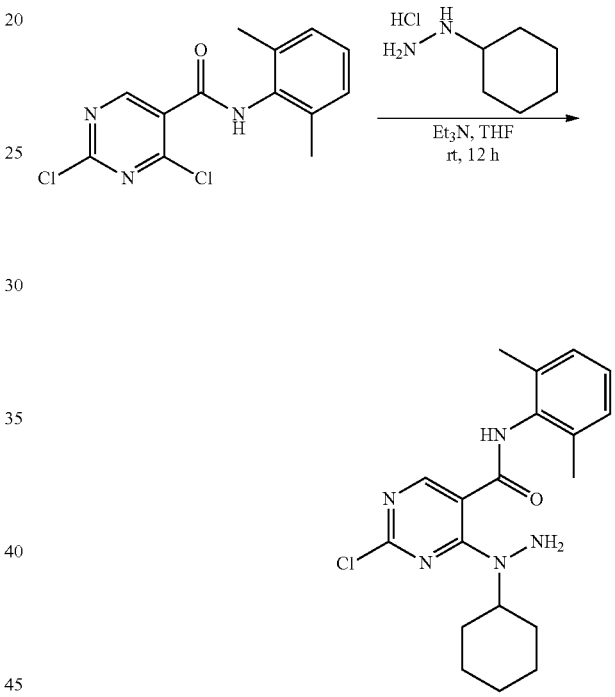

Et₃N (0.18 mL, 1.26 mmol) was added to 2,4-dichloro-N-(2,6-dimethylphenyl)pyrimidine-5-carboxamide (150 mg, 0.506 mmol) in THF (10 mL), to which cyclohexyl hydrazine HCl (84 mg, 0.557 mmol) was added at room temperature. The mixture was stirred at room temperature for 12 hours, which was concentrated to eliminate THF. The reaction mixture was washed with water, and the organic layer was dried over sodium sulfate, followed by concentration under reduced pressure. The obtained crude product was purified by column chromatography using EtOAc/Hx (1/4). As a result, 2-chloro-4-(1-cyclohexylhydrazinyl)-N-(2,6-dimethylphenyl)pyrimidine-5-carboxamide (140 mg, 0.374 mmol, 74%) was obtained as a white solid.

¹H NMR (500 MHz, CDCl₃) δ 8.29 (s, 1H), 7.34 (s, br, 1H), 7.18-7.12 (m, 3H), 4.75 4.65 (m, 1H), 3.85 (s, 2H), 2.34 (s, 6H), 1.95-1.90 (m, 2H), 1.85-1.77 (m, 2H), 1.76-1.74 (m, 2H), 1.55-1.45 (m, 4H), 1.22-1.11 (n, 1H): LC/MS 373.9 [M+H⁺].

Step 2: Preparation of 6-chloro-1-cyclohexyl-N-(2,6-dimethylphenyl)-1H-pyrazolo[3,4-d]pyrimidine-3-amine

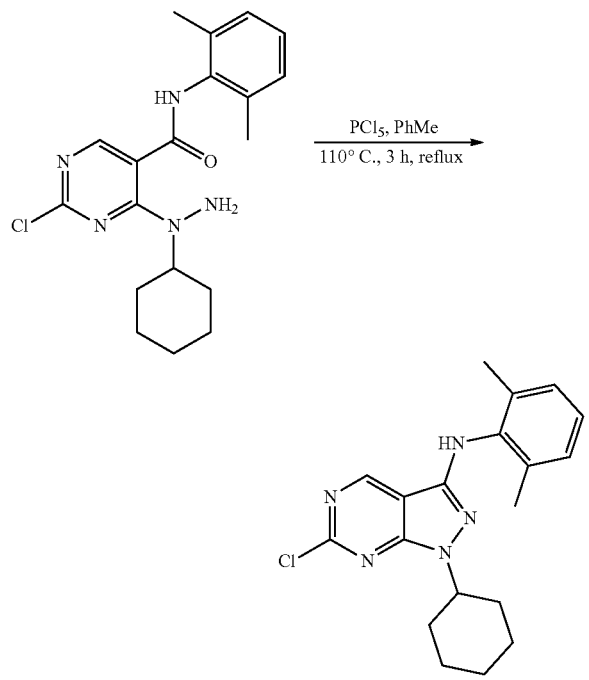

PCl$_5$ (72 mg, 0.347 mmol) was added to 2-chloro-4-(1-cyclohexylhydrazinyl)-N-(2,6-dimethylphenyl)pyrimidine-5-carboxamide (130 mg, 0.347 mmol) in toluene (20 mL) at mom temperature. The mixture was stirred at 110° C. for 3 hours, which was concentrated to eliminate toluene. The reaction mixture was washed with sodium bicarbonate, and the organic layer was dried over sodium sulfate, followed by concentration under reduced pressure. The obtained crude product was purified by column chromatography using EtOAc/Hx (1/4). As a result, 6-chloro-1-cyclohexyl-N-(2,6-dimethylphenyl)-1H-pyrazolo[3,4-d]pyrimidine-3-amine (90 mg, 0.253 mmol, 73%) was obtained as a yellow solid.

$^1$H NMR (300 MHz, CDCl$_3$) δ 7.46 (s, 1H), 7.23-7.11 (m, 3H), 6.14 (s, br, 1H), 4.67 4.53 (m, 1H), 2.24 (s, 6H), 2.02-1.84 (m, 6H), 1.78-1.67 (m, 11H), 1.54-1.38 (m, 2H), 1.32-1.17 (m, 1H); LC/MS 356.2 [M+H$^+$].

Preparative Example B-7: Preparation of 6-chloro-N-(2,6-dimethylphenyl)-1-isopropyl-1H-pyrazolo[3,4-d]pyrimidine-3-amine

Step 1: Preparation of 2-chloro-N-(2,6-dimethylphenyl)-4-(1-isopropyhydrazinyl)pyrimidine-5-carboxamide

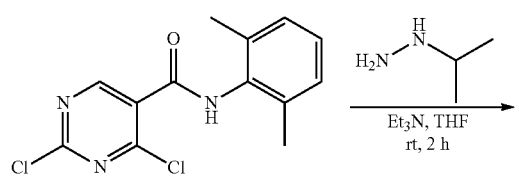

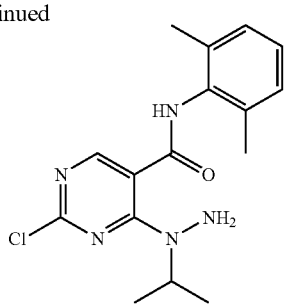

Et$_3$N (0.18 mL, 1.26 mmol) was added to 2,4-dichloro-N-(2,6-dimethylphenyl)pyrimidine-5-carboxamide (150 mg, 0.506 mmol) in THF (10 mL), to which isopropyl hydrazine (41 mg, 0.577 mmol) was added at room temperature. The mixture was stirred at room temperature for 2 hours, which was concentrated to eliminate THF. The reaction mixture was washed with water, and the organic layer was dried over sodium sulfate, followed by concentration under reduced pressure. The obtained crude product was purified by silica gel column chromatography using EtOAc/Hx (1/4). As a result, 2-chloro-N-(2,6-dimethylphenyl)-4-(1-isopropylhydrazinyl)pyrimidine-5-carboxamide (120 mg, 0.359 mmol, 71%) was obtained as a while solid.

$^1$H NMR (500 MHz, CDCl$_3$) δ 8.24 (s, 1H), 7.56 (s, br, 1H), 7.17-7.10 (m, 3H), 5.14 (sept, J=6.7 Hz, 1H), 3.81 (s, 2H), 2.32 (s, 6H), 1.24 (d, J=6.7 Hz, 6H); LC/MS 333.9 [M+H$^+$].

Step 2: Preparation of 6-choro-N-(2,6-dimethylphenyl)-1-isopropyl-1H-pyrazolo[3,4-d]pyrimidine-3-amine

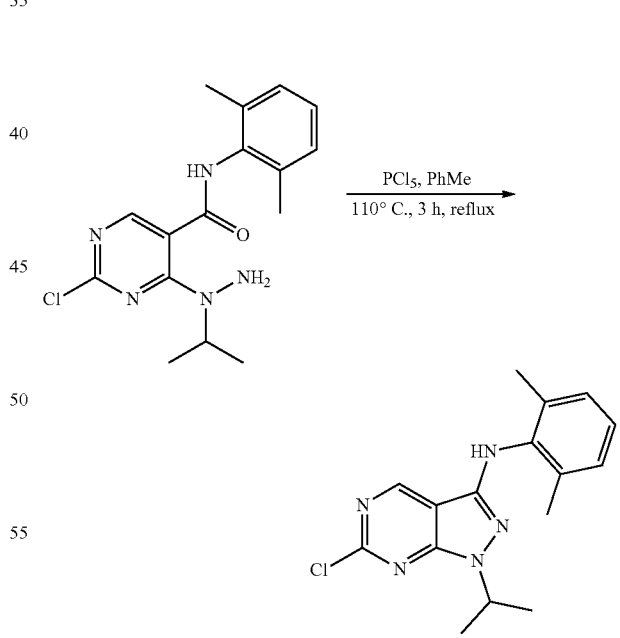

PCl$_5$ (68.6 mg, 0.329 mmol) was added to 2-chloro-N-(2,6-dimethylphenyl)-4-(1-isopropylhydrazinyl)pyrimidine-5-carboxamide (110 mg, 0.329 mmol) in toluene (20 mL) at room temperature. The mixture was stirred at 110° C. for 3 hours, which was concentrated to eliminate toluene. The reaction mixture was washed with sodium bicarbonate, and the organic layer was dried over sodium sulfate, followed by concentration under reduced pressure. The obtained crude product was purified by silica gel column chromatography using EtOAc/Hx (1/4). As a result, 6-chloro-N-(2,6-dimethylphenyl)-1-isopropyl-1H-pyrazolo[3,4-d]pyrimidine-3-amine (75 mg, 0.237 mmol, 72%) was obtained as a yellow solid.

¹H NMR (300 MHz, CDCl₃) δ 7.46 (s, 1H), 7.22-7.12 (m, 3H), 6.03 (s, br, 1H), 5.03 (sept, J=6.7 Hz, 1H), 2.25 (s, 6H), 1.51 (d, J=6.7 Hz, 6H): LC/MS 316.9 [M+H⁺].

Preparative Example B-8: Preparation of N-(3-((6-chloro-1-methyl-1H-pyrazolo[3,4-d]pyrimidin-3-yl)amino)-4-methylphenyl)-3-(trifluoromethyl)benzamide

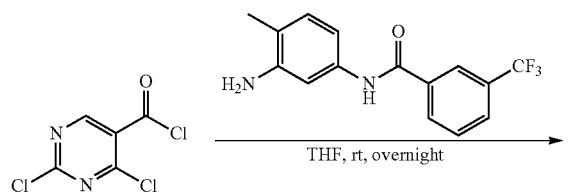

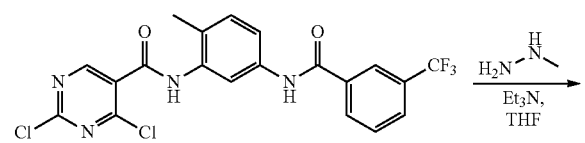

A target compound was prepared by the same manner as described in steps 2, 3, and 4 of Preparative Example B-1 except that N-(3-amino-4-methylphenyl)-3-(trifluoromethyl)benzamide prepared in step 4 above was used instead of 2,6-dimethylaniline in step 2 of Preparative Example B-1.

¹H NMR (300 MHz, CDCl₃) δ 9.14 (s, 1H), 8.25 (s, 1H), 8.23-8.17 (m, 1H), 8.14 (s, 1H), 8.09-8.03 (m, 1H), 7.93-7.92 (m, 1H), 7.84-7.81 (m, 1H), 7.67-7.61 (m, 2H), 2.35 (s, 3H); LC/MS 468.8 [M+H⁺]

Preparative Example B-9: Preparation of N-(3-((6-chloro-1-methyl-1H-pyrazolo[3,4-d]pyrimidine-3-yl)amino)-2,4-dimethylphenyl)-3-(trifluoromethyl)benzamide Step 1: Preparation of 1,3-dimethyl-2,4-dinitrobenzene

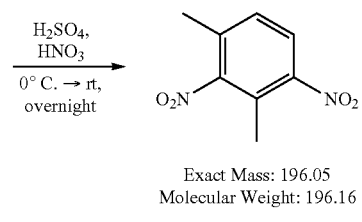

Exact Mass: 151.06
Molecular Weight: 151.17

Exact Mass: 196.05
Molecular Weight: 196.16

Sulfuric acid (1.65 mL) was slowly added to 1,3-dimethyl-2-nitrobenzene (5.00 g, 33.1 mmol) at 0° C. Nitric acid (0.41 mL) was slowly added thereto at 0° C. The reaction mixture was stirred at room temperature for 1 hour. The reaction was terminated with ice water and the precipitate was filtered. The Filtrate was distillated under reduced pressure. As a result, the target compound (6.0 g, 30.6 mmol, 92%) was obtained as a yellow solid.

¹H NMR (300 MHz, CDCl₃) δ 7.95 (d, J=8.4 Hz, 1H), 7.32 (d, J=8.4 Hz, 1H), 2.47 (s, 3H), 2.39 (s, 3H); LC/MS 196.8 [M+H⁺]

Step 2: Preparation of 2,4-dimethyl-3-nitroaniline

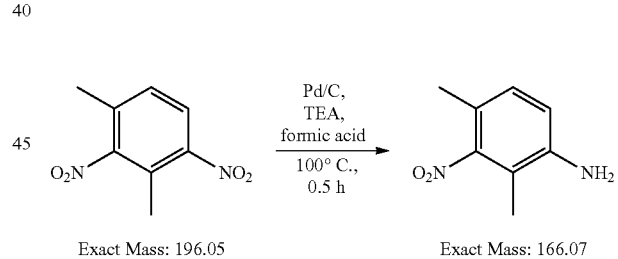

Exact Mass: 196.05
Molecular Weight: 196.16

Exact Mass: 166.07
Molecular Weight: 166.18

Formic acid (4.04 mL, 107 mmol) was slowly added to TEA (16.0 mL, 115 mmol) solution containing the compound prepared in step 1 (5.00 g, 25.5 mmol) and 10% Pd/C (500 mg) at room temperature. The reaction mixture was stirred at 100° C. for 0.5 hour. The reaction was terminated with NaHCO₃ (aq), followed by extraction with EtOAc (2×25 mL). The combined organic layer was dried over NaSO₄ and the solvent was eliminated under reduced pressure. The residue mixture was purified by silica gel column chromatography using EtOAc/Hex (3/7). As a result, the target compound (2.0 g, 12 mmol, 47%) was obtained as a yellow solid.

¹H NMR (300 MHz, CDCl₃) δ 6.92 (d, J=8.2 Hz, 1H), 6.68 (d, J=8.2 Hz, 1H), 3.71 (s, 2H), 2.18 (s, 3H), 2.05 (s, 3H).

Step 3: Preparation of N-(2,4-dimethyl-3-nitrophenyl)-3-(trifluoromethyl)benzamide

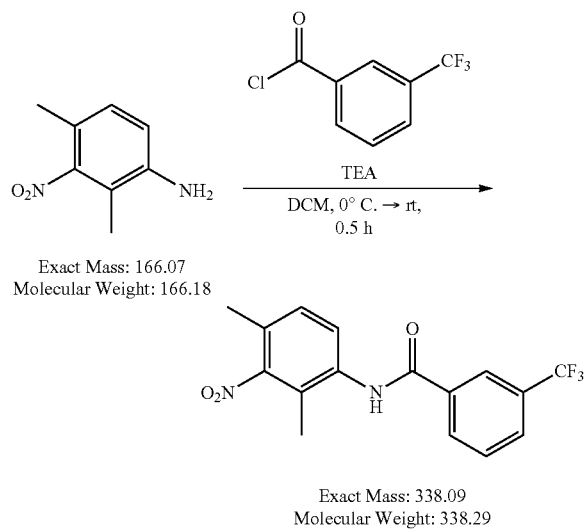

3-(trifluoromethyl)benzoyl chloride (1.09 mL, 7.22 mmol) was added to DCM solution containing the compound prepared in step 2 (1.0 g, 6.02 mmol), to which TEA (1.68 mL, 12.0 mmol) was added at 0° C. The mixture was stirred at room temperature for 0.5 hour. The reaction was terminated with water, followed by extraction with DCM (2×25 mL). The residue mixture was purified by silica gel column chromatography using EtOAc/Hex (3/7). As a result, the target compound (1.25 g, 3.70 mmol, 62%) was obtained as a white solid.

$^1$H NMR (300 MHz, CDCl$_3$) δ 8.15 (s, 1H), 8.06 (d, J=7.8 Hz, 1H), 7.75 (d, J=8.2 Hz, 2H), 7.66 (t, J=7.8 Hz, 1H), 7.20 (d, J=8.4 Hz, H), 2.31 (s, 3H), 2.10 (s, 3H); LC/MS 338.8 [M+H$^+$]

Step 4: Preparation of N-(3-amino-2,4-dimethylphenyl)-3-(trifluoromethyl)benzamide

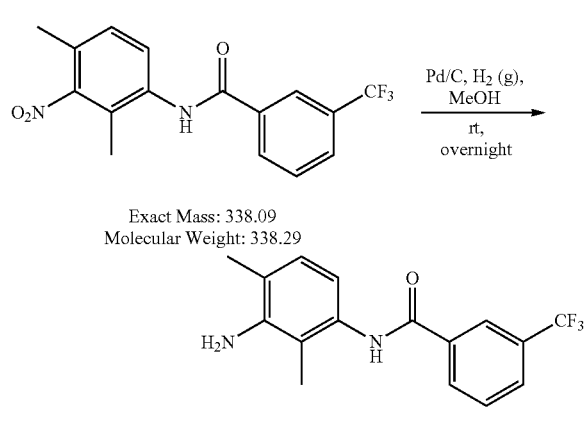

10% Pd/C (4 mg) was added to MeOH solution containing the compound prepared in step 3 (40 mg, 0.12 mmol) at room temperature. The reaction mixture was stirred at room temperature under hydrogen balloon pressure overnight. The reaction mixture was filtered with celite, and the solvent was eliminated. The mixture was purified by column chromatography using EtOAc/Hex as an eluent. As a result, the target compound (397 mg, 1.29 mmol, 36%) was obtained as a light yellow solid.

$^1$H NMR (300 MHz, CDCl$_3$) δ 8.16 (s, 1H), 8.07 (d, J=7.4 Hz, 1H), 7.81 (d, J=7.6 Hz, 1H), 7.65-7.60 (m, 2H), 6.98 (d, J=7.9 Hz, 1H), 6.87 (d, J=8.2 Hz, 1H), 3.67 (s, 2H), 2.19 (s, 3H), 2.11 (s, 3H); LC/MS 308.9 [M+H$^+$]

Step 5: Preparation of N-(3-((6-chloro-1-methyl-1H-pyrazolo[3,4-d]pyrimidin-3-yl)amino)-2,4-dimethylphenyl)-3-(trifluoromethyl)benzamide

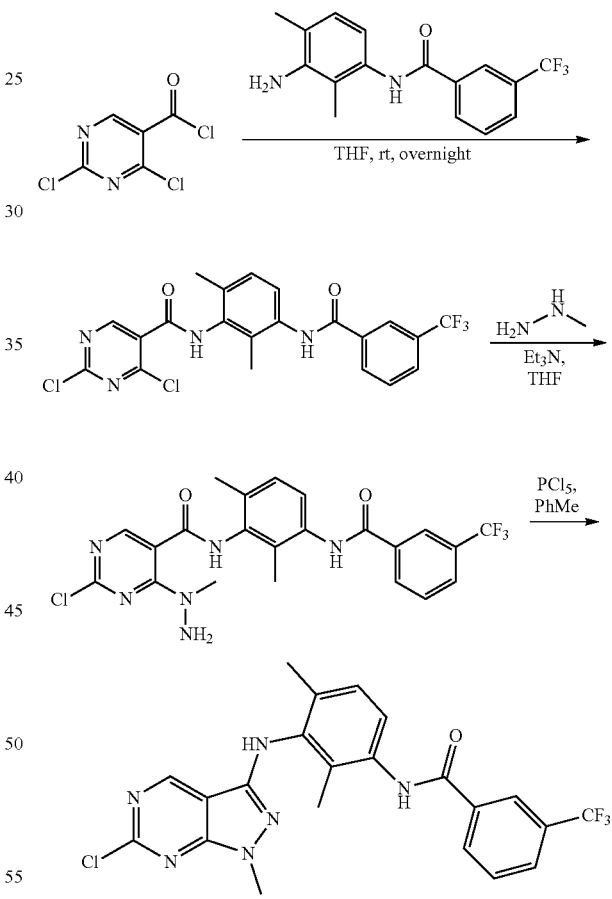

A target compound was prepared by the same manner as described in steps 2, 3, and 4 of Preparative Example B-1 except that N-(3-amino-2,4-dimethylphenyl)-3-(trifluoromethyl)benzamide prepared in step 4 above was used instead of 2,6-dimethylaniline in step 2 of Preparative Example B-1.

$^1$H NMR (300 MHz, CDCl$_3$) δ 8.15 (s, 1H), 8.07 (d, J=7.8 Hz, 1H), 7.71-7.52 (m, 3H), 7.22 (d, J=8.2 Hz, 1H), 6.25 (s, 1H), 3.87 (s, 3H), 2.25 (s, 3H), 2.22 (s, 3H); LC/MS 474.8 [M+H$^+$]

Preparative Example B-10: Preparation of 6-chloro-N-(4-(2-methoxyethoxy)-2,6-dimethylphenyl)-1-methyl-1H-pyrazolo[3,4-d]pyrimidine-3-amine Step 1: Preparation of 4-(2-methoxyethoxy)-2,6-dimethylaniline

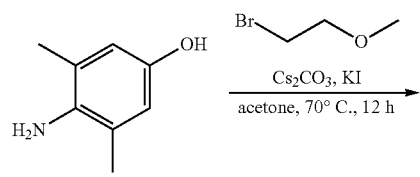

Exact Mass: 137.08
Molecular Weight: 137.18

Exact Mass: 195.13
Molecular Weight: 195.26

Cs$_2$CO$_3$ (3.53 g, 10.8 mmol) and KI (75.3 mg, 0.454 mmol) were added to acetone (10 mL) solution containing 4-amino-3,5-xylenol (1.00 g, 7.29 mmol) at room temperature. 1-Bromo-2-methoxyethane (1.22 g, 8.75 mmol) was added thereto at room temperature. The mixture was stirred at 70° C. for 7 hours. The reaction was terminated with water, followed by concentration until the volume was reduced to half. The mixture was extracted with EtOAc (2×). The extract was dried over Na$_2$SO$_4$ and then filtered. When the obtained product was concentrated to brown oil, the concentrated product was purified by silica gel column chromatography using EtOAc/hexane (1/1). As a result, the target compound (812 mg, 4.16 mmol, 39%) was obtained as brown oil.

$^1$H NMR (300 MHz, CDCl$_3$) δ 6.58 (s, 2H), 4.03 (t, J=4.8 Hz, 2H), 3.69 (t, J=4.8 Hz, 2H), 3.43 (s, 3H), 3.31 (s, br, 2H), 2.15 (s, 6H); LC/MS 195.8 [M+H$^+$]

Step 2: Preparation of 6-chloro-N-(4-(2-methoxyethoxy)-2,6-dimethylphenyl)-1-methyl-1H-pyrazolo[3,4-d]pyrimidine-3-amine

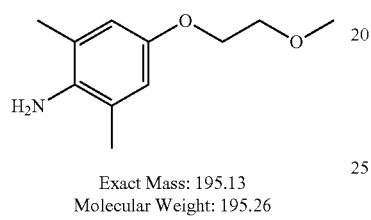

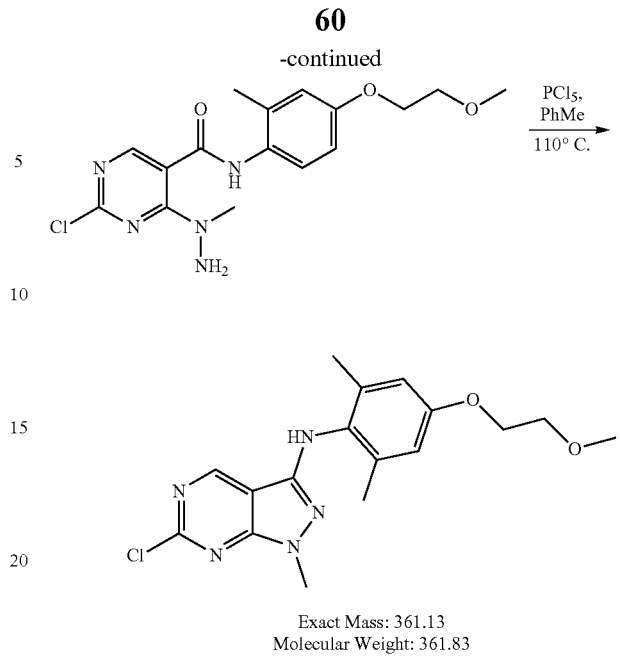

Exact Mass: 361.13
Molecular Weight: 361.83

A target compound was prepared by the same manner as described in steps 2, 3, and 4 of Preparative Example B-1 except that 4-(2-methoxyethoxy)-2,6-dimethylaniline prepared in step 1 above was used instead of 2,6-dimethylaniline in step 2 of Preparative Example B-1.

$^1$H NMR (300 MHz, CDCl$_3$) δ 7.49 (s, 1H), 6.73 (s, 2H), 5.98 (s, 1H), 4.15-4.08 (m, 2H), 3.87 (s, 3H), 3.80-3.74 (m, 2H), 3.47 (s, 3H), 2.20 (s, 6H); LC/MS 361.9 [M+H$^+$]

Preparative Example B-11: Preparation of 6-chloro-N-(2,6-dimethyl-4-phenoxyphenyl)-1-methyl-1H-pyrazolo[3,4-d]pyrimidine-3-amine

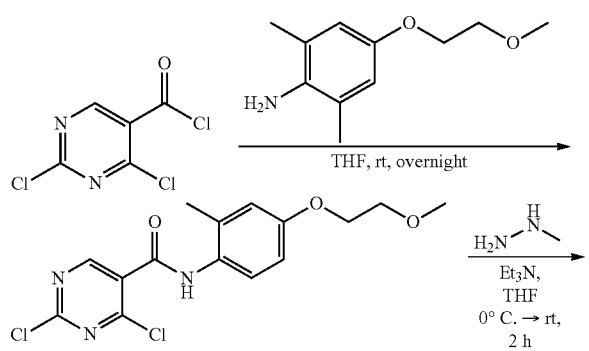

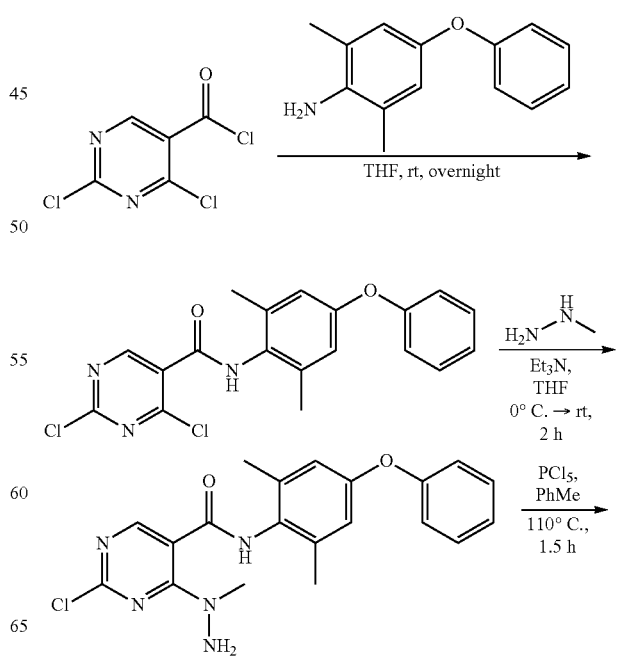

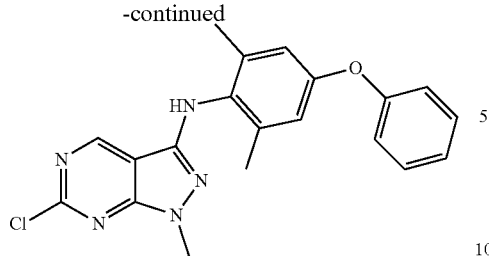

A target compound was prepared by the same manner as described in steps 2, 3, and 4 of Preparative Example B-1 except that 2,6-dimethyl-4-phenoxybenzamine was used instead of 2,6-dimethylaniline in step 2 of Preparative Example B-1.

$^1$H NMR (300 MHz, CDCl$_3$) δ 7.65 (s, 1H), 7.43-7.34 (m, 2H), 7.21-7.12 (m, 1H), 7.09-7.02 (m, 2H), 6.79 (s, 2H), 5.94 (s, 1H), 3.88 (s, 3H), 2.21 (s, 6H); LC/MS 379.9 [M+H$^+$]

Preparative Example B-12: Preparation of 4-((6-chloro-1-methyl-1H-pyrazolo[3,4-d]pyrimidin-3-yl)amino)-3,5-dimethyl-N-(pyridine-2-yl)benzamide Step 1: Preparation of 3,5-dimethyl-4-nitro-N-(pyridine-2-yl)benzamide

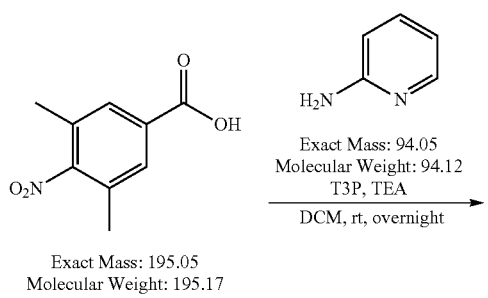

T3P (2.30 mL, 10.2 mmol) and TEA (1.42 mL, 10.2 mmol) were added to DCM (20 mL) solution containing 3,5-dimethyl-4-nitrobenzoic acid (1.00 g, 5.12 mmol) and 2-aminopyridine (482 mg, 5.12 mmol) at room temperature, followed by stirring at room temperature overnight. The reaction was terminated with NaHCO$_3$ (aq), followed by extraction with DCM (2×25 mL). The combined organic layer was dried over Na$_2$SO$_4$ and the solvent was eliminated under reduced pressure. The residue mixture was purified by silica gel column chromatography using EtOAc/Hex (3/7). As a result, the target compound (290 mg, 1.07 mmol, 21%) was obtained as a white solid.

$^1$H NMR (300 MHz, CDCl$_3$) δ 8.76 (s, 1H), 8.38-8.27 (m, 1H), 8.29-8.26 (m, 1H), 7.877.75 (m, 1H), 7.69 (s, 2H), 7.13-7.08 (m, 1H), 2.37 (s, 6H); LC/MS 271.8 [M+H$^+$]

Step 2: Preparation of 4-amino-3,5-dimethyl-N-(pyridine-2-yl)benzamide

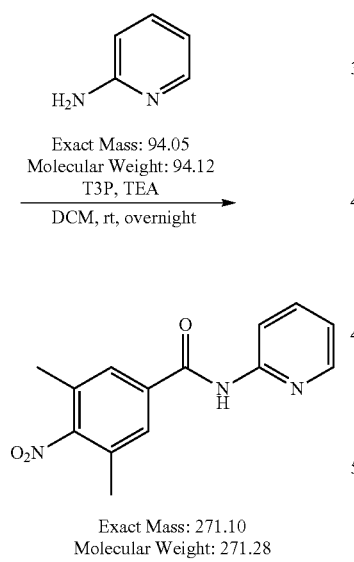

10% Pd/C (30 mg) was added to MeOH (20 mL) solution containing the compound prepared in step 1 above (290 mg, 1.07 mmol) at room temperature. The reaction mixture was stirred at room temperature under hydrogen balloon pressure overnight. The reaction mixture was filtered with celite and MeOH was eliminated under reduced pressure. As a result, the target compound (245 mg, 1.02 mmol, 95%) was obtained as a light yellow solid.

$^1$H NMR (300 MHz, CDCl$_3$) δ 8.51 (s, 1H), 8.38 (d, J=8.4 Hz, 1H), 8.328.25 (m, 1H), 7.797.68 (m, 1H), 7.56 (s, 2H), 7.096.99 (m, 1H), 3.99 (s, 2H), 2.23 (s, 6H); LC/MS 241.9 [M+H$^+$]

Step 3: Preparation of 4-((6-chloro-1-methyl-1H-pyrazolo[3,4-d]pyrimidine-3-yl)amino)-3,5-dimethyl-N-(pyridine-2-yl)benzamide

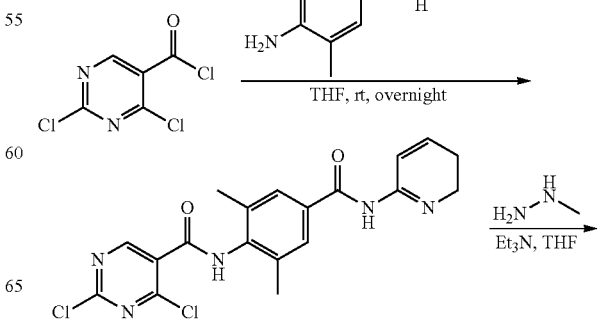

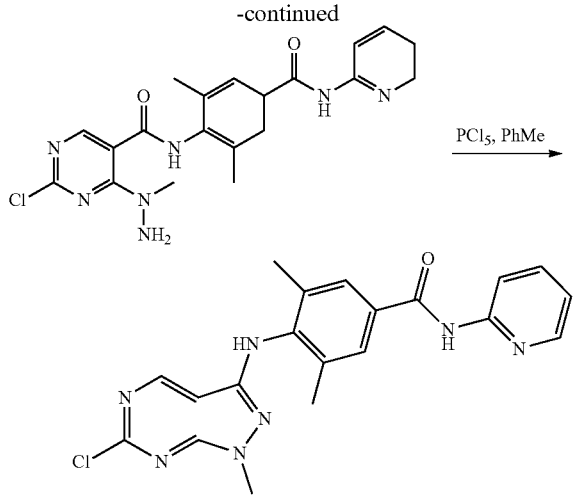

A target compound was prepared by the same manner as described in steps 2, 3, and 4 of Preparative Example B-1 except that 4-amino-3,5-dimenthyl-N-(pyridine-2-yl)benzamide in step 2 above was used instead of 2,6-dimethylaniline step 2 of Preparative Example B-1.

¹H NMR (300 MHz, CDCl₃) δ 8.69 (s, 1H), 8.40 (d, J=8.4 Hz, 1H), 8.34-8.29 (m, 1H) 8.02 (s, 1), 7.8-7.72 (m, 3H), 7.15-7.05 (m, 1H), 6.21 (s, 1H), 3.88 (s, 3H), 2.31 (s, 6H); LC/MS 407.8[M+H⁺]

Preparative Example B-13: Preparation of 6-chloro-N-(4-methoxy-2,6-dimethylphenyl)-1-methyl-1H-pyrazolo[3,4-d]pyrimidin-3-amine Step 1: Preparation of 4-methoxy-2,6-dimethylaniline

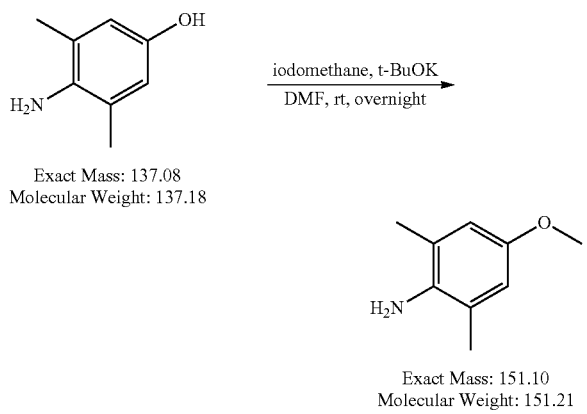

Iodomethane (0.41 mL, 6.63 mmol) was added to DMF (20 mL) solution containing 4-amino-3,5-dimethylphenol (1.00 g, 7.29 mmol) and t-BuOK (1.27 g, 11.3 mmol) at room temperature, followed by stirring at room temperature for 8 hours. The reaction was terminated with NaHCO₁ (aq), and the reaction mixture was washed with brine, followed by extraction with EtOAc (2×25 mL). The combined organic layer was dried over Na₂SO₄, and the solvent was eliminated under reduced pressure. The residue mixture was purified by silica gel column chromatography using EtOAc/Hex (3/7). As a result, the target compound (556 g, 3.68 mmol, 51%) was obtained as brown oil. ¹H NMR (300 MHz, chloroform) δ 6.54 (s, 2H), 3.71 (s, 3H) 3.27 (s, 2H) 2.15 (s, 6H).

Step 2: Preparation of 6-chloro-N-(4-methoxy-2,6-dimethylphenyl)-1-methyl-1H-pyrazolo[3,4-d]pyrimidine-3-amine

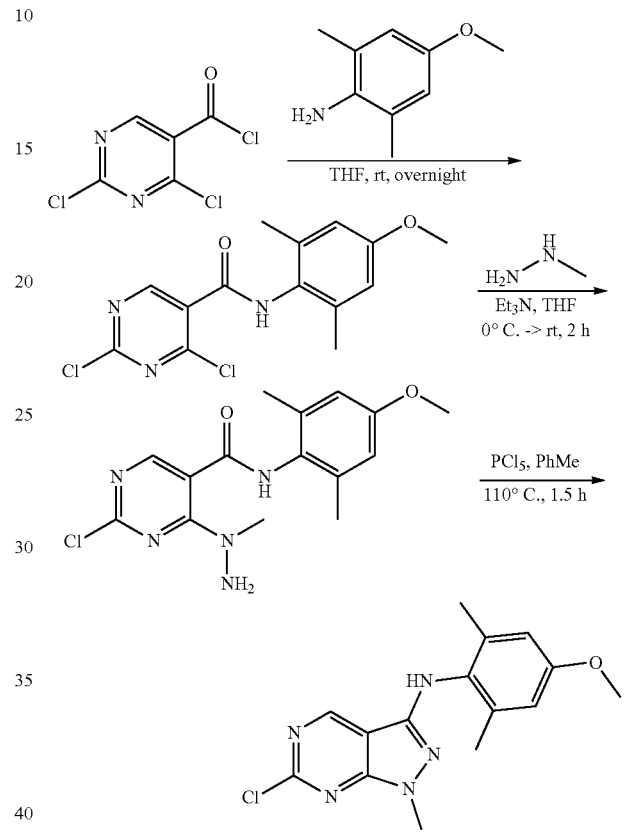

A target compound was prepared by the same manner as described in steps 2, 3, and 4 of Preparative Example B-1 except that 4-methoxy-2,6-dimethylaniline prepared in step 1 above was used instead of 2,6-dimethylaniline in step 2 of Preparative Example B-1.

1H NMR (300 MHz, CDCl₃) δ 7.49 (s, 1H), 6.70 (s, 2H), 5.95 (s, 1H), 3.87 (s, 3H), 3.81 (s, 3H), 2.21 (s, 6H), 317.9 [M+H⁺]

Preparative Example B-14: Preparation of 6-chloro-N-(2,6-diethylphenyl)-1-methyl-1H-pyrazolo[3,4-d]pyrimidine-3-amine

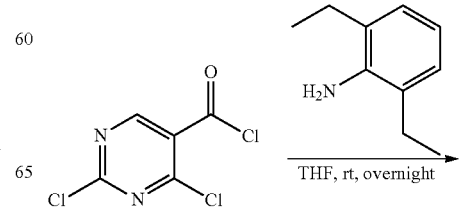

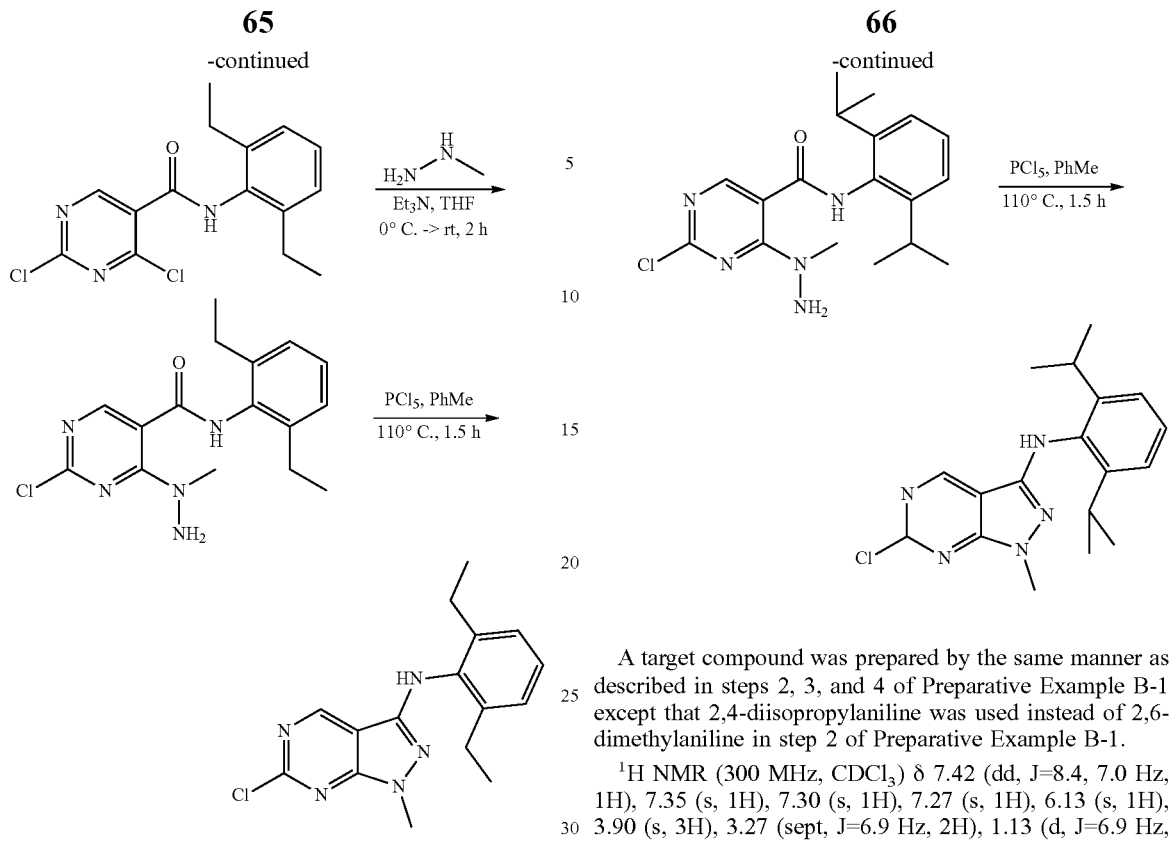

A target compound was prepared by the same manner as described in steps 2, 3, and 4 of Preparative Example B-1 except that 2,4-diethylaniline was used instead of 2,6-dimethylaniline in step 2 of Preparative Example B-1.

$^1$H NMR (300 MHz, CDCl$_3$) δ 7.42 (s, 1H), 7.34 (dd, J=8.5, 6.6 Hz, 1H), 7.23 (d, J=7.4 Hz, 2H), 6.06 (s, br, 1H), 3.90 (s, 3H), 2.63 (q, J=7.6 Hz, 4H), 1.15 (t, J=7.5 264 Hz, 6H); LC/MS 315.9 [M+H$^+$].

Preparative Example B-15: Preparation of 6-chloro-N-(2,6-diisopropylphenyl)-1-methyl-1H-pyrazolo[3,4-d]pyrimidine-3-amine

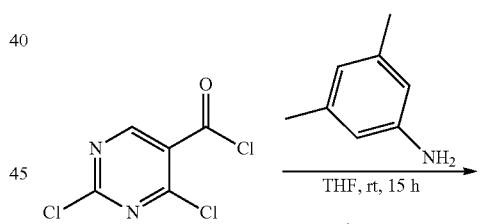

A target compound was prepared by the same manner as described in steps 2, 3, and 4 of Preparative Example B-1 except that 2,4-diisopropylaniline was used instead of 2,6-dimethylaniline in step 2 of Preparative Example B-1.

$^1$H NMR (300 MHz, CDCl$_3$) δ 7.42 (dd, J=8.4, 7.0 Hz, 1H), 7.35 (s, 1H), 7.30 (s, 1H), 7.27 (s, 1H), 6.13 (s, 1H), 3.90 (s, 3H), 3.27 (sept, J=6.9 Hz, 2H), 1.13 (d, J=6.9 Hz, 12H); LC/MS 343.9 [M+H$^+$].

Preparative Example B-16: Preparation of 6-chloro-N-(2-chloro-3,5-dimethylphenyl)-1-methyl-1H-pyrazolo[3,4-d]pyrimidine-3-amine

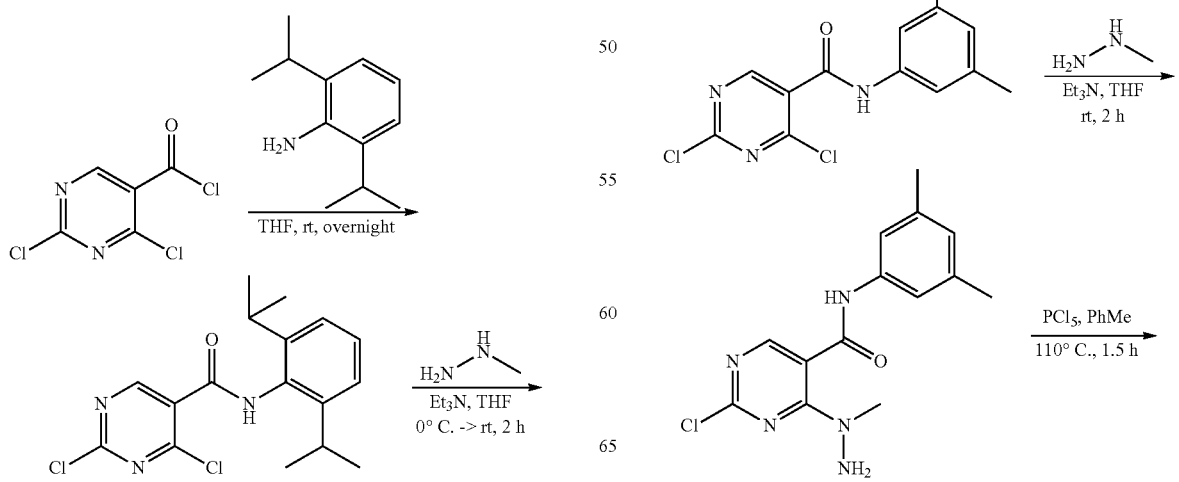

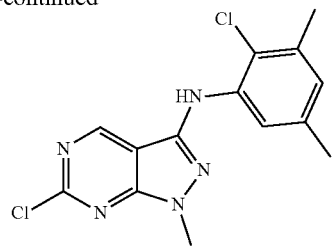

Step 1: Preparation of 2,4-dichloro-N-(3,5-dimethylphenyl)pyrimidine-5-carboxamide 3,5-Dimethyl aniline (143 mg, 1.18 mmol) was added to 2,4-dichloropyrimidine-5-carbonyl chloride (250 mg, 1.18 mmol) in THF (1.5 mL) at room temperature. The mixture was stirred at room temperature for 15 hours, followed by filtering. The filtrate was washed with water, 1.5 N HCl (15 mL), NaOH, and brine in that order. The combined organic layer was dried over sodium sulfate, and then concentrated under reduced pressure. The obtained crude product was recrystallized by using DCM. As a result, the target compound (251 mg, 0.847 mmol, 72%) was obtained as a white solid,
$^1$H NMR (300 MHz, CDCl$_3$) δ 9.03 (s, 1H), 7.99 (s, br, 1H), 7.24 (s, 2H), 6.88 (s, 1H), 2.34 (s, 6H); LC/MS 296.9 [M+H$^+$].

Step 2: Preparation of 2-chloro-N-(3,5-dimethylphenyl)-4-(1-methylhydrazinyl)pyrimidine-5-carboxamide Methyl hydrazine (26 mg, 0.557 mmol) and Et$_3$N (0.18 mL, 1.26 mmol) were added to THF (10 mL) solution containing the compound prepared in step 1 (150 mg, 0.506 mmol). The mixture was stirred at room temperature for 2 hours, which was concentrated to eliminate THF. The reaction mixture was washed with water, and the organic layer was dried over sodium sulfate, followed by concentration under reduced pressure. The obtained crude product was purified by silica gel column chromatography using EtOAc/Hx (1/4) as an eluent. As a result, 2-chloro-N-(3,5-dimethylphenyl)-4-(1-methylhydrazinyl)pyrimidine-5-carboxamide (124 mg, 0.405 mmol, 80%) was obtained as a white solid.
$^1$H NMR (300 MHz, CDCl$_3$) δ 8.10 (s, 1H), 7.82 (s, br, 1H), 7.26 (s, 2H), 6.83 (s, 1H), 4.09 (s, 2H), 3.43 (s, 3H), 2.34 (s, 6H); LC/MS 306.9 [M+H$^+$]1.

Step 3: Preparation of 6-chloro-N-(2-chloro-3,5-dimethylphenyl)-1-methyl-1H-pyrazolo[3,4-d]pyrimidine-3-amine PCl$_3$ (82 mg, 0.392 mmol) was added to 2-chloro-N-(3,5-dimethylphenyl)-4-(1-methylhydrazinyl)pyrimidine-5-carboxamide (120 mg, 0.392 mmol) in toluene (20 mL) at room temperature. The mixture was stirred at 110° C. for 2 hours, which was concentrated to eliminate toluene. The reaction mixture was washed with sodium bicarbonate, and the organic layer was dried over sodium sulfate, followed by concentration under reduced pressure. The obtained crude product was purified by silica gel column chromatography using EtOAc/Hx (1/4) as an eluent. As a result, 6-chloro-N-(2-chloro-3,5-dimethylphenyl)-1-methyl-1H-pyrazolo[3,4-d]pyrimidine-3-amine (40 mg, 0.124 mmol, 32%) was obtained as a yellow solid.
$^1$H NMR (300 MHz, CDCl$_3$) δ 8.83 (s, 1H), 7.72 (s, 1H), 7.02 (s, 1H), 6.78 (s, 1H), 4.01 (s, 3H), 2.41 (s, 3H), 2.34 (s, 3H); LC/MS 321.9 [M+H$^+$].

Preparative Example B-17: Preparation of 6-chloro-N-(2,4-dimethylphenyl)-1-methyl-1H-pyrazolo[3,4-d]pyrimidine-3-amine

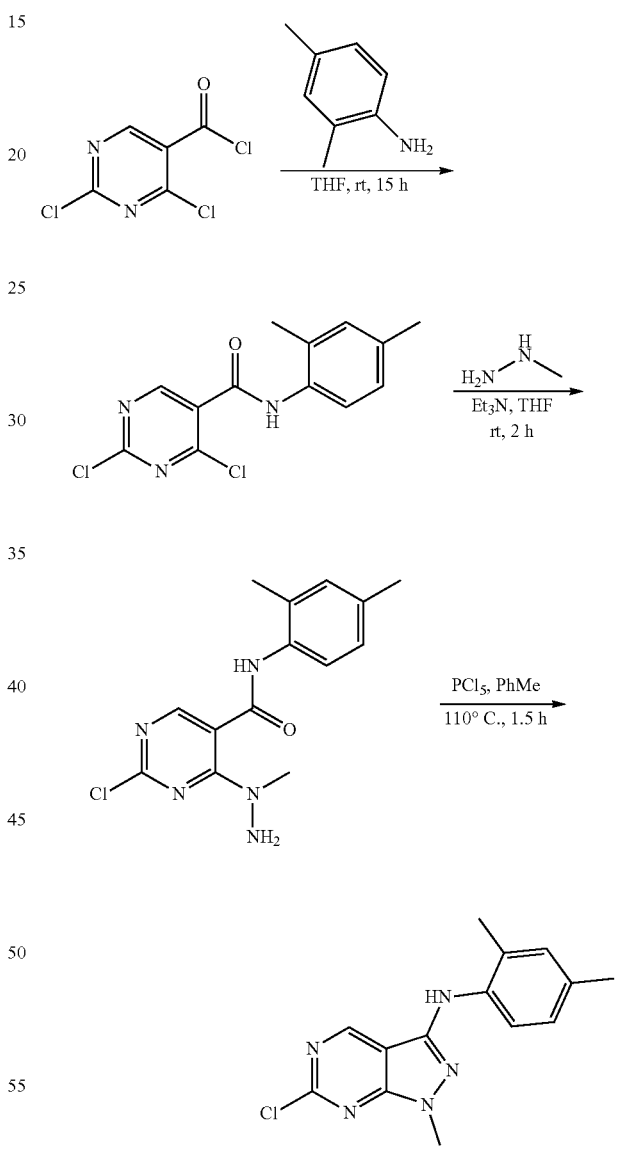

A target compound was prepared by the same manner as described in steps 2, 3, and 4 of Preparative Example B-1 except that 2,4-dimethylaniline was used instead of 2,6-dimethylaniline in step 2 of Preparative Example B-1.
$^1$H NMR (300 MHz, CDCl$_3$) δ 8.29 (s, 1H), 7.38 (d, J=8.1 Hz, 1H), 7.11 (s, 1H), 7.05 (d, J=8.2 Hz, 1H), 6.12 (s, br, 1H), 3.94 (s, 3H), 2.35 (s, 3H), 2.31 (s, 3H); LC/MS 287.9 [M+H$^+$].

Preparative Example B-18: Preparation of 6-chloro-1-methyl-N-(o-tolyl)-1H-pyrazolo[3,4-d]pyrimidine-3-amine

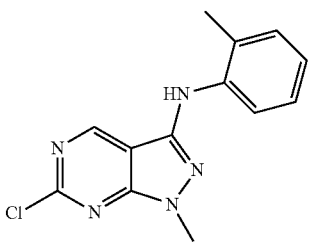 [SMILES: Cc1ccccc1Nc1nn(C)c2nc(Cl)ncc12]

A target compound was prepared by the same manner as described in steps 2, 3, and 4 of Preparative Example B-1 except that 2-methylaniline was used instead of 2,6-dimethylaniline in step 2 of Preparative Example B-1.

$^1$H NMR (300 MHz, CDCl$_3$) 8.47 (s, 1H), 7.56 (d, J=7.9 Hz, 1H), 7.28-7.20 (m, 2H), 7.09 (t, J=7.4 Hz, 1H), 6.22 (s, 1H), 3.96 (s, 3H), 2.37 (s, 3H); LC/MS 273.9 [M+H$^+$].

Preparative Example B-19: Preparation of 6-chloro-N-(3,5-dimethylphenyl)-1-methyl-1H-pyrazolo[3,4-d]pyrimidine-3-amine

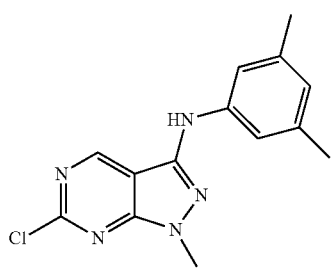 [SMILES: Cc1cc(C)cc(Nc2nn(C)c3nc(Cl)ncc23)c1]

A target compound was prepared by the same manner as described in steps 2, 3, and 4 of Preparative Example B-1 except that 3,5-dimethylaniline was used instead of 2,6-dimethylaniline in step 2 of Preparative Example B-1.

$^1$H NMR (300 MHz, CDCl$_3$) 8.72 (s, 1H), 7.05 (s, 2H), 6.74 (s, 1H), 6.39 (s, 1H), 3.98 (s, 3H), 2.34 (s, 6H); LC/MS 287.9 [M+H$^+$].

Preparative Example B-20: Preparation of 6-chloro-N-(2,6-difluorophenyl)-1-methyl-1H-pyrazolo[3,4-d]pyrimidine-3-amine

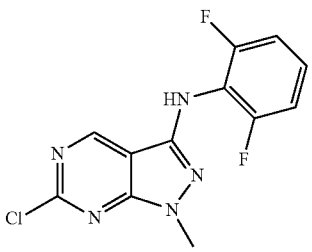 [SMILES: Cn1nc(Nc2c(F)cccc2F)c2cnc(Cl)nc21]

A target compound was prepared by the same manner as described in steps 2, 3, and 4 of Preparative Example B-1 except that 2,6-difluoroaniline was used instead of 2,6-dimethylaniline in step 2 of Preparative Example B-1.

$^1$H NMR (300 MHz, CDCl$_3$) δ 8.21 (s, 1H), 7.37 (s, 1H), 7.327.20 (n, 1H), 6.99 (t, J=8.2 Hz, 2H), 4.11 (s, 2H), 3.42 (s, 3H), 313.8 [M+H$^+$]

Preparative Example B-21: Preparation of 6-chloro-N-(2,6-dimethoxyphenyl)-1-methyl-1H-pyrazolo[3,4-d]pyrimidine-3-amine

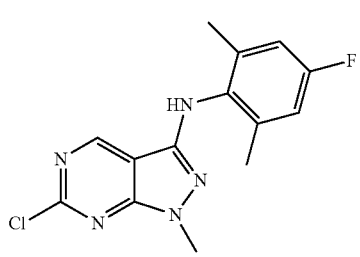 [SMILES: Cc1cc(F)cc(C)c1Nc1nn(C)c2nc(Cl)ncc12]

A target compound was prepared by the same manner as described in steps 2, 3, and 4 of Preparative Example B-1 except that 2,6-dimethoxyaniline was used instead of 2,6-dimethylaniline in step 2 of Preparative Example B-1.

$^1$H NMR (300 MHz, CDCl$_3$) δ 8.13 (s, 1H), 7.18 (t, J=8.4 Hz, 1H), 6.66 (d, J=8.4 Hz, 2H), 6.28 (s, 1H), 3.89 (s, 3H), 3.79 (s, 6H), 335.9 [M+H$^+$]

Preparative Example B-22: Preparation of 6-chloro-N-(4-fluoro-2,6-dimethylphenyl)-1-methyl-1H-pyrazolo[3,4-d]pyrimidine-3-amine A target compound was prepared by the same manner as described in steps 2, 3, and 4 of Preparative Example B-1 except that 2,5-dimethyl-4-fluoroaniline was used instead of 2,6-dimethylaniline in step 2 of Preparative Example B-1.

$^1$H NMR (300 MHz, CDCl$_3$) δ 7.64 (s, 1H), 6.89 (d, J=8.9 Hz, 2H), 5.94 (s, 1H), 3.88 (d, J=0.7 Hz, 3H), 2.24 (s, 6H), 305.9 [M+H$^+$]

Preparative Example B-23: Preparation of 6-chloro-N-(2,5-dimethylphenyl)-1-methyl-1H-pyrazolo[3,4-d]pyrimidine-3-amine

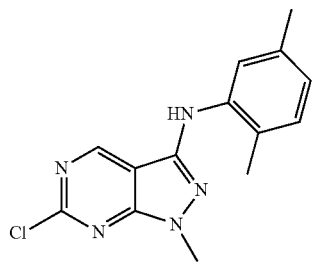 [SMILES: Cc1ccc(C)c(Nc2nn(C)c3nc(Cl)ncc23)c1]

A target compound was prepared by the same manner as described in steps 2, 3, and 4 of Preparative Example B-1 except that 2,5-dimethylaniline was used instead of 2,6-dimethylaniline in step 2 of Preparative Example B-1.

$^1$H NMR (300 MHz, CDCl$_3$) δ 8.41 (s, 1H), 7.31 (s, 1H), 7.14 (d, J=7.6 Hz, 1H), 6.89 (d, J=7.6 Hz, 1H), 6.16 (s, 1H), 3.94 (s, 3H), 2.30 (s, 3H), 2.29 (s, 3H), 287.9 [M+H$^+$]

Preparative Example B-24: Preparation of 6-chloro-N-(2-chloro-6-methylphenyl)-1-methyl-1H-pyrazolo[3,4-d]pyrimidine-3-amine

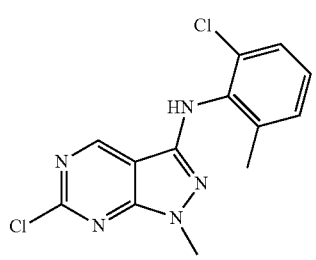 [SMILES: Cc1cccc(Cl)c1Nc1nn(C)c2nc(Cl)ncc12]

A target compound was prepared by the same manner as described in steps 2, 3, and 4 of Preparative Example B-1 except that 2-chloro-6-methylaniline was used instead of 2,6-dimethylaniline in step 2 of Preparative Example B-1.

$^1$H NMR (300 MHz, CDCl$_3$) δ 8.00 (s, 1H), 7.39 (dd, J=7.3, 2.2 Hz, H), 7.27 7.17 (m, 2H), 6.26 (s, 1H), 3.92 (s, 3H), 2.30 (s, 3H); LC/MS 308.9 [M+H$^+$].

Preparative Example B-25: Preparation of 6-chloro-N-(5-(2-methoxyethoxy)-2-methylphenyl)-1-methyl-1H-pyrazolo[3,4-d]pyrimidine-3-amine Step 1: Preparation of 3-amino-4-methylphenol

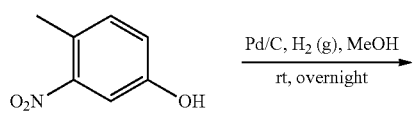

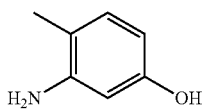

Exact Mass: 123.07
Molecular Weight: 123.16

10% Pd/C (100 mg) was added to 4-methyl-3-nitrophenol (1.00 g, 6.53 mmol) methanol (100 mL) solution. The mixture was stirred at room temperature under hydrogen balloon pressure overnight. The reaction mixture was filtered with celite, and MeOH was eliminated. As a result, 3-amino-4-methylphenol (750 mg, 6.09 mmol, 93%) was obtained as a light brown solid.

$^1$H NMR (300 MHz, CDCl$_3$) δ 6.87 (d, J=8.1 Hz, 1H), 6.276.15 (m 2H), 4.70 (s, 1H), 3.89 (s, 2H), 2.08 (s, 3H).

Step 2: Preparation of 5-(2-methoxyethoxy)-2-methylaniline

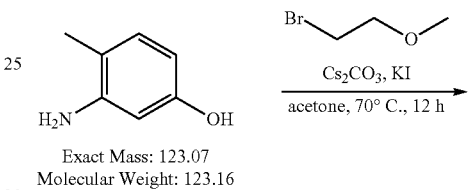

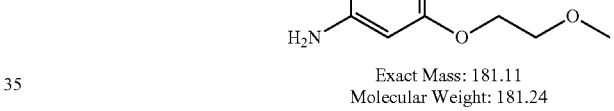

Exact Mass: 181.11
Molecular Weight: 181.24

Cs$_2$CO$_3$ (1.98 g, 6.09 mmol) and KI (40 mg, 0.244 mmol) were added to 3-amino-4-methylphenol (500 mg, 4.06 mmol) acetone (20 mL) solution. The mixture was stirred at 70° C. overnight. The reaction was terminated with water, followed by extraction with EtOAc (2×25 mL). The residue mixture was purified by silica gel column chromatography using EtOAc/Hex (3/7) as an eluent. As a result, 5-(2-methoxyethoxy)-2-methylaniline (600 mg, 3.31 mmol, 82%) was obtained as yellow oil.

$^1$H NMR (300 MHz, CDCl$_3$) δ 6.946.89 (m, 1H), 6.326.24 (m, 2H), 4.084.02 (m, 2H), 3.743.68 (m, 2H), 3.60 (s, 2H), 3.43 (s, 3H), 2.08 (s, 3H), 182.0 [M+H$^+$]

Step 3: Preparation of 6-chloro-N-(5-(2-methoxyethoxy)-2-methylphenyl)-1-methyl-1H-pyrazolo[3,4-d]pyrimidine-3-amine

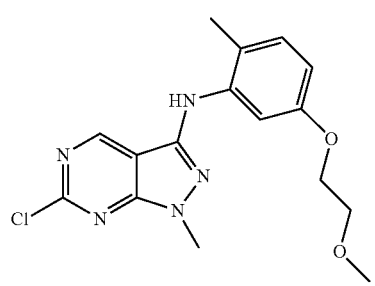 [SMILES: COCCOc1ccc(C)c(Nc2nn(C)c3nc(Cl)ncc23)c1]

A target compound was prepared by the same manner as described in steps 2, 3, and 4 of Preparative Example B-1 except that 5-(2-methoxyethoxy)-2-methylaniline prepared in step 2 above was used instead of 2,6-dimethylaniline in step 2 of Preparative Example B-1.

$^1$H NMR (300 MHz, CDCl$_3$) δ 8.56 (s, 1H), 7.25-7.20 (m, 1H), 7.12 (d, J=8.3 Hz, 1H), 6.62 (dd, J=8.3, 2.6 Hz, 1H), 6.19 (s, 1H), 4.09-4.02 (m, 2H), 3.95 (s, 3H), 3.75-3.69 (m, 2H), 3.43 (s, 3H), 2.26 (s, 3H), 347.9 [M+H$^+$]

Preparative Example B-26: Preparation of N-(3-((6-chloro-1-methyl-1H-pyrazolo[3,4-d]pyrimidine-3-yl)amino)-4-methylphenyl)picolineamide Step 1: Preparation of 6-chloro-1-methyl-N-(2-methyl-5-nitrophenyl)-1H-pyrazolo[3,4-d]pyrimidine-3-amine

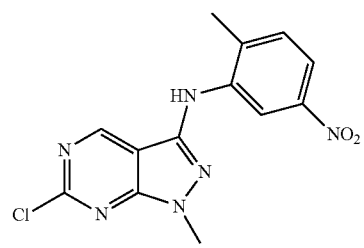 [SMILES: Cc1ccc([N+](=O)[O-])cc1Nc1nn(C)c2nc(Cl)ncc12]

A target compound was prepared by the same manner as described in steps 2, 3, and 4 of Preparative Example B-1 except that 2-methyl-5-nitroanilyl was used instead of 2,6-dimethylaniline in step 2 of Preparative Example B-1.

$^1$H NMR (300 MHz, DMSO-d$_6$) δ 9.34 (s, 1H), 8.99 (d, J=2.4 Hz, 1H), 8.89 (s, 1H), 7.80 (dd, J=8.3, 2.5 Hz, 1H), 7.50 (d, J=8.3 Hz, 1H), 3.89 (s, 3H), 318.9 [M+H$^+$]

Step 2: Preparation of N1-(6-chloro-1-methyl-1H-pyrazolo[3,4-d]pyrimidine-3-yl)-6-methylbenzene-1,3-diamine

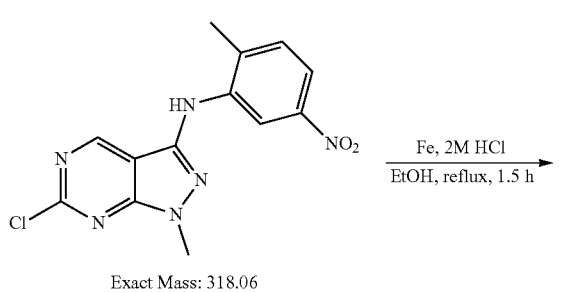

Exact Mass: 318.06
Molecular Weight: 318.72

Exact Mass: 288.09
Molecular Weight: 288.74

Fe (150 mg) and 2 M HCl (2 mL) were added to EtOH (2 mL) solution containing the compound prepared in step 1 above (100 mg, 0.314 mmol) at room temperature. The reaction mixture was stirred at 70° C. for 1.5 hour. The reaction was terminated with NaHCO$_3$ (aq), followed by extraction with EtOAc (2×25 mL). The combined organic layer was dried over Na$_2$SO$_4$ and the solvent was eliminated under reduced pressure. The residue mixture was purified by silica gel column chromatography using DCM/MeOH (9/1) as an eluent. As a result, the target compound (40 mg, 0.14 mmol, 44%) was obtained as a yellow solid.

$^1$H NMR (300 MHz, CDCl$_3$) δ 8.54 (s, 1H), 7.00 (d, J=8.0 Hz, 1H), 6.96 (d, J=2.3 Hz, 1H), 6.40 (dd, J=8.1, 2.4 Hz, 1H), 6.19 (s, 1H), 3.94 (s, 3H), 3.63 (s, 2H), 2.22 (s, 3H), 290.0 [M+H$^+$]

Step 3: Preparation of N-(3-((6-chloro-1-methyl-1H-pyrazolo[3,4-d]pyrimidine-3-yl)amino)-4-methylphenyl)picolineamide

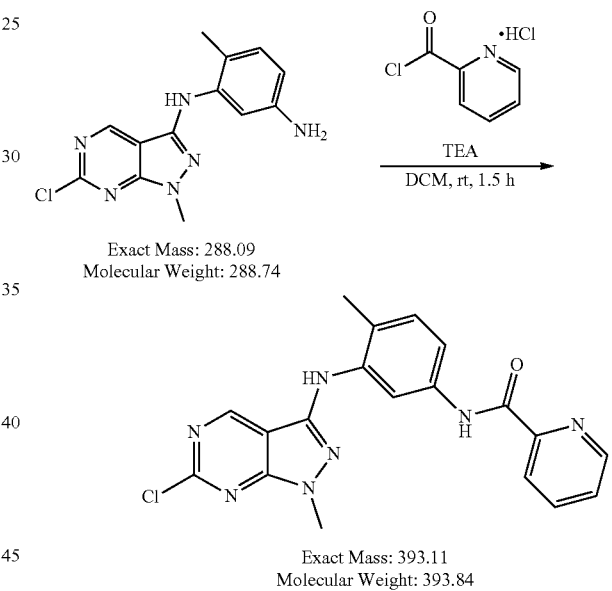

Exact Mass: 288.09
Molecular Weight: 288.74

Exact Mass: 393.11
Molecular Weight: 393.84

Pyridine-2-carbonylchloride hydrochloride (25 mg, 0.314 mmol) and TEA (0.04 mL, 0.268 mmol) were added to DCM (2 mL) solution containing the compound prepared in step 2 above (40 mg, 0.134 mmol) at room temperature. The reaction mixture was stirred at room temperature for 1.5 hour. The reaction was terminated with 1 M HCl (aq), followed by extraction with EtOAc (2×25 mL). The combined organic layer was dried over Na$_2$SO$_4$ and the solvent was eliminated under reduced pressure. The residue mixture was purified by silica gel column chromatography using EtOAc/Hex (5/5) as an eluent. As a result, the target compound (48 mg, 0.12 mmol, 87%) was obtained as a yellow solid.

$^1$H NMR (300 MHz, DMSO-d$_6$) δ 10.52 (s, 1H), 9.11 (s, 1H), 8.74 (d, J=4.7 Hz, 1H), 8.24 (d, J=2.1 Hz, 1H), 8.15 (d, J=7.8 Hz, 1H), 8.11-8.05 (m, 1H), 7.72-7.65 (m, 1H), 7.52 (dd, J=8.1, 2.2 Hz, 1H), 7.21 (d, J=8.2 Hz, 1H), 3.69 (s, 3H), 2.29 (s, 3H), 393.9 [M+H$^+$]

Preparative Example B-27: Preparation of 3-((6-chloro-1-methyl-1H-pyrazolo[3,4-d]pyrimidine-3-yl)amino)-4-methyl-N-(3-(trifluoromethyl)phenyl)benzamide

Step 1: Preparation of N-(4-methyl-3-nitrophenyl)-3-(trifluoromethyl)benzamide

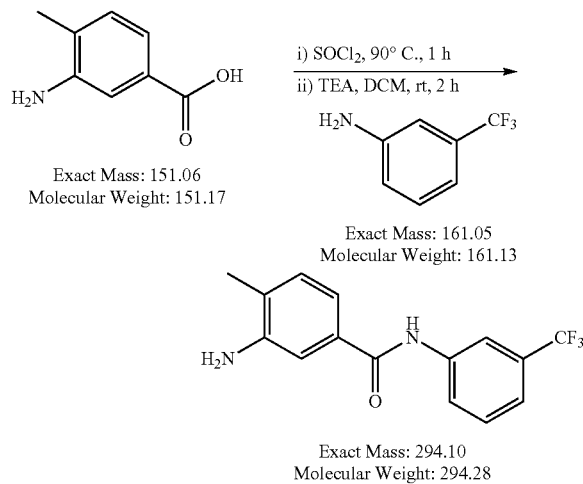

SOCl$_2$ (5 mL) was added to 3-amino-4-methylbenzoic acid (500 mg, 3.31 mmol) solution at room temperature, followed by stirring at 90° C. for 1 hour. The reaction mixture was concentrated to eliminate SOCl$_2$. 3-(Trifluoromethyl) aniline (799 mg, 4.96 mmol) DCM (10 mL) solution and TEA (0.92 mL, 6.62 mmol) were added thereto, followed by stirring at room temperature for 2 hours. The reaction was terminated with water, followed by extraction with DCM (2×25 mL). The combined organic layer was dried over NaSO$_4$ and the solvent was eliminated under reduced pressure. The mixture was concentrated and slurried with DCM (30 mL). The precipitated solid was filtered and washed with DCM (2×20 mL). The filtrate was dried under reduced pressure. As a result, the target compound (480 mg, 1.63 mmol, 49%) was obtained as an ivory solid.

$^1$H NMR (300 MHz, DMSO-d$_6$) δ 10.3 (s, 1H), 8.25 (s, 1H), 8.05 (d, J=8.0 Hz, 1H), 7.58 (t, J=8.0 Hz, 1H), 7.42 (d, J=7.8 Hz, H), 7.18 (s, 1H), 7.147.03 (m, 2H), 5.12 (s, 2H), 2.13 (s, 3H), 295.0 [M+H$^+$]

Step 2: Preparation of 3-((6-chloro-1-methyl-1H-pyrazolo[3,4-d]pyrimidine-3-yl)amino)-4-methyl-N-(3-(trifluoromethyl)phenyl)benzamide

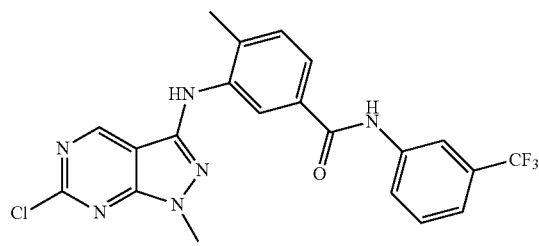 [SMILES: Cc1ccc(C(=O)Nc2cccc(C(F)(F)F)c2)cc1Nc1nn(C)c2nc(Cl)ncc12]

A target compound was prepared by the same manner as described in steps 2, 3, and 4 of Preparative Example B-1 except that N-(4-methyl-3-nitrophenyl)-3-(trifluoromethyl)benzamide prepared in step 1 above was used instead of 2,6-dimethylaniline in step 2 of Preparative Example B-1.

$^1$H NMR (300 MHz, chloroform-d) δ 8.69 (s, 1H), 8.31 (s, 1H), 7.95 (d, J=15.2 Hz, 2H), 7.85 (d, J=8.2 Hz, 1H), 7.557.30 (m, 4H), 6.35 (s, 1H), 3.97 (s, 3H), 2.43 (s, 3H), 460.9[M+H$^+$]

Preparative Example B-28: Preparation of 1-(3-((6-chloro-1-methyl-1H-pyrazolo[3,4-d]pyrimidine-3-yl)amino)-4-methylphenyl)-3-(3-(trifluoromethyl)phenyl) urea

Step 1: Preparation of N$^1$-(6-chloro-1-methyl-1H-pyrazolo[3,4-d]pyrimidine-3-yl)-6-methylbenzene-1,3-diamine

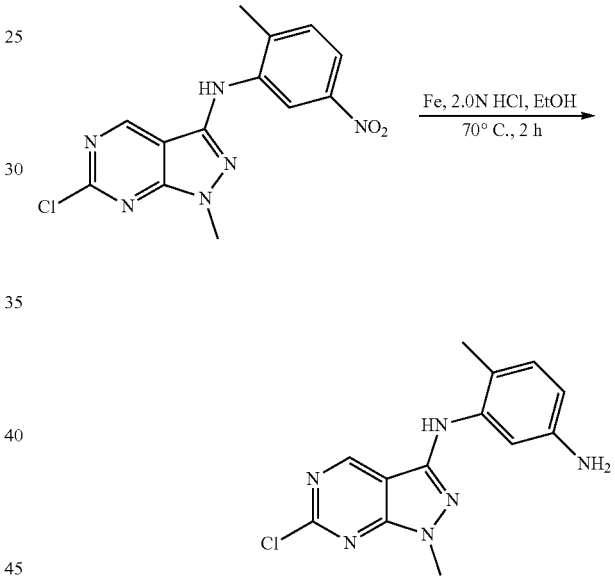

2.0 N HCl (5.0 mL) and Fe powder (150 mg) were added to 6-chloro-1-methyl-N-(2-methyl-5-nitrophenyl)-1H-pyrazolo[3,4-d]pyrimidine-3-amine (100 mg, 0.313 mmol) EtOH (5.0 mL) solution at room temperature, followed by stirring at 70° C. for 2 hours. TLC analysis indicated the complete consumption of the starting material. The reaction mixture was concentrated to eliminate ethanol. Sat. NaHCO$_3$ solution (15 mL) was added thereto, followed by extraction with EtOAc (15 mL×2). The combined organic layer was concentrated under reduced pressure. The obtained crude product was purified by column chromatography (EtOAc/Hexane (1:1)). As a result, N$^1$-(6-chloro-1-methyl-1H-pyrazolo[3,4-d]pyrimidine-3-yl)-6-methylbenzene-1,3-diamine (60 mg, 0.207 mmol, 66%) was obtained as a yellow solid.

$^1$H NMR (300 MHz, CDCl$_3$) 8.57 (s, 1H), 7.03 (d, J=8.0 Hz, 1H), 6.98 (d, J=2.4 Hz, 1H), 6.43 (dd, J=8.0, 2.3 Hz, 1H), 6.17 (s, 1H), 3.97 (s, 3H), 3.63 (s, 2H), 2.24 (s, 3H); LC/MS 289.2 [M+H$^+$].

Step 2: Preparation of 1-(3-((6-chloro-1-methyl-1H-pyrazolo[3,4-d]pyrimidine-3-yl)amino)-4-methylphenyl)-3-(3-(trifluoromethyl)phenyl) urea

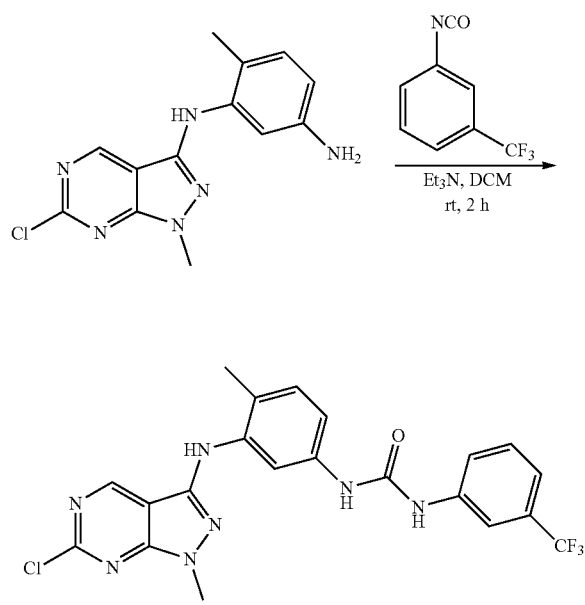

1-Isocyanato-3-(trifluoromethyl)benzene (21 mg, 0.113 mmol) was added to N1-(6-chloro-1-methyl-1H-pyrazolo[3,4-d]pyrimidine-3-yl)-6-methylbenzene-1,3-diamine (30 mg, 0.103 mmol) DCM (10 mL) solution at 0° C., to which Et₃N (20 mg, 0.206 mmol) was added, followed by stirring for 2 hours. TLC analysis indicated the complete consumption of the starting material. The reaction mixture was quenched with water, followed by extraction with DCM (25 mL×2). The organic layer was washed with saturated brine solution. The combined organic layer was concentrated under reduced pressure. The obtained crude product was purified by column chromatography (EtOAc/Hexane (1:1)). As a result, 1-(3-((6-chloro-1-methyl-1H-pyrazolo[3,4-d]pyrimidine-3-yl)amino)-4-methylphenyl)-3-(3-(trifluoromethyl)phenyl) urea (30 mg, 0.063 mmol, 61%) was obtained as a yellow solid.

$^1$H NMR (300 MHz, CD$_6$OD) δ 8.88 (s, 1H), 7.82 (s, 1H), 7.71 (s, 1H), 7.57 (d, J=8.4 Hz, 1H), 7.42 (t, J=7.8 Hz, 1H), 7.25 (d, J=8.1 Hz, 1H), 1H), 7.17 (d, J=7.8 Hz, 1H), 7.13 (d, J=7.8 Hz, 1H), 3.88 (s, 3H), 2.31 (s, 3H); LC/MS 475.2 [M+H$^+$].

Example 1: Preparation of 1-(7-(3-(2,6-dimethylphenylamino)-1-methyl-1H-pyrazolo[3,4-d]pyrimidine-6-ylamino)-3,4-dihydroisoquinoline-2(1H)-yl)ethaneone

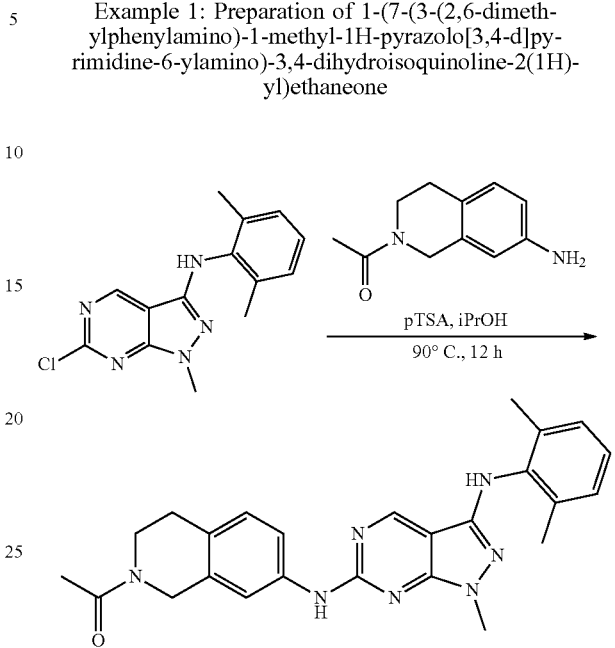

The compound prepared in Preparative Example A-1 (29.7 mg, 0.156 mmol) and pTSA.H₂O (33 mg, 0.173 mmol) were added to IPA (2.0 mL) solution containing the compound prepared in Preparative Example B-1 (50 mg, 0.173 mmol) at room temperature, followed by stirring at 90° C. for 12 hours. TLC analysis indicated the complete consumption of the staling material. The solid obtained from the reaction mixture was filtered and washed with ethanol (2 mL). The filtered solid was dissolved in EtOAc (15 mL) and washed with saturated NaHCO₃ solution. The combined organic layer was concentrated under reduced pressure. The obtained crude product was purified by column chromatography using MeOH/DCM (1/4) as an eluent. As a result, 1-(7-(3-(2,6-dimethylphenylamino)-1-methyl-1H-pyrazolo[3,4-d]pyrimidine-6-ylamino)-3,4-dihydroisoquinoline-2(1H)-yl)ethaneone (60 mg, 0.135 mmol, 78%) was obtained as a grey-white solid.

Example 2: Preparation of N³-(2,6-dimethylphenyl)-1-methyl-N⁶-(1,2,3,4-tetrahydroisoquinoline-7-yl)-1H-pyrazolo[3,4-d]pyrimidine-3,6-diamine

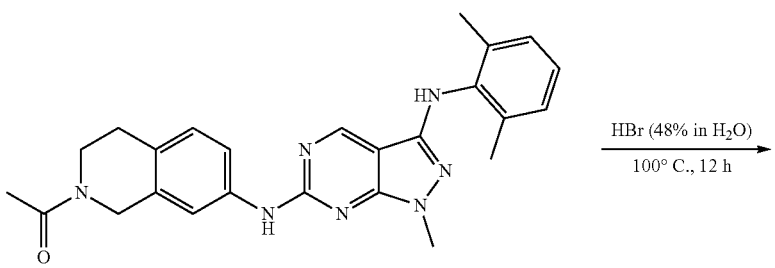

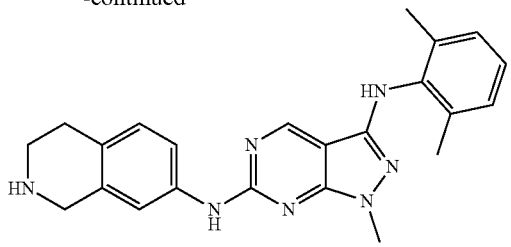

HBr (48% in H₂O) (10 mL) was added to the compound of Example 1 (45 mg, 0.101 mmol) at room temperature. The mixture was heated to reflux at 100° C. for 12 hours. TLC analysis indicated the complete consumption of the starting material. Saturated NaHCO₃ solution was added to the reaction mixture which was extracted with EtOAc. The combined organic layer was concentrated under reduced pressure. The obtained crude product was purified by column chromatography using MeOH/DCM (1/4) as an eluent. As a result, N3-(2,6-dimethylphenyl)-1-methyl-N6-(1,2,3,4-tetrahydroisoquinoline-7-yl)-1H-pyrazolo[3,4-d]pyrimidin-3,6-diamine (20 mg, 0.050 mmol, 50%) was obtained as a grey-white solid.

Example 3: Preparation of 1-(6-(3-(2,6-dimethylphenylamino)-1-methyl-1H-pyrazolo[3,4-d]pyrimidine-6-ylamino)-7-methoxy-3,4-dihydroisoquinoline-2(1H)-yl)-2,2,2-trifluoroethanone

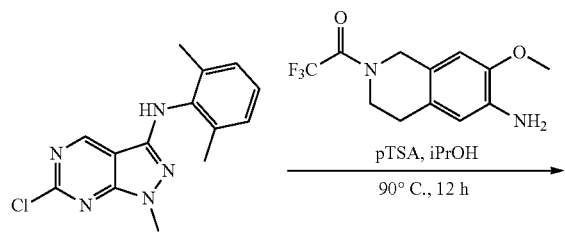

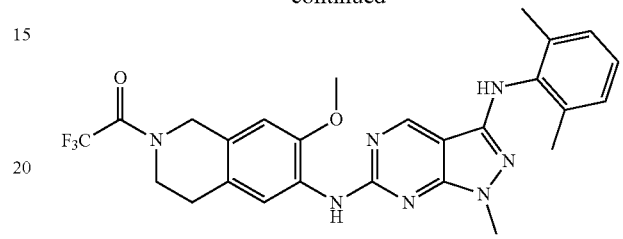

1-(6-amino-7-methoxy-3,4 dihydroisoquinoline-2(1H)-yl)-2,2,2-trifluoroethane-1-one (17 mg, 0.062 mmol) and pTSA.H₂O (13 mg, 0.069 mmol) were added to IPA (2.0 mL) solution containing the compound prepared in Preparative Example B-1 (6-CHLORO-N-(2,6-DIMETHYLPHENYL)-1-METHYL-1H-PYRAZOLO[3,4-D]PYRIMIDINE-3-AMINE, 20 mg, 0.069 mmol) at room temperature, followed by stirring at 90° C. for 12 hours. TLC analysis indicated the complete consumption of the starting material. The solid obtained from the reaction mixture was filtered and washed with ethanol (2 mL). The filtered solid was dissolved in EtOAc (15 mL) and washed with saturated NaHCO₃ solution. The combined organic layer was concentrated under reduced pressure. The obtained crude product was purified by column chromatography using EtOAc/hexane (1/1) as an eluent. As a result, 1-(6-(3-(2,6-dimethylphenylamino)-1-methyl-1H-pyrazolo[3,4-d]pyrimidine-6-ylamino)-7-methoxy-3,4-dihydroisoquinoline-2(1H)-yl)-2,2,2-trifluoroethaneone (28 mg, 0.053 mmol, 77%) was obtained as a grey-white solid.

Example 4: Preparation of N¹-(2,6-dimethylphenyl)-N⁶-(7-methoxy-1,2,3,4-tetrahydroisoquinoline-6-yl)-1-methyl-1H-pyrazolo[3,4-d]pyrimidine-3,6-diamine

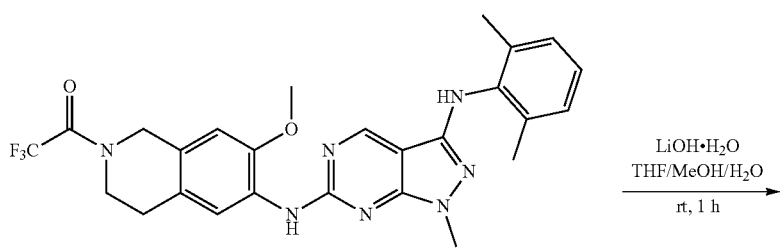

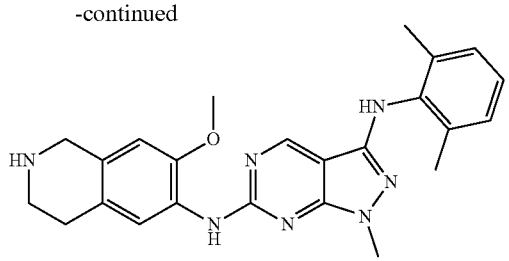

Lithium hydroxide monohydrate (2.5 mg, 0.057 mmol) was added to THF (1.0 mL), MeOH (0.5 mL), and H$_2$O (0.5 mL) containing the compound of Example 3 (1-(6-(3-(2,6-dimethylphenylamino)-1-methyl-1H-pyrazolo[3,4-d]pyrimidine-6-ylamino)-7-methoxy-3,4-dihydroisoquinoline-2(1H)-yl)-2,2,2-trifluoroethaneone, 15 mg, 0.028 mmol) at room temperature, followed by stirring at room temperature for 1 hour. TLC analysis indicated the complete consumption of the starting material. The reaction mixture was concentrated to eliminate THF and methanol. Water (5.0 mL) was added thereto, followed by extraction with EtOAc (15 mLX2). The combined organic layer was concentrated under reduced pressure. The obtained crude product was purified by column chromatography using MeOH/DCM (1:9) as an eluent. As a result, N3-(2,6-dimethylphenyl)-N6-(7-methoxy-1,2,3,4-tetrahydroisoquinoline-6-yl)-1-methyl-1H-pyrazolo[3,4-d]pyrimidine-3,6-diamine (10 mg, 0.023 mmol, 83%) was obtained as a grey-white solid.

Example 5: Preparation of 1-(6-(3-(2,6-dimethylphenylamino)-1-methyl-1H-pyrazolo[3,4-d]pyrimidine-6-ylamino)-7-methoxy-3,4-dihydroisoquinoline-2(1H)-yl)ethaneone

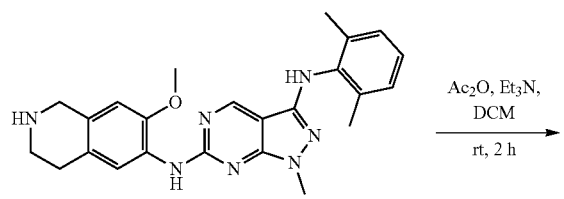

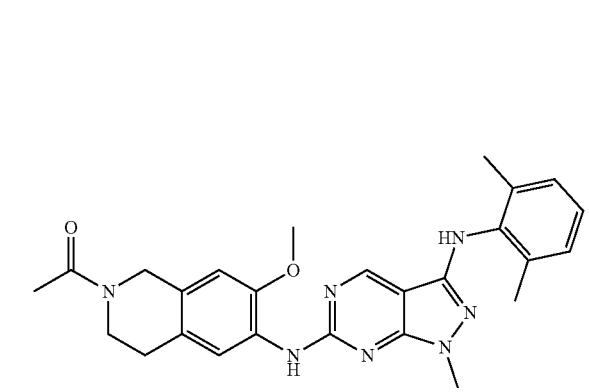

Acetic anhydride (8.5 mg, 0.084 mmol) and Et$_3$N (17.6 mg, 0.175 mmol) were added to DCM (10 mL) solution containing the compound of Example 4 (30 mg, 0.070 mmol) at 0° C., followed by stirring at room temperature for 2 hours. TLC analysis indicated the complete consumption of the starting material. Water was added thereto, followed by extraction with DCM (15 mL). The mixture was washed with saturated NaHCO$_3$ solution. The combined organic layer was concentrated under reduced pressure. The obtained crude product was purified by column chromatography using MeOH/DCM (1/4) as an eluent. As a result, 1-(6-(3-(2,6-dimethylphenylamino)-1-methyl-1H-pyrazolo[3,4-d]pyrimidine-6-ylamino)-7-methoxy-3,4-dihydroisoquinoline-2(1H)-yl)ethaneone (28 mg, 0.059 mmol, 85%) was obtained as a grey-white solid.

Example 6: Preparation of 1-(6-(3-(2,6-dimethylphenylamino)-1-methyl-1H-pyrazolo[3,4-d]pyrimidine-6-ylamino)-3,4-dihydroisoquinoline-2(1H)-yl)-2,2,2-trifluoroethaneone

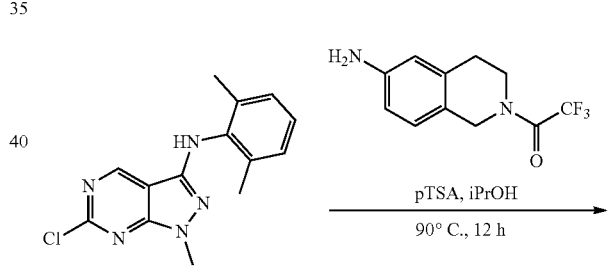

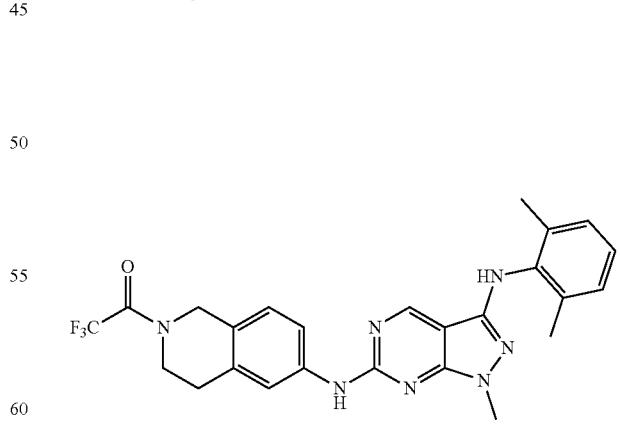

A target compound was prepared by the same manner as described in Example 3 except that the compound prepared in Preparative Example A-2 was used instead of 1-(6-amino-7-methoxy-3,4 dihydroisoquinoline-2(1H)-yl)-2,2,2-trifluoroethane-1-one in Example 3.

Example 7: Preparation of N³-(2,6-dimethylphenyl)-1-methyl-N⁶-(1,2,3,4-tetrahydroisoquinoline-6-yl)-1H-pyrazolo[3,4-d]pyrimidine-3,6-diamine

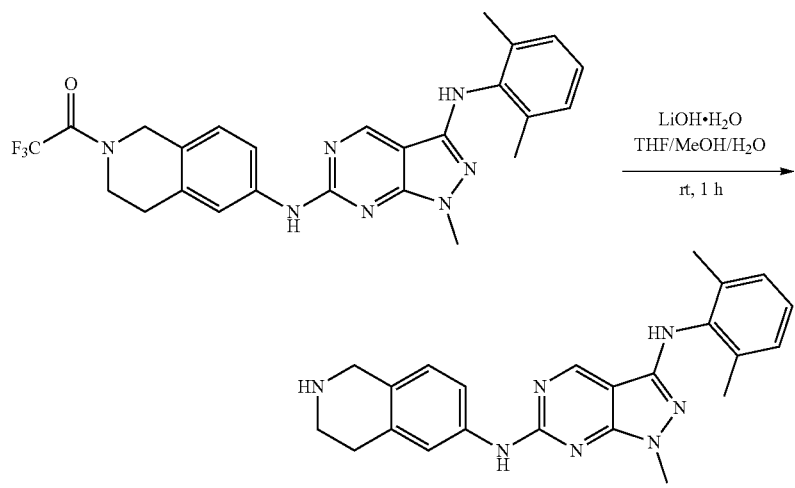

A target compound was prepared by the same manner as described in Example 4 except that the compound of Example 6 was used instead of the compound of Example 3 in Example 4.

Example 8: Preparation of 1-(6-(3-(2,6-dimethylphenylamino)-1-methyl-1H-pyrazolo[3,4-d]pyrimidine-6-ylamino)-3,4-dihydroisoquinoline-2(1H)-yl)ethaneone

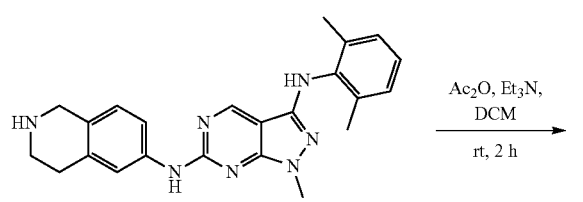

A target compound was prepared by the same manner as described in Example 5 except that the compound of Example 7 was used instead of the compound of Example 4 in Example 5.

Example 9: Preparation of 2,2,2-trifluoro-1-(7-(1-methyl-3-(phenylamino)-1H-pyrazolo[3,4-d]pyrimidine-6-ylamino)-3,4-dihydroisoquinoline-2(1H)-yl) ethaneone

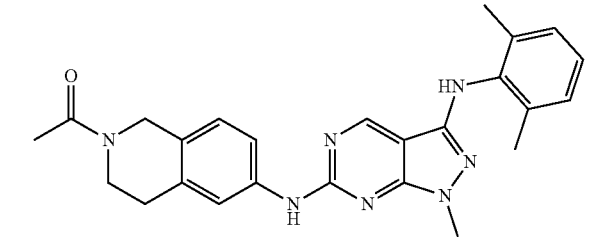

A target compound was prepared by the same manner as described in Example 3 except that the compound prepared in Preparative Example A-3 was used instead of 1-(6-amino-7-methoxy-3,4 dihydroisoquinoline-2(1H)-yl)-2,2,2-trifluoroethane-1-one and the compound prepared in Preparative Example B-2 was used instead of the compound prepared in Preparative Example B-1 in Example 3

Example 10: Preparation of 1-methyl-N³-phenyl-N⁶-(1,2,3,4-tetrahydroisoquinoline-7-yl)-1H-pyrazolo[3,4-d]pyrimidine-3,6-diamine

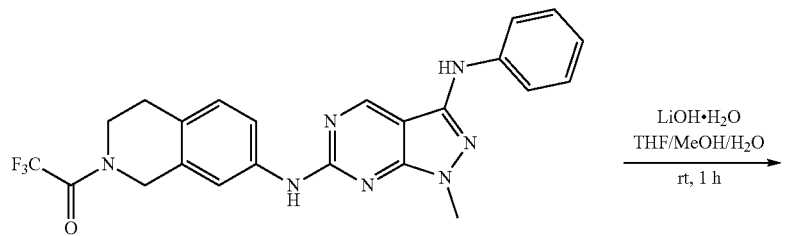

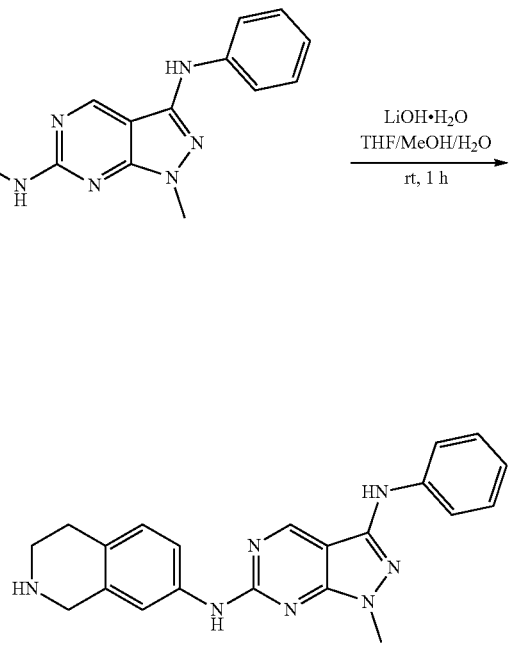

A target compound was prepared by the same manner as described in Example 4 except that the compound of Example 9 was used instead of the compound of Example 3 in Example 4.

Example 11: Preparation of 1-(7-(3-(2,6-dichlorophenylamino)-1-methyl-1H-pyrazolo[3,4-d]pyrimidine-6-ylamino)-3,4-dihydroisoquinoline-2(1H)-yl)-2,2,2-trifluoroethaneone

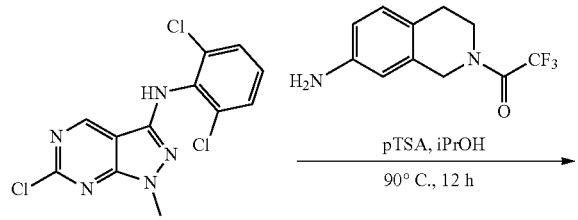

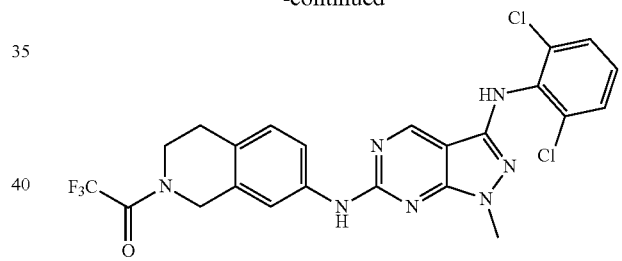

A target compound was prepared by the same manner as described in Example 9 except that the compound of Preparative Example B-3 was used instead of the compound of Preparative Example B-2 in Example 9.

Example 12: Preparation of N³-(2,6-dichlorophenyl)-1-methyl-N⁶ (1,2,3,4-tetrahydroisoquinoline-7-yl)-1H-pyrazolo[3,4-d]pyrimidine-3,6-diamine

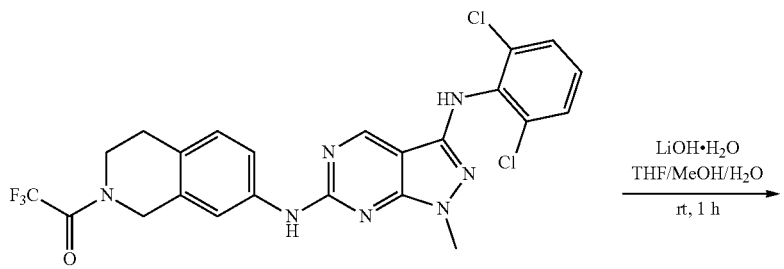

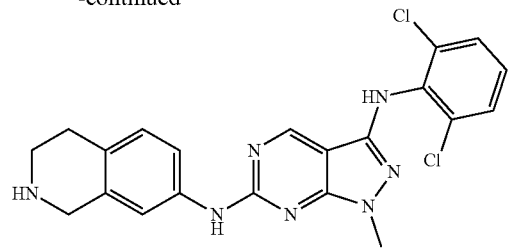

A target compound was prepared by the same manner as described in Example 10 except that the compound of Example 11 was used instead of the compound of Example 9 in Example 10.

Example 13: Preparation of 1-(7-(3-(2,6-dichlorophenylamino)-1-methyl-1H-pyrazolo[3,4-d]pyrimidine-6-ylamino)-3,4-dihydroisoquinoline-2(1H)-yl)ethaneone Example 14: Preparation of 1-(7-(3-(2,6-dimethylphenylamino)-1-methyl-1H-pyrazolo[3,4-d]pyrimidine-6-ylamino)-3,4-dihydroisoquinoline-2(1H)-yl)prop-2-en-1-one

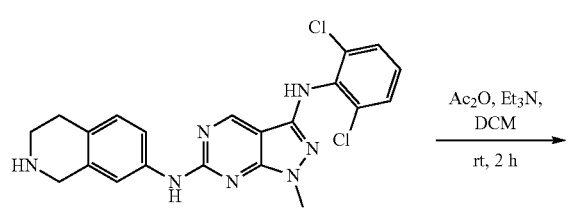

Acetic anhydride (2.7 mg, 0.027 mmol) and Et$_3$N (5.5 mg, 0.055 mmol) were added to DCM (10 mL) solution containing the compound of Example 12 (N3-(2,6-dichlorophenyl)-1-methyl-N6-(1,2,3,4-tetrahydroisoquinoline-7-yl)-1H-pyrazolo[3,4-d]pyrimidine-3,6-diamine, 10 mg, 0.022 mmol) at 0° C. followed by stirring at room temperature for 2 hours. TLC analysis indicated the complete consumption of the starting material. Water was added thereto, followed by extraction with DCM (15 mL).

The mixture was washed with saturated NaHCO$_3$ solution. The combined organic layer was concentrated under reduced pressure. The obtained crude product was purified by column chromatography using MeOH/DCM (1/4) as an eluent. As a result, 1-(7-(3-(2,6-dichlorophenylamino)-1-methyl-1H-pyrazolo[3,4-d]pyrimidine-6-ylamino)-3,4-dihydroisoquinoline-2(1H)-yl)ethaneone (10 mg, 0.020 mmol, 90%) was obtained as a grey-white solid.

Acryloyl chloride (2.7 mg, 0.03 mmol) and Et$_3$N (6.3 mg, 0.06 mmol) were added to DCM (10 mL) solution containing the compound of Example 2 (N3-(2,6-dimethylphenyl)-1-methyl-N6-(1,2,3,4-tetrahydroisoquinoline-7-yl)-1H-pyrazolo[3,4-d]pyrimidine-3,6-diamine, 10 mg, 0.02 mmol) at 0° C., followed by stirring at room temperature for 2 hours. TLC analysis indicated the complete consumption of the sailing material. Water was added thereto, followed by extraction with DCM (15 mL). The mixture was washed with saturated NaHCO$_3$ solution. The combined organic layer was concentrated under reduced pressure. The obtained crude product was purified by column chromatography using MeOH/DCM (1/4) as an eluent. As a result, 1-(7-(3-(2,6-dimethylphenylamino)-1-methyl-1H-pyrazolo[3,4-d]pyrimidine-6-ylamino)-3,4-dihydroisoquinolin-2(1H)-yl)prop-2-en-1-one (10 mg, 0.022 mmol, 88%) was obtained as a grey-white solid.

Example 15: Preparation of N³-(2,6-dichlorophenyl)-1-methyl-N⁶-(1,2,3,4-tetrahydroisoquinoline-6-yl)-1H-pyrazolo[3,4-d]pyrimidine-3,6-diamine

Step 1: Preparation of 1-(6-((3-((2,6-dichlorophenyl)amino)-1-methyl-1H-pyrazolo[3,4-d]pyrimidine-6-yl)amino)-3,4-dihydroisoquinoline-2(1H)-yl)-2,2,2-trifluoroethane-1-one

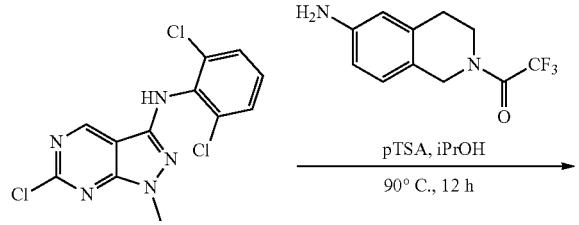

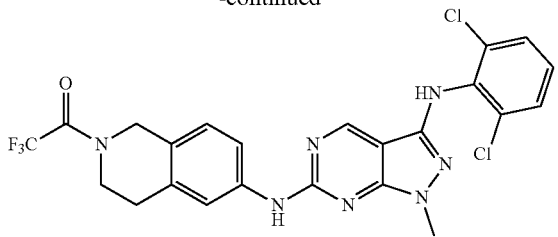

A target compound was prepared by the same manner as described in Example 6 except that the compound prepared in Preparative Example B-3 was used instead of the compound of Preparative Example B-1 in Example 6.

¹H NMR (300 MHz, CDCl₃) δ 8.10 (s, 1H), 7.57 (d, J=8.6 Hz, 2H), 7.44 (s, 1H), 7.42 (s, 1H), 7.38 (s, 1H), 7.20-7.09 (m, 2H), 6.38 (s, 1H), 4.79-4.75 (m, 2H), 3.96-3.83 (m, 5H), 3.02-2.96 (m, 2H); LC/MS 537.2 [M+H⁺].

Step 2: Preparation of N³-(2,6-dichlorophenyl)-1-methyl-N⁶-(1,2,3,4-tetrahydroisoquinoline-6-yl)-1H-pyrazolo[3,4-d]pyrimidine-3,6-diamine

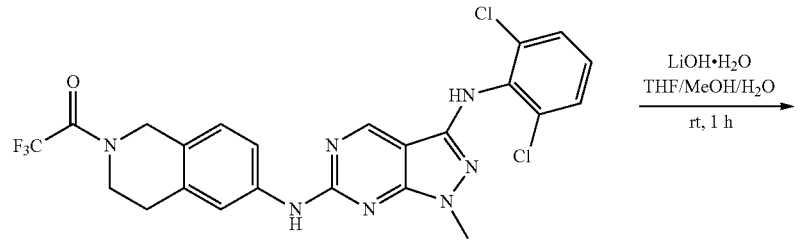

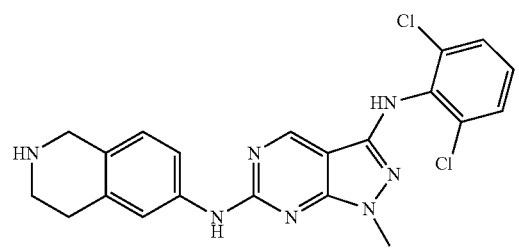

A target compound was prepared by the same manner as described in Example 7 except that the compound prepared in step 1 above was used instead of the compound of Example 6 in Example 7.

Example 16: Preparation of 1-(6-(3-(2,6-dichlorophenylamino)-1-methyl-1H-pyrazolo[3,4-d]pyrimidine-6-ylamino)-3,4-dihydroisoquinoline-2(1H)-yl)ethaneone

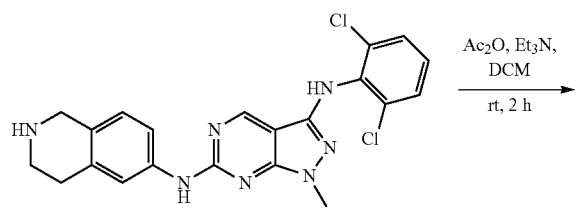

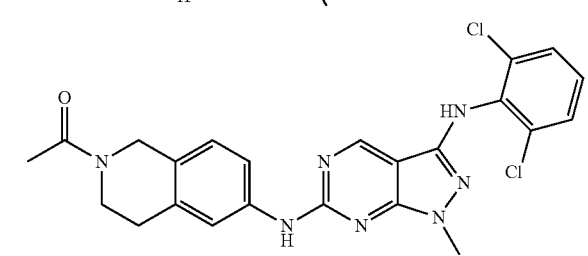

A target compound was prepared by the same manner as described in Example 13 except that the compound of Example 15 was used instead of the compound of Example 12 in Example 13.

Example 17: Preparation of $N^3$-(2,6-dimethylphenyl)-1-methyl-$N^6$-(2-methyl-1,2,3,4-tetrahydroisoquinoline-7-yl)-1H-pyrazolo[3,4-d]pyrimidine-3,6-diamine

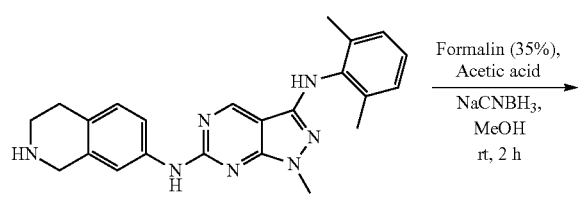

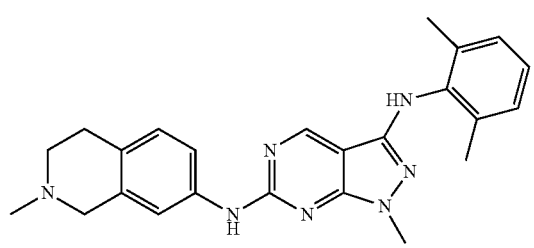

Formalin (35%) (1.5 mg, 0.05 mmol) was added to MeOH (1.0 mL) and acetic acid (0.1 mL) containing the compound of Example 2 (1-(7-(3-(2,6-dimethylphenylamino)-1-methyl-1H-pyrazolo[3,4-d]pyrimidine-6-ylamino)-3,4-dihydroisoquinolin-2(1H)-yl)prop-2-en-1-one, 10 mg, 0.025 mmol) at 0° C., followed by stirring at room temperature for 30 minutes. NaCNBH₃ (2.3 mg, 0.037 mmol) was added to the reaction mixture, which was stirred for 30 minutes. The reaction mixture was quenched with NaHCO₃ solution, followed by extraction with EtOAc. The reactant was dried over sodium sulfate and concentrated. The obtained crude mixture was purified by column chromatography using MeOH/MC as an eluent. As a result, N3-(2,6-dimethylphenyl)-1-methyl-N6-(2-methyl-1,2,3,4-tetrahydroisoquinoline-7-yl)1H-pyrazolo[3,4-d]pyrimidine-3,6-diamine (8.0 mg, 0.019 mmol, 77%) was obtained as a grey-white solid.

Example 18: Preparation of $N^3$(2,6-dimethylphenyl)-$N^6$ (isochroman-7-yl)-1-methyl-1H-pyrazolo[3,4-d]pyrimidine-3,6-diamine

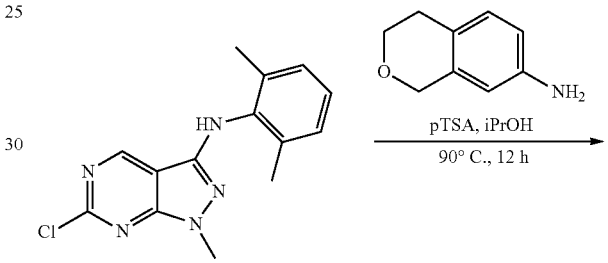

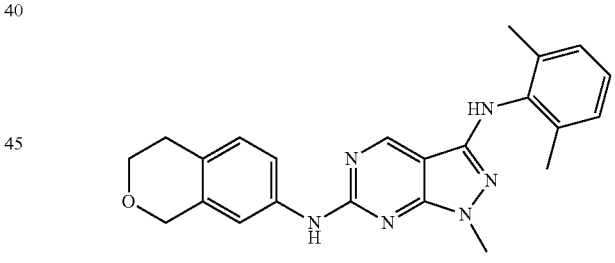

The compound prepared in Preparative Example A-4 (25 mg, 0.165 mmol), and pTSA.H₂O (33 mg, 0.173 mmol) were added to IPA (1.0 mL) solution containing the compound prepared in Preparative Example B-1 (50 mg, 0.173 mmol) at room temperature, followed by stirring at 90° C. for 12 hours. TLC analysis indicated the complete consumption of the starting material. The solid obtained from the reaction mixture was filtered and washed with ethanol (2 mL). The filtered solid was dissolved in EtOAc (50 mL) and washed with saturated NaHCO₃ solution. The combined organic layer was concentrated under reduced pressure. The obtained crude product was purified by column chromatography using MeOH/DCM (1/4) as an eluent. As a result, N3-(2,6-dimethylphenyl)-N6-(isochroman-7-yl)-1-methyl-1H-pyrazolo[3,4-d]pyrimidine-3,6-diamine (50 mg, 0.125 mmol, 75%) was obtained as a grey-white solid.

Example 19: Preparation of N3-(2,6-dimethylphenyl)-N6-(1,2,3,4-tetrahydroisoquinoline-7-yl)-1H-pyrazolo[3,4-d]pyrimidine-3,6-diamine

Step 1: Preparation of 1-(7-((3-((2,6-dimethylphenyl)amino)-1H-pyrazolo[3,4-d]pyrimidine-6-yl)amino)-3,4-dihydroisoquinoline-2(1H)-yl)-2,2,2-trifluoroethane-1-one

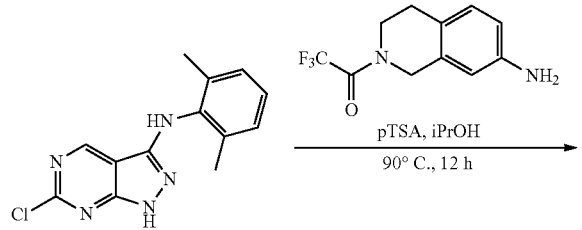

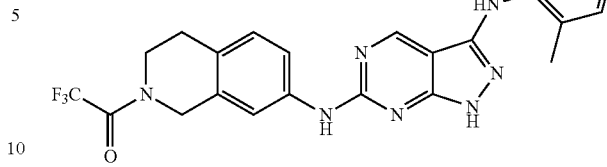

A target compound was prepared by the same manner as described in Example 9 except that the compound of Preparative Example B-4 was used instead of the compound of Preparative Example B-2 in Example 9.

$^1$H NMR (300 MHz, CDCl$_3$) δ 9.65 (s, br, H), 7.63 (s, 1H), 7.58-7.52 (m, 1H), 7.38-7.31 (m, 2H), 7.23-7.14 (m, 3H), 7.11 ((, J=8.1 Hz, 1H), 6.05 (s, 1H), 4.80-4.75 (m, 2H), 3.89-3.82 (m, 2H), 2.97-2.86 (m, 2H), 2.29 (s, 6H); LC/MS 481.9 [M+H$^+$].

Step 2: Preparation of N3-(2,6-dimethylphenyl)-N6-(1,2,3,4-tetrahydroisoquinoline-7-yl)-1H-pyrazolo[3,4-d]pyrimidine-3,6-diamine

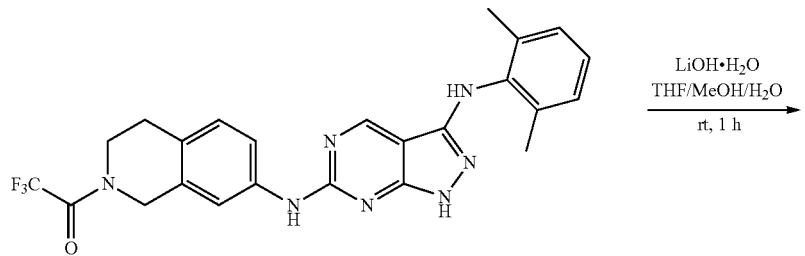

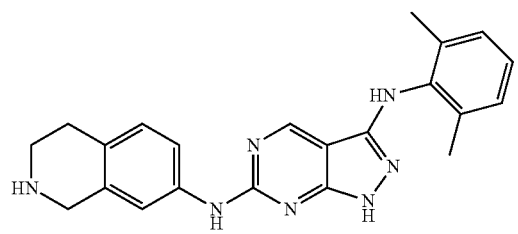

A target compound was prepared by the same manner as described in Example 10 except that the compound prepared in step 1 above was used instead of the compound of Example 9 in Example 10.
Example 20: Preparation of $N^3$-(2,6-dimethylphenyl)-1-methyl-$N^6$-(1-methyl-1,2,3,4-tetrahydroisoquinoline-7-yl)-1H-pyrazolo[3,4-d]pyrimidine-3,6-diamine
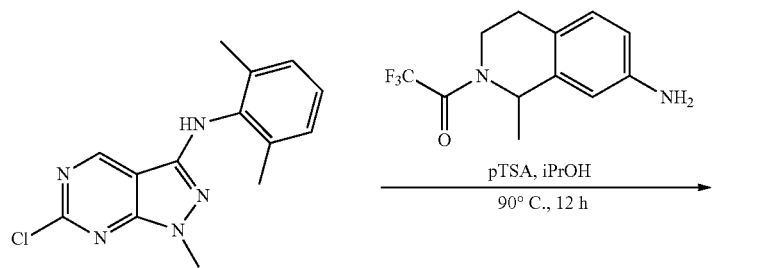
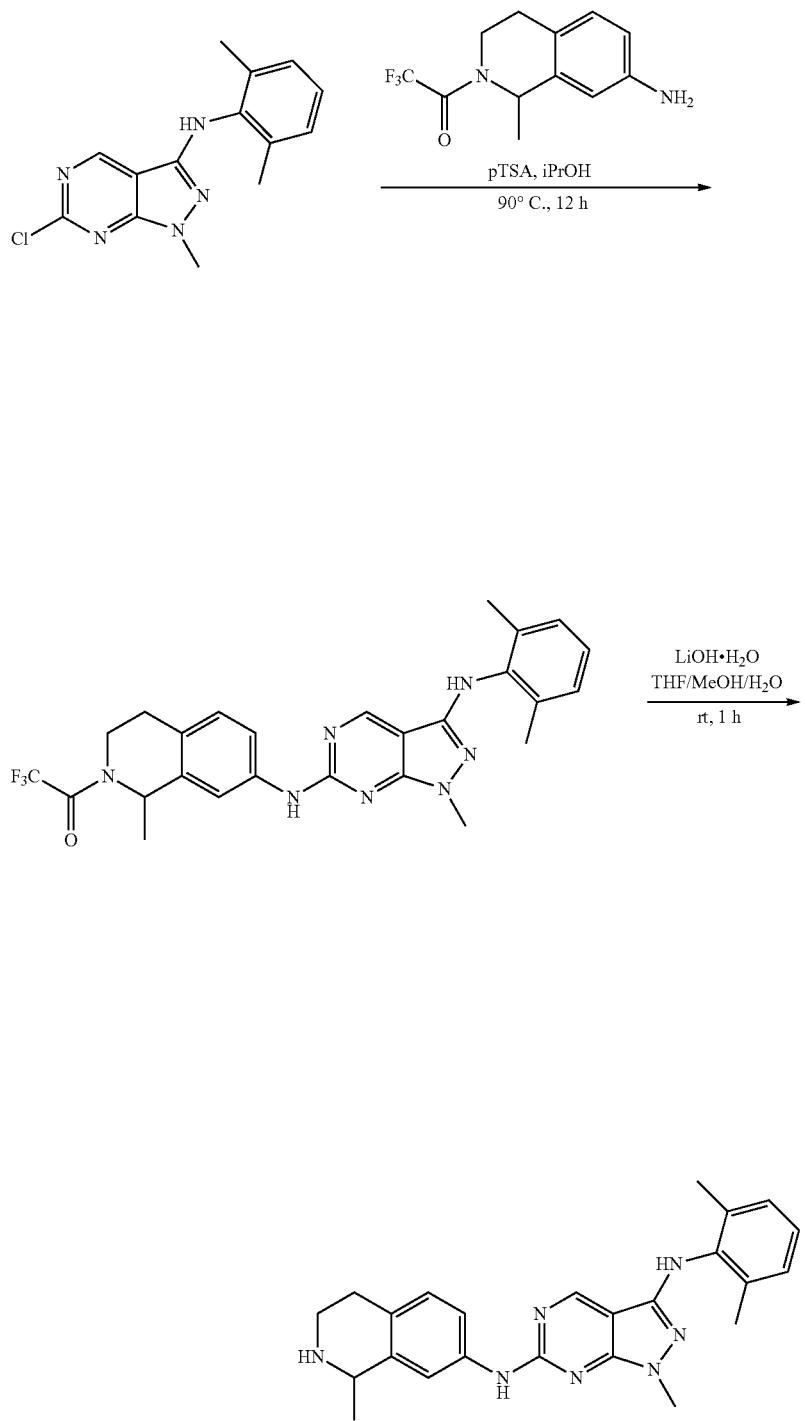

Step 1: A target compound was prepared by the same manner as described in Example 3 except that 1-methyl-1,2,3,4-tetrahydroisoquinoline-7-amine was used instead of 1-(6-amino-7-methoxy-3,4-dihydroisoquinoline-2(1H)-yl)-2,2,2-trifluoroethane-1-one in Example 3.

Step 2: A target compound was prepared by the same manner as described in Example 4 except that the compound prepared in step 1 above was used instead of the compound of Example 3 in Example 4.

Example 21: Preparation of N-(2,6-dimethylphenyl)-$N^6$ (2-isopropyl-1,2,3,4-tetrahydroisoquinoline-7-yl)-1-methyl-1H-pyrazolo[3,4-d]pyrimidine-3,6-diamine Acetone (0.01 mL) and $NaCNBH_3$ (9.4 mg, 0.15 mmol) were added to MeOH (4 mL) and acetic acid solution (0.05 mL) containing the compound of Example 2 (40 mg, 0.10 mmol) at room temperature, followed by stirring at room temperature for 10 hours. The aqueous solution layer was washed with pH 2 DCM (2×25 mL). The combined organic layer was dried over $Na_2SO_4$, and the solvent was eliminated under reduced pressure. The residue mixture was purified by silica gel column chromatography using DCM/MeOH (9/1) as an eluent. As a result, the target compound (17 mg, 0.038 mmol, 39%) was obtained as a yellow solid.

Example 22: Preparation of 1-(7-(3-(2,6-dimethylphenylamino)-1-methyl-1H-pyrazolo[3,4-d]pyrimidine-6-ylamino)-3,4-dihydroisoquinoline-2(1H)-yl)-2-hydroxyethanone

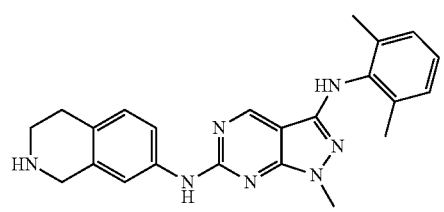

Exact Mass: 399.22
Molecular Weight: 399.50

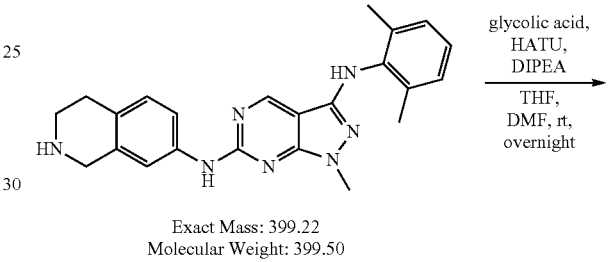

Exact Mass: 399.22
Molecular Weight: 399.50

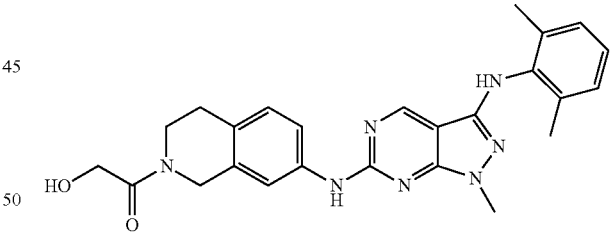

Exact Mass: 457.22
Molecular Weight: 457.54

Exact Mass: 441.26
Molecular Weight: 441.58

Glycolic acid (9.2 mg, 0.12 mmol), HATU (56 mg, 0.15 mmol) and DIPEA (0.44 mL, 0.25 mmol) were added to THF (4 mL) and DMF (2 mL) containing the compound of Example 2 (40 mg, 0.10 mmol) at room temperature, followed by stirring at room temperature for 10 hours. The reaction was terminated with water and brine, followed by extraction with EtOAc (2×25 mL). The combined organic layer was dried over $Na_2SO_4$, and the solvent was eliminated under reduced pressure. The residue mixture was purified by silica gel column chromatography using DCM/MeOH (9/1) as an eluent. As a result, the target compound (27 mg, 0.059 mmol, 59%) was obtained as a while solid.

Example 23: Preparation of cyclopropyl(7-(3-(2,6-dimethylphenylamino)-1-methyl-1H-pyrazolo[3,4-d]pyrimidine-6-ylamino)-3,4-dihydroisoquinoline-2(1H)-yl)methanone Example 24: Preparation of 2-(7-((3-((2,6-dimethylphenyl)amino)-1-methyl-1H-pyrazolo[3,4-d]pyrimidine-6-yl)amino)-3,4-dihydroisoquinoline-2(1H)-yl)ethane-1-ol

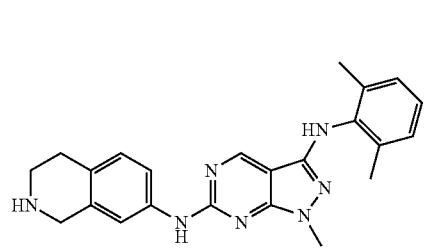

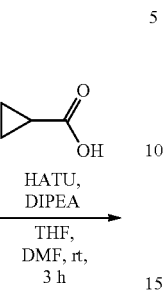

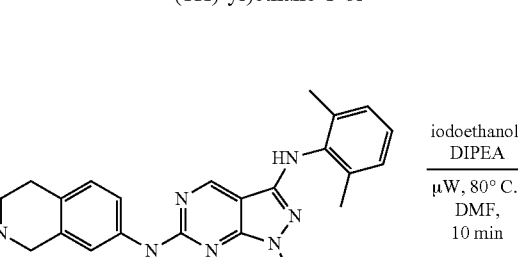

Exact Mass: 399.22
Molecular Weight: 399.50

Exact Mass: 399.22
Molecular Weight: 399.50

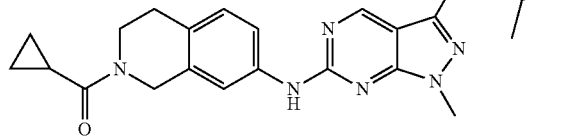

Exact Mass: 443.24
Molecular Weight: 443.56

Exact Mass: 467.24
Molecular Weight: 467.58

A target compound was prepared by the same manner as described in Example 22 except that iodoethanol was used instead of glycolic acid in Example 22.

A target compound was prepared by the same manner as described in Example 22 except that cyclopropanecarboxylic acid was used instead of glycolic acid in Example 22.

Example 25: Preparation of 1-cyclopentyl-$N^3$-(2,6-dimethylphenyl)-$N^6$-(1,2,3,4-tetrahydroisoquinoline-7-yl)-1H-pyrazolo[3,4-d]pyrimidine-3,6-diamine

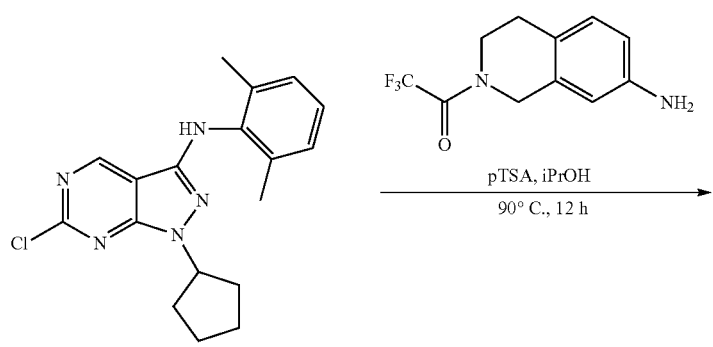

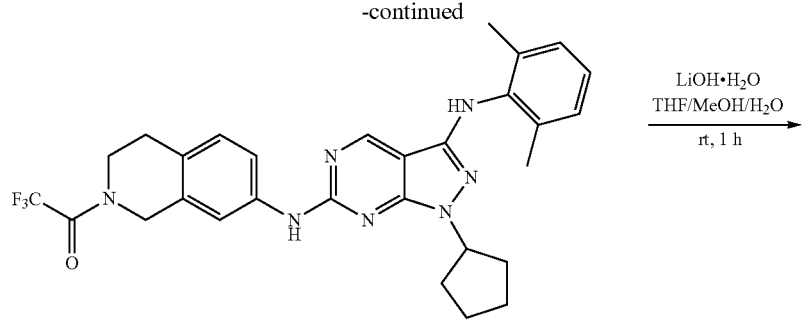
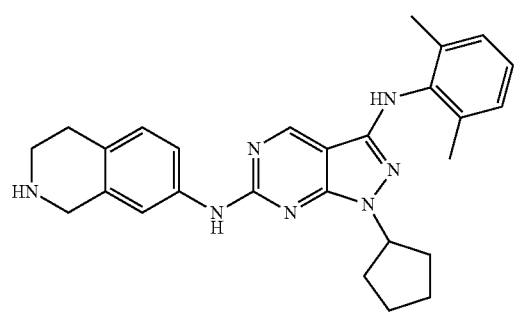
A target compound was prepared by the same manner as described in Example 19 except that the compound of Preparative Example B-5 was used instead of the compound of Preparative Example B-4 in Example 19.
Example 26: Preparation of 1-cyclohexyl-$N^3$-(2,6-dimethylphenyl)-$N^6$ (1,2,3,4-tetrahydroisoquinoline-7-yl)-1H-pyrazolo[3,4-d]pyrimidine-3,6-diamine
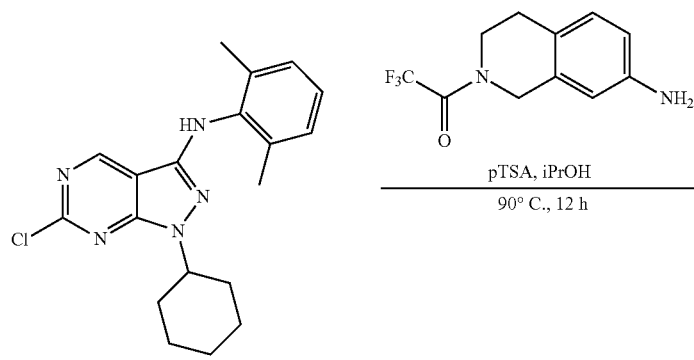
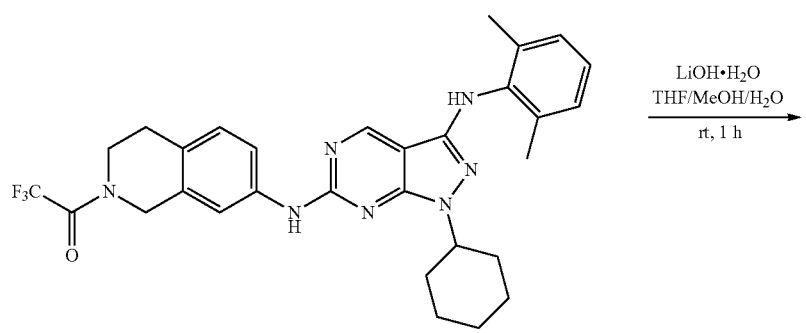

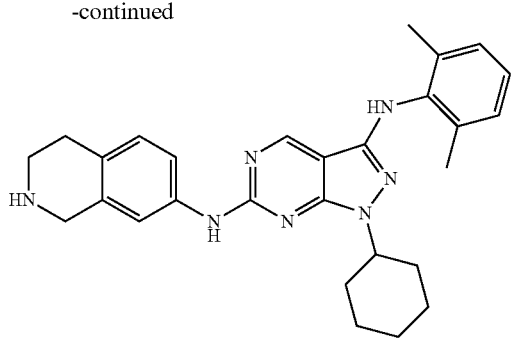
A target compound was prepared by the same manner as described in Example 19 except that the compound of Preparative Example B-6 was used instead of the compound of Preparative Example B-4 in Example 19.
Example 27: Preparation of N³ (2,6-dimethylphenyl)-1-isopropyl-N6-(1,2,3,4-tetrahydroisoquinoline-7-yl)-1H-pyrazolo[3,4-d]pyrimidine-3,6-diamine
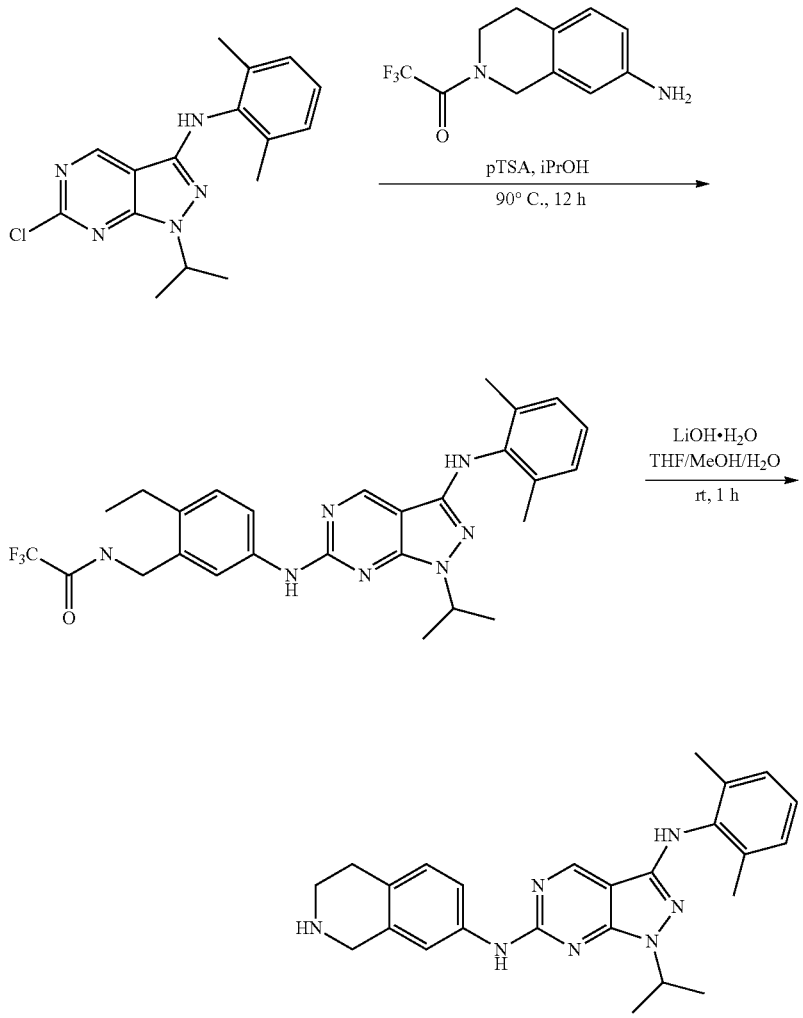

A target compound was prepared by the same manner as described in Example 19 except that the compound of Preparative Example B-7 was used instead of the compound of Preparative Example B-4 in Example 19.

Example 28: Preparation of N-(4-methyl-3-((1-methyl-6-((1,2,3,4-tetrahydroisoquinoline-7-yl)amino)-1H-pyrazolo[3, 4-d]pyrimidine-3-yl)amino)phenyl)-3-(trifluoromethyl)benzamide A target compound was prepared by the same manner as described in Example 19 except that the compound of Preparative Example B-8 was used instead of the compound of Preparative Example B-4 in Example 19.

Example 29: Preparation of N-(2,4-dimethyl-3-(1-methyl-6-(1,2,3,4-tetrahydroisoquinoline-7-ylamino)-1H-pyrazolo[3,4-d]pyrimidine-3-ylamino)phenyl)-3-(trifluoromethyl)benzamide A target compound was prepared by the same manner as described in Example 19 except that the compound of Preparative Example B-9 was used instead of the compound of Preparative Example B-4 in Example 19.

Example 30: Preparation of $N^3$-(4-(2-methoxyethoxy)-2,6-dimethylphenyl)-1-methyl-N-(1,2,3,4-tetrahydroisoquinoline-7-yl)-1H-pyrazolo[3,4-d]pyrimidine-3,6-diamine A target compound was prepared by the same manner as described in Example 19 except that the compound of Preparative Example B-10 was used instead of the compound of Preparative Example B-4 in Example 19.

Example 31: Preparation of 2-(dimethylamino)-1-(7-(3-(2,6-dimethylphenylamino)-1-methyl-1H-pyrazolo[3,4-d]pyrimidine-6-ylamino)-3,4-dihydroisoquinolin-2(1H)-yl)ethanone

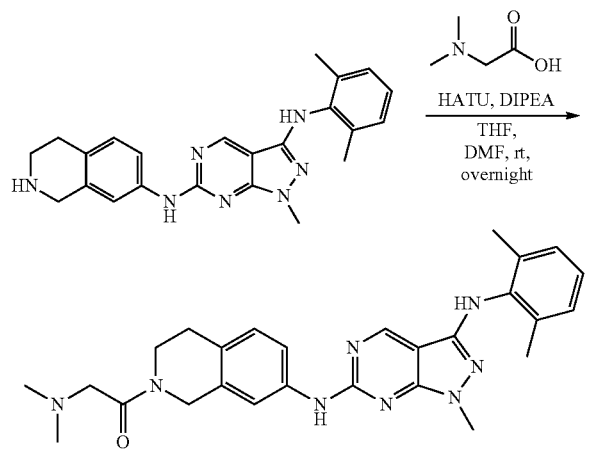

A target compound was prepared by the same manner as described in Example 22 except that N,N-dimethylglycine was used instead of glycolic acid in Example 22.

Example 32: Preparation of N3-(2,6-dimethylphenyl)-$N^6$-(2-ethyl-1,2,3,4-tetrahydroisoquinoline-7-yl)-1-methyl-1H-pyrazolo[3,4-d]pyrimidine-3,6-diamine

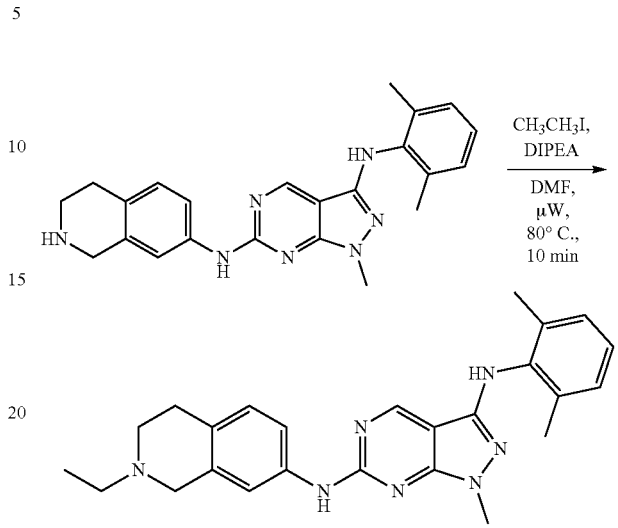

A target compound was prepared by the same manner as described in Example 22 except that iodoethane was used instead of glycolic acid in Example 22.

Example 33: Preparation of N-(2,6-dimethyl-4-phenoxyphenyl)-1-methyl-$N^6$ (1,2,3,4-tetrahydroisoquinoline-7-yl)-1H-pyrazolo[3,4-d]pyrimidine-3,6-diamine A target compound was prepared by the same manner as described in Example 19 except that the compound of Preparative Example B-11 was used instead of the compound of Preparative Example B-4 in Example 19.

Example 34: Preparation of 3,5-dimethyl-4-(1-methyl-6-(1,2,3,4-tetrahydroisoquinoline-7-ylamino)-1H-pyrazolo[3,4-d]pyrimidine-3-ylamino)-N-(pyridine-2-yl)benzamide A target compound was prepared by the same manner as described in Example 19 except that the compound of Preparative Example B-12 was used instead of the compound of Preparative Example B-4 in Example 19.

Example 35: Preparation of $N^3$-(4-methoxy-2,6-dimethylphenyl)-1-methyl-$N^6$-(1,2,3,4-tetrahydroisoquinoline-7-yl)-1H-pyrazolo[3,4-d]pyrimidine-3,6-diamine A target compound was prepared by the same manner as described in Example 19 except that the compound of Preparative Example B-13 was used instead of the compound of Preparative Example B-4 in Example 19.

Example 36: Preparation of $N^3$-(2,6-diethylphenyl)-1-methyl-$N^6$-(1,2,3,4-tetrahydroisoquinoline-7-yl)-1H-pyrazolo[3,4-d]pyrimidine-3,6-diamine A target compound was prepared by the same manner as described in Example 19 except that the compound of Preparative Example B-14 was used instead of the compound of Preparative Example B-4 in Example 19.

Example 37: Preparation of $N^3$-(2,6-diisopropylphenyl)-1-methyl-$N^6$-(1,2,3,4-tetrahydroisoquinoline-7-yl)-1H-pyrazolo[3,4-d]pyrimidine-3,6-diamine A target compound was prepared by the same manner as described in Example 19 except that the compound of Preparative Example B-15 was used instead of the compound of Preparative Example B-4 in Example 19.

Example 38: Preparation of $N^3$-(2-chloro-3,5-dimethylphenyl)-1-methyl-$N^6$-(1,2,3,4-tetrahydroisoquinoline-7-yl)-1H-pyrazolo[3,4-d]pyrimidine-3,6-diamine A target compound was prepared by the same manner as described in Example 10 except that the compound of Preparative Example B-16 was used instead of the compound of Preparative Example B-4 in Example 19.

Example 39: Preparation of $N^3$-(2,4-dimethylphenyl)-1-methyl-$N^6$ (1,2,3,4-tetrahydroisoquinoline-7-yl)-1H-pyrazolo[3,4-d]pyrimidine-3,6-diamine A target compound was prepared by the same manner as described in Example 19 except that the compound of Preparative Example B-17 was used instead of the compound of Preparative Example B-4 in Example 19.

Example 40: Preparation of 1-methyl-$N^3$-(1,2,3,4-tetrahydroisoquinoline-7-yl)-$N^6$-o-tolyl-1H-pyrazolo[3,4-d]pyrimidine-3,6-diamine A target compound was prepared by the same manner as described in Example 19 except that the compound of Preparative Example B-18 was used instead of the compound of Preparative Example B-4 in Example 19.

Example 41: Preparation of $N^3$-(3,5-dimethylphenyl)-1-methyl-$N^6$-(1,2,3,4-tetrahydroisoquinoline-7-yl)-1H-pyrazolo[3,4-d]pyrimidine-3,6-diamine A target compound was prepared by the same manner as described in Example 19 except that the compound of Preparative Example B-19 was used instead of the compound of Preparative Example B-4 in Example 19.

Example 42: Preparation of $N^3$-(2,6-difluorophenyl)-1-methyl-$N^6$-(1,2,3,4-tetrahydroisoquinoline-7-yl)-1H-pyrazolo[3,4-d]pyrimidine-3,6-diamine A target compound was prepared by the same manner as described in Example 19 except that the compound of Preparative Example B-20 was used instead of the compound of Preparative Example B-4 in Example 19.

Example 43: Preparation of $N^3$-(2,6-dimethoxyphenyl)-1-methyl-$N^6$ (1,2,3,4-tetrahydroisoquinoline-7-yl)-1H-pyrazolo[3,4-d]pyrimidine-3,6-diamine A target compound was prepared by the same manner as described in Example 19 except that the compound of Preparative Example B-21 was used instead of the compound of Preparative Example B-4 in Example 19.

Example 44: Preparation of $N^3$-(4-fluoro-2,6-dimethylphenyl)-1-methyl-$N^6$-(1,2,3,4-tetrahydroisoquinoline-7-yl)-1H-pyrazolo[3,4-d]pyrimidine-3,6-diamine A target compound was prepared by the same manner as described in Example 19 except that the compound of Preparative Example B-22 was used instead of the compound of Preparative Example B-4 in Example 19.

Example 45: Preparation of $N^3$-(2,5-dimethylphenyl)-1-methyl-$N^6$ (1,2,3,4-tetrahydroisoquinoline-7-yl)-1H-pyrazolo[3,4-d]pyrimidine-3,6-diamine A target compound was prepared by the same manner as described in Example 19 except that the compound of Preparative Example B-23 was used instead of the compound of Preparative Example B-4 in Example 19.

Example 46: Preparation of $N^3$-(4,4-dimethyl-1,2,3,4-tetrahydroisoquinoline-7-yl)-$N^6$-(2,6-dimethylphenyl)-1-methyl-1H-pyrazolo[3,4-d]pyrimidine-3,6-diamine A target compound was prepared by the same manner as described in Example 20 except that the compound of Preparative Example A-5 was used instead of 1-methyl-1,2,3,4-tetrahydroisoquinoline-7-amine in Example 20.

Example 47: Preparation of N-(4-methyl-3-(1-methyl-6-(1-methyl-1,2,3,4-tetrahydroisoquinoline-7-ylamino)-1H-pyrazolo[3,4-d]pyrimidine-3-ylamino)phenyl)-3-(trifluoromethyl)benzamide A target compound was prepared by the same manner as described in Example 20 except that the compound of Preparative Example B-8 was used instead of the compound of Preparative Example B-1 in Example 20.

Example 48: Preparation of $N^3$-(2-chloro-6-methylphenyl)-1-methyl-$N^6$ (1,2,3,4-tetrahydroisoquinoline-7-yl)-1H-pyrazolo[3,4-d]pyrimidine-3,6-diamine A target compound was prepared by the same manner as described in Example 19 except that the compound of Preparative Example B-24 was used instead of the compound of Preparative Example B-4 in Example 19.

Example 49: Preparation of $N^3$-(2,6-dimethylphenyl)-$N^6$-(1-isopropyl-1,2,3,4-tetrahydroisoquinoline-7-yl)-1-methyl-1H-pyrazolo[3,4-d]pyrimidine-3,6-diamine A target compound was prepared by the same manner as described in Example 20 except that the compound of Preparative Example A-6 was used instead of 1-methyl-1,2,3,4-tetrahydroisoquinoline-7-amine in Example 20.

Example 50: Preparation of $N^3$-(5-(2-methoxyethoxy)-2-methylphenyl)-1-methyl-$N^6$-(1,2,3,4-tetrahydroisoquinoline-7-yl)-1H-pyrazolo[3,4-d]pyrimidine-3,6-diamine A target compound was prepared by the same manner as described in Example 19 except that the compound of Preparative Example B-25 was used instead of the compound of Preparative Example B-4 in Example 19.

Example 51: Preparation of N-(4-methyl-3-(1-methyl-6-(1,2,3,4-tetrahydroisoquinoline-7-ylamino)-1H-pyrazolo[3,4-d]pyrimidine-3-ylamino)phenyl)picolinamide A target compound was prepared by the same manner as described in Example 19 except that the compound of Preparative Example B-26 was used instead of the compound of Preparative Example B-4 in Example 19.

Example 52: Preparation of 4-methyl-3-(1-methyl-6-(1,2,3,4-tetrahydroisoquinoline-7-ylamino)-1H-pyrazolo[3,4-d]pyrimidine-3-ylamino)-N-(3-(trifluoromethyl)phenyl)benzamide A target compound was prepared by the same manner as described in Example 19 except that the compound of Preparative Example B-27 was used instead of the compound of Preparative Example B-4 in Example 19.

Example 53: Preparation of $N^6$-(3,3-dimethyl-1,2,3,4-tetrahydroisoquinoline-7-yl)-$N^3$-(2,6-dimethylphenyl)-1-methyl-1H-pyrazolo[3,4-d]pyrimidine-3,6-diamine A target compound was prepared by the same manner as described in Example 20 except that 3,3-dimethyl-1,2,3,4-tetrahydroisoquinoline-7-amine was used instead of 1-methyl-1,2,3,4-tetrahydroisoquinoline-7-amine in Example 20.

Example 54: Preparation of 4-(3-((2,6-dimethylphenyl)amino)-6-((1,2,3,4-tetrahydroisoquinoline-7-yl)amino)-1H-pyrazolo[3,4-d]pyrimidine-1-yl)cyclohexane-1-ol Step 1: Preparation of tert-butyl-2-(1,4-dioxaspiro[4,5]decane-8-yl)hydrazine-1-carboxylate

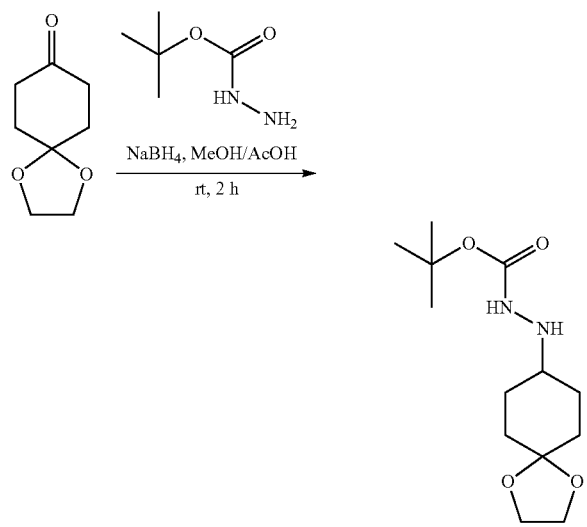

Methanol (30 mL) solution containing 1,4-dioxaspiro[4,5]decane-8-one (1.0 g, 6.40 mmol) and t-butylcarbazate (0.84 g, 6.40 mmol) was stirred at room temperature for 20 hours. Then, the reaction mixture was concentrated under reduced pressure. Acetic acid, water, and NaCNBH$_3$ (400 mg, 6.40 mmol) were added thereto, followed by stirring at room temperature for 3 hours. Upon completion of the reaction, the reaction mixture was concentrated under reduced pressure, and the residue was basified with 1 NaOH (pH 8). The residue was diluted with DCM, and the organic layer was concentrated under reduced pressure. The crude product was purified by column chromatography using EtOAc/Hx (1:2). As a result, the target compound (1.34 g, 4.92 mmol, 77%) was obtained as a white solid.

$^1$H NMR (500 MHz, CDCl$_6$) δ 6.13 (s, 1H), 4.02 (s, 1H), 3.92 (s, 4H), 3.00-2.85 (m, 1H), 1.84-1.72 (m, 4H), 1.58-1.46 (m, 4H), 1.44 (s, 9H); LC/MS 273.2 [M+H$^+$].

Step 2: Preparation of tert-butyl-2-(2-chloro-5-((2,6-dimethylphenyl)carbamoyl)pyridine-4-yl-2-(1,4-dioxaspiro[4,5]decane-8-yl)hydrazine-1-carboxylate

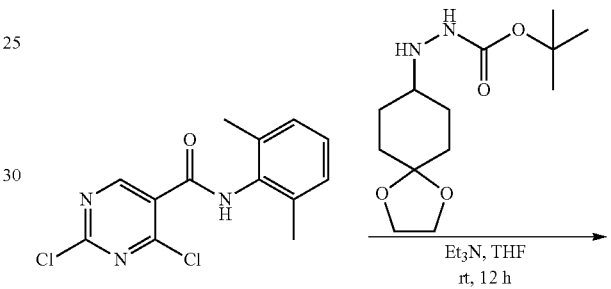

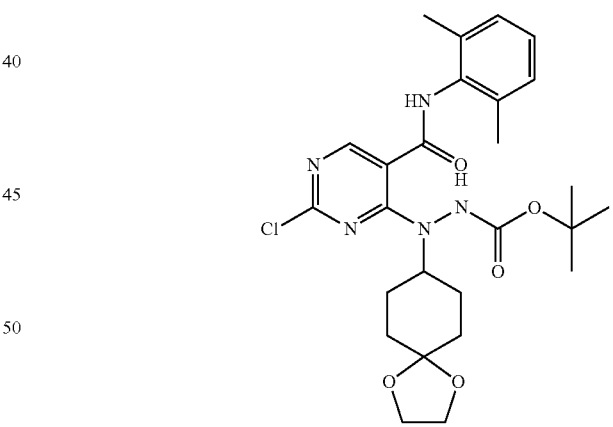

The compound prepared in step 1 above (202 mg, 0.742 mmol) and Et$_3$N (0.24 mL, 1.68 mmol) were added to THF (10 mL) solution containing the compound prepared in step 2 of Preparative Example B-1 (200 mg, 0.675 mmol) at room temperature, followed by stirring at room temperature for 12 hours. The mixture was concentrated under reduced pressure. The reaction mixture was washed with water, and the organic layer was dried over sodium sulfate, followed by concentration under reduced pressure. The crude product was purified by column chromatography (EtOAc/Hx (1/4)). As a result, the target compound (200 mg, 0.375 mmol, 55%) was obtained as a white solid.

¹H NMR (300 MHz, CDCl₃) δ 8.68 (s, 1H), 8.42 (s, 1H), 7.23-7.11 (m, 3H), 6.98 (s, 1H), 4.36 (s, 1H), 3.96 (s, 4H), 2.32 (s, 6H), 2.07 (s, 1H), 1.87-1.67 (m, 7H), 1.43 (s, 9H); LC/MS 532.9 [M+H⁺].

Step 3: Preparation of 6-chloro-N-(2,6-dimethylphenyl)-1-(1,4-dioxaspiro[4,5]decan-8-yl)-1H-pyrazole[3,4-d]pyrimidine-3-amine Step 4: Preparation of 4-(6-chloro-3-((2,6-dimethylphenyl)amino)-1H-pyrazole[3,4-d]pyrimidine-1-yl)cyclohexane-1-one

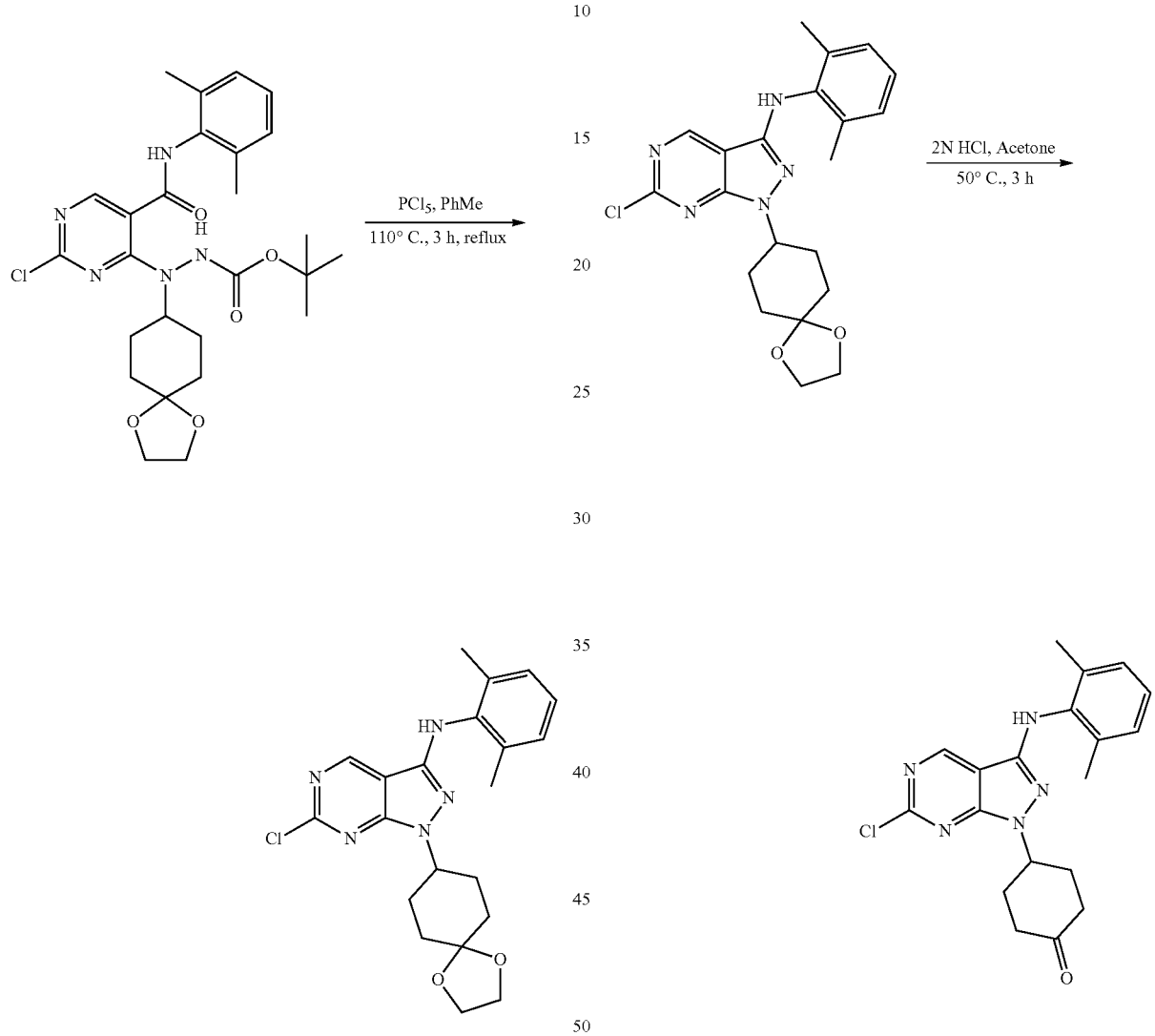

PCl₅ (78 mg, 0.375 mmol) was added to toluene (20 mL) solution containing the compound prepared in step 2 above (200 mg, 0.375 mmol) at room temperature, followed by stirring at 110° C. for 3 hours. The mixture was concentrated under reduced pressure to eliminate toluene. The reaction mixture was washed with sodium bicarbonate, and the organic layer was dried over sodium sulfate, followed by concentration under reduced pressure. The crude product was purified by column chromatography (EtOAc/Hx (1/4)). As a result, the target compound (80 mg, 0.193 mmol, 51%) was obtained as a yellow solid.

¹H NMR (300 MHz, CDCl₃) δ 7.48 (s, 1H), 7.25-7.12 (m, 3H), 6.17 (s, 1H), 4.72 (tt, J=11.7, 3.9 Hz, 1H), 4.01 (s, 4H), 2.43-2.27 (m, 2H), 2.25 (s, 6H), 2.02-1.89 (m, 4H), 1.87-1.73 (m, 2H); LC/MS 413.9 [M+H⁺].

2 N HCl (3.0 mL) was added to acetone (10 mL) solution containing the compound prepared in step 3 above (60 mg, 0.145 mmol) at room temperature, followed by stirring at 50° C. for 3 hours. The mixture was concentrated under reduced pressure to eliminate acetone. The reaction mixture was washed with sodium bicarbonate, and the organic layer was dried over sodium sulfate, followed by concentration under reduced pressure. The crude product was purified by column chromatography (EtOAc/Hx (1/4)). As a result, the target compound (45 mg, 0.121 mmol, 84%) was obtained as a yellow solid.

¹H NMR (300 MHz, CDCl₃) δ 7.56 (s, 1H), 7.27-7.13 (m, 3H), 6.12 (s, 1H), 5.19-5.05 (m, 1H), 2.67-2.40 (m, 6H), 2.35-2.28 (m, 2H), 2.26 (s, 6H); LC/MS 369.9 [M+H⁺].

Step 5: Preparation of 4-(6-chloro-3-((2,6-dimethylphenyl)amino)-1H-pyrazole[3,4-d]pyrimidine-1-yl)cyclohexane-1-ol

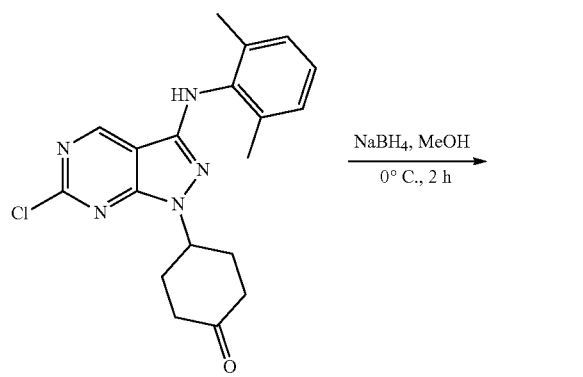

NaBH$_4$ (1.53 mg, 0.040 mmol) MeOH was slowly added to methanol (1.0 mL) solution containing the compound prepared in step 4 above (15 mg, 0.040 mmol) at room temperature. Then, methanol was eliminated therefrom, and the residue was extracted with EtOAc (2×20 mL). The EtOAc layer was dried over MgSO$_4$, and filtered, followed by reducing pressure. The obtained crude product was purified by column chromatography (EtOAc/Hx (1/4)). As a result, the target compound (8 mg, 0.021 mmol, 53%) was obtained as a yellow solid.

$^1$H NMR (300 MHz, CDCl$_3$) δ 7.50 (s, 1H), 7.24-7.15 (m, 3H), 6.12 (s, 1H), 4.74-4.60 (m, 1H), 3.87-3.68 (m, 1H), 2.26 (s, 6H), 2.19-2.11 (m, 2H), 2.05-1.98 (m, 2H), 1.65-1.49 (m, 4H); LC/MS 372.2 [M+H$^+$].

Step 6: Preparation of 1-(7-((3-((2,6-dimethylphenyl)amino)-1-(4-hydroxycyclohexyl)-1H-pyrazolo[3,4-d]pyrimidine-1-yl)amino)-3,4-dihydroquinoline-2(1H)-yl)-2,2,2-trifluoroethane-1-one

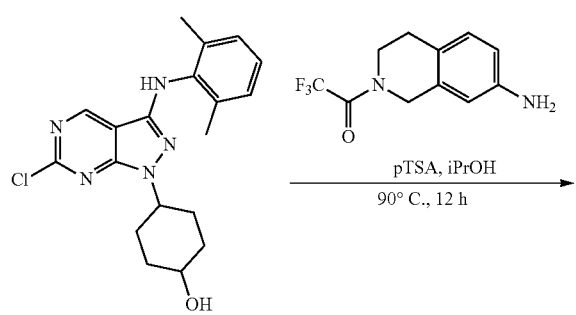

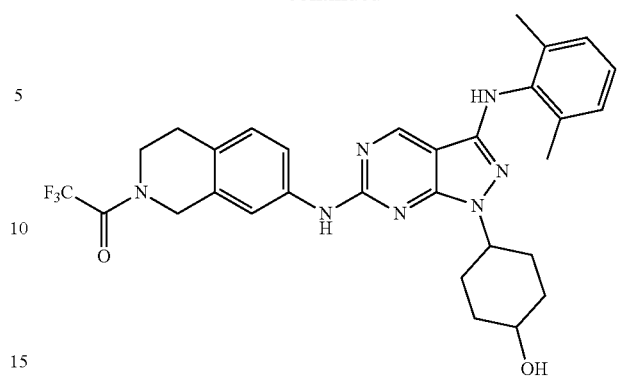

A target compound was prepared by the same manner as described in Example 9 except that the compound of Preparative Example B-4 was used instead of the compound of Preparative Example B-2 in Example 9.

$^1$H NMR (300 MHz, CDCl$_3$) δ 7.73-7.61 (m, 1H), 7.44-7.30 (m, 2H), 7.25-7.07 (m, 5H), 5.92 (d, J=4.6 Hz, 1H), 4.85-4.76 (m, 2H), 4.52-4.39 (m, 1H), 3.95-3.86 (m, 2H), 3.85-3.75 (m, 1H), 2.95 (q, J=5.9 Hz, 2H), 2.29 (s, 6H), 2.26-2.12 (m, 4H), 2.11-2.08 (m, 2H), 1.65-1.47 (m, 4H); LC/MS 580.2 [M+H$^+$].

Step 7: Preparation of 4-(3-((2,6-dimethylphenyl)amino)-6-((1,2,3,4-tetrahydroisoquinoline-7-yl)amino)-1H-pyrazolo[3,4-d]pyrimidine-1-yl)cyclohexane-1-ol

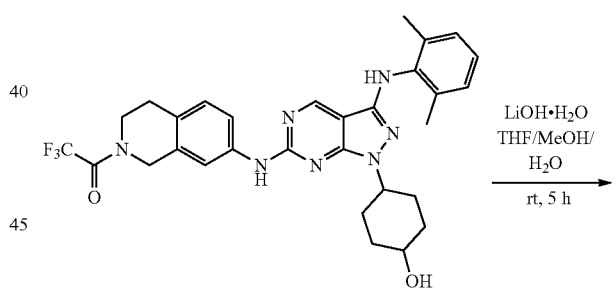

A target compound was prepared by the same manner as described in Example 10 except that the compound prepared in step 1 above was used instead of the compound of Example 9 in Example 10.

Example 55: Preparation of N3-(2,6-dimethylphenyl)-1-methyl-N 6-(1,3,3-trimethyl-1,2,3,4-tetrahydroisoquinoline-7-yl)-1H-pyrazolo[3,4-d]pyrimidine-3,6-diamine Step 1: Preparation of 1-(7-((3-((2,6-dimethylphenyl)amino)-1-methyl-1H-pyrazolo[3,4-d]pyrimidine-6-yl)amino)-1,3,3-trimethyl-3,4-dihydroisoquinoline-2(1H)-yl)-2,2,2-trifluoroethane-1-one

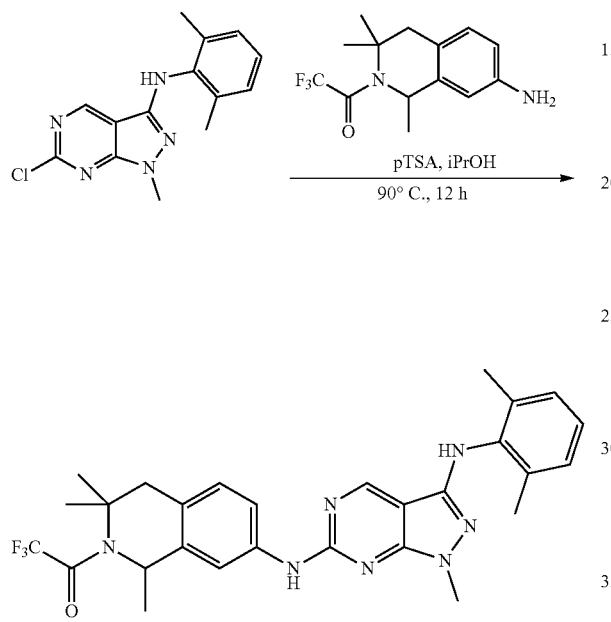

1-(7-amino-1,3,3-trimethyl-3,4-dihydroisoquinoline-2(1H)-yl)-2,2,2-trifluoroethane-1-one (47.2 mg, 0.165 mmol) and pTSA.H$_2$O (33 mg, 0.173 mmol) were added to IPA (1.0 mL) solution containing the compound prepared in Preparative Example B-1 (6-CHLORO-N-(2,6-DIMETHYLPHENYL)-1-METHYL-1H-PYRAZOLO[3,4-D]PYRIMIDINE-3-AMINE (50 mg, 0.173 mmol)) at room temperature, followed by stirring at 90° C. for 12 hours. TLC analysis indicated the complete consumption of the starling material. The solid obtained from the reaction mixture was filtered and washed with ethanol (2.0 mL). The filtered solid was dissolved in EtOAc (50 mL), which was washed with sat. NaHCO$_4$ solution. The combined organic layer was concentrated under reduced pressure. The obtained crude product was purified by column chromatography (MeOH/DCM (1/4)). As a result, 1-(7-((3-((2,6-dimethylphenyl)amino)-1-methyl-1H-pyrazolo[3,4-d]pyrimidine-6-yl)amino)-1,3,3-trimethyl-3,4-dihydroisoquinoline-2(1H)-yl)-2,2,2-trifluoroethane-1-one (70 mg, 0.130 mmol, 75%) was obtained as a light yellow solid.

$^1$H NMR (300 MHz, CDCl$_3$) δ 7.65 (d, J=2.2 Hz, 1H), 7.48 (dd, J=8.1, 2.2 Hz, 1H), 7.42 (s, 1H), 7.35 (s, 1H), 7.17 (d, J=7.8 Hz, 4H), 6.03 (s, 1H), 5.02 (q, J=6.9 Hz, 1H), 3.82 (s, 3H), 3.36 (d, J=15.4 Hz, H), 2.65 (d, J=15.4 Hz, 1H), 2.29 (s, 6H), 1.80 (s, 3H), 1.60 (d, J=6.9 Hz, 3H), 1.31 (s, 3H); LC/MS 538.2 [M+H$^+$].

Step 2: Preparation of N3-(2,6-dimethylphenyl)-1-methyl-N 6-(1,3,3-trimethyl-1,2,3,4-tetrahydroisoquinoline-7-yl)-1H-pyrazolo[3,4-d]pyrimidine-3,6-diamine

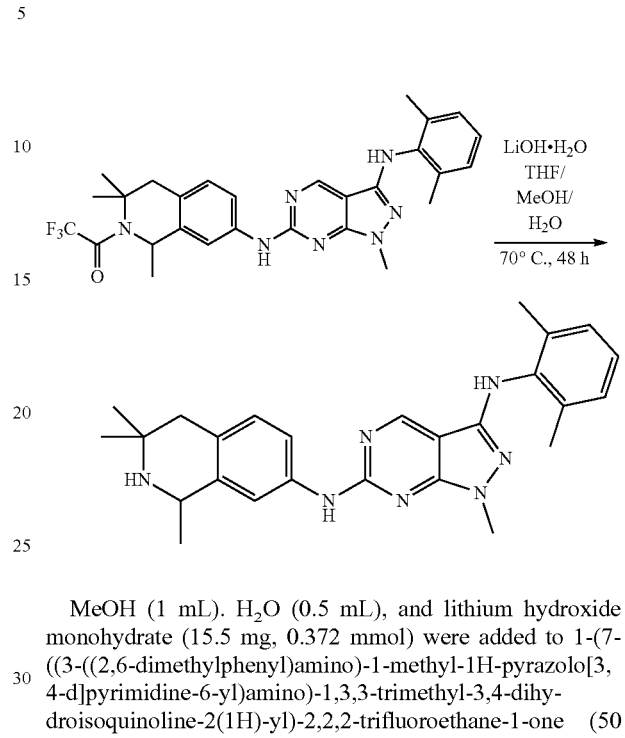

MeOH (1 mL). H$_2$O (0.5 mL), and lithium hydroxide monohydrate (15.5 mg, 0.372 mmol) were added to 1-(7-((3-((2,6-dimethylphenyl)amino)-1-methyl-1H-pyrazolo[3,4-d]pyrimidine-6-yl)amino)-1,3,3-trimethyl-3,4-dihydroisoquinoline-2(1H)-yl)-2,2,2-trifluoroethane-1-one (50 mg, 0.093 mmol) THF (5 mL) solution at room temperature, followed by stirring at 70° C. for 48 hours. TLC analysis indicated the complete consumption of the starting material. The reaction mixture was concentrated to eliminate THF. Methanol and water (5 mL) were added thereto, followed by extraction with EtOAc (15 mL×2). The combined organic layer was concentrated under reduced pressure. The obtained crude product was purified by column chromatography (MeOH/DCM (1:9)). As a result, the target compound (30 mg, 0.067 mmol, 73%) was obtained as a light yellow solid.

Example 56: Preparation of N$^3$-(2,6-dimethylphenyl)-N$^6$-(isoindolin-5-yl)-1-methyl-1H-pyrazolo[3,4-d]pyrimidine-3,6-diamine hydrochloride Step 1: Preparation of 1-(5-((3-((2,6-dimethylphenyl)amino)-1-methyl-1H-pyrazolo[3,4-d]pyrimidine-6-yl)amino)isoindolin-2-yl)-2,2,2-trifluoroethane-1-one

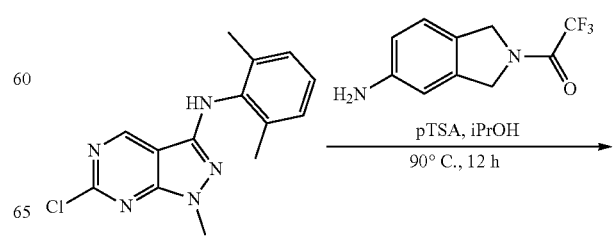

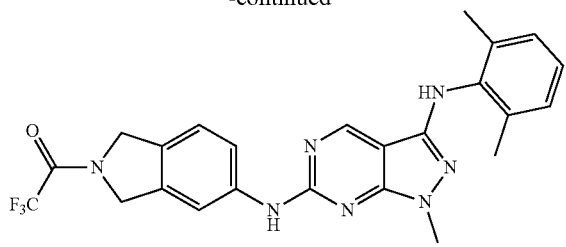

A target compound was prepared by the same manner as described in step 1 of Example 55 except that the compound prepared in Preparative Example A-8 was used instead of 1-(7-amino-1,3,3-trimethyl-3,4-dihydroisoquinoline-2(1H)-yl)-2,2,2-trifluoroethane-1-one.

¹H NMR (300 MHz, CDCl₃) δ 7.85 (d, J=15.6 Hz, 1H), 7.52-7.45 (m, 1H), 7.44 (s, 1H), 7.31-7.24 (m, 2H), 7.23-7.15 (m, 3H), 5.92 (s, 1H), 5.04 (d, J=10.4 Hz, 2H), 4.93 (d, J=13.3 Hz, 2H), 3.84 (s, 3H), 2.30 (s, 6H); LC/MS 482.2 [M+H⁺]

Step 2: Preparation of tert-butyl-5-((3-((2,6-dimethylphenyl)amino)-1-methyl-1H-pyrazolo-(3,4-dipyrimidine-6-yl)amino)isoindolin-2-carboxylate

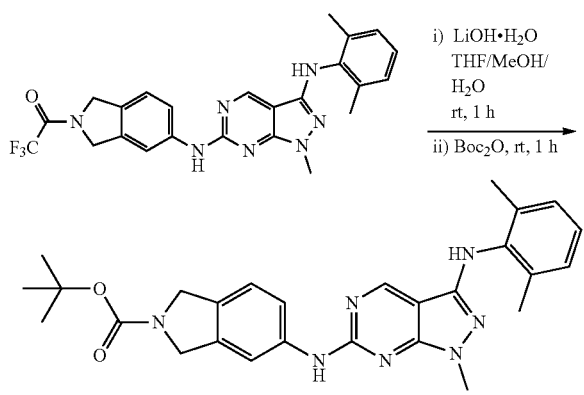

A target compound was prepared by the same manner as described in step 2 of Example 55 except that 1-(5-((3-((2,6-dimethylphenyl)amino)-1-methyl-1H-pyrazolo[3,4-d]pyrimidine-6-yl)amino)isoindolin-2-yl)-2,2,2-trifluoroethane-1-one prepared in step 1 above was used instead of 1-(7-((3-((2,6-dimethylphenyl)amino)-1-methyl-1H-pyrazolo[3,4-d]pyrimidine-6-yl)amino)-1,3,3-trimethyl-3,4-dihydroisoquinoline-2(1H)-yl)-2,2,2-trifluoroethane-1-one.

¹H NMR (300 MHz, CDCl₃) δ 7.70 (d, J=7.5 Hz, 1H), 7.46 (t, J=7.7 Hz, 1H), 7.42 (s, 1H), 7.37 (s, 1H), 7.25-7.11 (m, 4H), 5.99 (s, 1H), 4.76-4.61 (m, 4H), 3.82 (d, J=2.6 Hz, 3H), 2.29 (s, 6H), 1.54 (s, 9H); LC/MS 486.2 [M+H⁺].

Step 3: Preparation of N3-(2,6-dimethylphenyl)-N6-(isoindolin-5-yl)-1-methyl-1H-pyrazolo[3,4-d]pyrimidine-3,6-diamine hydrochloride

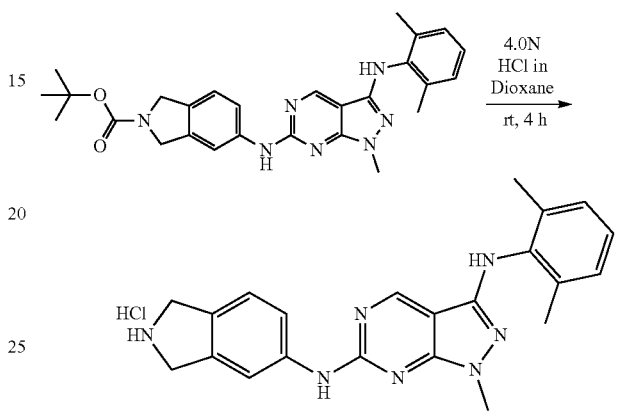

4.0 N HCl dioxane (0.2 mL) solution was added to tertbutyl-5-((3-((2,6-dimethylphenyl)amino)-1-methyl-1H-pyrazolo[3,4-d]pyrimidine-6-yl)amino)isoindolin-2-carboxylat (22 mg, 0.045 mmol) DCM (5 mL) solution a room temperature, followed by stirring at room temperature for 1 hour. TLC analysis indicated the complete consumption of the starting material. The solid obtained from the reaction mixture was filtered and washed with DCM. As a result, the target compound (N3-(2,6-dimethylphenyl)-N6-(isoindolin-5-yl)-1-methyl-1H-pyrazolo[3,4-d]pyrimidin c-3,6-diamine hydrochloride (16 mg, 0.041 mmol, 84%)) was obtained as a white solid HCL salt.

Example 57: Preparation of 1-(4-methyl-3-((1-methyl-6-((1,2,3,4-tetrahydroisoquinoline-7-yl)amino)-1H-pyrazolo[3,4-d]pyrimidine-3-yl)amino)phenyl)-3-(3-(trifluoromethyl)phenyl)urea Step 1: Preparation of 1-(4-methyl-3-((1-methyl-6-((2-(2,2,2-trifluoroacetyl)-1,2,3,4-tetrahydroisoquinoline-7-yl)amino)-1H-pyrazolo[3,4-d]pyrimidine-3-yl)amino)phenyl)-3-(3-(trifluoromethyl)phenyl)urea

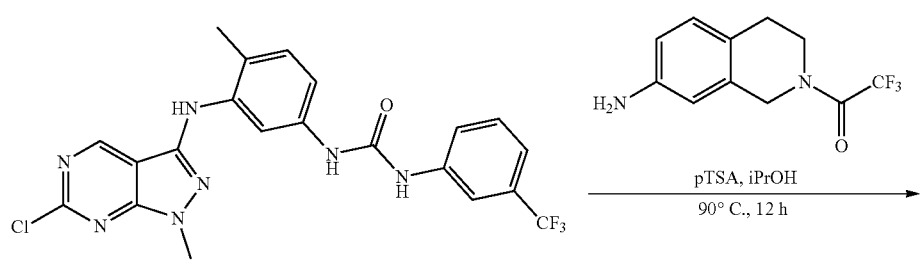

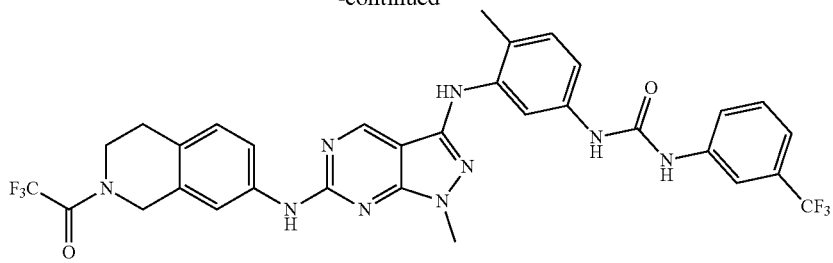

A target compound was prepared by the same manner as described in step 1 of Example 55 except that the compound prepared in Preparative Example B-28 was used instead of the compound prepared in Preparative Example B-1 and the compound prepared in Preparative Example A-2 was used instead of 1-(7-amino-1,3,3-trimethyl-3,4-dihydroisoquinoline-2(1H)-yl)-2,2,2-trifluoroethane-1one.

$^1$H NMR (300 MHz, MeOD) δ 8.48 (s, 1H), 7.72-7.46 (m, 5H), 7.34 (t, J=7.9 Hz, 1H), 7.20 (d, J=7.7 Hz, 1H), 7.17-7.04 (m, 3H), 4.83-4.71 (m, 2H), 3.87-3.81 (m, 2H), 3.81-3.75 (m, 3H), 2.98-2.88 (m, 3H), 2.25 (s, 3H); LC/MS 683.8 [M+H$^+$].

Step 2: Preparation of 1-(4-methyl-3-((1-methyl-6-((1,2,3,4-tetrahydroisoquinoline-7-yl)amino)-1H-pyrazolo[3,4-d]pyrimidine-3-yl)amino)phenyl)-3-(3-(trifluoromethyl)phenyl)urea

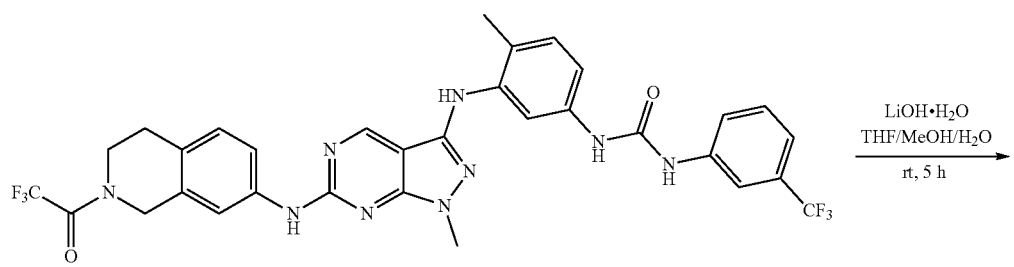

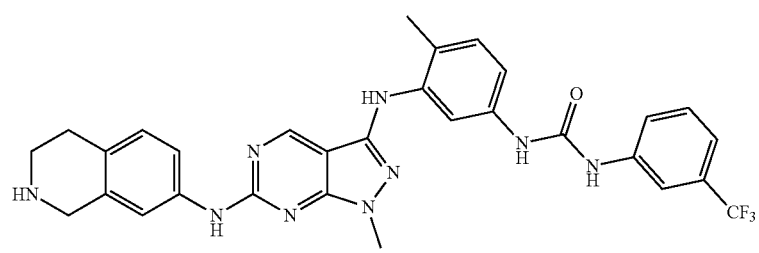

A target compound was prepared by the same manner as described in step 2 of Example 55 except that 1-(4-methyl-3-((1-methyl-6-((2-(2,2,2-trifluoroacetyl)-1,2,3,4-tetrahydroisoquinoline-7-yl)amino)-1H-pyrazolo[3,4-d]pyrimidine-3-yl)amino)phenyl)-3-(3-(trifluoromethyl)phenyl)urea prepared in step 1 above was used instead of 1-(7-((3-((2,6-dimethylphenyl)amino)-1-methyl-1H-pyrazolo[3,4-d]pyrimidine-6-yl)amino)-1,3,3-trimethyl-3,4-dihydroisoquinoline-2(1H)-yl)-2,2,2-trifluoromethane-1-one.

Example 58: Preparation of N6-(1,1-dimethyl-1,2,3,4-tetrahydroisoquinolin-7-yl)-N 3-(2,6-dimethylphenyl)-1-methyl-1H-pyrazolo[3,4-d]pyrimidine-3,6-diamine Step 1: Preparation of 1-(7-((3-((2,6-dimethylphenyl)amino)-1-methyl-1H-pyrazolo[3,4-d]pyrimidine-6-yl)amino)-1,1-dimethyl-3,4-dihydroisoquinoline-2(1H)-yl)-2,2,2-trifluoroethane-1-one

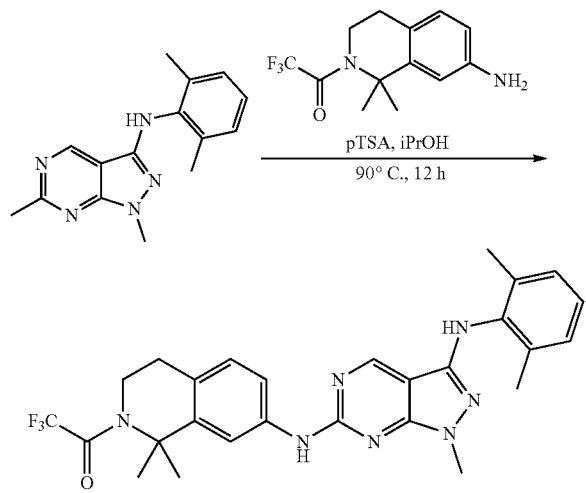

A target compound was prepared by the same manner as described in step 1 of Example 55 except that the compound prepared in Preparative Example A-9 was used instead of 1-(7-amino-1,3,3-trimethyl-3,4-dihydroisoquinoline-2(1H)-yl)-2,2,2-trifluoroethane-1-one.
¹H NMR (300 MH-z, CDCl₃) δ 7.94 (s, 1H), 7.42 (s, 1H), 7.28-7.21 (m, 2H), 7.20-7.13 (m, 3H), 7.06 (d, J=8.2 Hz, 1H), 5.91 (s, 1H), 3.80 (s, 3H), 3.66 (t, J=5.2 Hz, 2H), 2.87 (t, J=5.2 Hz, 2H), 2.27 (s, 6H), 1.88 (s, 6H); LC/MS 523.9 [M+H⁺].

Step 2: Preparation of N6-(1,1-dimethyl-1,2,3,4-tetrahydroisoquinoline-7-yl)-N 3-(2,6-dimethylphenyl)-1-methyl-1H-pyrazolo[3,4-d]pyrimidine-3,6-diamine

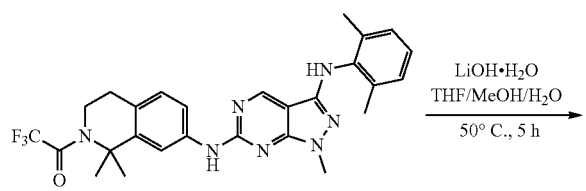

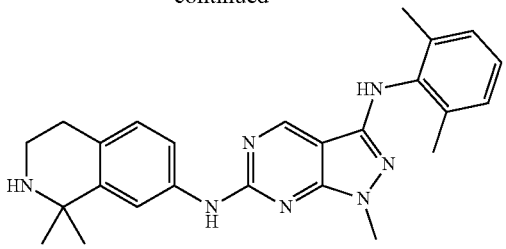

A target compound was prepared by the same manner as described in step 2 of Example 55 except that 1-(7-((3-((2,6-dimethylphenyl)amino)-1-methyl-1H-pyrazolo[3,4-d]pyrimidine-6-yl)amino)-1,1-dimethyl-3,4-dihydroisoquinoline-2(1H)-yl)-2,2,2-trifluoroethane-1-one prepared in step 1 above was used instead of 1-(7-((3-((2,6-dimethylphenyl)amino)-1-methyl-1H-pyrazolo[3,4-d]pyrimidine-6-yl)amino)-1,3,3-trimethyl-3,4-dihydroisoquinoline-2(1H)-yl)-2,2,2-trifluoroethane-1-one.

Example 59: Preparation of N3-(2,6-dimethylphenyl)-1-methyl-N 6-(1,1,2-trimethyl-1,2,3,4-tetrahydroisoquinoline-7-yl)-1H-pyrazolo[3,4-d]pyrimidine-3,6-diamine

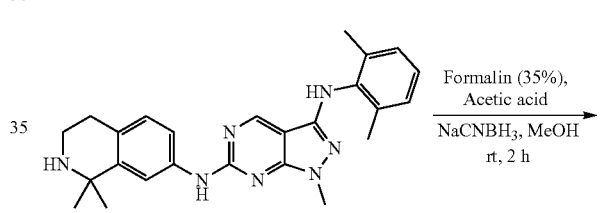

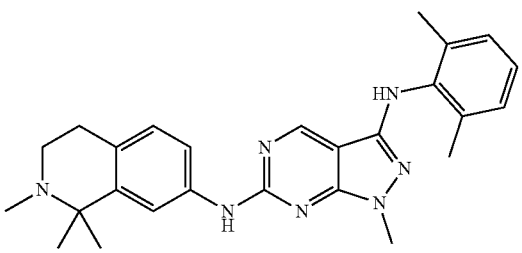

A target compound was prepared by the same manner as described in Example 17 except that N6-(1,1-dimethyl-1,2,3,4-tetrahydrisoquinoline-7-yl)-N3-(2,6-dimethylphenyl)-1-methyl-1H-pyrazolo[3,4-d]pyrimidine-3,6-diamine prepared in Example 58 was used instead of N3-(2,6-dimethylphenyl)-1-methyl-N6-(1,2,3,4-tetrahydroisoquinoline-7-yl)-1H-pyrazolo[3,4-d]pyrimidine-3,6-diamine.

Example 60: Preparation of 1-(7-((3-((2,6-dimethylphenyl)amino)-1-methyl-1H-pyrazolo[3,4-d]pyrimidine-6-yl)amino)-1,1-dimethyl-3,4-dihydroisoquinoline-2(1H)-yl)ethane-1-one

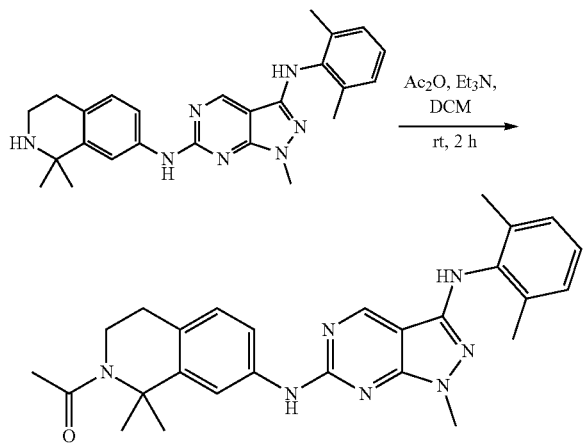

A target compound was prepared by the same manner as described in Example 13 except that N6-(1,1-dimethyl-1,2,3,4-tetrahydroisoquinoline-7-yl)-N3-(2,6-dimethylphenyl)-1-methyl-1H-pyrazolo[3,4-d]pyrimidine-3,6-diamine prepared in Example 58 was used instead of N3-(2,6-dichlorophenyl)-1-methyl-N6-(1,2,3,4-tetrahydroisoquinoline-7-yl)-1H-pyrazolo[3,4-d]pyrimidine-3,6-diamine.

Example 61: Preparation of 1-(7-((3-((2,6-dimethylphenyl)amino)-1-methyl-1H-pyrazolo[3,4-d]pyrimidine-6-yl)amino)-1-methyl-3,4-dihydroisoquinoline-2(1H)-yl)ethane-1-one

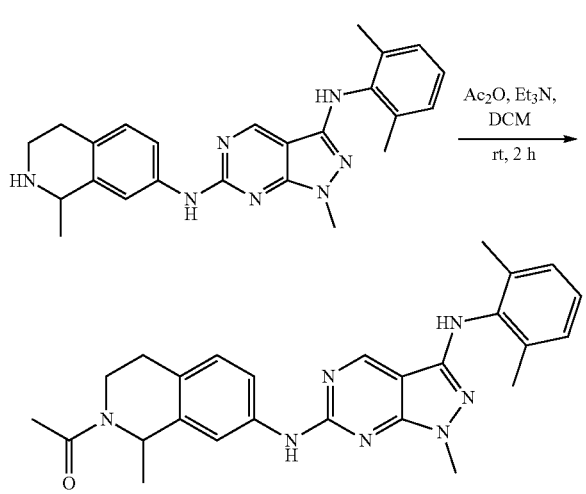

A target compound was prepared by the same manner as described in Example 13 except that the compound prepared in Example 20 was used instead of N3-(2,6-dichlorophenyl)-1-methyl-N6-(1,2,3,4-tetrahydroisoquinoline-7-yl)-1H-pyrazolo[3,4-d]pyrimidine-3,6-diamine.

Example 62: Preparation of N6-(1,2-dimethyl-1,2,3,4-tetrahydroisoquinoline-7-yl)-N 3-(2,6-dimethylphenyl)-1-methyl-1H-pyrazolo[3,4-d]pyrimidine-3,6-diamine

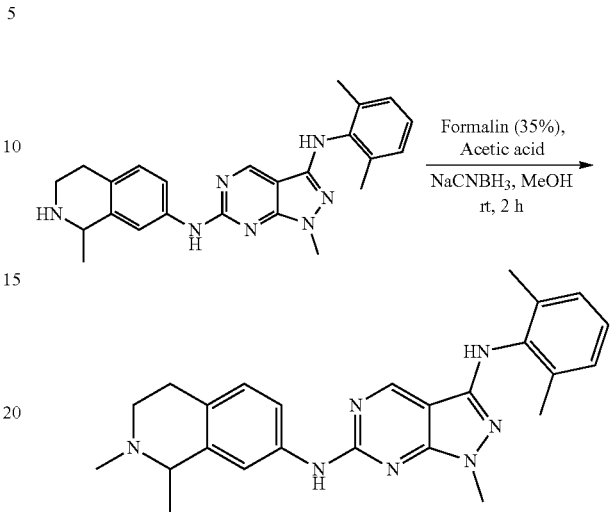

A target compound was prepared by the same manner as described in Example 17 except that the compound prepared in Example 20 was used instead of N3-(2,6-dimethylphenyl)-1-methyl-N6-(1,2,3,4-tetrahydroisoquinoline-7-yl)-1H-pyrazolo[3,4-d]pyrimidine-3,6-diamine.

Example 63: Preparation of N3-(2,6-dimethylphenyl)-1-methyl-N 6-(2,4,4-trimethyl-1,2,3,4-tetrahydroisoquinoline-7-yl)-1H-pyrazolo[3,4-d]pyrimidine-3,6-diamine

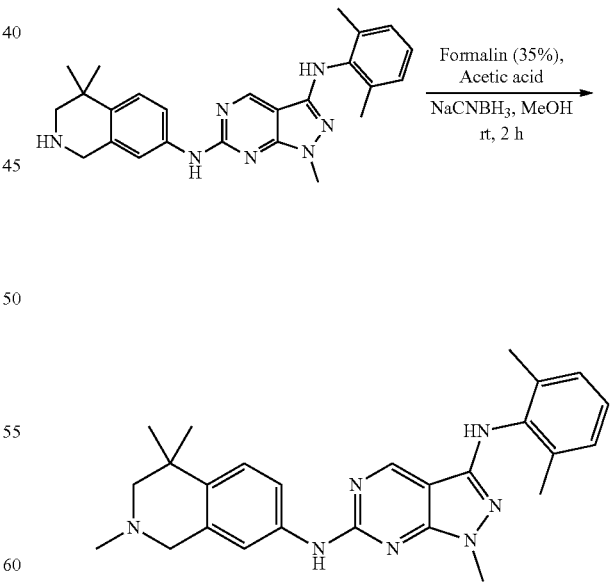

A target compound was prepared by the same manner as described in Example 17 except that the compound prepared in Example 46 was used instead of N3-(2,6-dimethylphenyl)-1-methyl-N6-(1,2,3,4-tetrahydroisoquinoline-7-yl)-1H-pyrazolo[3,4-d]pyrimidine-3,6-diamine.

Example 64: Preparation of N-(3-((6-((1,2-dimethyl-1,2,3,4-tetrahydroisoquinolin-7-yl)amino)-1-methyl-1H-pyrazolo[3,4-d]pyrimidine-3-yl)amino)-4-methylphenyl)-3-(trifluoromethyl)benzamide

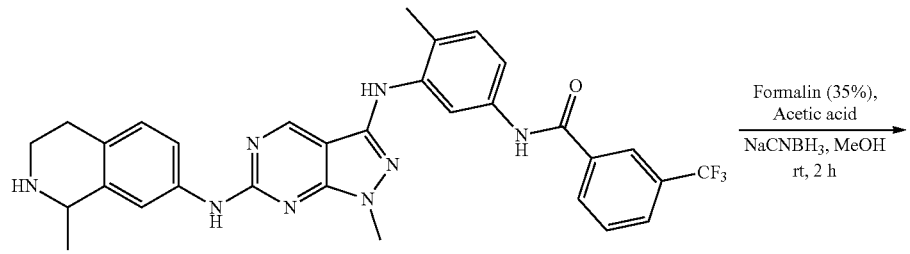

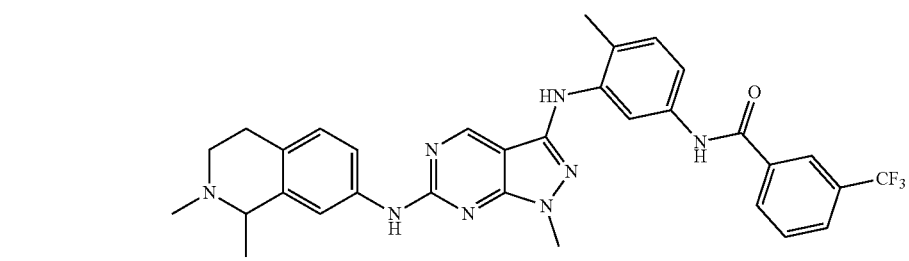

A target compound was prepared by the same manner as described in Example 17 except that the compound prepared in Example 47 was used instead of N3-(2,6-dimethylphenyl)-1-methyl-N6-(1,2,3,4-tetrahydroisoquinoline-7-yl)-1H-pyrazolo[3,4-d]pyrimidine-3,6-diamine.

Example 65: Preparation of N3-(2,6-dimethylphenyl)-N 6-(1-isopropyl-2-methyl-1,2,3,4-tetrahydroisoquinoline-7-yl)-1-methyl-1H-pyrazolo[3, 4-d]pyrimidine-3,6-diamine

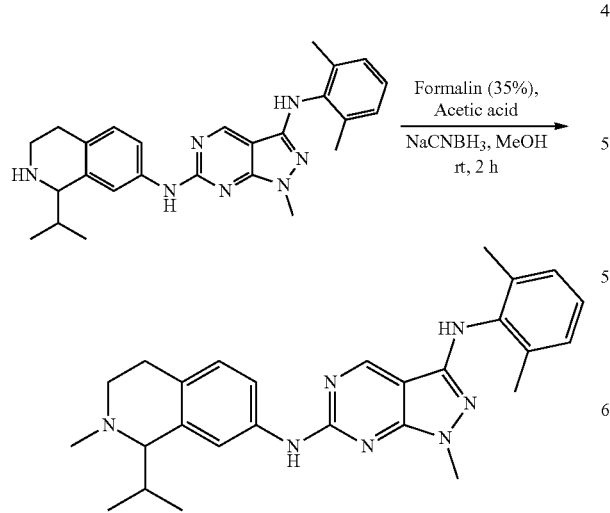

A target compound was prepared by the same manner as described in Example 17 except that the compound prepared in Example 49 was used instead of N3-(2,6-dimethylphenyl)-1-methyl-N6-(1,2,3,4-tetrahydroisoquinoline-7-yl)-1H-pyrazolo[3,4-d]pyrimidine-3,6-diamine.

Example 66: Preparation of N3-(2,6-dimethylphenyl)-1-methyl-N 6-(2,3,3-trimethyl-1,2,3,4-tetrahydroisoquinoline-7-yl)-1H-pyrazolo[3,4-d]pyrimidine-3,6-diamine

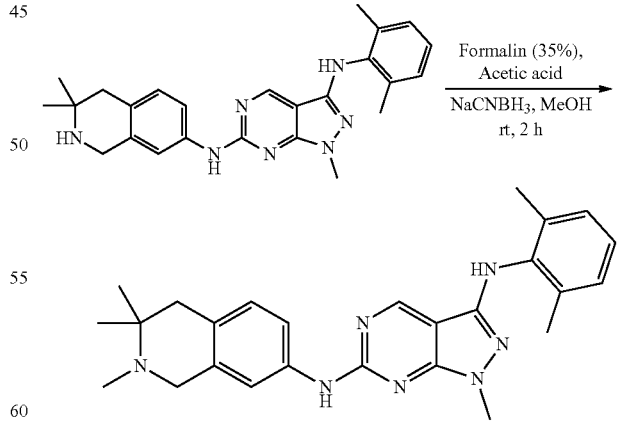

A target compound was prepared by the same manner as described in Example 17 except that the compound prepared in Example 53 was used instead of N3-(2,6-dimethylphenyl)-1-methyl-N6-(1,2,3,4-tetrahydroisoquinoline-7-yl)-1H-pyrazolo[3,4-d]pyrimidine-3,6-diamine.

Example 67: Preparation of N3-(2,6-dimethylphenyl)-1-methyl-N 6-(1,2,3,3-tetramethyl-1,2,3,4-tetrahydroisoquinoline-7-yl)-1H-pyrazolo[3,4-d]pyrimidine-3,6-diamine

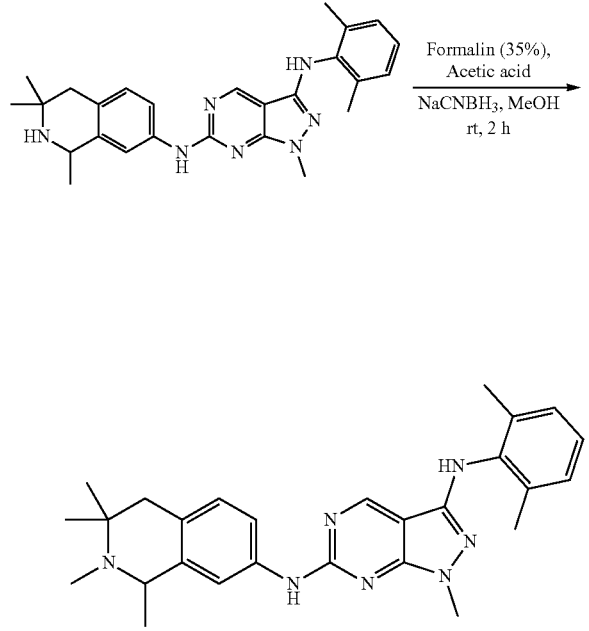

A target compound was prepared by the same manner as described in Example 17 except that the compound prepared in Example 55 was used instead of N3-(2,6-dimethylphenyl)-1-methyl-N6-(1,2,3,4-tetrahydroisoquinoline-7-yl)-1H-pyrazolo[3,4-d]pyrimidine-3,6-diamine.

Example 68: Preparation of 1-(7-((3-((2,6-dimethylphenyl)amino)-1-methyl-1H-pyrazolo[3,4-d]pyrimidine-6-yl)amino)-4,4-dimethyl-3,4-dihydroisoquinoline-2(1H)-yl)ethane-1-one

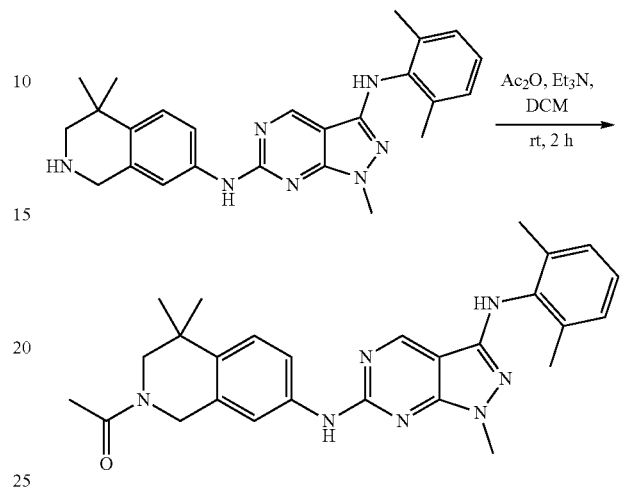

A target compound was prepared by the same manner as described in Example 13 except that the compound prepared in Example 46 was used instead of N3-(2,6-dichlorophenyl)-1-methyl-N6-(1,2,3,4-tetrahydroisoquinoline-7-yl)-1H-pyrazolo[3,4-d]pyrimidine-3,6-diamine.

Example 69: Preparation of N-(3-((6-((2-acctyl-1-methyl-1,2,3,4-tetrahydroisoquinoline-7-yl)amino)-1-methyl-1H-pyrazolo[3,4-d]pyrimidine-3-yl)amino)-4-methylphenyl)-3-(trifluoromethyl)benzamide

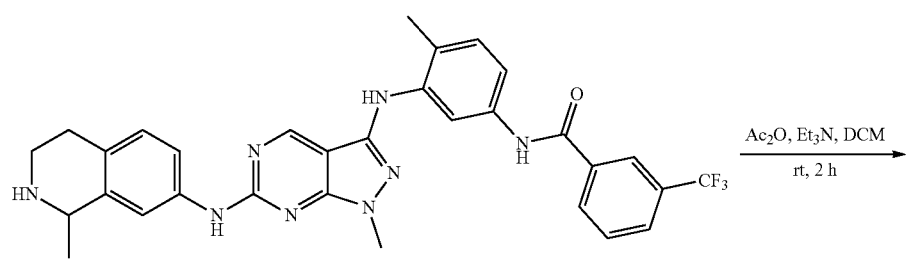

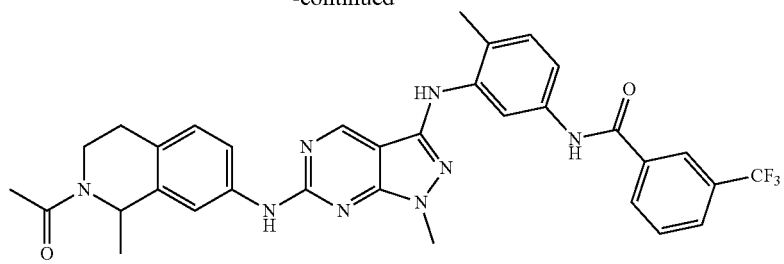

A target compound was prepared by the same manner as described in Example 13 except that the compound prepared in Example 47 was used instead of N3-(2,6-dichlorophenyl)-1-methyl-N6-(1,2,3,4-tetrahydroisoquinoline-7-yl)-1H-pyrazolo[3,4-d]pyrimidine-3,6-diamine.

Example 70: Preparation of 1-(7-((3-((2,6-dimethylphenyl)amino)-1-methyl-1H-pyrazolo[3,4-d]pyrimidine-6-yl)amino)-1-isopropyl-3,4-dihydroisoquinoline-2(1H)-yl) ethane-1-one

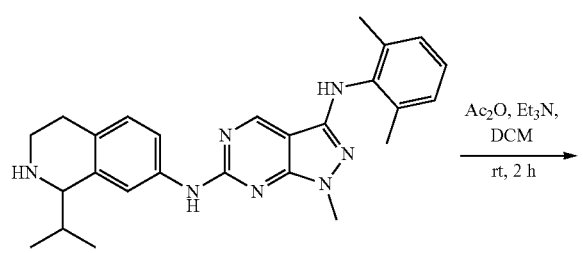

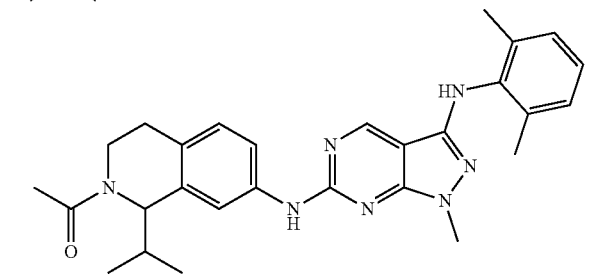

A target compound was prepared by the same manner as described in Example 13 except that the compound prepared in Example 49 was used instead of N3-(2,6-dichlorophenyl)-1-methyl-N6-(1,2,3,4-tetrahydroisoquinoline-7-yl)-1H-pyrazolo[3,4-d]pyrimidine-3,6-diamine.

Example 71: Preparation of 1-(7-((3-((2,6-dimethylphenyl)amino)-1-methyl-1H-pyrazolo[3,4-d]pyrimidine-6-yl)amino)-3,3-dimethyl-3,4-dihydroisoquinoline-2(1H)-yl)ethane-1-one

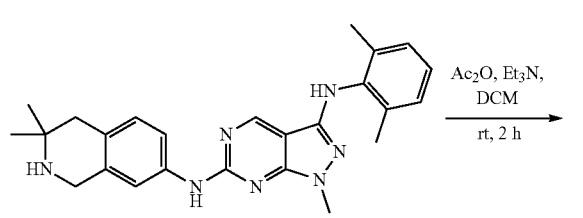

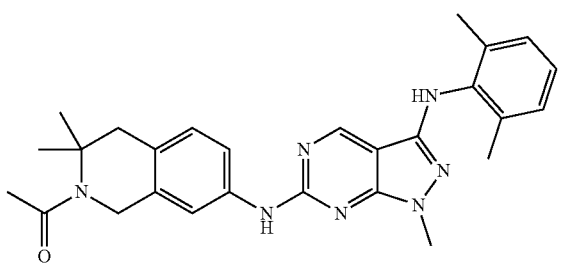

A target compound was prepared by the same manner as described in Example 13 except that the compound prepared in Example 53 was used instead of N3-(2,6-dichlorophenyl)-1-methyl-N6-(1,2,3,4-tetrahydroisoquinoline-7-yl)-1H-pyrazolo[3,4-d]pyrimidine-3,6-diamine.

Example 72: Preparation of 1-(5-((3-((2,6-dimethylphenyl)amino)-1-methyl-1H-pyrazolo[3,4-d]pyrimidine-6-yl)amino)isoindolin-2-yl)ethane-1-one

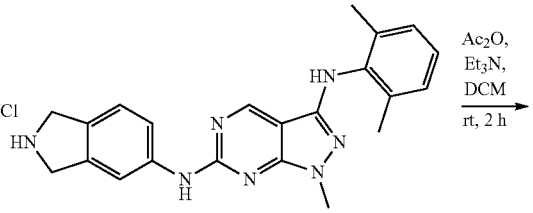

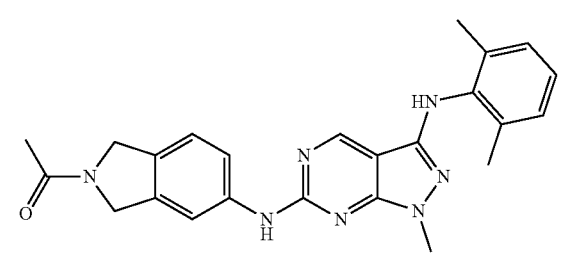

A target compound was prepared by the same manner as described in Example 13 except that the compound prepared in Example 55 was used instead of N3-(2,6-dichlorophenyl)-1-methyl-N6-(1,2,3,4-tetrahydroisoquinoline-7-yl)-1H-pyrazolo[3,4-d]pyrimidine-3,6-diamine.

Example 73: Preparation of 1-(7-((3-((2,6-dimethylphenyl)amino)-1-methyl-1H-pyrazolo[3,4-d]pyrimidine-6-yl)amino)-1,3,3-trimethyl-3,4-dihydroisoquinoline-2(1H)-yl)ethane-1-one

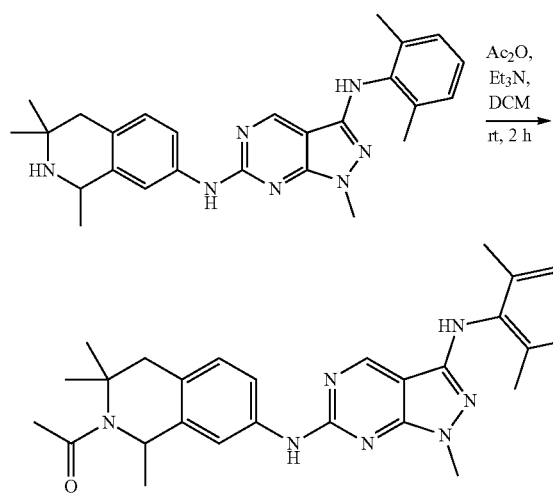

A target compound was prepared by the same manner as described in Example 13 except that the compound prepared in Example 55 was used instead of N3-(2,6-dichlorophenyl)-1-methyl-N6-(1,2,3,4-tetrahydroisoquinoline-7-yl)-1H-pyrazolo[3,4-d]pyrimidine-3,6-diamine.

Example 74: Preparation of N3-(2,6-dimethylphenyl)-1-methyl-N 6-(2-methylisoindolin-5-yl)-1H-pyrazolo[3,4-d]pyrimidine-3,6-diamine

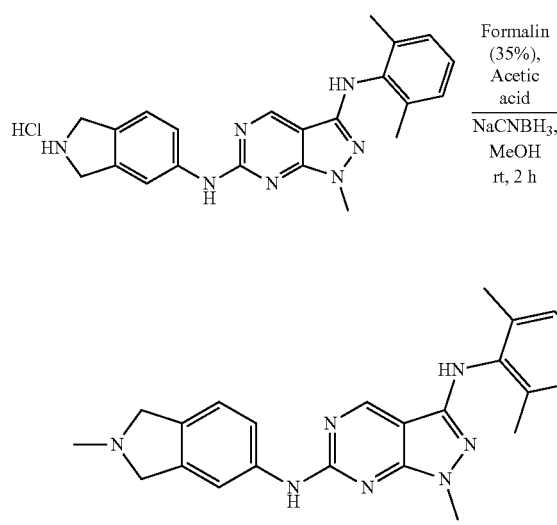

A target compound was prepared by the same manner as described in Example 17 except that the compound prepared in Example 56 was used instead of N3-(2,6-dimethylphenyl)-1-methyl-N6-(1,2,3,4-tetrahydroisoquinoline-7-yl)-1H-pyrazolo[3,4-d]pyrimidine-3,6-diamine.

Example 75: Preparation of N3-(2,6-dimethylphenyl)-1-methyl-N 6-(5,6,7,8-tetrahydronaphthalen-2-yl)-1H-pyrazolo[3,4-d]pyrimidine-3,6-diamine

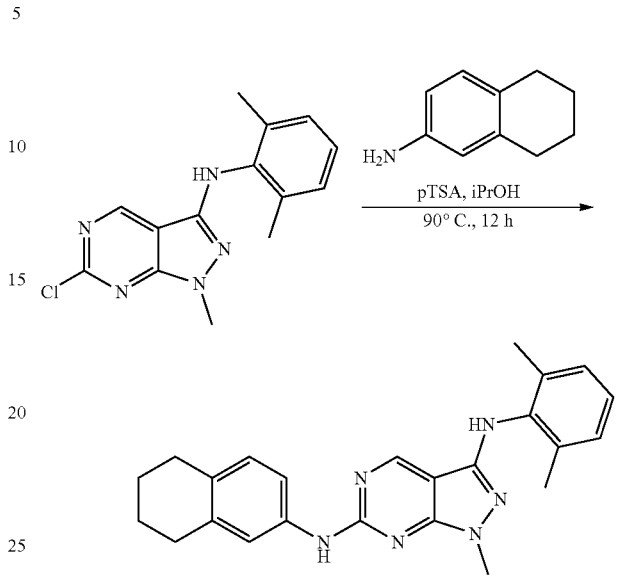

A target compound was prepared by the same manner as described in step 1 of Example 55 except that 5,6,7,8-tetrahydronaphthalene-2-amine was used instead of 1-(7-amino-1,3,3-trimethyl-3,4-dihydroisoquinoline-2(1H)-yl)-2,2,2-trifluoroethane-1-one.

Example 76: Preparation of N-(4-((3-((2,6-dimethylphenyl)amino)-1-methyl-1H-pyrazolo[3,4-d]pyrimidine-6-yl)amino)phenyl)acrylamide

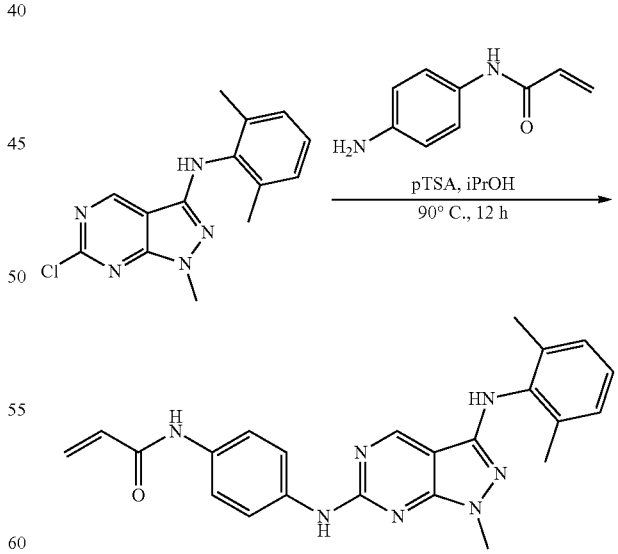

A target compound was prepared by the same manner as described in step 1 of Example 55 except that the compound prepared in Preparative Example A-10 was used instead of 1-(7-amino-1,3,3-trimethyl-3,4-dihydroisoquinoline-2(1H)-yl)-2,2,2-trifluoroethane-1-one.

Example 77: Preparation of 7-((3-((2,6-dimethylphenyl)amino)-1-methyl-1H-pyrazolo[3,4-d]pyrimidine-6-yl)amino)-3,4-dihydroisoquinoline-1(2H)-one

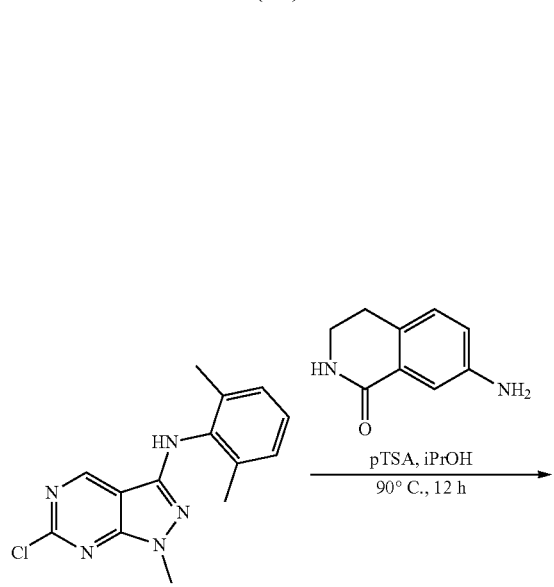

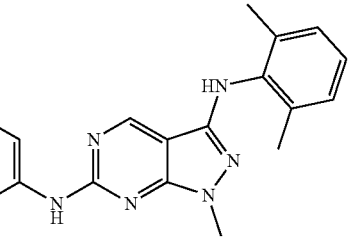

A target compound was prepared by the same manner as described in step 1 of Example 55 except that the compound prepared in Preparative Example A-11 was used instead of 1-(7-amino-1,3,3-trimethyl-3,4-dihydroisoquinoline-2(1H)-yl)-2,2,2-trifluoroethane-1-one.

Example 78: Preparation of N6-(1-isopropyl-1,2,3,4-tetrahydroisoquinoline-7-yl)-N 3-(4-(2-methoxyethoxy)-2,6-dimethylphenyl)-1-methyl-1H-pyrazolo[3,4-d]pyrimidine-3,6-diamine

Step 1: Preparation of 2,2,2-trifluoro-1-(1-isopropyl-7-((3-((4-(2-methoxyethoxy)-2,6-dimethylphenyl)amino)-1-methyl-1H-pyrazolo[3,4-d]pyrimidine-6-yl)amino)-3,4-dihydroisoquinoline-2(1H)yl)ethane-1-one

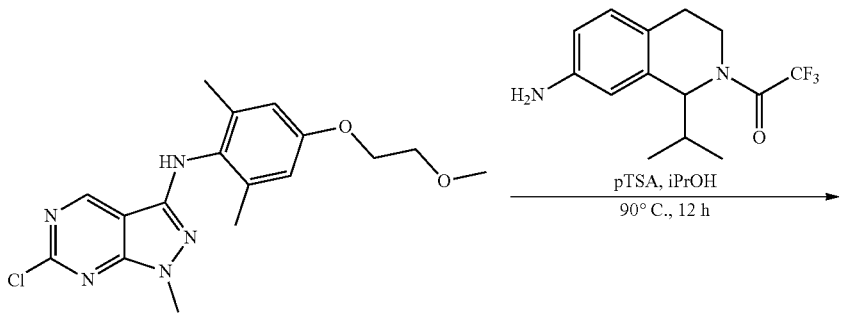

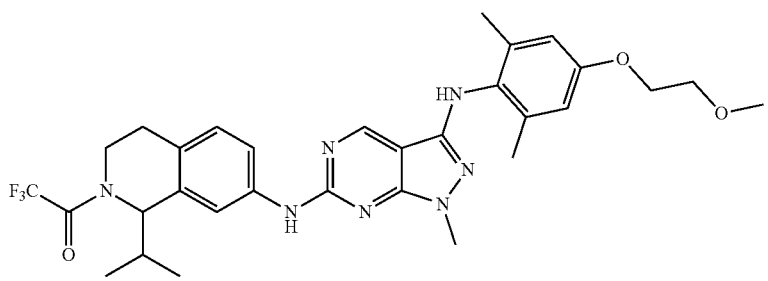

A target compound was prepared by the same manner as described in step 1 of Example 55 except that the compound prepared in Preparative Example B-10 was used instead of the compound prepared in Preparative Example B-1 and the compound prepared in Preparative Example A-6 was used instead of 1-(7-amino-1,3,3-trimethyl-3,4-dihydroisoquinoline-2(1H)-yl)-2,2,2-trifluoroethane-1-one.

$^1$H NMR (300 MHz, CDCl$_3$) δ 7.74-7.57 (m, 1H), 7.42-7.35 (m, 2H), 7.28 (s, 1H), 7.12 (dd, J=8.3, 3.8 Hz, 1H), 6.75 (s, 2H), 5.85 (s, 1H), 5.25 (d, J=9.0 Hz, 0.8H), 4.59-4.43 (m, 0.2H), 4.42-4.36 (m, 0.2H), 4.18-4.12 (m, 2H), 4.10-3.98 (m, 0.8H), 3.81 (s, 3H), 3.80-3.77 (m, 2H), 3.76-3.72 (m, 1H), 3.50 (s, 3H), 3.10-2.92 (m, 2H), 2.25 (s, 6H), 2.21-2.09 (m, 1H), 1.21-1.00 (m, 6H); LC/MS 611.9 [M+H$^+$].

Step 2: Preparation of N6-(1-isopropyl-1,2,3,4-tetrahydroisoquinoline-7-yl)-N 3-(4-(2-methoxyethoxy)-2,6-dimethylphenyl)-1-methyl-1H-pyrazolo[3,4-d]pyrimidine-3,6-diamine

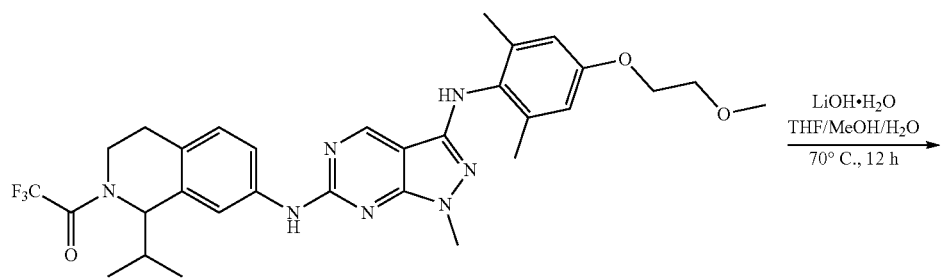

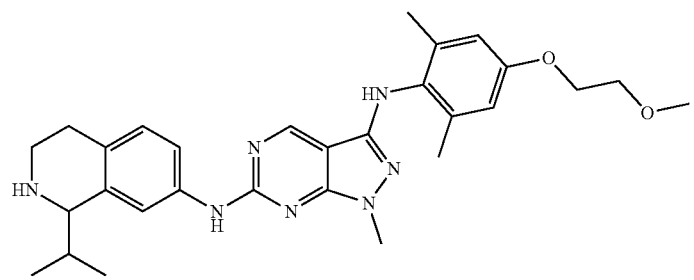

A target compound was prepared by the same manner as described in step 2 of Example 55 except that 2,2,2-trifluoro-1-(1-isopropyl-7-((3-((4-(2-methoxyethoxy)-2,6-dimethylphenyl)amino)-1-methyl-1H-pyrazolo[3,4-d]pyrimidine-6-yl)amino)-3,4-dihydroisoquinoline-2(1H)yl)ethane-1-one prepared in step 1 above was used instead of 1-(7-((3-((2,6-dimethylphenyl)amino)-1-methyl-1H-pyrazolo[3,4-d]pyrimidine-6-yl)amino)-1,3,3-trimethyl-3,4-dihydroisoquinoline-2(1H)-yl)-2,2,2-trifluoroethane-1-one.

Example 79: Preparation of N6-(1,1-dimethyl-1,2,3,4-tetrahydroisoquinoline-7-yl)-N 3-(4-(2-methoxyethoxy)-2,6-dimethylphenyl)-1-methyl-1H-pyrazolo[3,4-d]pyrimidine-3,6-diamine Step 1: Preparation of 2,2,2-trifluoro-1-(7-((3-((4-(2-methoxyethoxy)-2,6-dimethylphenyl)amino)-1-methyl-1H-pyrazolo[3,4-d]pyrimidine-6-yl)amino)-1,1-dimethyl-3,4-dihydroisoquinoline-2(1H)-yl)ethane-1-one

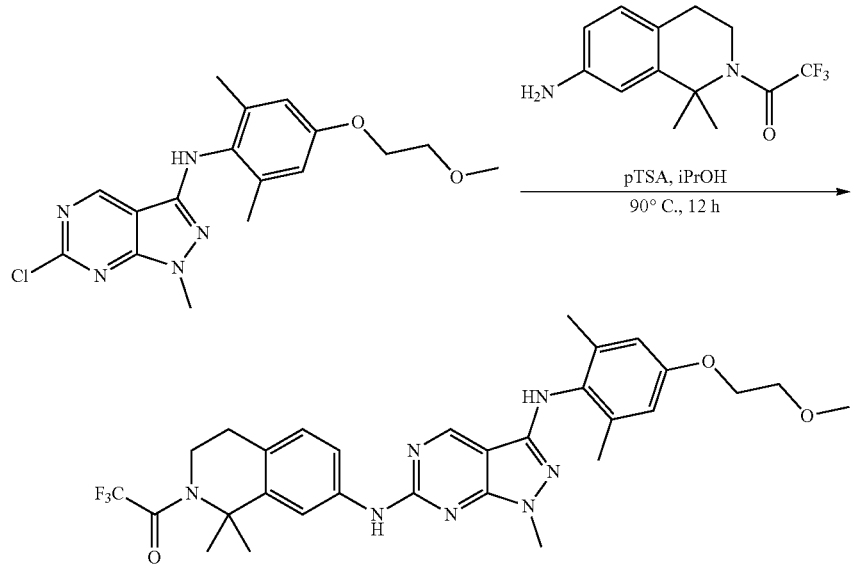

A target compound was prepared by the same manner as described in step 1 of Example 55 except that the compound prepared in Preparative Example B-10 was used instead of the compound prepared in Preparative Example B-1 and the compound prepared in Preparative Example A-9 was used instead of 1-(7-amino-1,3,3-trimethyl-3,4-dihydroisoquinoline-2(1H)-yl)-2,2,2-trifluoroethane-1-one.

$^1$H NMR (300 MHz, CDCl$_3$) δ 7.95 (s, 1H), 7.40 (s, 1H), 7.32-7.29 (m, 1H), 7.22 (s, 1H), 7.08 (d, J=8.2 Hz, 1H), 6.75 (s, 2H), 5.81 (s, 1H), 4.15 (dd, J=5.7, 3.6 Hz, 2H), 3.81 (s, 3H), 3.79 (dd, J=3.8, 2.5 Hz, 2H), 3.72-3.66 (m, 2H), 3.50 (s, 3H), 2.90 (d, J=5.2 Hz, 2H), 2.26 (s, 6H), 1.91 (s, 6H); LC/MS 597.9 [M+H$^+$].

Step 2: Preparation of N6-(1,1-dimethyl-1,2,3,4-tetrahydroisoquinoline-7-yl)-N 3-(4-(2-methoxyethoxy)-2,6-dimethylphenyl)-1-methyl-1H-pyrazolo[3,4-d]pyrimidine-3,6-diamine

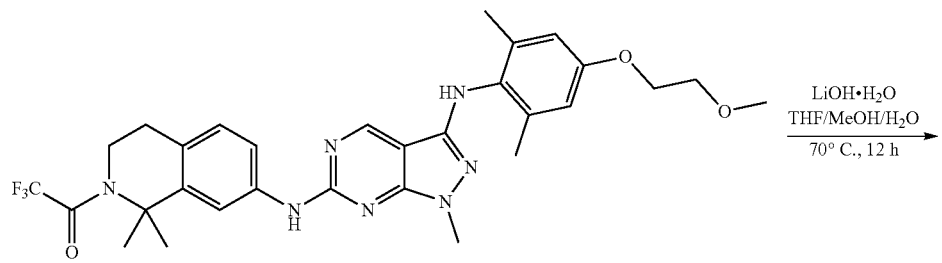

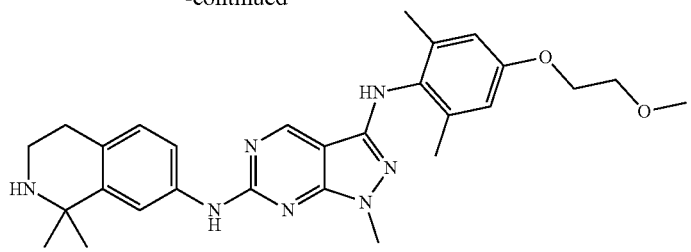

A target compound was prepared by the same manner as described in step 2 of Example 55 except that 2,2,2-trifluoro-1-(7-((3-((4-(2-methoxyethoxy)-2,6-dimethylphenyl)amino)-1-methyl-1H-pyrazolo[3,4-d]pyrimidine-6-yl)amino)-1,1-dimethyl-3,4-dihydroisoquinoline-2(1H)-yl)ethane-1-one prepared in step 2 above was used instead of 1-(7-((3-((2,6-dimethylphenyl)amino)-1-methyl-1H-pyrazolo[3,4-d]pyrimidine-6-yl)amino)-1,3,3-trimethyl-3,4-dihydroisoquinoline-2(1H)-yl)-2,2,2-trifluoroethane-1-one.

The chemical structures of the compounds of Examples 1 to 79 according to the present invention are shown in Tables 1 and 2 below, and the analytical data on the compound structure are shown in Tables 3 to 5 below.

TABLE 1

| Example | Chemical Structure |
|---|---|
| 1 | 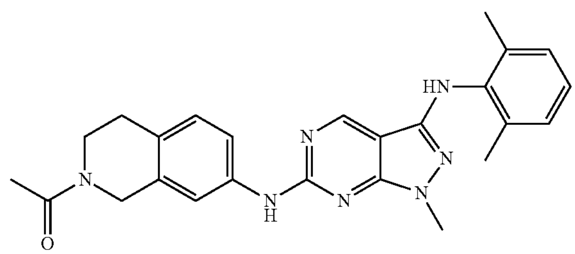 [SMILES: CC(=O)N1CCc2ccc(Nc3ncc4c(Nc5c(C)cccc5C)nn(C)c4n3)cc2C1] |
| 2 | 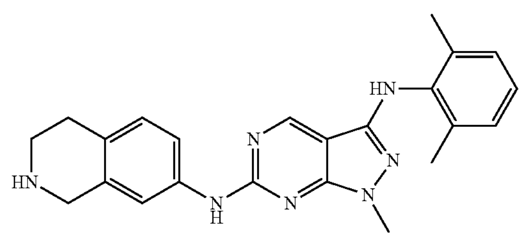 [SMILES: Cc1cccc(C)c1Nc1nn(C)c2nc(Nc3ccc4c(c3)CNCC4)ncc12] |
| 3 | 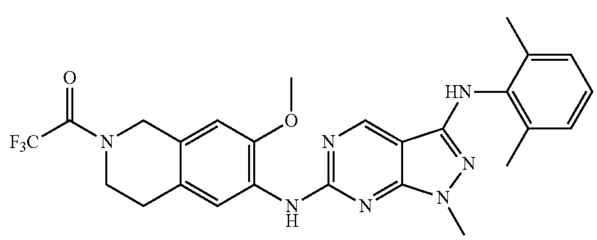 [SMILES: COc1cc2c(cc1Nc1ncc3c(Nc4c(C)cccc4C)nn(C)c3n1)CCN(C(=O)C(F)(F)F)C2] |
| 4 | 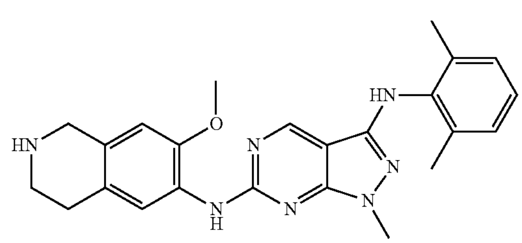 [SMILES: COc1cc2c(cc1Nc1ncc3c(Nc4c(C)cccc4C)nn(C)c3n1)CCNC2] |

TABLE 1-continued
| Example | Chemical Structure |
|---|---|
| 5 | 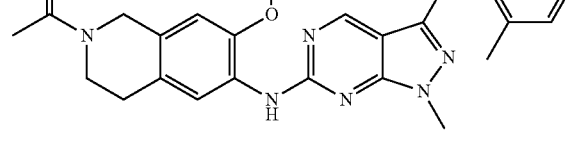 |
| 6 | 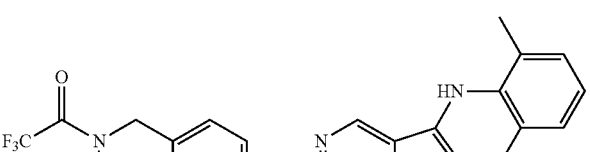 |
| 7 | 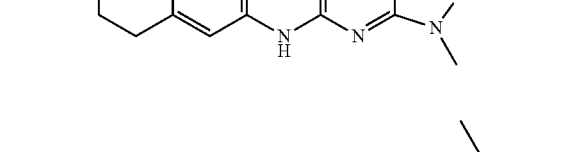 |
| 8 | 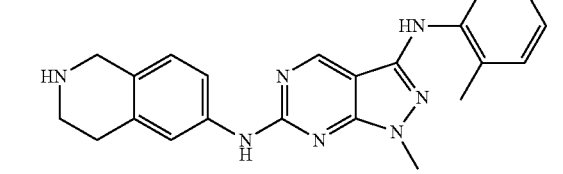 |
| 9 | 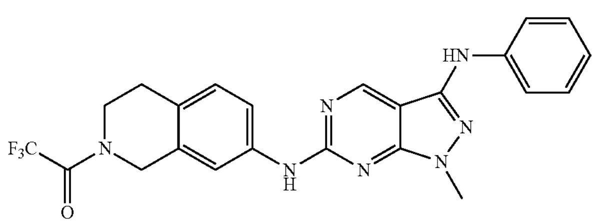 [SMILES: Cn1nc(Nc2ccccc2)c2cnc(Nc3ccc4c(c3)CN(C(=O)C(F)(F)F)CC4)nc21] |
| 10 | 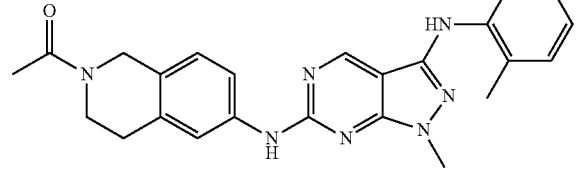 |

TABLE 1-continued
| Example | Chemical Structure |
|---|---|
| 11 | 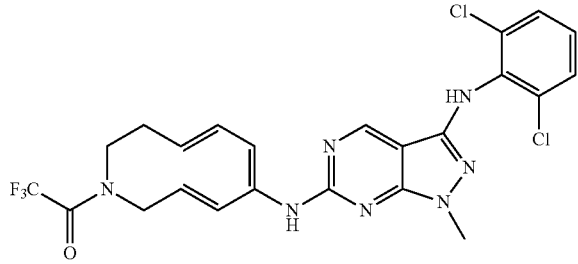 [SMILES: Cn1nc(Nc2c(Cl)cccc2Cl)c2cnc(NC3=C/C=C/CCN(C(=O)C(F)(F)F)C\C=C\3)nc21] |
| 12 | 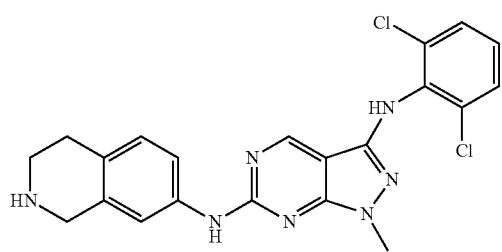 [SMILES: Cn1nc(Nc2c(Cl)cccc2Cl)c2cnc(Nc3ccc4c(c3)CNCC4)nc21] |
| 13 | 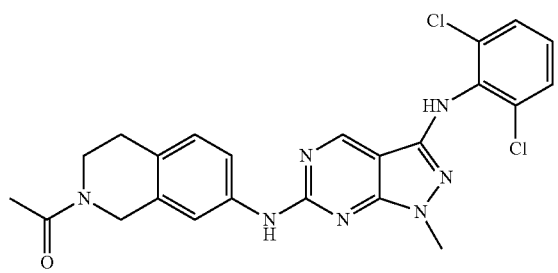 [SMILES: CC(=O)N1CCc2ccc(Nc3ncc4c(Nc5c(Cl)cccc5Cl)nn(C)c4n3)cc2C1] |
| 14 | 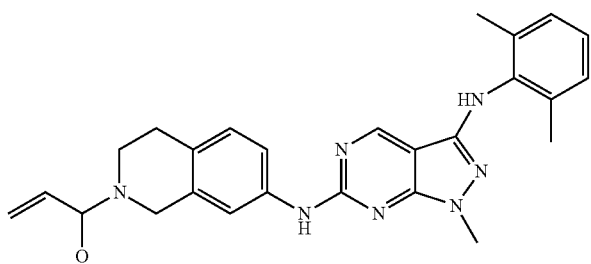 [SMILES: C=CC(O)N1CCc2ccc(Nc3ncc4c(Nc5c(C)cccc5C)nn(C)c4n3)cc2C1] |
| 15 | 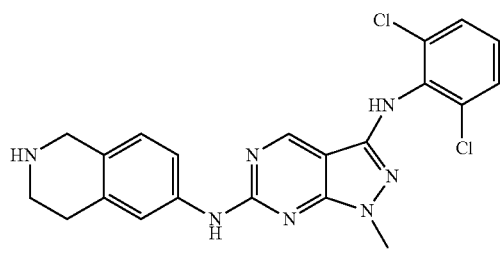 [SMILES: Cn1nc(Nc2c(Cl)cccc2Cl)c2cnc(Nc3ccc4c(c3)CCNC4)nc21] |

TABLE 1-continued
| Example | Chemical Structure |
|---|---|
| 16 | 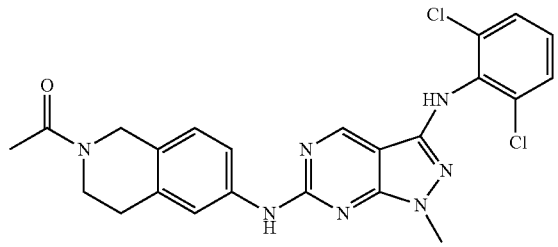 [SMILES: CC(=O)N1CCc2cc(Nc3ncc4c(Nc5c(Cl)cccc5Cl)nn(C)c4n3)ccc2C1] |
| 17 | 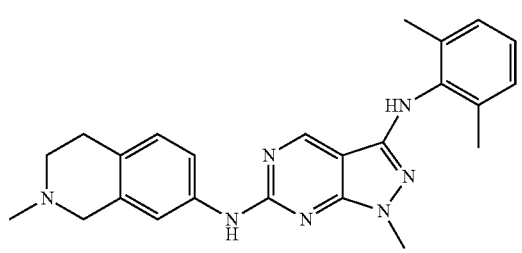 [SMILES: Cc1cccc(C)c1Nc1nn(C)c2nc(Nc3ccc4c(c3)CN(C)CC4)ncc12] |
| 18 | 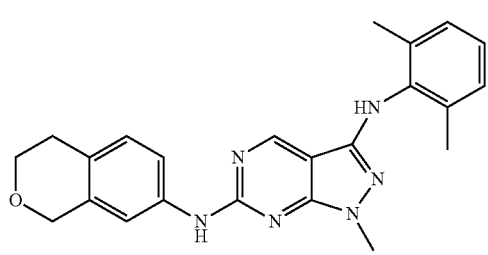 [SMILES: Cc1cccc(C)c1Nc1nn(C)c2nc(Nc3ccc4c(c3)COCC4)ncc12] |
| 19 | 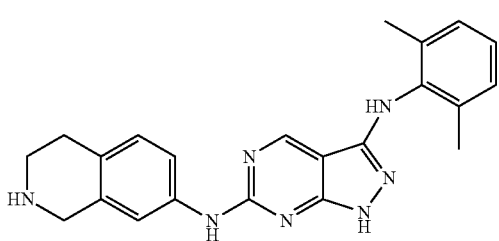 [SMILES: Cc1cccc(C)c1Nc1n[nH]c2nc(Nc3ccc4c(c3)CNCC4)ncc12] |
| 20 | 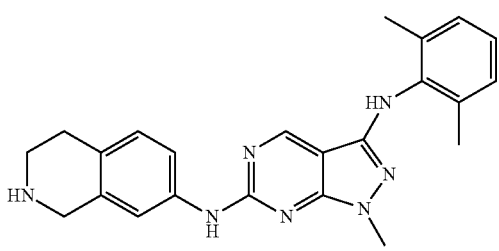 [SMILES: Cc1cccc(C)c1Nc1nn(C)c2nc(Nc3ccc4c(c3)CNCC4)ncc12] |
| 21 | 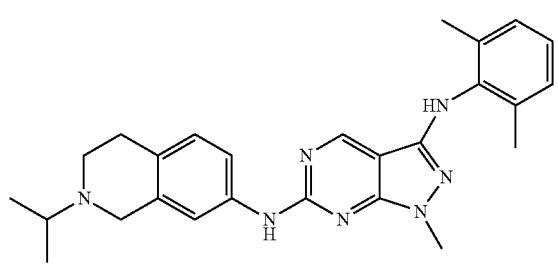 [SMILES: Cc1cccc(C)c1Nc1nn(C)c2nc(Nc3ccc4c(c3)CN(C(C)C)CC4)ncc12] |

TABLE 1-continued
| Example | Chemical Structure |
|---|---|
| 22 | 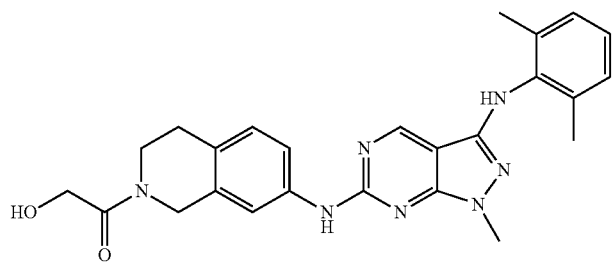 [SMILES: Cc1cccc(C)c1Nc1nn(C)c2nc(Nc3ccc4c(c3)CN(C(=O)CO)CC4)ncc12] |
| 23 | 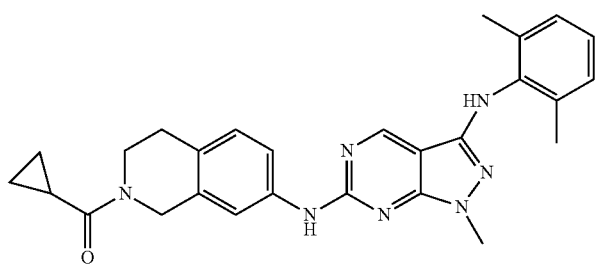 [SMILES: Cc1cccc(C)c1Nc1nn(C)c2nc(Nc3ccc4c(c3)CN(C(=O)C3CC3)CC4)ncc12] |
| 24 | 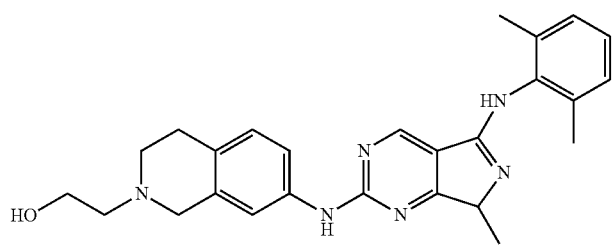 [SMILES: Cc1cccc(C)c1NC1=NC(C)c2nc(Nc3ccc4c(c3)CN(CCO)CC4)ncc21] |
| 25 | 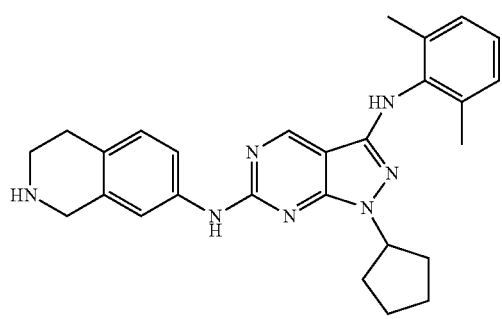 [SMILES: Cc1cccc(C)c1Nc1nn(C2CCCC2)c2nc(Nc3ccc4c(c3)CNCC4)ncc12] |
| 26 | 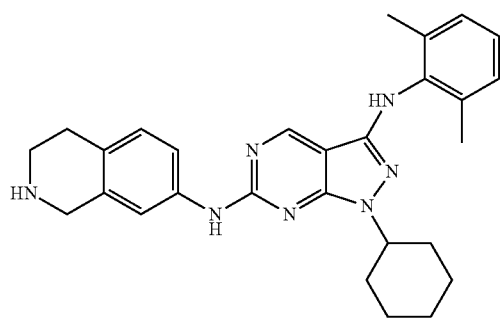 [SMILES: Cc1cccc(C)c1Nc1nn(C2CCCCC2)c2nc(Nc3ccc4c(c3)CNCC4)ncc12] |

TABLE 1-continued

| Example | Chemical Structure |
|---|---|
| 27 | 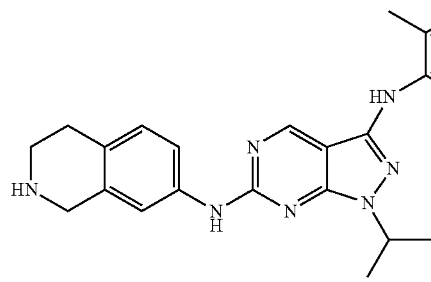 |
| 28 | 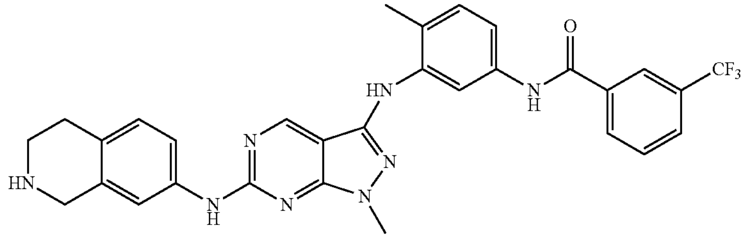 [SMILES: Cc1ccc(NC(=O)c2cccc(C(F)(F)F)c2)cc1Nc1nn(C)c2nc(Nc3ccc4c(c3)CNCC4)ncc12] |
| 29 | 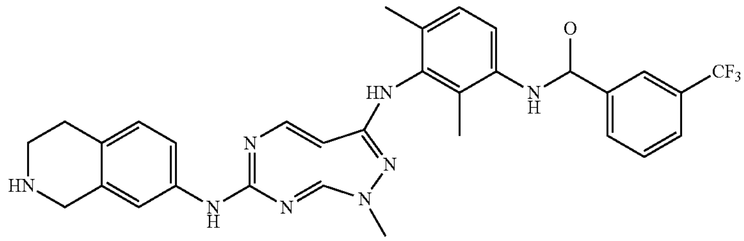 [SMILES: Cc1ccc(NC(O)c2cccc(C(F)(F)F)c2)c(C)c1Nc1ccnc(Nc2ccc3c(c2)CNCC3)ncn(C)n1] |
| 30 | 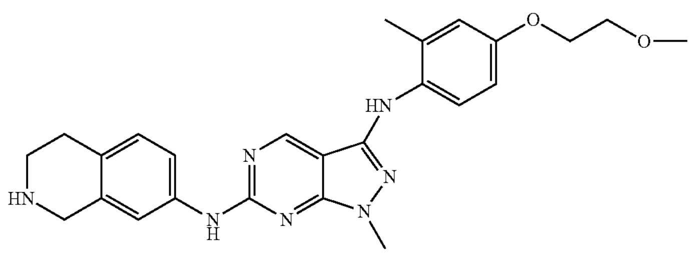 [SMILES: COCCOc1ccc(Nc2nn(C)c3nc(Nc4ccc5c(c4)CNCC5)ncc23)c(C)c1] |
| 31 | 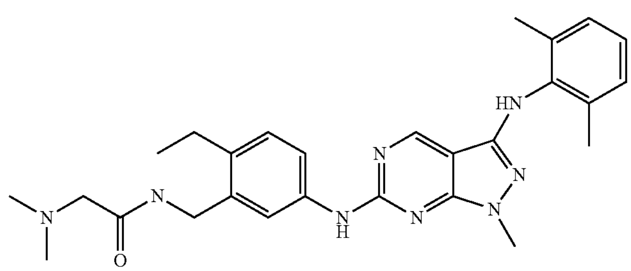 [SMILES: CCc1ccc(Nc2ncc3c(Nc4c(C)cccc4C)nn(C)c3n2)cc1CNC(=O)CN(C)C] |
| 32 | 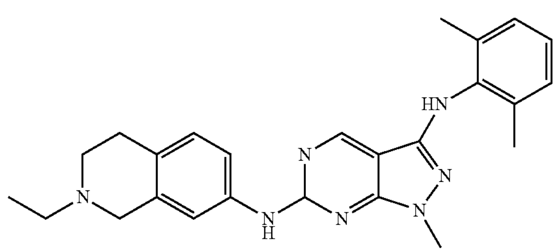 [SMILES: CCN1CCc2ccc(NC3N=c4c(c(Nc5c(C)cccc5C)nn4C)=CN3)cc2C1] |

TABLE 1-continued
| Example | Chemical Structure |
| --- | --- |
| 33 | 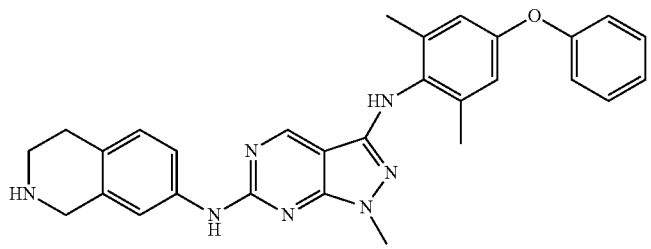 [SMILES: Cc1cc(Oc2ccccc2)cc(C)c1Nc1nn(C)c2nc(Nc3ccc4c(c3)CNCC4)ncc12] |
| 34 | 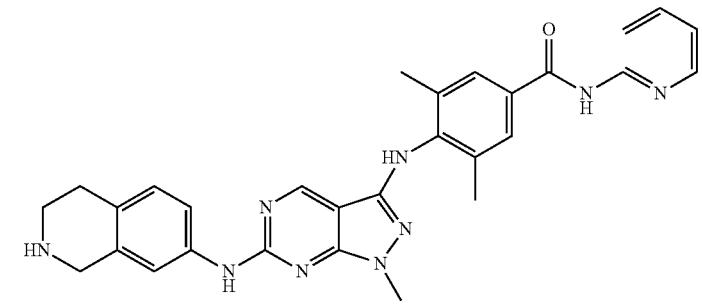 [SMILES: C=C/C=C\N=C\NC(=O)c1cc(C)c(Nc2nn(C)c3nc(Nc4ccc5c(c4)CNCC5)ncc23)c(C)c1] |
| 35 | 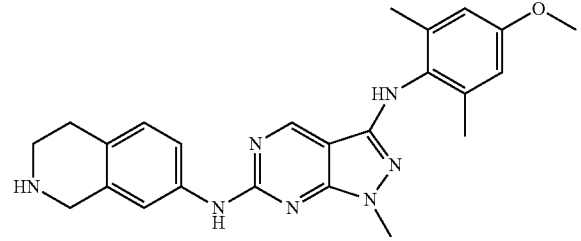 [SMILES: COc1cc(C)c(Nc2nn(C)c3nc(Nc4ccc5c(c4)CNCC5)ncc23)c(C)c1] |
| 36 | 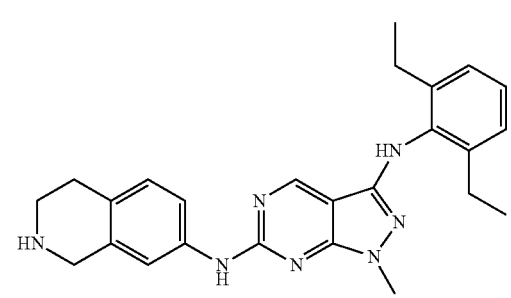 [SMILES: CCc1cccc(CC)c1Nc1nn(C)c2nc(Nc3ccc4c(c3)CNCC4)ncc12] |
| 37 | 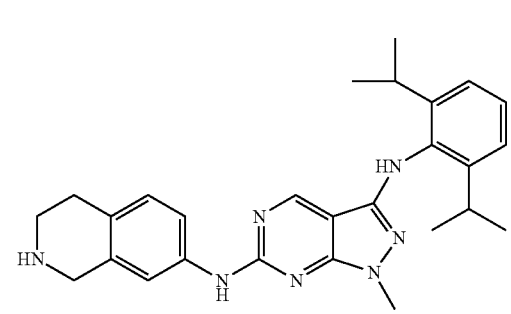 [SMILES: CC(C)c1cccc(C(C)C)c1Nc1nn(C)c2nc(Nc3ccc4c(c3)CNCC4)ncc12] |

TABLE 1-continued

| Example | Chemical Structure |
|---|---|
| 38 | (structure) |
| 39 | (structure) |
| 40 | (structure) |

TABLE 2

| Example | Chemical Structure |
|---|---|
| 41 | (structure) |
| 42 | (structure) |

TABLE 2-continued

| Example | Chemical Structure |
|---------|--------------------|
| 43 | 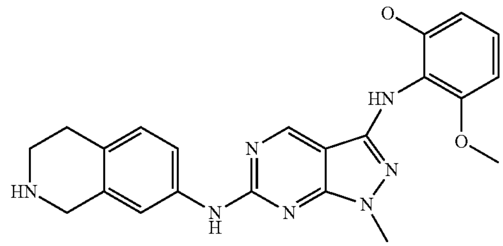 [SMILES: COc1cccc(O)c1Nc1nn(C)c2nc(Nc3ccc4c(c3)CNCC4)ncc12] |
| 44 | 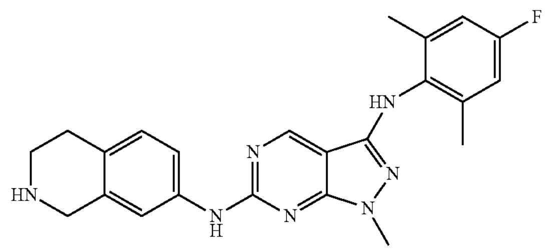 [SMILES: Cc1cc(F)cc(C)c1Nc1nn(C)c2nc(Nc3ccc4c(c3)CNCC4)ncc12] |
| 45 | 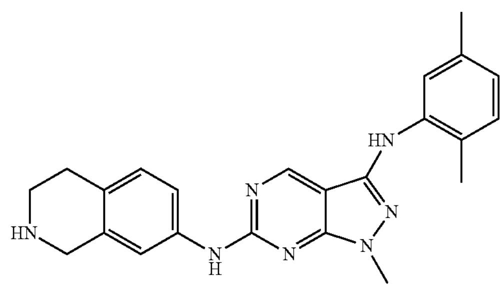 [SMILES: Cc1ccc(C)c(Nc2nn(C)c3nc(Nc4ccc5c(c4)CNCC5)ncc23)c1] |
| 46 | 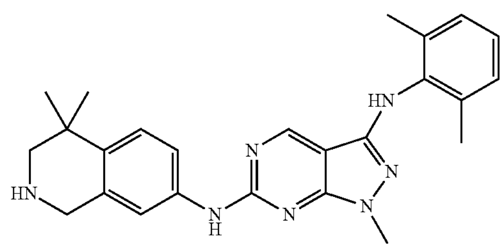 [SMILES: Cc1cccc(C)c1Nc1nn(C)c2nc(Nc3ccc4c(c3)CNCC4(C)C)ncc12] |
| 47 | 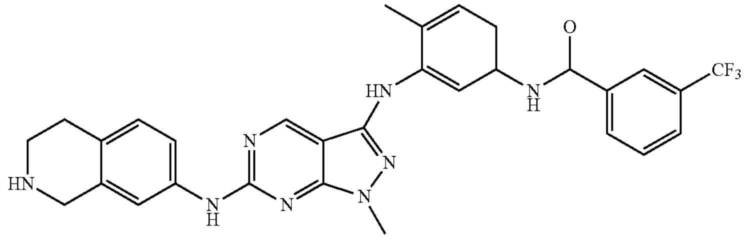 [SMILES: CC1=CCC(NC(O)c2cccc(C(F)(F)F)c2)C=C1Nc1nn(C)c2nc(Nc3ccc4c(c3)CNCC4)ncc12] |
| 48 | 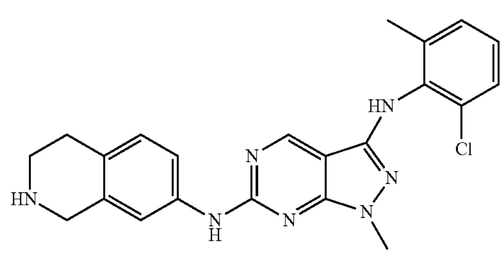 |

TABLE 2-continued

| Example | Chemical Structure |
| --- | --- |
| 49 | 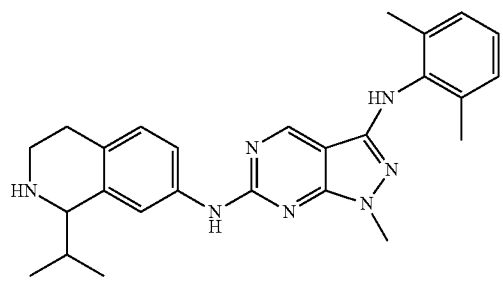 [SMILES: Cc1cccc(C)c1Nc1nn(C)c2nc(Nc3ccc4c(c3)C(C(C)C)NCC4)ncc12] |
| 50 | 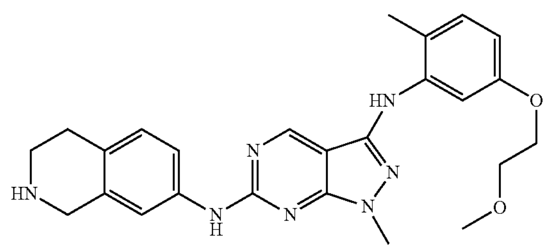 [SMILES: COCCOc1ccc(C)c(Nc2nn(C)c3nc(Nc4ccc5c(c4)CNCC5)ncc23)c1] |
| 51 | 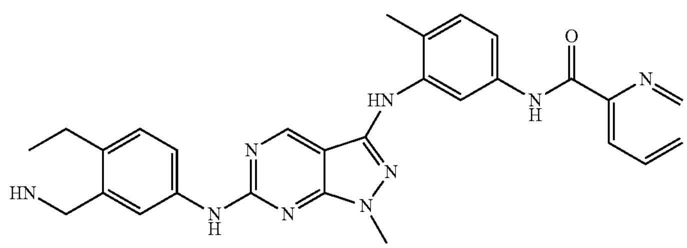 [SMILES: C=C/C=C(\N=C)C(=O)Nc1ccc(C)c(Nc2nn(C)c3nc(Nc4ccc(CC)c(CN)c4)ncc23)c1] |
| 52 | 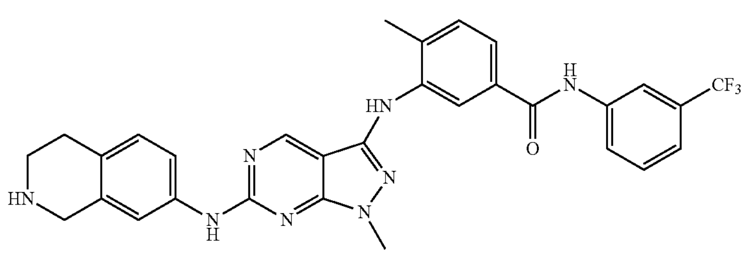 [SMILES: Cc1ccc(C(=O)Nc2cccc(C(F)(F)F)c2)cc1Nc1nn(C)c2nc(Nc3ccc4c(c3)CNCC4)ncc12] |
| 53 | 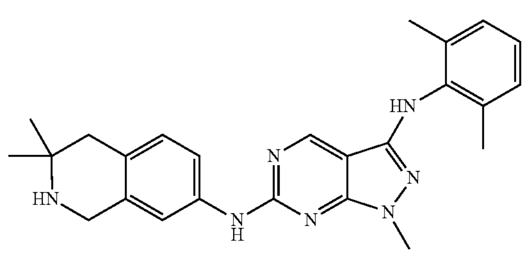 [SMILES: Cc1cccc(C)c1Nc1nn(C)c2nc(Nc3ccc4c(c3)CNC(C)(C)C4)ncc12] |

TABLE 2-continued

| Example | Chemical Structure |
|---|---|
| 54 | 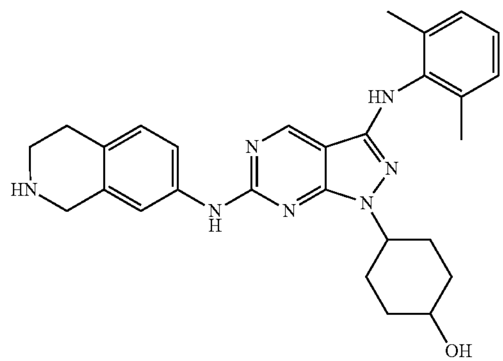 [SMILES: Cc1cccc(C)c1Nc1nn(C2CCC(O)CC2)c2nc(Nc3ccc4c(c3)CNCC4)ncc12] |
| 55 | 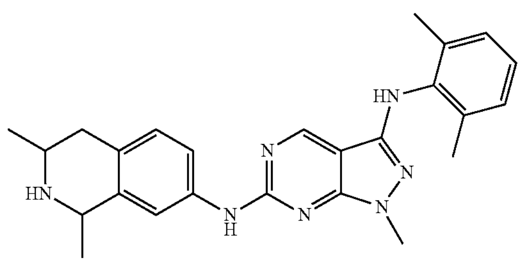 [SMILES: Cc1cccc(C)c1Nc1nn(C)c2nc(Nc3ccc4c(c3)C(C)NC(C)C4)ncc12] |
| 56 | 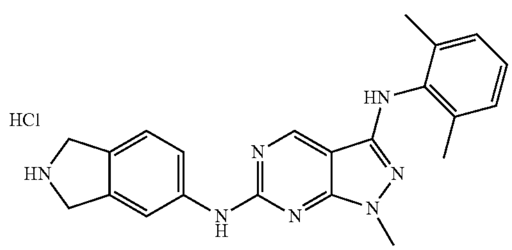 [SMILES: Cl ; Cc1cccc(C)c1Nc1nn(C)c2nc(Nc3ccc4c(c3)CNC4)ncc12] |
| 57 | 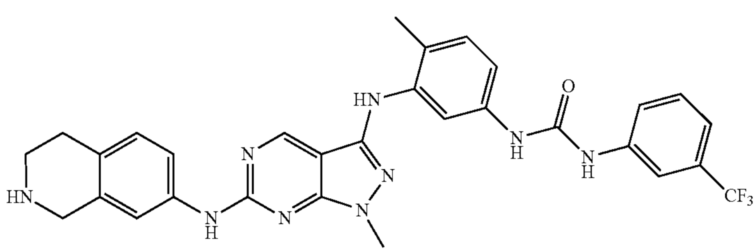 [SMILES: Cc1ccc(NC(=O)Nc2cccc(C(F)(F)F)c2)cc1Nc1nn(C)c2nc(Nc3ccc4c(c3)CNCC4)ncc12] |
| 58 | 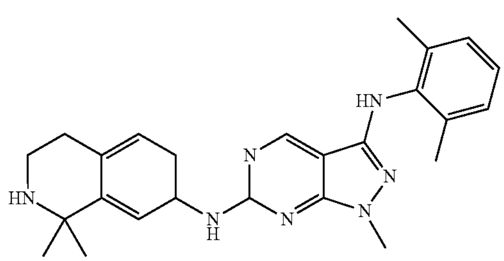 [SMILES: Cc1cccc(C)c1Nc1nn(C)c2c1=CNC(NC1C=C3C(=CC1)CCNC3(C)C)N=2] |

TABLE 2-continued

| Example | Chemical Structure |
|---|---|
| 59 | 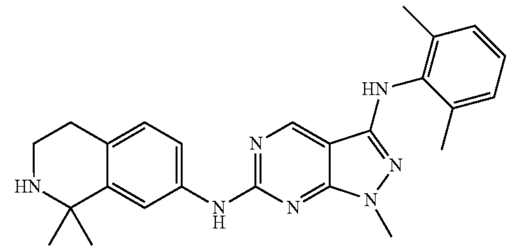 |
| 60 | 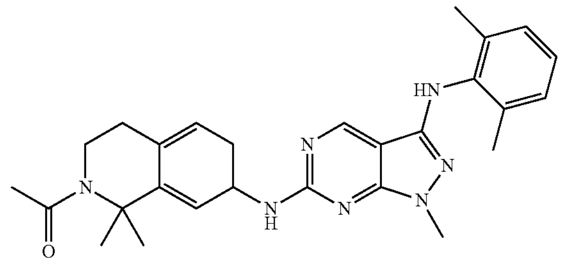 [SMILES: CC(=O)N1CCC2=CCC(Nc3ncc4c(Nc5c(C)cccc5C)nn(C)c4n3)C=C2C1(C)C] |
| 61 | 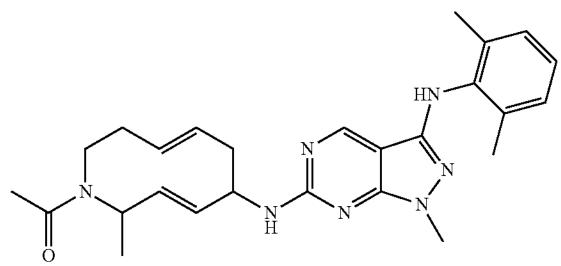 [SMILES: CC(=O)N1CC/C=C/CC(Nc2ncc3c(Nc4c(C)cccc4C)nn(C)c3n2)/C=C/C1C] |
| 62 | 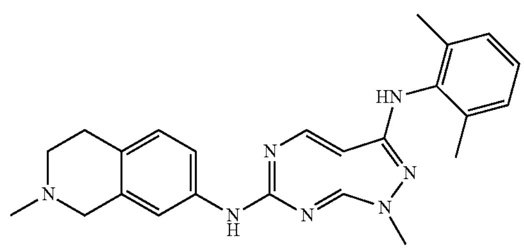 [SMILES: Cc1cccc(C)c1Nc1ccnc(Nc2ccc3c(c2)CN(C)CC3)ncn(C)n1] |
| 63 | 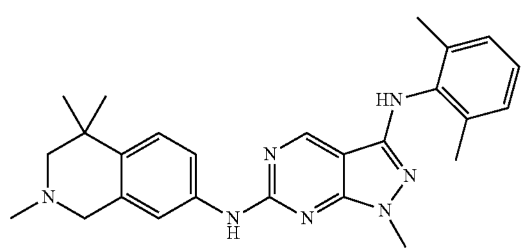 [SMILES: Cc1cccc(C)c1Nc1nn(C)c2nc(Nc3ccc4c(c3)CN(C)CC4(C)C)ncc12] |
| 64 | 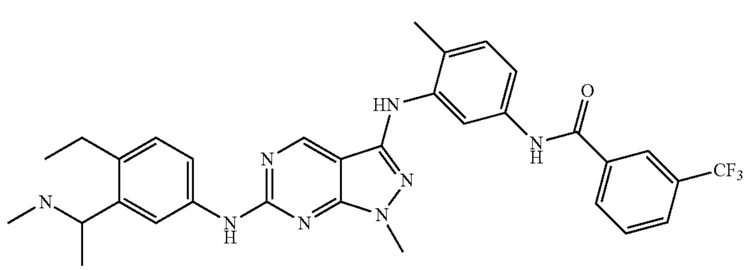 [SMILES: CCc1ccc(Nc2ncc3c(Nc4cc(NC(=O)c5cccc(C(F)(F)F)c5)ccc4C)nn(C)c3n2)cc1C(C)NC] |

TABLE 2-continued
| Example | Chemical Structure |
|---|---|
| 65 | 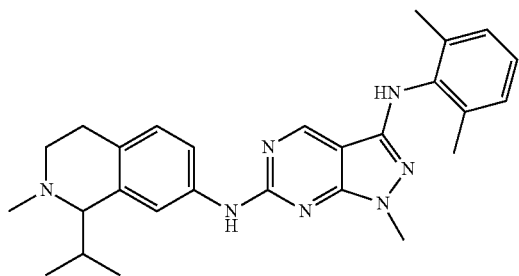 [SMILES: Cc1cccc(C)c1Nc1nn(C)c2nc(Nc3ccc4c(c3)C(C(C)C)N(C)CC4)ncc12] |
| 66 | 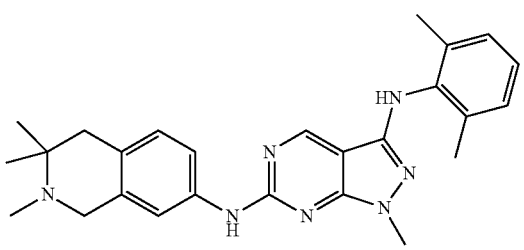 [SMILES: Cc1cccc(C)c1Nc1nn(C)c2nc(Nc3ccc4c(c3)CN(C)C(C)(C)C4)ncc12] |
| 67 | 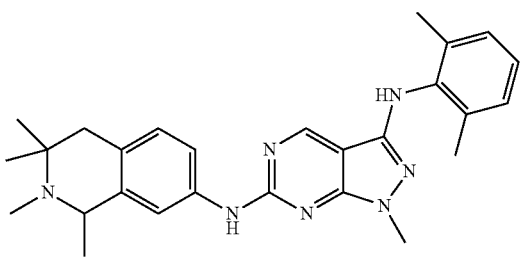 [SMILES: Cc1cccc(C)c1Nc1nn(C)c2nc(Nc3ccc4c(c3)C(C)N(C)C(C)(C)C4)ncc12] |
| 68 | 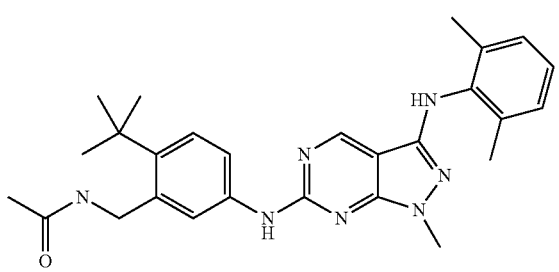 [SMILES: CC(=O)NCc1cc(Nc2ncc3c(Nc4c(C)cccc4C)nn(C)c3n2)ccc1C(C)(C)C] |
| 69 | 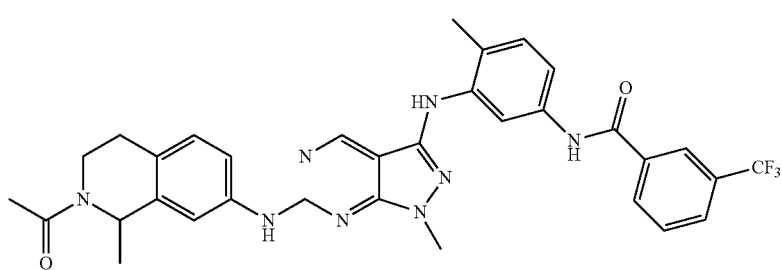 [SMILES: CC(=O)N1CCc2ccc(NC/N=C3\C(=C/N)C(Nc4cc(NC(=O)c5cccc(C(F)(F)F)c5)ccc4C)=NN3C)cc2C1C] |

TABLE 2-continued

| Example | Chemical Structure |
| --- | --- |
| 70 | 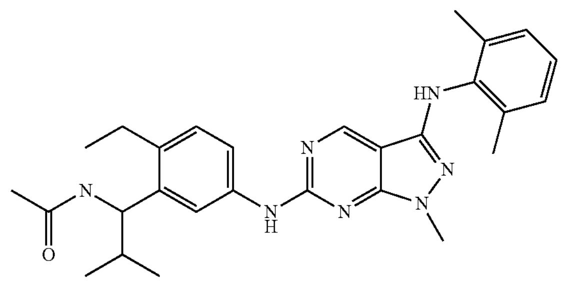 [SMILES: CCc1ccc(Nc2ncc3c(Nc4c(C)cccc4C)nn(C)c3n2)cc1C(NC(C)=O)C(C)C] |
| 71 | 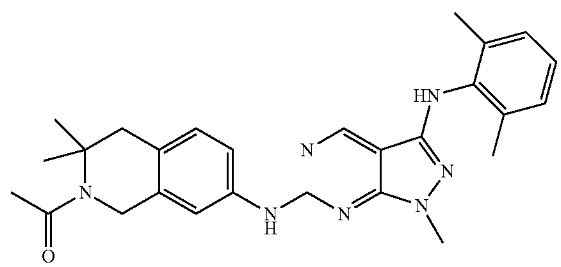 [SMILES: CC(=O)N1Cc2cc(NC/N=C3\C(=C/N)C(Nc4c(C)cccc4C)=NN3C)ccc2CC1(C)C] |
| 72 | 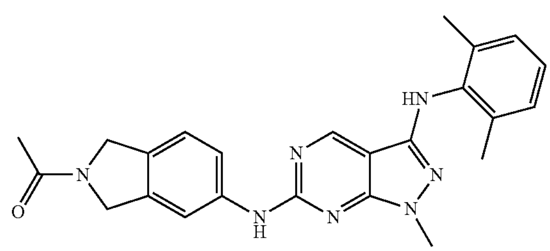 [SMILES: CC(=O)N1Cc2ccc(Nc3ncc4c(Nc5c(C)cccc5C)nn(C)c4n3)cc2C1] |
| 73 | 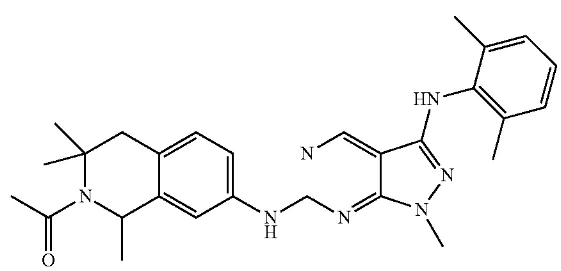 [SMILES: CC(=O)N1C(C)c2cc(NC/N=C3\C(=C/N)C(Nc4c(C)cccc4C)=NN3C)ccc2CC1(C)C] |
| 74 | 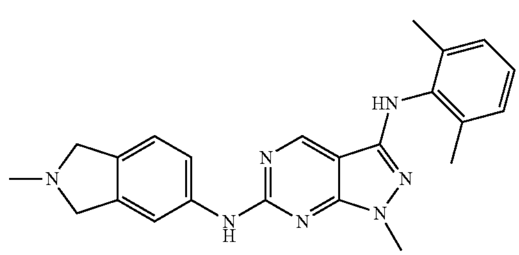 [SMILES: Cc1cccc(C)c1Nc1nn(C)c2nc(Nc3ccc4c(c3)CN(C)C4)ncc12] |

TABLE 2-continued

| Example | Chemical Structure |
|---|---|
| 75 | 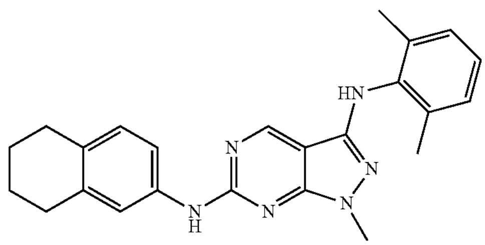 [SMILES: Cc1cccc(C)c1Nc1nn(C)c2nc(Nc3ccc4c(c3)CCCC4)ncc12] |
| 76 | 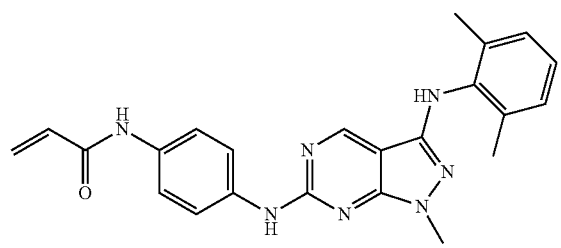 [SMILES: C=CC(=O)Nc1ccc(Nc2ncc3c(Nc4c(C)cccc4C)nn(C)c3n2)cc1] |
| 77 | 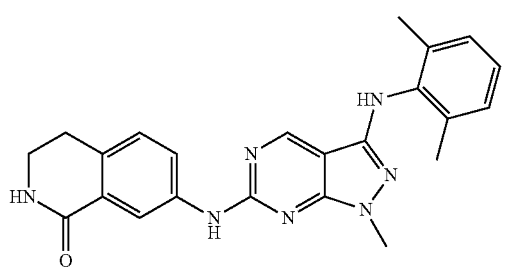 [SMILES: Cc1cccc(C)c1Nc1nn(C)c2nc(Nc3ccc4c(c3)C(=O)NCC4)ncc12] |
| 78 | 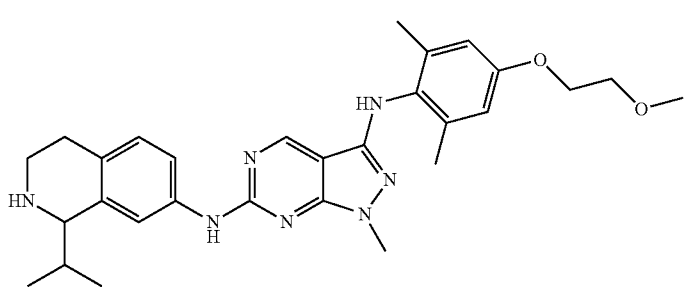 [SMILES: COCCOc1cc(C)c(Nc2nn(C)c3nc(Nc4ccc5c(c4)C(C(C)C)NCC5)ncc23)c(C)c1] |
| 79 | 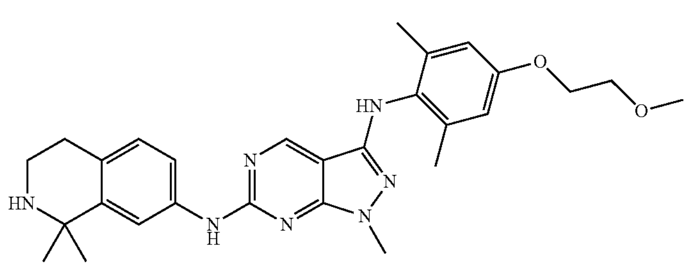 [SMILES: COCCOc1cc(C)c(Nc2nn(C)c3nc(Nc4ccc5c(c4)C(C)(C)NCC5)ncc23)c(C)c1] |

TABLE 3

| Example | NMR/Mass Data |
|---|---|
| 1 | ¹HNMR (300 MHz, CDCl₃) δ 9.65-9.63 (m, 1H), 8.35 (s, 1H), 8.10 (s, 1H), 7.68 (s, 1H), 7.62 (d, J = 8.3 Hz, 1H), 7.11-7.09 (m, 4H), 4.62-4.57 (m, 2H), 3.67-3.65 (m, 2H), 3.62 (s, 3H), 2.80-2.69 (m, 2H), 2.20 (s, 6H), 2.10-2.08 (m, 3H); LC/MS 442.2 [M + H⁺]. |
| 2 | ¹H NMR (300 MHz, CDCl₃) δ 7.39-7.37 (m, 2H), 7.34 (s, br, 1H), 7.18-7.12 (m, 3H), 7.07-7.03 (m, 2H), 5.85 (s, br, 1H), 4.02 (s, 2H), 3.79 (s, 3H), 3.14 (t, J = 6.0 Hz, 2H), 2.76 (t, J = 5.8 Hz, 2H), 2.26 (s, 6H), 1.77 (s, br, 1H); LC/MS 400.2 [M + H⁺]. |
| 3 | ¹H NMR (500 MHz, CDCl₃) δ 8.46-8.45 (m, 1H), 7.77 (s, 1H), 7.45 (s, 1H), 7.20-7.16 (m, 3H), 6.65-6.62 (m, 1H), 5.94 (s, br, 1H), 4.77-4.72 (m, 2H), 3.97-3.86 (m, 5H), 3.84 (s, 3H), 2.99-2.95 (m, 2H), 2.29 (s, 6H); LC/MS 526.2 [M + H⁺]. |
| 4 | ¹H NMR (300 MHz, CDCl₃) δ 8.32 (s, 1H), 7.69 (s, 1H), 7.41 (s, 1H), 7.18-7.11 (m, 3H), 6.51 (s, 1H), 5.87 (s, br, 1H), 3.97 (s, 2H), 3.83 (s, 3H), 3.81 (s, 3H), 3.14 (t, J = 5.9 Hz, 2H), 2.78 (t, J = 5.7 Hz, 2H), 2.27 (s, 6H), 1.80 (s, br, 1H); LC/MS 430.2 [M + H⁺]. |
| 5 | ¹H NMR (300 MHz, CDCl₃) δ 8.41-8.38 (m, 1H), 7.75 (s, 1H), 7.41 (s, 1H), 7.20-7.13 (m, 3H), 6.63-6.59 (m, 1H), 6.07 (s, br, 1H), 4.68-4.57 (m, 2H), 3.87-3.83 (m, 4H), 3.81 (s, 3H), 3.67 (t, J = 5.8 Hz, 1H), 2.91-2.81 (m, 2H), 2.27 (s, 6H), 2.18-2.17 (m, 3H); LC/MS 472.2 [M + H⁺]. |
| 6 | ¹H NMR (500 MHz, CDCl₃) δ 7.54-7.52 (m, 2H), 7.43 (s, 1H), 7.21-7.08 (m, 5H), 5.93 (s, 1H), 4.78-4.74 (m, 2H), 3.92-3.85 (m, 2H), 3.82 (s, 3H), 3.00-2.95 (m, 2H), 2.29 (s, 6H); LC/MS 496.2 [M + H⁺]. |
| 7 | ¹H NMR (500 MHz, CDCl₃) δ 7.44 (d, J = 8.3 Hz, 1H), 7.42 (s, 1H), 7.41 (s, 1H), 7.20 (s, br, 1H), 7.17-7.15 (m, 3H), 6.99 (d, J = 8.3 Hz, 1H), 5.95 (s, 1H), 4.01 (s, 2H), 3.81 (s, 3H), 3.16 (t, J = 5.9 Hz, 2H), 2.83 (t, J = 5.8 Hz, 2H), 2.29 (s, 6H), 1.87 (s, br, 1H); LC/MS 400.2 [M + H⁺]. |
| 8 | ¹H NMR (500 MHz, CDCl₃) δ 7.81-7.70 (m, 1H), 7.56-7.52 (m, 2H), 7.38 (s, 1H), 7.21-7.16 (m, 3H), 7.14-7.07 (m, 1H), 6.13 (s, 1H), 4.72-4.61 (m, 2H), 3.84 (t, J = 5.9 Hz, 2H), 3.82 (s, 3H), 3.69 (t, J = 5.9 Hz, 1H), 2.94-2.86 (m, 2H), 2.29 (s, 6H), 2.21-2.20 (m, 3H); LC/MS 442.2 [M + H⁺]. |
| 9 | ¹H NMR (300 MHz, CDCl₃) δ 8.62-8.61 (m, 1H), 7.70-7.61 (m, 1H), 7.56-7.32 (m, 6H), 7.18 (t, J = 8.5 Hz, 1H), 7.03 (t, J = 7.2 Hz, 1H), 6.46 (s, 1H), 4.85-4.79 (m, 2H), 3.96-3.86 (m, 5H), 2.98-2.95 (m, 2H); LC/MS 468.2 [M + H⁺] |
| 10 | ¹H NMR (500 MHz, DMSO) δ 9.64 (s, 1H), 9.30 (s, 1H), 9.00 (s, 1H), 7.68 (s, 1H), 7.59 (d, J = 7.8 Hz, 2H), 7.59 (d, J = 8.3 Hz, 1H), 7.55 (s, 1H), 7.31 (t, J = 7.9 Hz, 2H), 7.00 (d, J = 8.3 Hz, 1H), 6.88 (t, J = 7.3 Hz, 1H), 3.84 (s, 2H), 3.78 (s, 3H), 2.94 (t, J = 5.8 Hz, 2H), 2.64 (t, J = 5.6 Hz, 2H); LC/MS 372.2 [M + H⁺]. |
| 11 | ¹H NMR (300 MHz, CDCl₃) δ 8.09-8.08 (m, 1H), 7.69-7.59 (m, 1H), 7.52-7.41 (m, 4H), 7.16 (t, J = 8.1 Hz, 2H), 6.44 (s, 1H), 4.83-4.77 (m, 2H), 3.94-3.86 (m, 5H), 2.97-2.94 (m, 2H); LC/MS 536.2 [M + H⁺] |
| 12 | ¹H NMR (500 MHz, DMSO) δ 9.60 (s, 1H), 8.71 (s, 1H), 8.68 (s, 1H), 7.56 (d, J = 8.1 Hz, 3H), 7.52 (s, 1H), 7.30 (t, J = 8.1 Hz, 1H), 6.99 (d, J = 8.3 Hz, 1H), 3.83 (s, 2H), 3.63 (s, 3H), 2.94 (t, J = 5.8 Hz, 2H), 2.63 (t, J = 5.7 Hz, 2H); LC/MS 441.2 [M + H⁺]. |
| 13 | ¹H NMR (500 MHz, CDCl₃) δ 8.08-8.06 (m, 1H), 7.65-7.41 (m, 5H), 7.17-7.12 (m, 2H), 6.46 (s, 1H), 4.77-4.64 (m, 2H), 3.85 (s, 3H), 3.70 (t, J = 5.9 Hz, 2H), 2.91-2.83 (m, 2H), 2.21-2.20 (m, 3H); LC/MS 483.2 [M + H⁺]. |
| 14 | ¹H NMR (500 MHz, CDCl₃) δ 7.64-7.51 (m, 1H), 7.43-7.33 (m, 2H), 7.23-7.03 (m, 5H), 6.70-6.64 (m, 1H), 6.36 (d, J = 16.7 Hz, 1H), 5.93 (s, 1H), 5.75 (d, J = 10.6 Hz, 1H), 4.83-4.74 (m, 2H), 3.91-3.79 (m, 5H), 2.90-2.88 (m, 2H), 2.29-2.27 (m, 6H); LC/MS 454.2 [M + H⁺]. |
| 15 | ¹H NMR (300 MHz, CDCl₃) δ 8.08 (s, 1H), 7.48 (d, J = 8.5 Hz, 1H), 7.44 (s, 2H), 7.41 (s, 1H), 7.25 (s, 1H), 7.15 (s, J = 8.1 Hz, 1H), 7.02 (d, J = 8.3 Hz, 1H), 6.34 (s, 1H), 4.02 (s, 2H), 3.86 (s, 3H), 3.17 (t, J = 6.0 Hz, 2H), 2.84 (t, J = 5.7 Hz, 2H); LC/MS 441.2 [M + H⁺]. |
| 16 | ¹H NMR (300 MHz, CDCl₃) δ 8.07 (s, 1H), 7.52-7.50 (m, 2H), 7.42 (s, 1H), 7.39 (s, 1H), 7.34 (s, 1H), 7.18-7.05 (m, 2H), 6.36 (s, 1H), 4.70-4.59 (m, 2H), 3.83 (s, 3H), 3.82-3.81 (m, 1H), 3.68 (t, J = 5.9 Hz, 1H), 2.94-2.84 (m, 2H), 2.18-2.17 (m, 3H); LC/MS 483.2 [M + H⁺]. |
| 17 | ¹H NMR (300 MHz, CDCl₃) δ 7.43-7.40 (m, 3H), 7.20-7.15 (m, 3H), 7.10-7.08 (m, 2H), 5.86 (s, 1H), 3.82 (s, 3H), 3.64 (s, 2H), 2.92 (t, J = 5.8 Hz, 2H), 2.74 (t, J = 5.9 Hz, 2H), 2.50 (s, 3H), 2.29 (s, 6H)); LC/MS 414.2 [M + H⁺]. |
| 18 | ¹H NMR (300 MHz, CDCl₃) δ 7.39-7.36 (m, 3H), 7.20-7.11 (m, 4H), 7.08 (d, J = 8.0 Hz, 1H), 5.91 (s, 1H), 4.78 (s, 2H), 3.97 (t, J = 5.7 Hz, 2H), 3.79 (s, 3H), 2.82 (t, J = 5.7 Hz, 2H), 2.26 (s, 6H).; LC/MS 401.2 [M + H⁺]. |
| 19 | ¹H NMR (300 MHz, DMSO-d6) δ 11.86 (s, 1H), 9.39 (s, 1H), 8.34 (s, 1H), 7.92 (s, 1H), 7.53 (d, J = 8.2 Hz, 1H), 7.41 (s, 1H), 7.16-7.02 (m, 3H), 6.95 (d, J = 8.4 Hz, 1H), 3.79 (s, 2H), 2.92 (t, J = 5.6 Hz, 2H), 2.62 (d, J = 5.5 Hz, 2H), 2.19 (s, 6H); LC/MS 386.2 [M + H⁺]. |
| 20 | ¹H NMR (500 MHz, CDCl₃) δ 7.62 (s, 1H), 7.42 (s, 1H), 7.34 (dd, J = 8.2, 2.1 Hz, 1H), 7.31 (s, 1H), 7.20 7.15 (m, 3H), 7.06 (d, J = 8.2 Hz, 1H), 6.01 (s, 1H), 4.14 (q, J = 6.5 Hz, 1H), 3.82 (s, 3H), 3.30 (dt, J = 12.5, 5.0 Hz, 1H), 3.07 3.01 (m, 1H), 2.89-2.84 (m, 1H), 2.73 (dt, J = 16.2, 4.4 Hz, 1H), 2.29 (s, 6H), 1.74 (s, br, 1H), 1.52 (d, J = 6.7 Hz, 3H).; LC/MS 414.2 [M + H⁺] |
| 21 | ¹H NMR (300 MHz, DMSO + D2O) δ 8.34 (s, 1H), 7.75 (s, 1H), 7.70-7.66 (m, 1H), 7.27 7.10 (m, 4H), 4.38 (d, J = 9.0 Hz, 2H), 3.67-3.61(m, 5H), 3.32-3.22 (m, 2H), 3.15 2.94 (m, 22H), 2.20 (s, 6H), 1.37 (d, J = 6.5 Hz, 6H); 441.9 [M + H⁺] |
| 22 | ¹H NMR (300 MHz, DMSO) δ 9.65-9.62 (m, 1H), 8.34 (s, 1H), 8.09 (s, 1H), 7.73 7.59 (m, 2H), 7.16 7.04 (m, 4H), 4.63-4.54 (m, 3H), 4.19-4.17 (m, 2H), 3.73 3.53 (m, 5H), 2.82-2.69 (m, 2H), 2.20 (s, 6H). 457.9 [M + H⁺] |
| 23 | ¹H NMR (300 MHz, CDCl₃) δ 7.64 7.49 (m, 2H), 7.45-7.35 (m, 2H), 7.19 7.06 (m, 4H), 6.18 (s, 1H), 4.86-4.78 (m, 2H), 3.95 3.81 (m, 2H), 3.78 (s, 3H), 2.98-2.86 (m, 1H), 2.80 (s, 1H), 2.26 (s, 6H), 1.88-1.75 (m, 1H), 1.05-1.00 (m, 2H), 0.85 0.73 (m, 2H). 467.9 [M + H⁺] |
| 24 | ¹H NMR (300 MHz, CDCl₃) δ 7.45-7.36 (m, 3H), 7.33 (s, 1H), 7.18-7.16 (m, 3H), 7.08 (d, J = 7.9 Hz, 1H), 6.02 (s, 1H), 3.81 (s, 3H), 3.76-3.72 (m, 4H), 2.90-2.83 (m, 4H), 2.79 2.71 (m, 2H), 2.28 (s, 6H). 443.9 [M + H⁺] |
| 25 | ¹H NMR (300 MHz, CDCl₃) δ 7.3-7.33 (m, 3H), 7.21-7.10 (m, 3H), 7.06 7.01 (m, 2H), 5.86 (s, 1H), 4.99 (pent, J = 7.9 Hz, 1H), 4.02 (s, 2H), 3.14 (t, J = 5.9 Hz, 2H), 2.76 (t, J = 5.9 Hz, 2H), 2.27 (s, 6H), 2.20-2.05 (m, 4H), 2.03 1.89 (m, 2H), 1.84 (s, br, 1H), 1.76-1.68 (m, 1H); LC/MS 454.2 [M + H⁺]. |
| 26 | ¹H NMR (300 MHz, CDCl₃) δ 7.51 (s, 1H), 7.37 (s, 1H), 7.32 7.26 (m, 1H), 7.19 7.14 (m, 3H), 7.06 (d, J = 8.6 Hz, 2H), 5.97 (s, 1H), 4.51 4.38 (m, 1H), 4.05 (s, 2H), 3.17 (t, J = 6.0 Hz, 2H), 2.78 (t, J = 6.0 Hz, 2H), 2.29 (s, 6H), 2.10 1.99 (m, 4H), 1.99 1.90 (m, 2H), 1.82 1.75 (m, 1H), 1.53 1.40 (m, 2H), 1.38 1.27 (m, 1H); LC/MS 468.3 [M + H⁺] |
| 27 | ¹H NMR (300 MHz, CDCl₃) δ 7.44 7.33 (m, 3H), 7.22 7.14 (m, 3H), 7.11 7.03 (m, 2H), 5.90 (s, 1H), 4.89 (sept, J = 6.7 Hz, 1H), 4.04 (s, 2H), 3.16 (t, J = 5.9 Hz, 2H), 2.78 (t, J = 5.9 Hz, 2H), 2.29 (s, 6H), 1.55 (d, J = 6.7 Hz, 6H); LC/MS 428.2 [M + H⁺]. |

TABLE 4

| Example | NMR/Mass Data |
|---|---|
| 28 | ¹H NMR (500 MHz, CDCl₃) δ 8.59 (s, 1H), 8.10 (s, 1H), 8.02 (d, J = 7.8 Hz, 1H), 7.94 (d, J = 2.2 Hz, 1H), 7.85 (s, 1H), 7.78 (d, J = 7.8 Hz, 1H), 7.60 (t, J = 7.8 Hz, 1H), 7.46 (d, J = 8.6 Hz, 1H), 7.39 (s, 1H), 7.28 (s, 1H), 7.20 (d, J = 8.1 Hz, 1H), 7.07 (d, J = 8.3 Hz, 1H), 6.16 (s, 1H), 4.03 (s, 2H), 3.85 (s, 3H), 3.16 (t, J = 6.0 Hz, 2H), 2.78 (t, J = 6.0 Hz, 2H), 2.32 (s, 3H), 1.77 (s, 2H). 572.8 [M + H⁺] |
| 29 | ¹HNMR (300 MHz, CDCl₃) δ 8.17 (s, 1H), 8.07 (d, J = 7.7 Hz, 1H), 7.98 (s, 1H), 7.81 (d, J = 7.7 Hz, 1H), 7.66 7.54 (m, 3H), 7.46 7.39 (m, 2H), 7.32 (s, 1H), 7.21 (d, J = 8.2 Hz, 1H), 7.05 (d, J = 8.2 Hz, 1H), 6.10 (s, 1H), 4.00 (s, 2H), 3.79 (s, 2H), 3.14 (t, J = 5.9 Hz, 2H), 2.77 (t, J = 5.9 Hz, 2H), 2.28 (s, 3H), 2.25 (s, 3H). 586.9 [M + H⁺] |
| 30 | ¹H NMR (300 MHz, CDCl₃) δ 7.41 7.33 (m, 3H), 7.20 (s, 1H), 7.04 (d, J = 8.1 Hz, 1H), 6.72 (s, 2H), 5.85 (s, 1H), 4.15 4.09 (m, 2H), 4.02 (s, 2H), 3.80 3.74 (m, 5H), 3.47 (s, 3H), 3.14 (t, J = 5.9 Hz, 2H), 2.76 (t, J = 5.9 Hz, 2H), 2.22 (s, 6H), 1.84 (s, 2H). 473.9 [M + H⁺] |
| 31 | ¹H NMR (300 MHz, CDCl3) δ 7.60 (s, 1H), 7.45 7.33 (m, 3H), 7.17-7.07 (m, 5H), 5.87 (s, 1H), 4.76 (d, J = 9.6 Hz, 3H), |

TABLE 4-continued

| Example | NMR/Mass Data |
|---|---|
|  | 3.84 3.76 (m, 5H), 3.20 (s, 2H), 2.89 2.81 (m, 2H), 2.31 (s, 6H), 2.27 (s, 6H). 484.9 [M + H$^+$] |
| 32 | $^1$H NMR (300 MHz, CDCl$_3$) δ 7.44 7.34 (m, 3H), 7.25 7.10 (m, 4H), 7.06 (d, J = 8.1 Hz, 1H), 5.99 (s, 1H), 3.78 (s, 3H), 3.66 (s, 2H), 2.89 (t, J = 5.9 Hz, 2H), 2.77 (t, J = 5.9 Hz, 2H), 2.62 (q, J = 7.2 Hz, 2H), 2.26 (s, 26H), 1.28 1.18 (m, 3H). 428.0 [M + H$^+$] |
| 33 | $^1$H NMR (300 MHz, CDCl$_3$) δ 7.52 (s, 1H), 7.43 7.34 (m, 4H), 7.28 (s, 1H), 7.16 7.10 (m, 1H), 7.08 7.03 (m, 3H), 6.79 (s, 2H), 5.83 (s, 1H), 4.03 (s, 2H), 3.79 (s, 3H), 3.16 (t, J = 6.0 Hz, 2H), 2.78 (t, J = 6.0 Hz, 2H), 2.48 (s, 3H), 2.23 (s, 6H). 491.8 [M + H$^+$] |
| 34 | $^1$H NMR (300 MHz, CDCl$_3$) δ 8.61 (s, 1H), 8.40 (d, J = 8.4 Hz, 1H), 8.34 8.31 (m, 1H), 7.84-7.68 (m, 4H), 7.48 7.35 (m, 2H), 7.22 (s, 1H), 7.15 7.01 (m, 2H), 5.94 (s, 1H), 4.03 (s, 2H), 3.80 (s, 3H), 3.15 (s, 2H), 2.77 (t, J = 6.0 Hz, 2H), 2.33 (s, 6H), 1.79 (s, 2H). 519.8 [M + H$^+$] |
| 35 | $^1$H NMR (300 MHz, CDCl$_3$) δ 7.45 7.32 (m, 3H), 7.13 7.02 (m, 2H), 6.69 (s, 2H), 5.76 (s, 1H), 4.02 (s, 2H), 3.79 (d, J = 9.9 Hz, 6H), 3.14 (t, J = 5.9 Hz, 2H), 2.76 (t, J = 6.0 Hz, 2H), 2.24 (s, 6H). 429.9 [M + H$^+$] |
| 36 | $^1$H NMR (300 MHz, CDCl$_3$) δ 7.43 7.34 (m, 2H), 7.29-7.27 (m, 2H), 7.21 (d, J = 7.6 Hz, 2H), 7.15 (s, 1H), 7.07 (d, J = 8.2 Hz, 1H), 5.97 (s, 1H), 4.04 (s, 2H), 3.81 (s, 3H), 3.16 (t, J = 5.9 Hz, 2H), 2.78 (t, J = 6.0 Hz, 2H), 2.67 (d, J = 7.5 Hz, 4H), 1.16 (t, J = 7.5 Hz, 6H); LC/MS 428.3 [M + H$^+$]. |
| 37 | $^1$H NMR (300 MHz, CDCl$_3$) δ 7.44 7.34 (m, 3H), 7.26 (d, J = 7.6 Hz, 2H), 7.21 (s, 1H), 7.12 (s, 1H), 7.06 (d, J = 8.2 Hz, 1H), 5.99 (s, 1H), 4.04 (s, 2H), 3.81 (s, 3H), 3.34 (sept, J = 6.9 Hz, 2H), 3.16 (t, J = 5.9 Hz, 2H), 2.78 (t, J = 5.9 Hz, 2H), 1.14 (d, J = 6.9 Hz, 12H); LC/MS 456.2 [M + H$^+$]. |
| 38 | $^1$H NMR (300 MHz, DMSO-d6) δ 9.68 (s, 1H), 8.99 (s, 1H), 8.28 (s, 1H), 7.82 (s, 1H), 7.58 (d, J = 9.7 Hz, 2H), 7.00 (d, J = 8.1 Hz, 1H), 6.78 (d, J = 2.0 Hz, 1H), 3.84 (s, 2H), 3.78 (s, 3H), 2.94 (t, J = 5.8 Hz, 2H), 2.63 (t, J = 5.9 Hz, 2H), 2.33 (s, 3H), 2.26 (s, 3H); LC/MS 434.4 [M + H$^+$]. |
| 39 | $^1$H NMR (300 MHz, CDCl$_3$) δ 8.23 (s, 1H), 7.46 (dd, J = 8.2, 2.3 Hz, 1H), 7.43 7.37 (m, 2H), 7.25 (s, 1H), 7.12 7.06 (m, 2H), 7.02 (d, J = 8.1 Hz, 1H), 6.02 (s, 1H), 4.06 (s, 2H), 3.85 (s, 3H), 3.17 (t, J = 5.9 Hz, 2H), 2.79 (t, J = 5.9 Hz, 2H), 2.34 (s, 3H), 2.31 (s, 3H); LC/MS 400.2 [M + H$^+$]. |
| 40 | $^1$H NMR (300 MHz, CDCl$_3$) δ 8.39 (s, 1H), 7.56 (d, J = 8.0 Hz, 1H), 7.47 (dd, J = 8.2, 2.4 Hz, 1H), 7.43 (s, 1H), 7.28 7.19 (m, 3H), 7.10 (d, J = 8.3 Hz, 1H), 7.01 (d, J = 7.4 Hz, 1H), 6.11 (s, 1H), 4.06 (s, 2H), 3.87 (s, 3H), 3.18 (t, J = 5.9 Hz, 2H), 2.80 (t, J = 5.9 Hz, 2H), 2.36 (s, 3H); LC/MS 386.2 [M + H$^+$]. |
| 41 | $^1$H NMR (300 MHz, CDCl$_3$) δ 8.57 (s, 1H), 7.48 (d, J = 8.2 Hz, 1H), 7.43 (s, 1H), 7.24 (s, 1H), 7.11 (d, J = 8.3 Hz, 1H), 7.01 (s, 2H), 6.68 (s, 1H), 6.27 (s, 1H), 4.07 (s, 2H), 3.88 (s, 3H), 3.18 (t, J = 5.9 Hz, 2H), 2.80 (t, J = 6.0 Hz, 2H), 2.33 (s, 6H); LC/MS 400.2 [M + H$^+$]. |
| 42 | $^1$H NMR (300 MHz, DMSO) δ 9.62 (s, 1H), 8.79 (s, 1H), 8.68 (s, 1H), 7.60 7.51 (m, 2H), 7.25-7.14 (m, 3H), 7.00 (d, J = 8.3 Hz, 1H), 3.84 (s, 2H), 3.64 (s, 3H), 2.95 (t, J = 5.8 Hz, 2H), 2.65 (d, J = 5.9 Hz, 2H), 2.30 2.23 (m, 1H); LC/MS 407.9 [M + H$^+$] |
| 43 | $^1$H NMR (300 MHz, CDCl$_3$) δ 8.00 (s, 1H), 7.46 7.36 (m, 2H), 7.14 (t, J = 8.4 Hz, 1H), 7.06 (d, J = 7.5 Hz, 2H), 6.65 (d, J = 8.4 Hz, 2H), 6.13 (s, 1H), 4.03 (s, 2H), 3.82 3.76 (m, 9H), 3.19 3.11 (m, 2H), 2.76 (t, J = 6.0 Hz, 2H), 1.65 (s, 1H); LC/MS 431.9 [M + H$^+$] |
| 44 | $^1$H NMR (300 MHz, CDCl$_3$) δ 7.46 (s, 1H), 7.38 (d, J = 20.2 Hz, 3H), 7.10 6.99 (m, 2H), 6.87 (d, J = 9.0 Hz, 2H), 5.69 (s, 1H) 4.02 (s, 2H), 3.79 (s, 3H), 3.14 (t, J = 6.0 Hz, 2H), 2.79 2.73 (m, 2H), 2.26 (s, 6H); LC/MS 417.9 [M + H$^+$] |
| 45 | $^1$H NMR (300 MHz, CDCl$_3$) δ 8.34 (s, 1H), 7.49 7.35 (m, 2H), 7.33 (s, 1H), 7.22 (s, 1H), 7.09 (d, J = 6.8 Hz, 2H), 6.81 (d, J = 7.5 Hz, 2H), 6.03 (s, 1H), 4.04 (s, 2H), 3.85 (s, 3H), 3.15 (t, J = 6.0 Hz, 2H), 2.78 (t, J = 6.0 Hz, 2H), 2.29 (s, 3H), 2.28 (s, 3H). LC/MS 399.9 [M + H$^+$] |
| 46 | $^1$H NMR (500 MHz, CDCl$_3$) δ 7.47 (dd, J = 8.3, 2.4 Hz, 1H), 7.42 (s, 1H), 7.31 (d, J = 8.5 Hz, 2H), 7.22 7.15 (m, 3H), 7.10 (s, 1H), 5.88 (s, 1H), 4.04 (s, 2H), 3.82 (s, 3H), 2.89 (s, 2H), 2.29 (s, 6H), 1.84 (s, 1H), 1.29 (s, 6H); LC/MS 428.2 [M + H$^+$]. |
| 47 | $^1$H NMR (500 MHz, CDCl$_3$) δ 8.62 (s, 1H), 8.12 (s, 1H), 8.03 (d, J = 7.7 Hz, 1H), 7.95 (s, 1H), 7.91 (s, 1H), 7.79 (d, J = 7.9 Hz, 1H), 7.66 (s, 1H), 7.61 (t, J = 7.8 Hz, 1H), 7.40 (dd, J = 8.2, 2.3 Hz, 1H), 7.33 (s, 1H), 7.31 7.26 (m, 1H), 7.21 (d, J = 8.1 Hz, 1H), 7.08 (d, J = 8.3 Hz, 1H), 6.19 (s, 1H), 4.15 (d, J = 6.8 Hz, 1H), 3.88 (s, 3H), 3.31 (dt, J = 12.5, 5.0 Hz, 1H), 3.10 3.02 (m, 1H), 2.93 2.83 (m, 1H), 2.74 (dt, J = 16.2, 4.6 Hz, 1H), 2.34 (s, 3H), 1.69 (s, 1H), 1.54 (d, J = 6.7 Hz, 3H); LC/MS 587.4 [M + H$^+$]. |
| 48 | $^1$H NMR (300 MHz, DMSO) δ 9.57 (s, 1H), 8.56 (s, 1H), 8.40 (s, 1H), 7.56 (d, J = 8.7 Hz, 1H), 7.52 (s, 1H), 7.39 (d, J = 7.1 Hz, 1H), 7.27 (d, J = 7.4 Hz, 1H), 7.19 (t, J = 7.7 Hz, 1H), 6.98 (d, J = 8.3 Hz, 1H), 3.82 (s, 2H), 3.62 (s, 3H), 2.93 (t, J = 5.8 Hz, 2H), 2.62 (t, J = 5.8 Hz, 2H), 2.24 (s, 3H); LC/MS 420.2 [M + H$^+$]. |
| 49 | $^1$H NMR (500 MHz, CDCl$_3$) δ 7.60 (s, 1H), 7.42 (s, 1H), 7.35 (dd, J = 8.2, 2.2 Hz, 1H), 7.23 (s, 1H), 7.20 7.15 (m, 3H), 7.06 (d, J = 8.2 Hz, 1H), 5.97 (s, 1H), 3.96 (d, J = 3.8 Hz, 1H), 3.81 (s, 3H), 3.36 3.30 (m, 1H), 2.99 2.91 (m, 1H), 2.88 2.79 (m, 1H), 2.71 2.64 (m, 1H), 2.45 2.36 (m, 1H), 2.29 (s, 6H), 1.54 (s, 1H), 1.17 (d, J = 6.9 Hz, 3H), 0.83 (d, J = 6.8 Hz, 3H); LC/MS 442.2 [M + H$^+$]. |
| 50 | $^1$H NMR (300 MHz, CDCl$_3$) δ 8.46 (s, 1H), 7.50 7.38 (m, 2H), 7.22 (d, J = 2.7 Hz, 1H), 7.18 (s, 1H), 7.09 (d, J = 8.2 Hz, 2H), 6.55 (dd, J = 8.4, 2.6 Hz, 1H), 6.03 (s, 1H), 4.12 4.02 (m, 4H), 3.66 (s, 3H), 3.74 3.69 (m, 2H), 3.43 (s, 3H), 3.16 (t, J = 6.0 Hz, 2H), 2.79 (t, J = 5.9 Hz, 2H), 2.26 (s, 3H), 1.68 (s, 1H). LC/MS 459.9 [M + H$^+$] |
| 51 | $^1$H NMR (300 MHz, chloroform-d) δ 9.96 (s, 1H), 8.64 8.51 (m, 2H), 8.26 (d, J = 7.7 Hz, 1H), 8.07 8.03 (m, 1H), 7.91 7.83 (m, 1H), 7.50 7.32 (m, 5H), 7.20 (d, J = 8.2 Hz, 1H), 7.07 (d, J = 8.2 Hz, 1H), 6.22 (s, 1H), 4.03 (s, 2H), 3.87 (s, 3H), 3.15 (t, J = 5.9 Hz, 2H), 2.77 (t, J = 5.9 Hz, 2H), 2.31 (s, 3H), 1.79 (s, 2H). LC/MS 505.9 [M + H$^+$] |
| 52 | $^1$H NMR (300 MHz, chloroform-d) δ 8.53 (s, 1H), 8.25 (s, 1H), 8.13 (s, 1H), 7.93 (s, 1H), 7.86 (d, J = 8.5 Hz, 1H), 7.53 7.27 (m, 7H), 7.08 (d, J = 8.2 Hz, 1H), 6.21 (s, 1H), 4.03 (s, 2H), 3.86 (s, 3H), 3.15 (t, J = 5.9 Hz, 2H), 2.78 (t, J = 5.6 Hz, 1H), 2.40 (s, 3H), 2.40 (s, 3H). LC/MS 572.9 [M + H$^+$] |
| 53 | $^1$H NMR (300 MHz, CDCl$_3$) δ 7.47-7.37 (m, 3H), 7.22-7.14 (m, 4H), 7.03 (d, J = 8.0 Hz, 1H), 5.94 (s, 1H), 4.07 (s, 2H), 3.81 (s, 3H), 2.62 (s, 2H), 2.29 (s, 6H), 1.64 (s, 1H), 1.21 (s, 6H); LC/MS 428.2 [M + H$^+$]. |
| 54 | $^1$H NMR (300 MHz, MeOD) δ 7.95 (s, 1H), 7.57 (s, 1H), 7.43 (d, J = 8.7 Hz, 1H), 7.19-7.13 (m, 3H), 7.06 (d, J = 8.3 Hz, 1H), 4.45-4.32 (m, 1H), 3.98 (s, 2H), 3.74-3.63 (m, 1H), 3.10 (t, J = 6.0 Hz, 2H), 2.82 (t, J = 5.9 Hz, 2H), 2.27 (s, 6H), 2.19-2.02 (m, 4H), 2.01-1.92 (m, 2H), 1.58-1.38 (m, 2H); LC/MS 483.9 [M + H$^+$]. |

TABLE 5

| Example | NMR/Mass Data |
|---|---|
| 55 | $^1$H NMR (300 MHz, CDCl$_3$) δδ 7.69 (s, 1H), 7.42 (s, 1H), 7.35 (dd, J = 8.3, 2.3 Hz, 1H), 7.23-7.13 (m, 4H), 7.03 (d, J = 8.2 Hz, 1H), 5.89 (s, 1H), 4.16 (q, J = 6.7 Hz, 1H), 3.83 (s, 3H), 2.71 (d, J = 15.8 Hz, 1H), 2.57 (d, J = 15.9 Hz, 1H), 2.29 (s, 6H), 1.54 (d, J = 6.5 Hz, 3H), 1.29 (s, 3H), 1.13 (s, 3H); LC/MS 428.2 [M + H$^+$]. |
| 56 | $^1$H NMR (300 MHz, DMSO-d6) δδ 10.10 (s, 1H), 9.74 (s, 2H), 8.53 (s, 1H), 8.37 (s, 1H), 7.96 (s, 1H), 7.73 (d, J = 8.3 Hz, 1H), 7.34 (d, J = 8.3 Hz, 1H), 7.20-7.01 (m, 3H), 4.59-4.41 (m, 4H), 3.64 (s, 3H), 2.21 (s, 6H); LC/MS 386.2 [M + H$^+$]. |
| 57 | $^1$H NMR (300 MHz, MeOD) δδ 8.67 (s, 1H), 7.86 (s, 1H), 7.78 (s, 1H), 7.65-7.52 (m, 3H), 7.46 (t, J = 8.0 Hz, 1H), 7.28 (d, J = 7.7 Hz, 1H), 7.20-7.13 (m, 2H), 7.08 (d, J = 8.2 Hz, 1H), 4.00 (s, 2H), 3.78 (s, 3H), 3.12 (t, J = 6.1 Hz, 2H), 2.83 (t, J = 6.0 Hz, 2H), 2.31 (s, 3H); LC/MS 587.8 [M + H$^+$] |
| 58 | $^1$H NMR (500 MHz, CDCl$_3$) δδ 7.73 (s, 1H), 7.40 (s, 1H), 7.26-7.24 (m, 1H), 7.19-7.12 (m, 4H), 7.02 (d, J = 8.2 Hz, 1H), 5.87 (s, 1H), 3.80 (s, 3H), 3.14 (t, J = 5.9 Hz, 2H), 2.74 (t, J = 5.9 Hz, 2H), 2.27 (s, 6H), 1.50 (s, 6H); LC/MS 427.9 [M + H$^+$]. |
| 59 | $^1$H NMR (300 MHz, CDCl$_3$) δ 7.81 (s, 1H), 7.41 (s, 1H), 7.32-7.27 (m, 1H), 7.21-7.11 (m, 4H), 7.04 (d, J = 8.3 Hz, 1H), 5.87 (s, 1H), 3.80 (s, 3H), 3.14-3.04 (m, 2H), 2.99-2.91 (m, 2H), 2.58 (s, 3H), 2.27 (s, 6H), 1.59 (s, 6H); LC/MS 441.9 [M + H$^+$] |

TABLE 5-continued

| Example | NMR/Mass Data |
|---|---|
| 60 | ¹H NMR (300 MHz, CDCl₃) δδ 7.92 (s, 1H), 7.41 (s, 1H), 7.29 (s, 1H), 7.23 (dd, J = 8.2, 2.2 Hz, 1H), 7.18-7.11 (m, 3H), 7.03 (d, J = 8.2 Hz, 1H), 5.94 (s, 1H), 3.80 (s, 3H), 3.60-3.53 (m, 2H), 2.82 (t, J = 5.3 Hz, 2H), 2.27 (s, 6H), 2.21 (s, 3H), 1.88 (s, 6H); LC/MS 469.9 [M + H⁺]. |
| 61 | ¹H NMR (300 MHz, CDCl₃) δδ 7.66-7.51 (m, 1H), 7.40 (d, J = 6.0 Hz, 1H), 7.38-7.29 (m, 1H), 7.23 (s, 1H), 7.19-7.11 (m, 3H), 7.11-7.02 (m, 1H), 5.91 (s, 1H), 5.66 (q, J = 6.8 Hz, 0.6H), 4.94 (q, J = 6.8 Hz, 0.4H), 4.74-4.65 (m, 0.4H), 3.84-3.83 (m, 0.4H), 3.80 (s, 3H), 3.52 (ddd, J = 13.9, 10.6, 4.4 Hz, 0.7H), 3.07-2.64 (m, 2.5H), 2.27 (s, 6H), 2.20 (s, 1H), 2.17 (s, 2H), 1.58 (d, J = 6.8 Hz, 1H), 1.48 (d, J = 6.8 Hz, 2H); LC/MS 456.2 [M + H⁺]. |
| 62 | ¹H NMR (300 MHz, CDCl₃) δδ 7.59-7.52 (m, 1H), 7.40 (s, 1H), 7.33 (dd, J = 8.3, 2.4 Hz, 1H), 7.24-7.08 (m, 4H), 7.05 (d, J = 8.3 Hz, 1H), 5.86 (s, 0.7H), 5.18 (s, 0.3H), 3.83-3.78 (m, 3H), 3.66 (d, J = 6.7 Hz, 1H), 3.15-3.04 (m, 1H), 2.93-2.76 (m, 2H), 2.75-2.63 (m, 1H), 2.52 (s, 3H), 2.27 (s, 6H), 1.47 (d, J = 6.6 Hz, 3H); LC/MS 427.9 [M + H⁺]. |
| 63 | ¹H NMR (300 MHz, CDCl₃) δδ 7.45 (d, J = 8.4 Hz, 1H), 7.39 (s, 1H), 7.31 (s, 1H), 7.26-7.24 (m, 1H), 7.21-7.12 (m, 3H), 7.07 (s, 1H), 5.84 (s, 1H), 3.79 (s, 3H), 3.54 (s, 2H), 2.42 (s, 3H), 2.39 (s, 2H), 2.27 (s, 6H), 1.30 (s, 6H); LC/MS 441.9 [M + H⁺]. |
| 64 | ¹H NMR (500 MHz, CDCl₃) δδ 8.63 (s, 1H), 8.13 (s, 1H), 8.05 (d, J = 7.8 Hz, 1H), 7.98 (s, 1H), 7.92 (s, 1H), 7.80 (d, J = 7.8 Hz, 1H), 7.66 (s, 1H), 7.62 (t, J = 7.8 Hz, 1H), 7.41 (dd, J = 8.2, 2.3 Hz, 1H), 7.36 (s, 1H), 7.30-7.26 (m, 1H), 7.22 (d, J = 8.1 Hz, 1H), 7.10 (d, J = 8.3 Hz, 1H), 6.20 (s, 1H), 3.88 (s, 3H), 3.82-3.75 (m, 1H), 3.23-3.14 (m, 1H), 2.98-2.88 (m, 2H), 2.85-2.79 (m, 1H), 2.59 (s, 3H), 2.35 (s, 3H), 1.55 (d, J = 6.6 Hz, 3H); LC/MS 600.9 [M + H⁺]. |
| 65 | ¹H NMR (300 MHz, CDCl₃) δδ 7.53 (s, 1H), 7.40 (s, 1H), 7.32 (dd, J = 8.2, 2.3 Hz, 1H), 7.20-7.11 (m, 4H), 7.05 (d, J = 8.2 Hz, 1H), 5.88 (s, 1H), 3.79 (s, 3H), 3.33-3.20 (m, 2H), 2.84-2.64 (m, 3H), 2.50 (s, 3H), 2.27 (s, 6H), 2.10-1.98 (m, 1H), 1.09 (d, J = 6.8 Hz, 3H), 0.92 (d, J = 6.7 Hz, 3H); LC/MS 455.9 [M + H⁺]. |
| 66 | ¹H NMR (300 MHz, CDCl₃) δδ 7.44 (s, 1H), 7.41-7.35 (m, 2H), 7.22-7.10 (m, 4H), 7.03 (d, J = 8.2 Hz, 1H), 5.88 (s, 1H), 3.84 (s, 2H), 3.80 (s, 3H), 2.73 (s, 2H), 2.45 (s, 3H), 2.27 (s, 6H), 1.18 (s, 6H); LC/MS 441.9 [M + H⁺]. |
| 67 | ¹H NMR (500 MHz, CDCl₃) δδ 7.72 (s, 1H), 7.43 (s, 1H), 7.38-7.32 (m, 1H), 7.25 (s, 1H), 7.21-7.15 (m, 3H), 7.04 (d, J = 8.3 Hz, 1H), 5.93 (s, 1H), 3.82 (s, 3H), 3.14-3.03 (m, 1H), 2.64-2.45 (m, 5H), 2.29 (s, 6H), 1.69 (s, 3H), 1.47 (s, 3H), 1.15-1.04 (m, 3H); LC/MS 455.9 [M + H⁺]. |
| 68 | ¹H NMR (300 MHz, CDCl₃) δδ 7.57-7.46 (m, 1H), 7.43-7.38 (m, 72H), .34-7.28 (m, 1H), 7.25-7.22 (m, 1H), 7.19-7.12 (m, 3H), 5.90 (s, 1H), 4.82-4.62 (m, 2H), 3.80 (s, 3H), 3.64-3.34 (m, 2H), 2.27 (s, 6H), 2.23-2.16 (m, 1H), 1.35-1.23 (m, 6H); LC/MS 469.9 [M + H⁺]. |
| 69 | ¹H NMR (500 MHz, CDCl3) δδ 8.66-8.60 (m, 1H), 8.14 (d, J = 2.4 Hz, 1H), 8.05 (d, J = 8.3 Hz, 1H), 8.00 (d, J = 5.5 Hz, 1H), 7.97-7.93 (m, 1H), 7.80 (d, J = 7.6 Hz, 1H), 7.69-7.60 (m, 2H), 7.53-7.40 (m, 2H), 7.33-7.30 (m, 1H), 7.25-7.21 (m, 1H), 7.16-7.09 (m, 1H), 6.22-6.21 (m, 1H), 5.72-5.66 (m, 0.7H), 5.00-4.96 (m, 0.3H), 4.76-4.70 (m, 0.3H), 3.90-3.88 (m, 3H), 3.87-3.82 (m, 0.7H), 3.59-3.51 (m, 0.8H), 3.08-3.01 (m, 0.2H), 2.98-2.73 (m, 2H), 2.35 (s, 3H), 2.23 (s, 1H), 2.19 (s, 2H), 1.50 (d, J = 6.8 Hz, 3H), 1.30-1.28 (m, 1H); LC/MS 628.9 [M + H⁺]. |
| 70 | ¹H NMR (300 MHz, CDCl₃) δδ 7.64-7.53 (m, 1H), 7.43-7.31 (m, 2H), 7.22-7.04 (m, 5H), 5.88 (s, 1H), 5.34-5.25 (m, 0.65H), 4.57-4.44 (m, 0.36H), 4.31-4.24 (m, 0.35H), 3.79 (s, 3H), 3.70 (t, J = 6.6 Hz, 1.24H), 3.37-3.19 (m, 0.36H), 3.04-2.79 (m, 2H), 2.27 (s, 6H), 2.18-2.14 (m, 3H), 2.03-1.95 (m, 1H), 1.13-0.96 (m, 6H); LC/MS 483.9 [M + H⁺]. |
| 71 | ¹H NMR (300 MHz, CDCl₃) δδ 7.57 (s, 1H), 7.50 (dd, J = 8.0, 2.2 Hz, 1H), 7.42 (s, 1H), 7.21-7.08 (m, 5H), 5.87 (s, 1H), 4.39 (s, 2H), 3.81 (s, 3H), 2.73 (s, 2H), 2.27 (s, 6H), 2.20 (s, 3H), 1.46 (s, 6H); LC/MS 469.9 [M + H⁺]. |
| 72 | ¹H NMR (300 MHz, CDCl₃) δδ 7.85-7.72 (m, 1H), 7.46 (d, J = , 8.4 Hz 1H), 7.41 (s, 1H), 7.30-7.27 (m, 1H), 7.24-7.11 (m, 4H), 5.89 (s, 1H), 4.86-4.73 (m, 4H), 3.80 (d, J = 1.9 Hz, 3H), 2.27 (s, 6H), 2.17 (s, 3H); LC/MS 427.9 [M + H⁺]. |
| 73 | ¹H NMR (300 MHz, CDCl₃) δδ 7.51 (dd, J = 8.1, 2.2 Hz, 1H), 7.46 (s, 1H), 7.42 (s, 1H), 7.21-7.09 (m, 5H), 5.85 (s, 1H), 4.83-4.71 (m, 1H), 3.80 (s, 3H), 3.21 (d, J = 15.2 Hz, 1H), 2.52 (d, J = 15.2 Hz, 1H), 2.27 (s, 6H), 2.25 (s, 3H), 1.75 (s, 3H), 1.49 (d, J = 7.0 Hz, 3H), 1.24 (s, 3H); LC/MS 484.0 [M + H⁺]. |
| 74 | ¹H NMR (300 MHz, CDCl₃) δδ 7.61 (s, 1H), 7.47-7.38 (m, 2H), 7.22-7.08 (m, 5H), 5.83 (s, 1H), 4.04-3.95 (m, 4H), 3.79 (s, 3H), 2.65 (s, 3H), 2.27 (s, 6H); LC/MS 399.9 [M + H⁺]. |
| 75 | ¹H NMR (300 MHz, CDCl₃) δδ 7.42-7.31 (m, 3H), 7.15 (s, 3H), 7.02 (d, J = 8.5 Hz, 2H), 5.84 (s, 1H), 3.79 (s, 3H), 2.81-2.68 (m, 4H), 2.27 (s, 6H), 1.85-1.75 (m, 4H); LC/MS 399.5 [M + H⁺]. |
| 76 | ¹H NMR (300 MHz, CDCl₃) δδ 7.64 (d, J = 8.9 Hz, 2H), 7.55 (d, J = 8.7 Hz, 2H), 7.41 (s, 1H), 7.30 (s, 2H), 7.21-7.10 (m, 3H), 6.44 (d, J = 16.8 Hz, 1H), 6.24 (dd, J = 16.9, 10.1 Hz, 1H), 5.91 (s, 1H), 5.76 (d, J = 10.1 Hz, 1H), 3.80 (s, 3H), 2.27 (s, 6H); LC/MS 414.1 [M + H⁺]. |
| 77 | ¹H NMR (500 MHz, CDCl₃) δδ 8.33 (d, J = 2.4 Hz, 1H), 7.92 (dd, J = 8.2, 2.5 Hz, 1H), 7.54 (s, 1H), 7.44 (s, 1H), 7.22 (d, J = 8.3 Hz, 1H), 7.19-7.14 (m, 3H), 6.30 (s, 1H), 6.08 (s, 1H), 3.84 (s, 3H), 3.58 (td, J = 6.6, 2.8 Hz, 2H), 2.99 (t, J = 6.6 Hz, 2H), 2.29 (s, 6H); LC/MS 414.2 [M + H⁺]. |
| 78 | ¹H NMR (300 MHz, CDCl₃) δδ 7.59 (s, 1H), 7.41-7.33 (m, 2H), 7.13-7.02 (m, 2H), 6.75 (s, 2H), 5.75 (s, 1H), 4.18-4.12 (m, 2H), 3.96 (d, J = 3.7 Hz, 1H), 3.82-3.76 (m, 5H), 3.50 (s, 3H), 3.39-3.27 (m, 1H), 3.00-2.75 (m, 2H), 2.73-2.62 (m, 1H), 2.48-2.36 (m, 1H), 2.25 (s, 6H), 1.17 (d, J = 6.9 Hz, 3H), 0.82 (d, J = 6.8 Hz, 3H); LC/MS 516.2 [M + H⁺]. |
| 79 | ¹H NMR (300 MHz, CDCl₃) δδ 7.72 (s, 1H), 7.37 (s, 1H), 7.26-7.22 (m, 1H), 7.09 (s, 1H), 7.02 (d, J = 8.3 Hz, 1H), 6.72 (s, 2H), 5.74 (s, 1H), 4.15-4.10 (m, 2H), 3.79 (s, 3H), 3.78-3.71 (m, 2H), 3.47 (s, 3H), 3.14 (t, J = 5.9 Hz, 2H), 2.74 (t, J = 5.8 Hz, 2H), 2.23 (s, 6H), 1.59 (s, 1H), 1.50 (s, 6H); LC/MS 502.2 [M + H⁺]. |

Comparative Example 1: Preparation of N³-(2,6-dimethylphenyl)-1-methyl-N⁶-(4-(piperidine-4-yl)phenyl)-1H-pyrazolo[3,4-d]pyrimidine-3,6-diamine Step 1: Preparation of tert-butyl 4-(4-nitrophenyl)-3,6-dihydropyridine-1(2H)-carboxylate

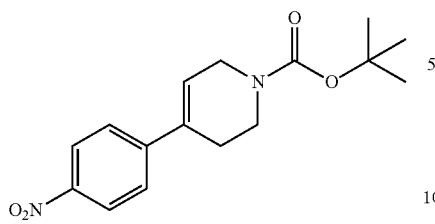

Tert-butyl 4-(4,4,5,5-tetramethyl-cyclohexyl-3-en-1-carboxylate (1.68 g, 5.44 mmol) and sodium carbonate 1.05 g, 9.90 mmol) were added to dioxane (40 mL) and H$_2$O (10 mL) containing 1-bromo-4-nitrobenzene (1.0 g, 4.95 mmol) at room temperature. The reaction mixture was purged with nitrogen for 10 minutes. PdCl$_2$ (dppf) (202 mg, 0.247 mmol) was added to the reaction mixture, which was heated to reflux for 2 hours. Upon completion of the reaction, the solvent was concentrated under reduced pressure to remove the solvent. The crude mixture was diluted with water (100 mL), followed by extraction with ethylacetate (2×150 mL). The combined organic layer was dried over Na$_2$SO$_4$ and concentrated under reduced pressure. The obtained crude mixture was purified by column chromatography using EtOAc/hexane (1:1) as an eluent. As a result, the target compound (1.15 g, 3.77 mmol, 76%) was obtained as a white solid.

$^1$H NMR (300 MHz, CDCl$_3$) δ 8.21 (d, J=8.9 Hz, 2H), 7.53 (d, J=8.9 Hz, 2H), 6.25 (s, br, 1H), 4.19-4.10 (m, 2H), 3.68 (1, J=5.7 Hz, 2H), 2.63-2.50 (m, 2H), 1.52 (s, 9H); LC/MS 305.2 [M+H$^+$].

Step 2: Preparation of tert-butyl 4-(4-aminophenyl)piperidine-1-carboxylate

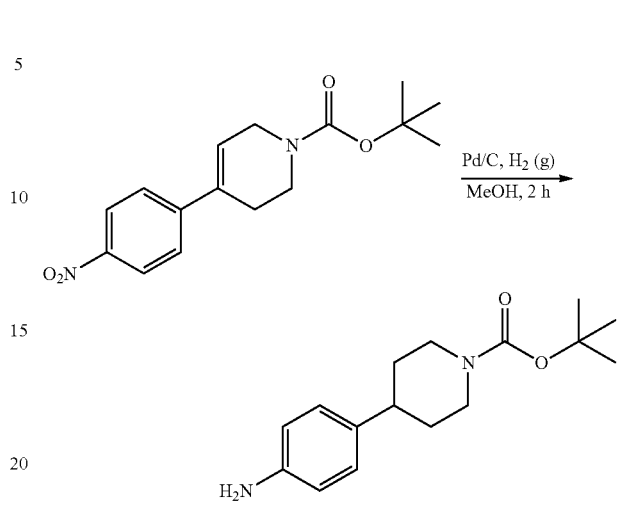

Pd/C (10 weight %) (110 mg, 1.04 mmol) was added to MeOH (10 mL) solution containing the compound prepared in step 1 above (1.1 g, 3.61 mmol) at room temperature. The reaction mixture was stirred at room temperature under hydrogen balloon pressure for 2 hours. TLC analysis indicated the complete consumption of the starting material. The reaction mixture was filtered with a celite bed and concentrated to remove MeOH. The obtained crude mixture was purified by column chromatography using EtOAc/hexane. As a result, the target compound (850 mg, 3.07 mmol, 85%) was obtained as a white solid.

$^1$H NMR (300 MHz, CDCl$_3$) δ 6.98 (d, J=8.3 Hz, 2H), 6.63 (d, J=8.4 Hz, 2H), 4.19-4.12 (m, 2H), 3.57 (s, br, 2H), 2.76 (t, J=12.3 Hz, 2H), 2.56-2.48 (m, 1H), 1.79-1.75 (m, 2H), 1.58-1.52 (m, 2H), 1.47 (s, 9H); LC/MS 277.2 [M+H$^+$].

Step 3: Preparation of N3-(2,6-dimethylphenyl)-1-methyl-N6-(4-(piperidine-4-yl)phenyl)-1H-pyrazolo[3,4-d]pyrimidine-3,6-diamine

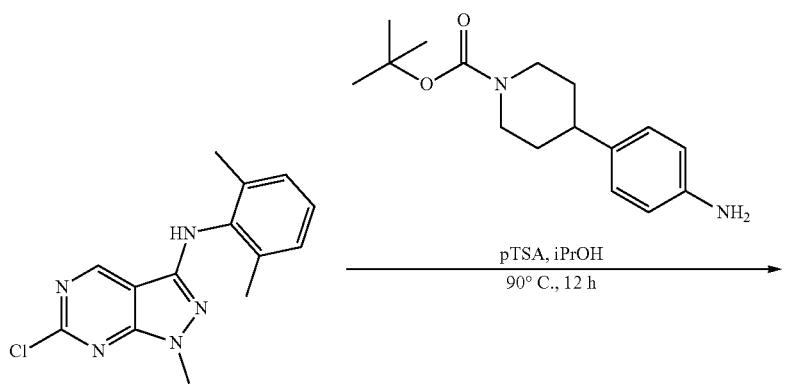

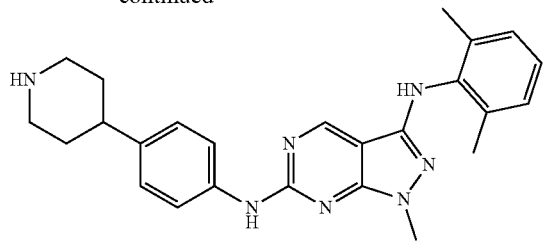

The compound prepared in step 2 above (17.1 mg, 0.062 mmol) and pTSA.H₂O (13.1 mg, 0.069 mmol) were added to IPA (1.0 mL) solution containing the compound of Preparative Example B-1 (20 mg, 0.069 mmol) at room temperature, followed by stirring at 90° C. for 12 hours. TLC analysis indicated the complete consumption of the starting material. The solid obtained from the reaction mixture was filtered and washed with ethanol (2 mL). The filtered solid was dissolved in EtOAc (15 mL) and washed with saturated NaHCO₃ solution. The combined organic layer was concentrated under reduce pressure. The obtained crude mixture was purified by column chromatography using MeOH/DCM (1/4) as an eluent. As a result, the target compound (20 mg, 0.046 mmol, 68%) was obtained as a grey-white solid.

¹H NMR (500 MHz, CDCl₃) δ 7.60 (d, J=8.5 Hz, 2H), 7.43 (s, 1H), 7.21 (d, J=8.5 Hz, 2H), 7.19-7.16 (m, 3H), 7.13 (s, br, 1H), 5.86 (s, br, 1H), 3.83 (s, 3H), 3.21 (d, J=12.1 Hz, 2H), 2.76 (t, J=12.2 Hz, 2H), 2.64-2.58 (n, 1H), 2.29 (s, 6H), 1.85 (d, J=12.4 Hz, 2H), 1.69-1.66 (m, 2H), 1.63 (s, br, 1H);

Comparative Example 2: Preparation of 1-(4-(4-(3-(2,6-dimethylphenylamino)-1-methyl-1H-pyrazolo[3,4-d]pyrimidine-6-ylamino)phenyl)piperidine-1-yl)ethaneone

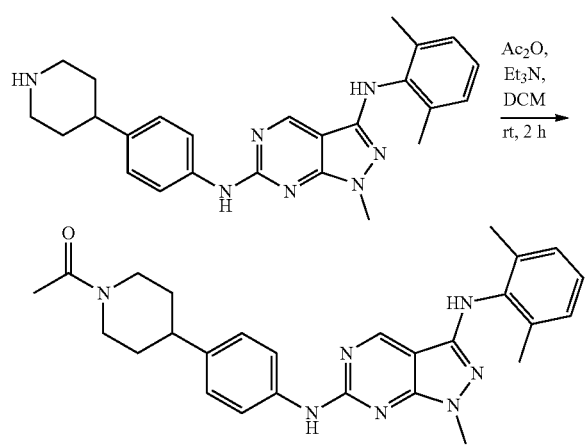

Acetic anhydride (8.5 mg, 0.084 mmol) and Et₃N (17.6 mg, 0.175 mmol) were added to DCM (10 mL) solution containing the compound of Comparative Example 1 (30 mg, 0.070 mmol) at 0° C., followed by stirring at room temperature for 2 hours. TLC analysis indicated the complete consumption of the starting material. Water was added to the reaction mixture, which was extracted with DCM (15 mL). The extract was washed with saturated NaHCO₃ solution. The combined organic layer was concentrated under reduced pressure. The obtained crude product was purified by column chromatography using MeOH/DCM (1/4) as an eluent. As a result, 1-(4-(4-(3-(2,6-dimethylphenylamino)-1-methyl-1H-pyrazolo[3,4-d]pyrimidine-6-ylamino)phenyl)piperidine-1-yl)ethaneone (28 mg, 0.059 mmol, 85%) was obtained as a grey-white solid.

¹H NMR (300 MHz, CDCl₃) δ 7.61 (d, J=8.5 Hz, 2H), 7.53 (s, br, 1H), 7.38 (s, 1H), 7.20-7.15 (m, 5H), 5.99 (s, br, 1H), 4.78 (d, J=13.4 Hz, 1H), 3.93 (d, J=13.4 Hz, 1H), 3.79 (s, 3H), 3.16 (t, J=12.8 Hz, 1H), 2.75-2.70 (m, 1H), 2.67-2.57 (m, 1H), 2.26 (s, 6H), 2.13 (s, 3H), 1.89 (t, J=9.6 Hz, 2H), 1.67-1.58 (m, 2H); LC/MS 470.2 [M+H⁺].

Experimental Example 1: Evaluation of BTK Inhibitory Activity of the Compound of the Present Invention 1-1. Experimental Method The following experiment was performed in order to evaluate the Bruton's tyrosine kinase inhibitory activity of the derivatives of the present invention and the result are shown in Table 5.

BTK enzyme evaluation with each compound of examples of the invention was performed by using BTK enzyme inhibition diagnosis kit (Cisbio, Codolet, France). ATP (adenosine triphosphate), BTK, peptide (biotin-Aca-AAAEEIYGEI-NH₂) and each compound of examples of the invention were mixed, followed by reaction for 30 minutes. Then, EDTA (ethylenediaminetetraacetic acid) was added thereto in order to terminate the reaction. At this time, the EDTA solution contained curopium-containing antibody (antiphosphoresidue antibody) and straptavidin-XL665 (SA-XL665, Cisbio). After incubation for 1 hour, fluorescence was measured. The emission values of 665 nm and 620 nm excited at 337 nm were measured with Envision reader. IC₅₀ values were determined using GraphPad prism (version 5). Herein, the curve indicates a nonlinear regression model, which was determined by logarithmic functions and reaction values.

1-2. Experiment Results

TABLE 6

| Example | Btk IC$_{50}$ (uM) |
| --- | --- |
| 1 | 0.0006 |
| 2 | 0.0006 |
| 4 | 0.1 |
| 6 | 0.01 |
| 7 | 0.0008 |
| 8 | 0.001 |
| 11 | 0.386 |
| 12 | 0.003752 |
| 13 | 0.003 |
| 14 | 0.002 |

TABLE 6-continued

| Example | Btk IC$_{50}$ (uM) |
|---|---|
| 15 | 0.00067 |
| 16 | 0.003 |
| 17 | 0.0012 |
| 18 | 0.0005 |
| 19 | 0.0003 |
| 20 | 0.0005 |
| 21 | 0.0002 |
| 22 | 0.0004 |
| 23 | 0.0003 |
| 24 | 0.0003 |
| 25 | 0.0003 |
| 26 | 0.002 |
| 27 | 0.001 |
| 28 | 0.003 |
| 29 | 0.008 |
| 30 | 0.002 |
| 31 | 0.0008 |
| 32 | 0.0007 |
| 33 | 0.005 |
| 34 | 0.015 |
| 35 | 0.003 |
| 36 | 0.044 |
| 39 | 0.0028 |
| 44 | 0.0017 |
| 46 | 0.002849 |
| 47 | 0.005421 |
| 48 | 0.001275 |
| 49 | 0.001615 |
| 53 | 0.0005228 |
| 54 | 0.001142 |
| 55 | 0.000847 |
| 56 | 0.0007455 |
| 57 | 0.02669 |
| 58 | 0.001687 |
| 59 | 0.001837 |
| 60 | 0.004012 |
| 61 | 0.001035 |
| 62 | 0.001208 |
| 63 | 0.002128 |
| 64 | 0.005223 |
| 65 | 0.007742 |
| Comparative Example 1 | 0.01 |
| Comparative Example 2 | 0.02 |

As shown in Table 6, the compounds of the present invention were confirmed to have excellent inhibitory activity against Bruton's tyrosine kinase (BTK). In particular, the compounds of the present invention having the structure in which an amine substituted at the 6-position of pyrazolopyrimidine is substituted with a phenyl to which a heterocyclic ring is conjugated have more excellent activity than the compound of Comparative Example 1 or Comparative Example 2 having the structure in which an amine substituted at the 6-position of pyrazolopyrimidine is substituted with a phenyl substituted with a heterocyclic ring.

Therefore, the pyrazolopyrimidine derivative compounds of the present invention are excellent in inhibiting Bruton's tyrosine kinase (BTK) activity, so that the compounds can be effectively used as an active ingredient for a pharmaceutical composition for the prevention or treatment of cancer, autoimmune disease and Parkinson's disease.

Experimental Example 2: Evaluation or BTK inhibitory activity in TMD8 cells 2-1. Experimental Method TDM-8 cells, the ABC (activated B-cell) type DLBCL (diffuse large B cell lymphoma) cell line sensitive to BTK signaling, were seeded in a 96-well plate at 30% confluency. Then, the compounds of the invention were treated thereto at different concentrations. 72 hours later, WST-1 reagent was added thereto. One hour later, absorbance was measured at 450 nm by using a spectramax spectrophotometer. IC$_{50}$ values were measured using GraphPad prism program and the results are shown in Table 7.

2-2. Experiment Results

TABLE 7

| Example | TMD8 IC$_{50}$ (uM) |
|---|---|
| 1 | 0.0411 |
| 2 | 0.0301 |
| 4 | 0.572 |
| 6 | 0.159 |
| 7 | 0.046 |
| 8 | 0.093 |
| 11 | 0.243 |
| 12 | 0.089 |
| 13 | 0.118 |
| 14 | 0.032 |
| 15 | 0.041 |
| 16 | 0.061 |
| 17 | 0.036 |
| 18 | 0.1339 |
| 19 | 0.0494 |
| 20 | 0.008277 |
| 21 | 0.1387 |
| 22 | 0.04637 |
| 23 | 0.08792 |
| 24 | 0.04007 |
| 25 | 0.09028 |
| 26 | 0.06495 |
| 27 | 0.03538 |
| 28 | 0.01795 |
| 29 | 0.117 |
| 30 | 0.04106 |
| 31 | 0.06425 |
| 32 | 0.0379 |
| 33 | 0.6687 |
| 34 | 0.1779 |
| 35 | 0.09935 |
| 36 | 0.9679 |
| 38 | 0.8316 |
| 39 | 0.2918 |
| 40 | 0.3971 |
| 42 | 0.397 |
| 44 | 0.06898 |
| 45 | 0.72 |
| 46 | 0.04723 |
| 47 | 0.01377 |
| 48 | 0.05019 |
| 49 | 0.01957 |
| 52 | 0.08323 |
| 53 | 0.0319 |
| 54 | 0.06086 |
| 55 | 0.01679 |
| 56 | 0.05887 |
| 57 | 0.2213 |
| 58 | 0.008772 |
| 59 | 0.009269 |
| 60 | 0.1594 |
| 61 | 0.09638 |
| 62 | 0.02791 |
| 63 | 0.02085 |
| 64 | 0.01007 |
| 65 | 0.2744 |
| 66 | 0.0285 |
| 67 | 0.02364 |
| 68 | 0.1213 |
| 69 | 0.02452 |
| 70 | 0.02452 |
| 71 | 0.1137 |
| 72 | 0.2660 |
| 73 | 0.0878 |
| 74 | 0.3578 |
| 75 | 0.6674 |
| 76 | 0.07518 |
| 77 | 0.1465 |
| 78 | 0.02624 |
| 79 | 0.01299 |

As shown in Table 7, the compounds of the present invention were confirmed to have excellent inhibitory activity against TMD8 cells. Based on such activity as the above, the compounds of the present invention were confirmed to be very effective in treating B-cell malignant tumor.

Therefore, the compounds of the present invention can be effectively used as an active ingredient for a pharmaceutical composition for the prevention or treatment of cancer, autoimmune disease and Parkinson's disease.

Experimental Example 3: Evaluation of BTK Inhibitory Activity in Human Peripheral Blood Mononuclear Cells (HPBMC)

3-1. Experimental Method 20 ug/ml of human serum albumin (HAS) solution was prepared and distributed in a 96-well plate (200 μl/well). Reaction was induced at 4° C. for overnight and then 10% FBS solution was treated thereto (200 μl/well), followed by elimination. Lastly, 10 ug/ml of anti-HSA antibody was treated thereto (200 μl/well) for 1 hour, followed by elimination. An appropriate number of monocytes of human peripheral blood mononuclear cells (human PBMC) were distributed in the prepared 96-well plate. The target compounds were treated thereto at different concentration via serial dilution method, followed by culture for overnight. TNFa concentration in the culture medium was measured by ELISA (enzyme-linked immunosorbent assay) as shown in the FIGURE. A schematic diagram of the experimental procedure is shown in the FIGURE. $IC_{50}$ values of the compounds were determined by confirming the TNFa inhibition activity of the compounds between the maximum concentration (positive control) and the minimum concentration (negative control) of TNFa, and the results are shown in Table 8.

3-2. Experiment Results

TABLE 8

| Example | hPBMC $IC_{50}$ (uM) |
|---|---|
| 1 | 0.035 |
| 2 | 0.0077 |
| 4 | 0.209 |
| 6 | 0.113 |
| 7 | 0.020 |
| 8 | 0.0048 |
| 10 | 0.202 |
| 12 | 0.0026 |
| 13 | 0.0055 |
| 14 | 0.031 |
| 15 | 0.0013 |
| 16 | 0.0032 |

As shown in Table 8, the compounds of the present invention were confirmed to have excelling inhibitory activity against human PBMC. Therefore, the compounds of the present invention can be effectively used as an active ingredient for a pharmaceutical composition for the prevention or treatment of cancer, autoimmune disease and Parkinson's disease.

The pyrazolopyrimidine derivative of the present invention displays an excellent Bruton's tyrosine kinase (BTK) inhibitory activity, so that a composition comprising the derivative as an active ingredient can be effectively used as a pharmaceutical composition for the prevention or treatment of cancer, autoimmune disease and Parkinson's disease. The pyrazolopyrimidine derivative of the present invention can be used for immunotherapy because it does not inhibit ITK (Interlukin-2 receptor inducible T-cell kinase) and can b used as an autoimmune disease therapeutic agent for long-term administration because it is a reversible inhibitor. The derivative of the invention also shows an excellent pharmaceutical effect on Ab1 and Ab1 mutants along with excellent BBB permeability, so that it can be effectively used for the treatment of Parkinson's disease.

Manufacturing Example 1: Preparation of Powders

| Derivative of formula 1 | 2 g |
|---|---|
| Lactose | 1 g |

Powders were prepared by mixing all the above components, which were filled in airtight packs according to the conventional method for preparing powders.

Manufacturing Example 2: Preparation of Tablets

| Derivative of formula 1 | 100 mg |
|---|---|
| Corn starch | 100 mg |
| Lactose | 100 mg |
| Magnesium stearate | 2 mg |

Tablets were prepared by mixing all the above components by the conventional method for preparing tablets.

Manufacturing Example 3: Preparation of Capsules

| Derivative of formula 1 | 100 mg |
|---|---|
| Corn starch | 100 mg |
| Lactose | 100 mg |
| Magnesium stearate | 2 mg |

Capsules were prepared by mixing all the above components, which were filled in gelatin capsules according to the conventional method for preparing capsules.

Manufacturing Example 4: Preparation of Injectable Solution

| Derivative of formula 1 | 100 mg |
|---|---|
| Mannitol | 180 mg |
| $Na_2HPO_4 \cdot 2H_2O$ | 26 mg |
| Distilled water | 974 mg |

Injectable solutions were prepared by mixing all the above components by the conventional method for preparing injectable solutions.

Manufacturing Example 5: Preparation of Health Food

| Derivative of formula 1 | 500 ng |
|---|---|
| Vitamin complex proper amount | |
| Vitamin A acetate | 70 mg |
| Vitamin E | 1.0 mg |

183
-continued

| | | |
|---|---|---|
| Vitamin B1 | 0.13 mg | |
| Vitamin B2 | 0.15 mg | |
| Vitamin B6 | 0.5 mg | |
| Vitamin B12 | 0.2 µg | |
| Vitamin C | 10 mg | |
| Biotin | 10 µg | |
| Nicotinic acid amide | 1.7 mg | |
| Folic acid | 50 µg | |
| Calcium pantothenate | 0.5 mg | |
| Minerals proper amount | | |
| Ferrous sulfate | 1.75 mg | |
| Zinc oxide | 0.82 mg | |
| Magnesium carbonate | 25.3 mg | |
| Potassium phosphate monobasic | 15 mg | |
| Potassium phosphate dibasic | 55 mg | |
| Potassium citrate | 90 mg | |
| Calcium carbonate | 100 mg | |
| Magnesium chloride | 24.8 mg | |

Vitamins and minerals were mixed according to the preferable composition rate for health food. However, the composition rate can be adjusted. The constituents were mixed according to the conventional method for preparing health food and then the composition for health food was prepared according to the conventional method.

Manufacturing Example 6: Preparation of Health Beverages

| | |
|---|---|
| Derivative of formula 1 | 1000 mg |
| Citric acid | 1000 mg |
| Oligosaccharide | 100 g |
| Maesil (*Prunus mume*) Extract | 2 g |
| Taurine | 1 g |
| Purified water | up to 900 ml |

The above constituents were mixed according to the conventional method for preparing health beverages. The mixture was heated at 85° C. for 1 hour with stirring and then filtered. The filtrate was loaded in 2 liter sterilized containers, which were scaled and sterilized again, stored in a refrigerator until they would be used for the preparation of a composition for health beverages.

The constituents appropriate for favorite beverages were mixed according to the preferred mixing ratio but the composition ratio can be adjusted according to regional and national preferences, etc.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

INDUSTRIAL APPLICABILITY

The pyrazolopyrimidine derivative of the present invention demonstrates an excellent Bruton's tyrosine kinase (BTK) inhibitory activity, so that a pharmaceutical composition comprising the compound of the invention as an active ingredient can be effectively used for the prevention or treatment of cancer, autoimmune disease and Parkinson's disease.

184

The invention claimed is:

1. A compound represented by formula 1 or a pharmaceutically acceptable salt thereof:

[Formula 1]

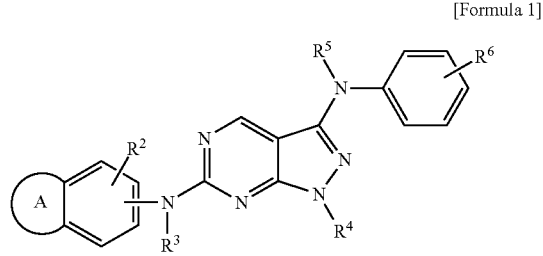

wherein:
A is piperndine, tetrahydropyrane, pyrrolidine, or cyclohexane;
wherein A is unsubstituted or substituted by one or more substituents selected from the group consisting of oxo (=), —CH$_3$, —CH$_2$CH$_3$, —CH(CH$_3$)$_2$, —CH$_2$CH$_2$OH, —(C=O)CH$_3$, —(C=O)CF$_3$, —(C=O)CHCH$_2$, —(C=O)cyclopropyl, —(C=O)CH$_2$OH, and —(C=O)CH$_2$N(CH$_3$)$_2$;
R$^2$ is hydrogen or methoxy;
R$^3$ is hydrogen;
R$^4$ is hydrogen, methyl, isopropyl, cyclopentyl, cyclohexyl, or (4-hydroxy)cyclohexyl;
R$^5$ is hydrogen; and
R$^6$ is one or more substituents selected from the group consisting of hydrogen, methyl, ethyl, isopropyl, methoxy, chloro, fluoro, methoxyethoxy, phenoxy,

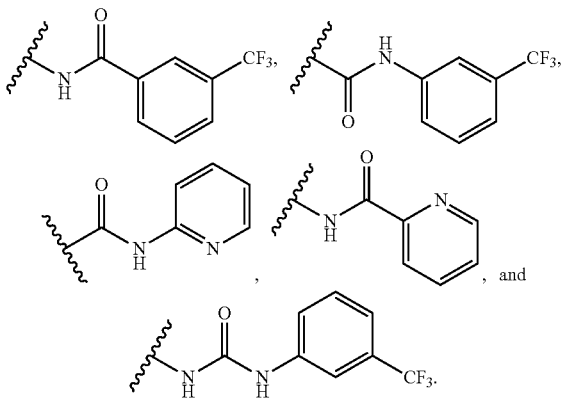

2. The compound of formula 1 according to claim 1 or the pharmaceutically acceptable salt thereof, wherein the compound represented by formula 1 is selected from the group consisting of the following compounds:
(1) 1-(7-(3-(2,6-dimethylphenylamino)-1-methyl-1H-pyrazolo[3,4-d]pyrimidine-6-ylamino)-3,4-dihydroisoquinoline-2(1H)-yl)ethaneone;
(2) N$^3$-(2,6-dimethylphenyl)-1-methyl-N$^6$-(1,2,3,4-tetrahydroisoquinoline-7-yl)-1H-pyrazolo[3,4-d]pyrimidine-3,6-diamine;
(3) 1-(6-(3-(2,6-dimethylphenylamino)-1-methyl-1H-pyrazolo[3,4-d]pyrimidine-6-ylamino)-7-methoxy-3,4-dihydroisoquinoline-2(1H)-yl)-2,2,2-trifluoroethaneone;
(4) N$^3$-(2,6-dimethylphenyl)-N$^6$-(7-methoxy-1,2,3,4-tetrahydroisoquinoline-6-yl)-1-methyl-1H-pyrazolo[3,4-d]pyrimidine-3,6-diamine;

(5) 1-(6-(3-(2,6-dimethylphenylamino)-1-methyl-1H-pyrazolo[3,4-d]pyrimidine-6-ylamino)-7-methoxy-3,4-dihydroisoquinoline-2(1H)-yl)ethaneone;

(6) 1-(6-(3-(2,6-dimethylphenylamino)-1-methyl-1H-pyrazolo[3,4-d]pyrimidine-6-ylamino)-3,4-dihydroisoquinoline-2(1H)-yl)-2,2,2-trifluoroethaneone;

(7) $N^3$-(2,6-dimethylphenyl)-1-methyl-$N^6$-(1,2,3,4-tetrahydroisoquinoline-6-yl)-1H-pyrazolo[3,4-d]pyrimidine-3,6-diamine;

(8) 1-(6-(3-(2,6-dimethylphenylamino)-1-methyl-1H-pyrazolo[3,4-d]pyrimidine-6-ylamino)-3,4-dihydroisoquinoline-2(1H)-yl)ethaneone;

(9) 2,2,2-trifluoro-1-(7-(1-methyl-3-(phenylamino)-1H-pyrazolo[3,4-d]pyrimidine-6-ylamino)-3,4-dihydroisoquinoline-2(1H)-yl)ethaneone;

(10) 1-methyl-$N^3$-phenyl-$N^6$-(1,2,3,4-tetrahydroisoquinoline-7-yl)-1H-pyrazolo[3,4-d]pyrimidine-3,6-diamine;

(11) 1-(7-(3-(2,6-dichlorophenylamino)-1-methyl-1H-pyrazolo[3,4-d]pyrimidine-6-ylamino)-3,4-dihydroisoquinoline-2(1H)-yl)-2,2,2-trifluoroethaneone;

(12) $N^3$-(2,6-dichlorophenyl)-1-methyl-$N^6$-(1,2,3,4-tetrahydroisoquinoline-7-yl)-1H-pyrazolo[3,4-d]pyrimidine-3,6-diamine;

(13) 1-(7-(3-(2,6-dichlorophenylamino)-1-methyl-1H-pyrazolo[3,4-d]pyrimidine-6-ylamino)-3,4-dihydroisoquinoline-2(1H)-yl)ethaneone;

(14) 1-(7-(3-(2,6-dimethylphenylamino)-1-methyl-1H-pyrazolo[3,4-d]pyrimidine-6-ylamino)-3,4-dihydroisoquinoline-2(1H)-yl)prop-2-en-1-one;

(15) $N^3$-(2,6-dichlorophenyl)-1-methyl-$N^6$-(1,2,3,4-tetrahydroisoquinoline-6-yl)-1H-pyrazolo[3,4-d]pyrimidine-3,6-diamine;

(16) 1-(6-(3-(2,6-dichlorophenylamino)-1-methyl-1H-pyrazolo[3,4-d]pyrimidine-6-ylamino)-3,4-dihydroisoquinoline-2(1H)-yl)ethaneone;

(17) $N^3$-(2,6-dimethylphenyl)-1-methyl-$N^6$-(2-methyl-1,2,3,4-tetrahydroisoquinoline-7-yl)-1H-pyrazolo[3,4-d]pyrimidine-3,6-diamine;

(18) $N^3$-(2,6-dimethylphenyl)-$N^6$-(isochroman-7-yl)-1-methyl-1H-pyrazolo[3,4-d]pyrimidine-3,6-diamine;

(19) $N^3$-(2,6-dimethylphenyl)-$N^6$-(1,2,3,4-tetrahydroisoquinoline-7-yl)-1H-pyrazolo[3,4-d]pyrimidine-3,6-diamine;

(20) $N^3$-(2,6-dimethylphenyl)-1-methyl-$N^6$-(1-methyl-1,2,3,4-tetrahydroisoquinoline-7-yl)-1H-pyrazolo[3,4-d]pyrimidine-3,6-diamine;

(21) $N^3$-(2,6-dimethylphenyl)-$N^6$-(2-isopropyl-1,2,3,4-tetrahydroisoquinoline-7-yl)-1-methyl-1H-pyrazolo[3,4-d]pyrimidine-3,6-diamine;

(22) 1-(7-(3-(2,6-dimethylphenylamino)-1-methyl-1H-pyrazolo[3,4-d]pyrimidine-6-ylamino)-3,4-dihydroisoquinoline-2(1H)-yl)-2-hydroxyethanone;

(23) cyclopropyl(7-(3-(2,6-dimethylphenylamino)-1-methyl-1H-pyrazolo[3,4-d]pyrimidine-6-ylamino)-3,4-dihydroisoquinoline-2(1H)-yl)methanone;

(24) 2-(7-((3-((2,6-dimethylphenyl)amino)-1-methyl-1H-pyrazolo[3,4-d]pyrimidine-6-yl)amino)-3,4-dihydroisoquinoline-2(1H)-yl)ethane-1-ol;

(25) 1-cyclopentyl-$N^3$-(2,6-dimethylphenyl)-$N^6$-(1,2,3,4-tetrahydroisoquinoline-7-yl)1H-pyrazolo[3,4-d]pyrimidine-3,6-diamine;

(26) 1-cyclohexyl-$N^3$-(2,6-dimethylphenyl)-$N^6$-(1,2,3,4-tetrahydroisoquinoline-7-yl)1H-pyrazolo[3,4-d]pyrimidine-3,6-diamine;

(27) $N^3$-(2,6-dimethylphenyl)-1-isopropyl-N6-(1,2,3,4-tetrahydroisoquinoline-7-yl)-1H-pyrazolo[3,4-d]pyrimidine-3,6-diamine;

(28) N-(4-methyl-3-((1-methyl-6-((1,2,3,4-tetrahydroisoquinoline-7-yl)amino)-1H-pyrazolo[3,4-d]pyrimidine-3-yl)amino)phenyl)-3-(trifluoromethyl)benzamide;

(29) N-(2,4-dimethyl-3-(1-methyl-6-(1,2,3,4-tetrahydroisoquinoline-7-ylamino)-1H-pyrazolo[3,4-d]pyrimidine-3-ylamino)phenyl)-3-(trifluoromethyl)benzamide;

(30) $N^3$-(4-(2-methoxyethoxy)-2,6-dimethylphenyl)-1-methyl-$N^6$-(1,2,3,4-tetrahydroisoquinoline-7-yl)-1H-pyrazolo[3,4-d]pyrimidine-3,6-diamine;

(31) 2-(dimethylamino)-1-(7-(3-(2,6-dimethylphenylamino)-1-methyl-1H-pyrazolo[3,4-d]pyrimidine-6-ylamino)-3,4-dihydroisoquinoline-2(1H)-yl)ethanone;

(32) $N^3$-(2,6-dimethylphenyl)-$N^6$-(2-ethyl-1,2,3,4-tetrahydroisoquinoline-7-yl)-1-methyl-1H-pyrazolo[3,4-d]pyrimidine-3,6-diamine;

(33) $N^3$-(2,6-dimethyl-4-phenoxyphenyl)-1-methyl-$N^6$-(1,2,3,4-tetrahydroisoquinoline-7-yl)-1H-pyrazolo[3,4-d]pyrimidine-3,6-diamine;

(34) 3,5-dimethyl-4-(1-methyl-6-(1,2,3,4-tetrahydroisoquinoline-7-ylamino)-1H-pyrazolo[3,4-d]pyrimidine-3-ylamino)-N-(pyridine-2-yl)benzamide;

(35) $N^3$-(4-methoxy-2,6-dimethylphenyl)-1-methyl-$N^6$-(1,2,3,4-tetrahydroisoquinoline-7-yl)-1H-pyrazolo[3,4-d]pyrimidine-3,6-diamine;

(36) $N^3$-(2,6-diethylphenyl)-1-methyl-$N^6$-(1,2,3,4-tetrahydroisoquinoline-7-yl)-1H-pyrazolo[3,4-d]pyrimidine-3,6-diamine;

(37) $N^3$-(2,6-diisopropylphenyl)-1-methyl-$N^6$-(1,2,3,4-tetrahydroisoquinoline-7-yl)-1H-pyrazolo[3,4-d]pyrimidine-3,6-diamine;

(38) $N^3$-(2-chloro-3,5-dimethylphenyl)-1-methyl-$N^6$-(1,2,3,4-tetrahydroisoquinoline-7-yl)-1H-pyrazolo[3,4-d]pyrimidine-3,6-diamine;

(39) $N^3$-(2,4-dimethylphenyl)-1-methyl-$N^6$-(1,2,3,4-tetrahydroisoquinoline-7-yl)-1H-pyrazolo[3,4-d]pyrimidine-3,6-diamine;

(40) 1-methyl-$N^6$-(1,2,3,4-tetrahydroisoquinoline-7-yl)-$N^3$-o-tolyl-1H-pyrazolo[3,4-d]pyrimidine-3,6-diamine;

(41) $N^3$-(3,5-dimethylphenyl)-1-methyl-$N^6$-(1,2,3,4-tetrahydroisoquinoline-7-yl)-1H-pyrazolo[3,4-d]pyrimidine-3,6-diamine;

(42) $N^3$-(2,6-difluorophenyl)-1-methyl-$N^6$-(1,2,3,4-tetrahydroisoquinoline-7-yl)-1H-pyrazolo[3,4-d]pyrimidine-3,6-diamine;

(43) $N^3$-(2,6-dimethoxyphenyl)-1-methyl-$N^6$-(1,2,3,4-tetrahydroisoquinoline-7-yl)-1H-pyrazolo[3,4-d]pyrimidine-3,6-diamine;

(44) $N^3$-(4-fluoro-2,6-dimethylphenyl)-1-methyl-$N^6$-(1,2,3,4-tetrahydroisoquinoline-7-yl)-1H-pyrazolo[3,4-d]pyrimidine-3,6-diamine;

(45) $N^3$-(2,5-dimethylphenyl)-1-methyl-$N^6$-(1,2,3,4-tetrahydroisoquinoline-7-yl)-1H-pyrazolo[3,4-d]pyrimidine-3,6-diamine;

(46) $N^6$-(4,4-dimethyl-1,2,3,4-tetrahydroisoquinoline-7-yl)-$N^3$-(2,6-dimethylphenyl)-1-methyl-1H-pyrazolo[3,4-d]pyrimidine-3,6-diamine;

(47) N-(4-methyl-3-(1-methyl-6-(1-methyl-1,2,3,4-tetrahydroisoquinoline-7-ylamino)1H-pyrazolo[3,4-d]pyrimidine-3-ylamino)phenyl)-3-(trifluoromethyl)benzamide;

(48) N³-(2-chloro-6-methylphenyl)-1-methyl-N⁶-(1,2,3,4-tetrahydroisoquinoline-7-yl)1H-pyrazolo[3,4-d]pyrimidine-3,6-diamine;
(49) N³-(2,6-dimethylphenyl)-N⁶-(1-isopropyl-1,2,3,4-tetrahydroisoquinoline-7-yl)-1-methyl-1H-pyrazolo[3,4-d]pyrimidine-3,6-diamine;
(50) N³-(5-(2-methoxyethoxy)-2-methylphenyl)-1-methyl-N⁶-(1,2,3,4-tetrahydroisoquinoline-7-yl)-1H-pyrazolo[3,4-d]pyrimidine-3,6-diamine;
(51) N-(4-methyl-3-(1-methyl-6-(1,2,3,4-tetrahydroisoquinoline-7-ylamino)-1H-pyrazolo[3,4-d]pyrimidine-3-ylamino)phenyl)picolineamide;
(52) 4-methyl-3-(1-methyl-6-(1,2,3,4-tetrahydroisoquinoline-7-ylamino)-1H-pyrazolo[3,4-d]pyrimidine-3-ylamino)-N-(3-(trifluoromethyl)phenyl)benzamide;
(53) N⁶-(3,3-dimethyl-1,2,3,4-tetrahydroisoquinoline-7-yl)-N³-(2,6-dimethylphenyl)-1-methyl-1H-pyrazolo[3,4-d]pyrimidine-3,6-diamine;
(54) 4-(3-((2,6-dimethylphenyl)amino)-6-((1,2,3,4-tetrahydroisoquinoline-7-yl)amino)1H-pyrazolo[3,4-d]pyrimidine-1-yl)cyclohexane-1-ol;
(55) N³-(2,6-dimethylphenyl)-1-methyl-N⁶-(1,3,3-trimethyl-1,2,3,4-tetrahydroisoquinoline-7-yl)-1H-pyrazolo[3,4-d]pyrimidine-3,6-diamine;
(56) N³-(2,6-dimethylphenyl)-N⁶-(isoindolin-5-yl)-1-methyl-1H-pyrazolo[3,4-d]pyrimidine-3,6-diamine;
(57) 1-(4-methyl-3-((1-methyl-6-((1,2,3,4-tetrahydroisoquinoline-7-yl)amino)-1H-pyrazolo[3,4-d]pyrimidine-3-yl)amino)phenyl)-3-(3-(trifluoromethyl)phenyl)urea;
(58) N⁶-(1,1-dimethyl-1,2,3,4-tetrahydroisoquinoline-7-yl)-N³-(2,6-dimethylphenyl)-1-methyl-1H-pyrazolo[3,4-d]pyrimidine-3,6-diamine;
(59) N³-(2,6-dimethylphenyl)-1-methyl-N⁶-(1,1,2-trimethyl-1,2,3,4-tetrahydroisoquinoline-7-yl)-1H-pyrazolo[3,4-d]pyrimidine-3,6-diamine;
(60) 1-(7-((3-((2,6-dimethylphenyl)amino)-1-methyl-1H-pyrazolo[3,4-d]pyrimidine-6-yl)amino)-1,1-dimethyl-3,4-dihydroisoquinoline-2(1H)-yl)ethane-1-one;
(61) 1-(7-((3-((2,6-dimethylphenyl)amino)-1-methyl-1H-pyrazolo[3,4-d]pyrimidine-6-yl)amino)-1-methyl-3,4-dihydroisoquinoline-2(1H)-yl)ethane-1-one;
(62) N⁶-(1,2-dimethyl-1,2,3,4-tetrahydroisoquinoline-7-yl)-N³-(2,6-dimethylphenyl)-1-methyl-1H-pyrazolo[3,4-d]pyrimidine-3,6-diamine;
(63) N³-(2,6-dimethylphenyl)-1-methyl-N⁶-(2,4,4-trimethyl-1,2,3,4-tetrahydroisoquinoline-7-yl)-1H-pyrazolo[3,4-d]pyrimidine-3,6-diamine;
(64) N-(3-((6-((1,2-dimethyl-1,2,3,4-tetrahydroisoquinoline-7-yl)amino)-1-methyl-1H-pyrazolo[3,4-d]pyrimidine-3-yl)amino)-4-methylphenyl)-3-(trifluoromethyl)benzamide;
(65) N³-(2,6-dimethylphenyl)-N⁶-(1-isopropyl-2-methyl-1,2,3,4-tetrahydroisoquinoline-7-yl)-1-methyl-1H-pyrazolo[3,4-d]pyrimidine-3,6-diamine;
(66) N³-(2,6-dimethylphenyl)-1-methyl-N⁶-(2,3,3-trimethyl-1,2,3,4-tetrahydroisoquinoline-7-yl)-1H-pyrazolo[3,4-d]pyrimidine-3,6-diamine;
(67) N³-(2,6-dimethylphenyl)-1-methyl-N⁶-(1,2,3,3-tetramethyl-1,2,3,4-tetrahydroisoquinoline-7-yl)-1H-pyrazolo[3,4-d]pyrimidine-3,6-diamine;
(68) 1-(7-((3-((2,6-dimethylphenyl)amino)-1-methyl-1H-pyrazolo[3,4-d]pyrimidine-6-yl)amino)-4,4-dimethyl-3,4-dihydroisoquinoline-2(1H)-yl)ethane-1-one;
(69) N-(3-((6-((2-acetyl-1-methyl-1,2,3,4-tetrahydroisoquinoline-7-yl)amino)-1-methyl-1H-pyrazolo[3,4-d]pyrimidine-3-yl)amino)-4-methylphenyl)-3-(trifluoromethyl)benzamide;
(70) 1-(7-((3-((2,6-dimethylphenyl)amino)-1-methyl-1H-pyrazolo[3,4-d]pyrimidine-6-yl)amino)-1-isopropyl-3,4-dihydroisoquinoline-2(1H)-yl)ethane-1-one;
(71) 1-(7-((3-((2,6-dimethylphenyl)amino)-1-methyl-1H-pyrazolo[3,4-d]pyrimidine-6-yl)amino)-3,3-dimethyl-3,4-dihydroisoquinoline-2(1H)-yl)ethane-1-one;
(72) 1-(5-((3-((2,6-dimethylphenyl)amino)-1-methyl-1H-pyrazolo[3,4-d]pyrimidine-6-yl)amino)isoindolin-2-yl)ethane-1-one;
(73) 1-(7-((3-((2,6-dimethylphenyl)amino)-1-methyl-1H-pyrazolo[3,4-d]pyrimidine-6-yl)amino)-1,3,3-trimethyl-3,4-dihydroisoquinoline-2(1H)-yl)ethane-1-one;
(74) N³-(2,6-dimethylphenyl)-1-methyl-N⁶-(2-methylisoindolin-5-yl)-1H-pyrazolo[3,4-d]pyrimidine-3,6-diamine;
(75) N³-(2,6-dimethylphenyl)-1-methyl-N⁶-(5,6,7,8-tetrahydronaphthalene-2-yl)-1H-pyrazolo[3,4-d]pyrimidine-3,6-diamine;
(76) 7-((3-((2,6-dimethylphenyl)amino)-1-methyl-1H-pyrazolo[3,4-d]pyrimidine-6-yl)amino)-3,4-dihydroisoquinoline-1(2H)-one;
(77) N⁶-(1-isopropyl-1,2,3,4-tetrahydroisoquinoline-7-yl)-N³-(4-(2-methoxyethoxy)-2,6-dimethylphenyl)-1-methyl-1H-pyrazolo[3,4-d]pyrimidine-3,6-diamine; and
(78) N⁶-(1,1-dimethyl-1,2,3,4-tetrahydroisoquinoline-7-yl)-N³-(4-(2-methoxyethoxy)-2,6-dimethylphenyl)-1-methyl-1H-pyrazolo[3,4-d]pyrimidine-3,6-diamine.

3. A method of preparing a compound represented by formula 1 comprising the step of reacting a compound represented by formula 2 with a compound represented by formula 3 (step 1), as shown in reaction formula 1 below:

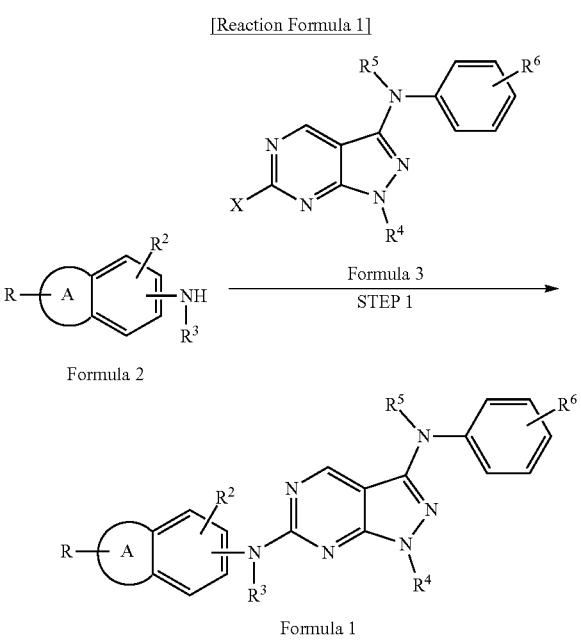

wherein:
A is piperidine, tetrahydropyrane, pyrrolidine, or cyclohexane;
wherein A is unsubstituted or substituted by one or more substituents selected from the group consisting of oxo (=O), —CH₃, —CH₂CH₃, —CH(CH₃)₂, —CH₂CH₂OH, —(C=O)CH₃, —(C=O)CF₃, —(C=O)CHCH₂, —(C=O)cyclopropyl, —(C=O)CH₂OH, and —(C=O)CH₂N(CH₃)₂;

R² is hydrogen or methoxy;

R³ is hydrogen;

R⁴ is hydrogen, methyl, isopropyl, cyclopentyl, cyclohexyl, or (4-hydroxy)cyclohexyl;

R⁵ is hydrogen;

R⁶ is one or more substituents selected from the group consisting of hydrogen, methyl, ethyl, isopropyl, methoxy, chloro, fluoro, methoxyethoxy, phenoxy,

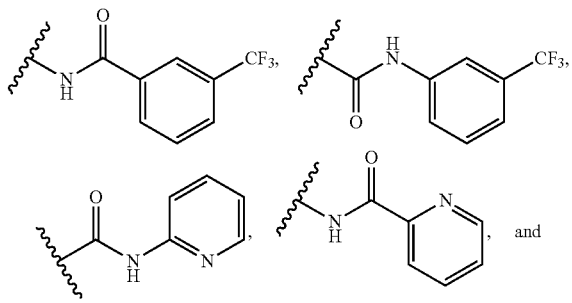

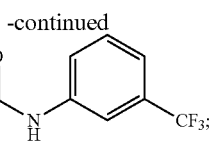

and

X is F, Br, Cl, or I.

4. A pharmaceutical composition comprising the compound of formula 1 according to claim 1 or the pharmaceutically acceptable salt thereof as an active ingredient for the treatment of diffuse large B-cell lymphoma.

5. A method of treating a subject having diffuse large B-cell lymphoma comprising administering an effective amount of the compound of formula 1 according to claim 1 or the pharmaceutically acceptable salt thereof to the subject.

6. A method for the treatment of diffuse large B-cell lymphoma comprising the step of administering the pharmaceutical composition comprising the compound formula 1 according to claim 1 or the pharmaceutically acceptable salt thereof as an active ingredient to a subject in need.

* * * * *